United States Patent
Kim et al.

(10) Patent No.: US 10,096,784 B2
(45) Date of Patent: Oct. 9, 2018

(54) COMPOUND FOR ORGANIC OPTOELECTRIC DEVICE, COMPOSITION FOR ORGANIC OPTOELECTRIC DEVICE AND ORGANIC OPTOELECTRIC DEVICE AND DISPLAY DEVICE

(71) Applicants: SAMSUNG SDI CO., LTD., Yongin-si, Gyeonggi-do (KR); SAMSUNG ELECTRONICS CO., LTD., Suwon-si, Gyeonggi-do (KR)

(72) Inventors: Byungku Kim, Suwon-si (KR); Dong Min Kang, Suwon-si (KR); Jinhyun Lui, Suwon-si (KR); Bum Woo Park, Suwon-si (KR); Eun Sun Yu, Suwon-si (KR); Yuna Jang, Suwon-si (KR); Sung-Hyun Jung, Suwon-si (KR); Pyeongseok Cho, Suwon-si (KR)

(73) Assignees: Samsung SDI Co., Ltd., Yongin-si, Gyeonggi-do (KR); Samsung Electronics Co., Ltd., Suwon-Si, Gyeonggi-do (KR)

( * ) Notice: Subject to any disclaimer, the term of this patent is extended or adjusted under 35 U.S.C. 154(b) by 0 days.

(21) Appl. No.: 15/677,491

(22) Filed: Aug. 15, 2017

(65) Prior Publication Data

US 2018/0083202 A1  Mar. 22, 2018

(30) Foreign Application Priority Data

Sep. 21, 2016 (KR) .................. 10-2016-0120645

(51) Int. Cl.
C07D 491/048 (2006.01)
C07D 495/04 (2006.01)
H01L 51/00 (2006.01)

(52) U.S. Cl.
CPC ...... *H01L 51/0072* (2013.01); *C07D 491/048* (2013.01); *C07D 495/04* (2013.01); *H01L 51/0067* (2013.01); *H01L 51/0071* (2013.01); *H01L 51/0073* (2013.01); *H01L 51/0074* (2013.01)

(58) Field of Classification Search
CPC ............. C07D 487/22; C07D 491/048; C07D 495/04; C07F 7/02; H01L 51/0067; H01L 51/0071–51/0074
See application file for complete search history.

(56) References Cited

U.S. PATENT DOCUMENTS 9,017,829 B2 * 4/2015 Hong .................. C07D 209/80
257/40

FOREIGN PATENT DOCUMENTS

| KR | 10-2012-0072784 A | 7/2012 |
|---|---|---|
| KR | 10-1196093 B | 11/2012 |
| KR | 10-1219492 B | 1/2013 |
| KR | 10-2013-0050237 A | 5/2013 |
| KR | 10-2013-0057397 A | 5/2013 |
| KR | 10-1456521 B | 10/2014 |
| KR | 10-1470055 B | 12/2014 |

* cited by examiner

*Primary Examiner* — Daniel Shook
(74) *Attorney, Agent, or Firm* — Lee & Morse, P.C.

(57) ABSTRACT

Disclosed are a compound for an organic optoelectric device represented by Chemical Formula 1, a composition for an organic optoelectric device, an organic optoelectric device including the same, and a display device. Details of Chemical Formula 1 are the same as those defined in the specification.

18 Claims, 1 Drawing Sheet

COMPOUND FOR ORGANIC OPTOELECTRIC DEVICE, COMPOSITION FOR ORGANIC OPTOELECTRIC DEVICE AND ORGANIC OPTOELECTRIC DEVICE AND DISPLAY DEVICE

CROSS-REFERENCE TO RELATED APPLICATION

This application claims priority to and the benefit of Korean Patent Application No. 10-2016-0120645 filed in the Korean Intellectual Property Office on Sep. 21, 2016, the entire contents of which are incorporated herein by reference.

BACKGROUND OF THE INVENTION

1. Field of the Invention

A compound for an organic optoelectric device, a composition for an organic optoelectric device, an organic optoelectric device, and a display device are disclosed.

2. Description of the Related Art

An organic optoelectric device (organic optoelectric diode) is a device that converts electrical energy into photoenergy, and vice versa.

An organic optoelectric device may be classified as follows in accordance with its driving principles. One is a photoelectric device where excitons are generated by photoenergy, separated into electrons and holes, and are transferred to different electrodes to generate electrical energy, and the other is a light emitting device where a voltage or a current is supplied to an electrode to generate photoenergy from electrical energy.

The organic optoelectric device may for example include an organic photoelectric device, an organic light emitting diode, an organic solar cell, an organic photo conductor drum, and the like.

Of these, an organic light emitting diode (OLED) has recently drawn attention due to an increase in demand for flat panel displays. The organic light emitting diode is a device converting electrical energy into light by applying current to an organic light emitting material, and has a structure in which an organic layer is disposed between an anode and a cathode. Herein, the organic layer may include a light emitting layer and optionally an auxiliary layer, and the auxiliary layer may be, for example at least one layer selected from a hole injection layer, a hole transport layer, an electron blocking layer, an electron transport layer, an electron injection layer, and a hole blocking layer.

Performance of an organic light emitting diode may be affected by characteristics of the organic layer, and among them, may be mainly affected by characteristics of an organic material of the organic layer.

Particularly, development for an organic material being capable of increasing hole and electron mobility and simultaneously increasing electrochemical stability is needed so that the organic light emitting diode may be applied to a large-size flat panel display.

SUMMARY OF THE INVENTION

An embodiment provides a compound for an organic optoelectric device capable of realizing an organic optoelectric device having high efficiency and a long life-span.

Another embodiment provides a composition for an organic optoelectric device including the compound for an organic optoelectric device.

Yet another embodiment provides an organic optoelectric device including the compound.

According to an embodiment, a compound for an organic optoelectric device represented by Chemical Formula 1 is provided.

[Chemical Formula 1]

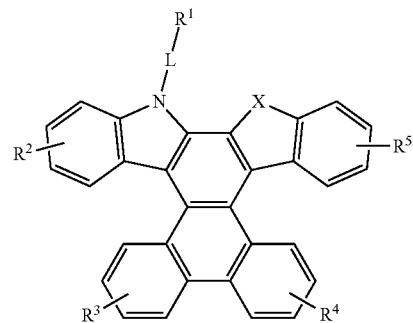

In Chemical Formula 1,

X is O, S, $CR^6R^7$, or $SiR^8R^9$, $R^1$ is a substituted or unsubstituted C6 to C30 aryl group, a substituted or unsubstituted C2 to C30 heterocyclic group, or a combination thereof, $R^2$ to $R^9$ are independently hydrogen, deuterium, a substituted or unsubstituted C1 to C20 alkyl group, a substituted or unsubstituted C6 to C30 aryl group, a substituted or unsubstituted C2 to C30 heterocyclic group, or a combination thereof, L is a single bond, a substituted or unsubstituted C6 to C30 arylene group, a substituted or unsubstituted C2 to C30 heteroarylene group, or a combination thereof, and the "substituted" refers to replacement of at least one hydrogen by deuterium, a C1 to C4 alkyl group, a C6 to C18 aryl group, or a C2 to C18 heteroaryl group.

According to another embodiment, a composition for an organic optoelectric device includes a first compound for an organic optoelectric device that is the above compound; and at least one second compound for an organic optoelectric device selected from a compound represented by Chemical Formula 2 and a compound consisting of a combination of a moiety represented by Chemical Formula 3 and a moiety represented by Chemical Formula 4.

[Chemical Formula 2]

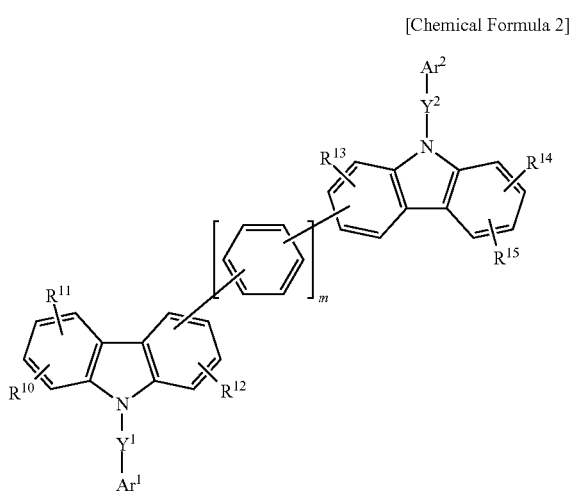

In Chemical Formula 2, $Y^1$ and $Y^2$ are independently a single bond, a substituted or unsubstituted C6 to C30 arylene group, a substituted or unsubstituted C2 to C30 heteroarylene group, or a combination thereof, $Ar^1$ and $Ar^2$ are independently a substituted or unsubstituted C6 to C30 aryl group, a substituted or unsubstituted C2 to C30 heterocyclic group, or a combination thereof, $R^{10}$ to $R^{15}$ are independently hydrogen, deuterium, a substituted or unsubstituted C1 to C20 alkyl group, a substituted or unsubstituted C6 to C30 aryl group, a substituted or unsubstituted C2 to C50 heterocyclic group, or a combination thereof, and m is an integer of 0 to 2;

[Chemical Formula 3]

[Chemical Formula 4]

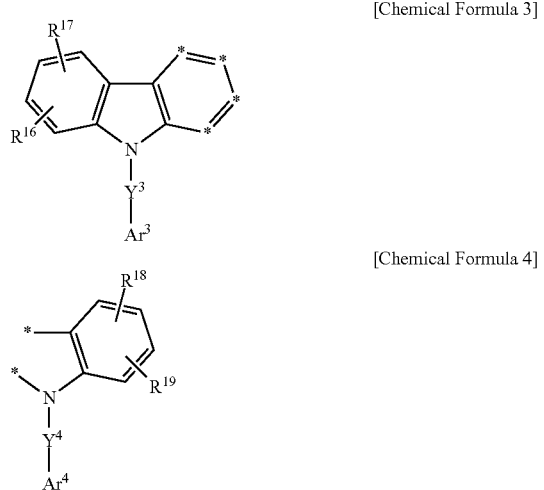

wherein, in Chemical Formulae 3 and 4, $Y^3$ and $Y^4$ are independently a single bond, a substituted or unsubstituted C6 to C30 arylene group, a substituted or unsubstituted C2 to C30 heteroarylene group, or a combination thereof, $Ar^3$ and $Ar^4$ are independently a substituted or unsubstituted C6 to C30 aryl group, a substituted or unsubstituted C2 to C30 heterocyclic group, or a combination thereof, $R^{16}$ to $R^{19}$ are independently hydrogen, deuterium, a substituted or unsubstituted C1 to C20 alkyl group, a substituted or unsubstituted C6 to C50 aryl group, a substituted or unsubstituted C2 to C50 heterocyclic group, or a combination thereof, two adjacent *'s of Chemical Formula 3 are bound to two adjacent *'s of Chemical Formula 4 to provide a fused ring and *'s of not providing the fused ring in Chemical Formula 3 are independently $CR^a$, and $R^a$ is hydrogen, deuterium, a substituted or unsubstituted C1 to C10 alkyl group, a substituted or unsubstituted C6 to C12 aryl group, a substituted or unsubstituted C2 to C12 heterocyclic group, or a combination thereof;

wherein the "substituted" refers to replacement of at least one hydrogen by deuterium, a C1 to C4 alkyl group, a C6 to C18 aryl group, or a C2 to C18 heteroaryl group.

According to another embodiment, an organic optoelectric device includes an anode and a cathode facing each other and at least one organic layer disposed between the anode and the cathode, wherein the organic layer includes the compound for an organic optoelectric device or the composition for an organic optoelectric device.

According to another embodiment, a display device includes the organic optoelectric device.

An organic optoelectric device having high efficiency and a long life-span may be realized.

DETAILED DESCRIPTION

Figure 1:
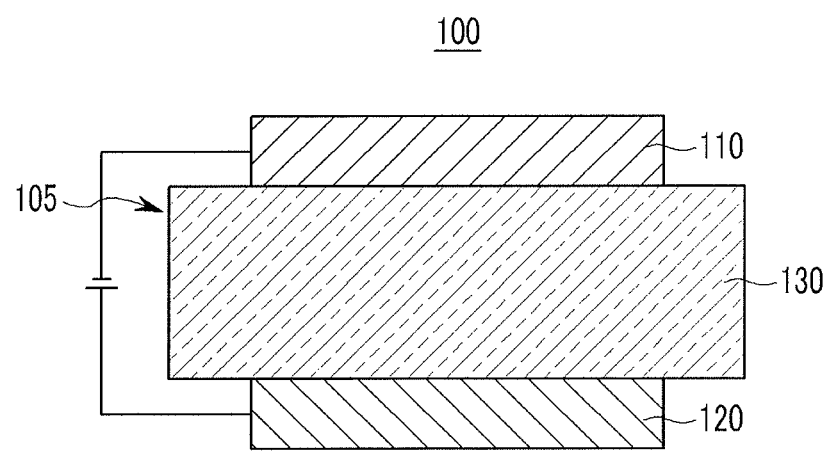
FIGS. 1 and 2 are cross-sectional views showing organic light emitting diodes according to embodiments.

Hereinafter, embodiments of the present disclosure are described in detail. However, these embodiments are exemplary, the present disclosure is not limited thereto and the present invention is defined by the scope of claims.

As used herein, when a definition is not otherwise provided, "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C6 to C30 heteroaryl group, a C1 to C20 alkoxy group, a fluoro group, a C1 to C10 trifluoroalkyl group such as a trifluoromethyl group, or a cyano group.

In one example of the present disclosure, the "substituted" refers to replacement of at least one hydrogen of a substituent or a compound by deuterium, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, or a C6 to C30 heteroaryl group. In addition, in specific examples of the present disclosure, the "substituted" refers to replacement of at least one hydrogen of a substituent or a compound by deuterium, a C1 to C30 alkyl group, a C6 to C18 aryl group, or a C6 to C20 heteroaryl group. In addition, in more specific examples of the present disclosure, the "substituted" refers to replacement of at least one hydrogen of a substituent or a compound by deuterium, a C1 to C4 alkyl group, a C6 to C18 aryl group, or a C2 to C18 heteroaryl group.

As used herein, when a definition is not otherwise provided, "hetero" refers to one including one to three heteroatoms selected from N, O, S, P, and Si, and remaining carbons in one functional group.

As used herein, when a definition is not otherwise provided, "alkyl group" refers to an aliphatic hydrocarbon group. The alkyl group may be "a saturated alkyl group" without any double bond or triple bond.

The alkyl group may be a C1 to C30 alkyl group. More specifically, the alkyl group may be a C1 to C20 alkyl group or a C1 to C10 alkyl group. For example, a C1 to C4 alkyl group may have one to four carbon atoms in an alkyl chain, and may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

As used herein, "an aryl group" refers to a group including at least one hydrocarbon aromatic moiety, and all elements of the hydrocarbon aromatic moiety have p-orbitals which form conjugation, for example a phenyl group, a naphthyl group, and the like, two or more hydrocarbon aromatic moieties may be linked by a sigma bond and may be, for example a biphenyl group, a terphenyl group, a quarterphenyl group, and the like, and two or more hydrocarbon aromatic moieties are fused directly or indirectly to provide a non-aromatic fused ring. For example, it may be a fluorenyl group.

The aryl group may include a monocyclic, polycyclic, or fused ring polycyclic (i.e., rings sharing adjacent pairs of carbon atoms) functional group.

As used herein, "a heterocyclic group" is a generic concept of a heteroaryl group, and may include at least one heteroatom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

For example, "a heteroaryl group" may refer to an aryl group including at least one heteroatom selected from N, O, S, P, and Si. Two or more heteroaryl groups are linked by a sigma bond directly, or when the heteroaryl group includes two or more rings, the two or more rings may be fused. When the heteroaryl group is a fused ring, each ring may include one to three heteroatoms.

Specific examples of the heterocyclic group may be a pyridinyl group, a pyrimidinyl group, a pyrazinyl group, a pyridazinyl group, a triazinyl group, a quinolinyl group, an isoquinolinyl group, and the like.

More specifically, the substituted or unsubstituted C6 to C30 aryl group and/or the substituted or unsubstituted C2 to C30 heterocyclic group may be a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted fluorenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted dibenzofuranyl group, or a substituted or unsubstituted dibenzothiophenyl group, or a combination thereof, but are not limited thereto.

As used herein, hole characteristics refer to an ability to donate an electron to form a hole when an electric field is applied and that a hole formed in the anode may be easily injected into the light emitting layer and transported in the light emitting layer due to conductive characteristics according to a highest occupied molecular orbital (HOMO) level.

In addition, electron characteristics refer to an ability to accept an electron when an electric field is applied and that electron formed in the cathode may be easily injected into the light emitting layer and transported in the light emitting layer due to conductive characteristics according to a lowest unoccupied molecular orbital (LUMO) level.

Hereinafter, a compound for an organic optoelectric device according to an embodiment is described.

A compound for an organic optoelectric device according to an embodiment is represented by Chemical Formula 1.

[Chemical Formula 1]

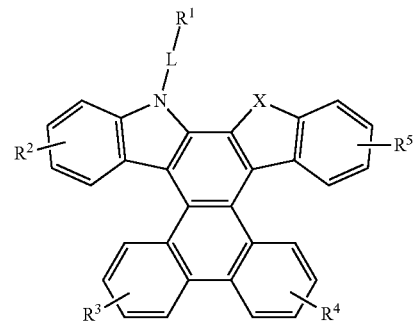

In Chemical Formula 1,

X is O, S, $CR^6R^7$, or $SiR^8R^9$, $R^1$ is a substituted or unsubstituted C6 to C30 aryl group, a substituted or unsubstituted C2 to C30 heterocyclic group, or a combination thereof, $R^2$ to $R^9$ are independently hydrogen, deuterium, a substituted or unsubstituted C1 to C20 alkyl group, a substituted or unsubstituted C6 to C30 aryl group, a substituted or unsubstituted C2 to C30 heterocyclic group, or a combination thereof, L is a single bond, a substituted or unsubstituted C6 to C30 arylene group, a substituted or unsubstituted C2 to C30 heteroarylene group, or a combination thereof, and the "substituted" refers to replacement of at least one hydrogen by deuterium, a C1 to C4 alkyl group, a C6 to C18 aryl group, or a C2 to C18 heteroaryl group.

The compound for an organic optoelectric device according to an embodiment has a structure that phenanthrene is fused with an indolocarbazole derivative and thus may show device performance such as a low driving voltage and high efficiency, since excellent hole characteristics of the indolocarbazole derivative are not only used, but holes are also transferred much faster due to the additionally fused moiety.

In an example embodiment, $R^1$ of Chemical Formula 1 may be a substituted or unsubstituted phenyl group, a substituted or unsubstituted biphenyl group, a substituted or unsubstituted terphenyl group, a substituted or unsubstituted naphthyl group, a substituted or unsubstituted phenanthrenyl group, a substituted or unsubstituted triphenylene group, a substituted or unsubstituted fluorenyl group, a substituted or unsubstituted fluoranthenyl group, a substituted or unsubstituted carbazolyl group, a substituted or unsubstituted dibenzofuranyl group, a substituted or unsubstituted dibenzothiophenyl group, a substituted or unsubstituted pyridinyl group, a substituted or unsubstituted pyrimidinyl group, a substituted or unsubstituted triazinyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzofuranpyrimidinyl group, a substituted or unsubstituted benzothiophenepyrimidinyl group, or a substituted or unsubstituted phenanthrolinyl group, in a specific example embodiment, R' of Chemical Formula 1 may be a substituted or unsubstituted phenyl group, a substituted or unsubstituted biphenyl group, a substituted or unsubstituted terphenyl group, a substituted or unsubstituted phenanthrenyl group, a substituted or unsubstituted triphenylene group, a substituted or unsubstituted carbazolyl group, a substituted or unsubstituted dibenzofuranyl group, a substituted or unsubstituted dibenzothiophenyl group, a substituted or unsubstituted triazinyl group, a substituted or unsubstituted quinazolinyl group, a substituted or unsubstituted benzofuranpyrimidinyl group, or a substituted or unsubstituted benzothiophenepyrimidinyl group, and for example, it may be selected from substituents of Group I.

[Group I]

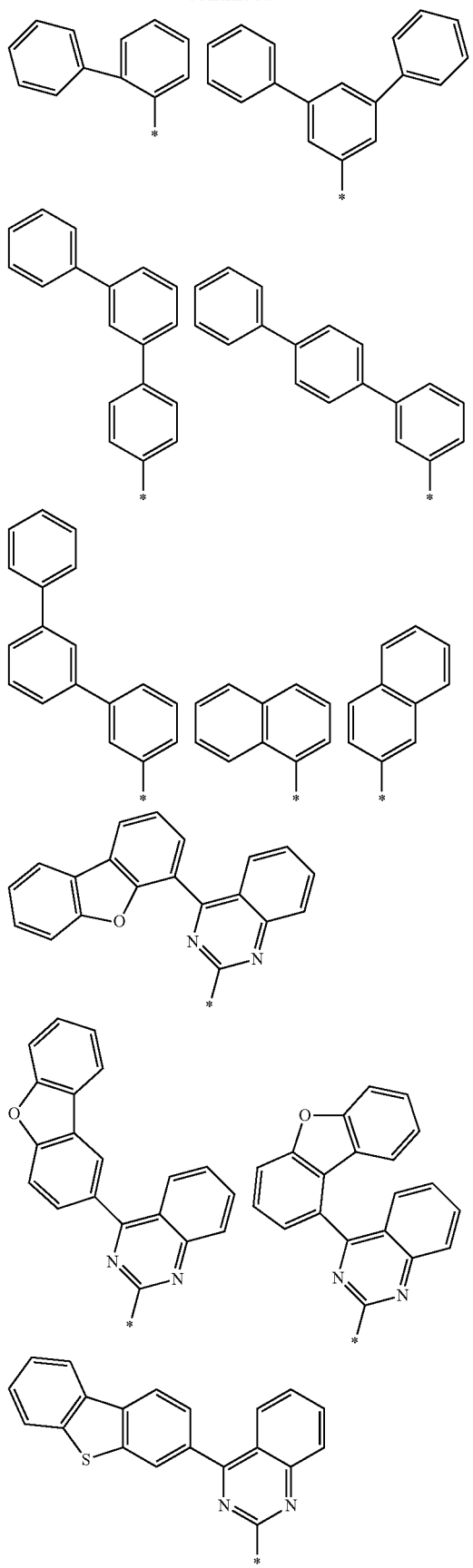

-continued
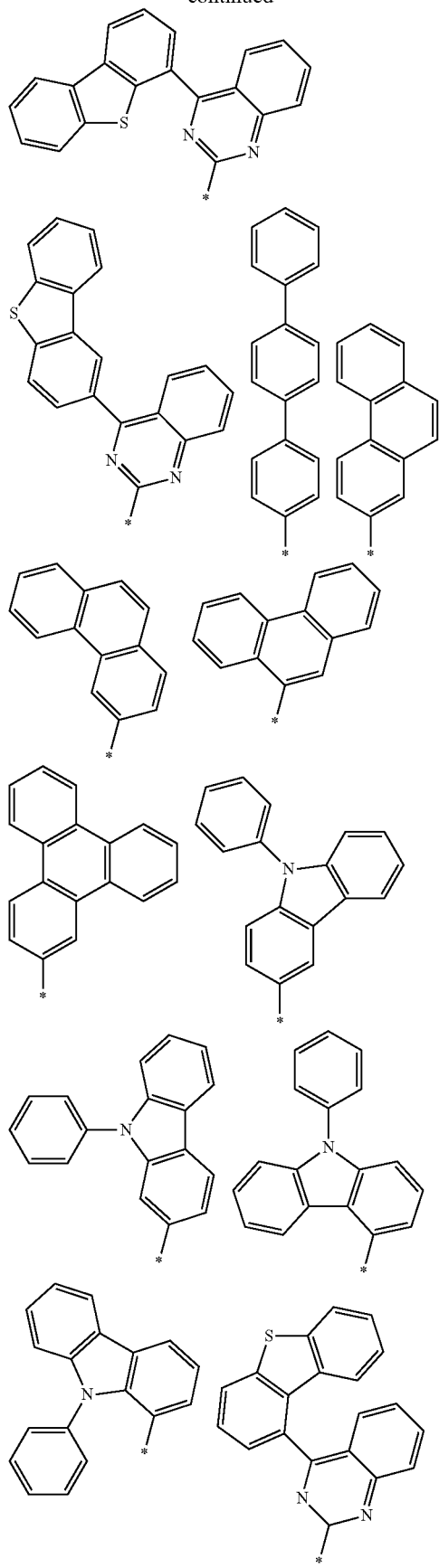
-continued
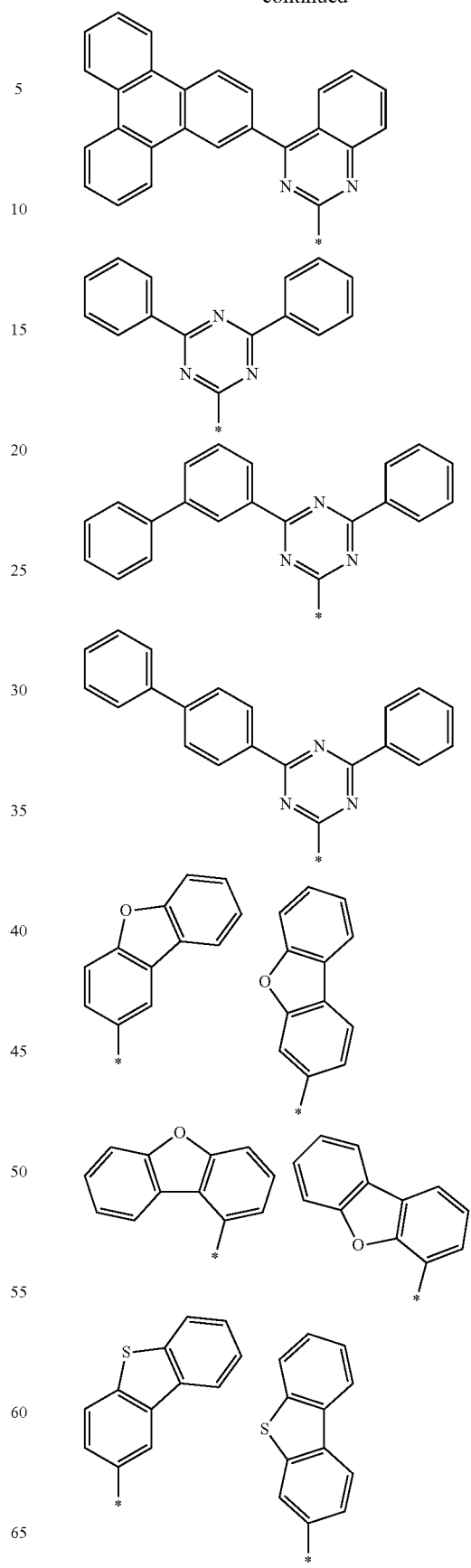

-continued
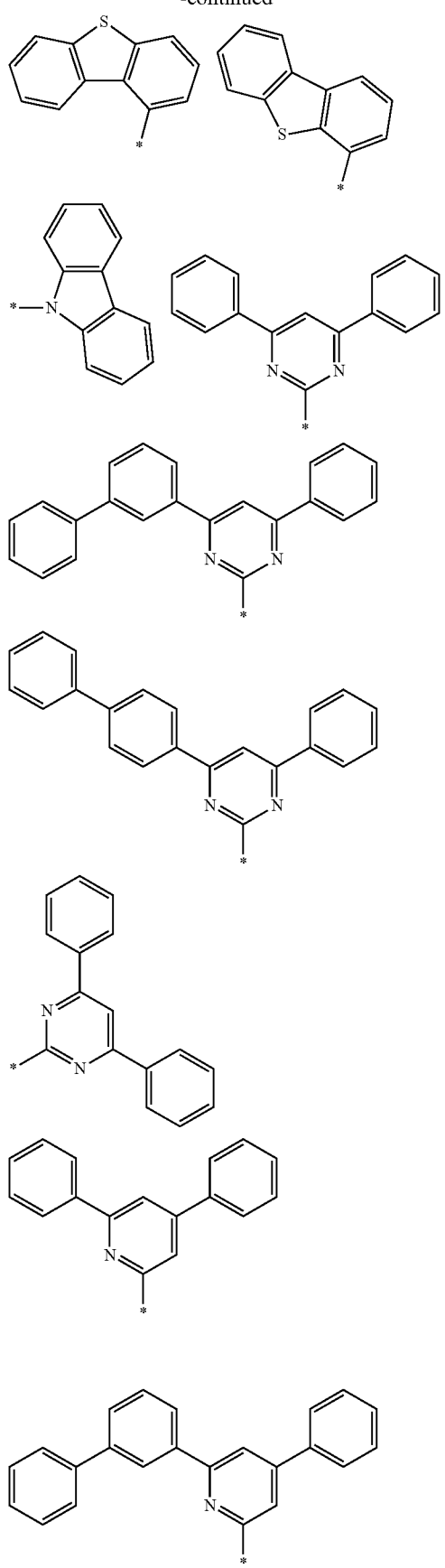
-continued
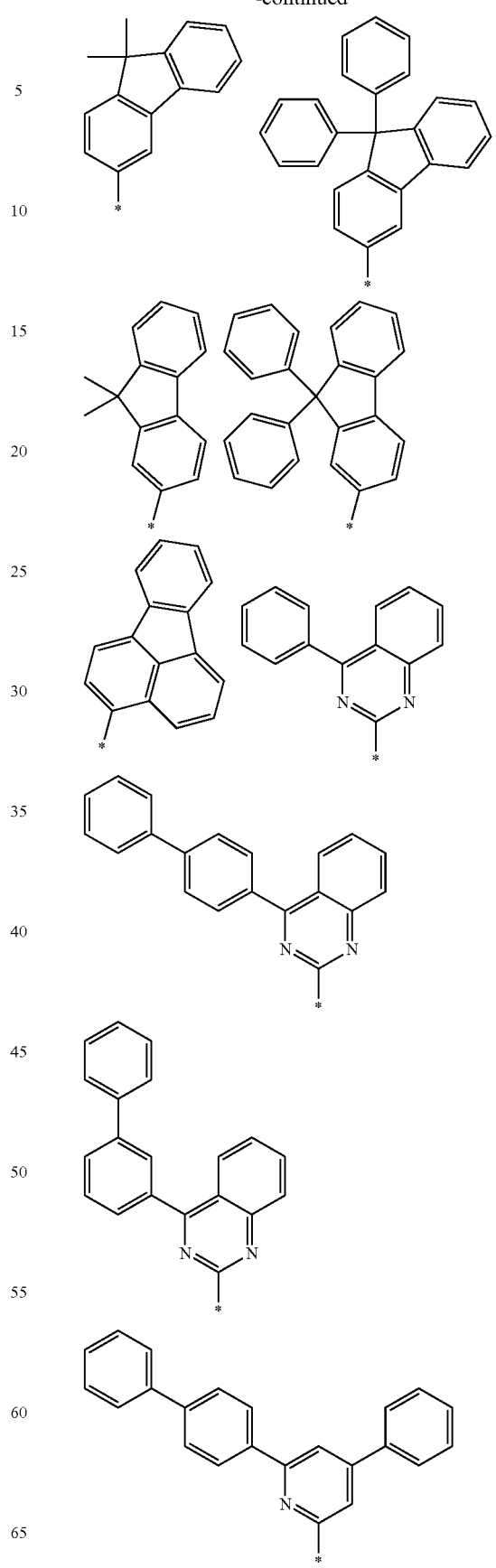

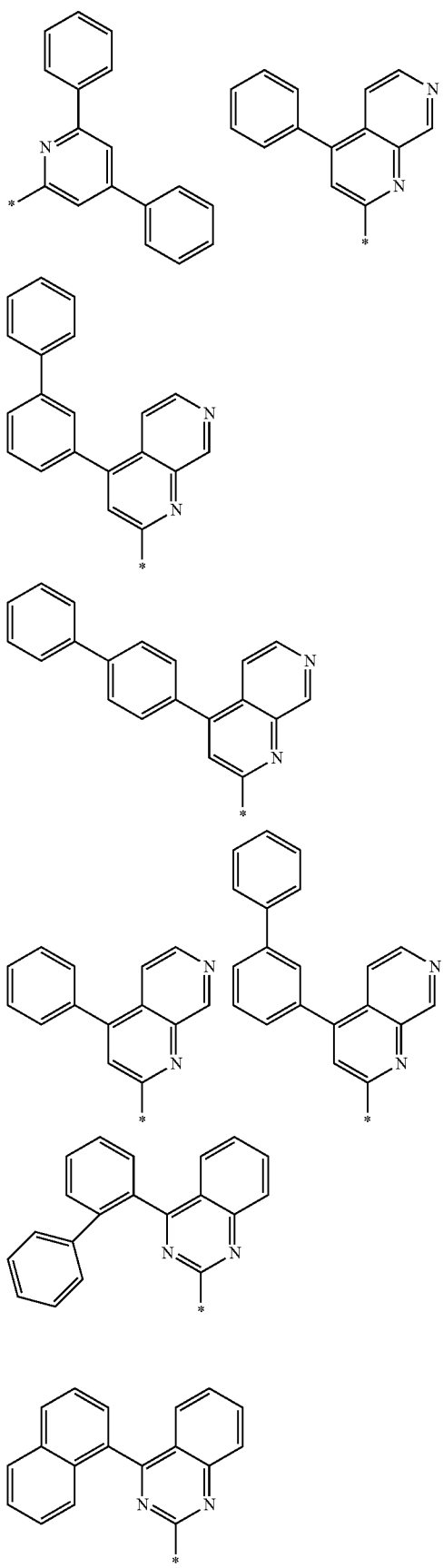
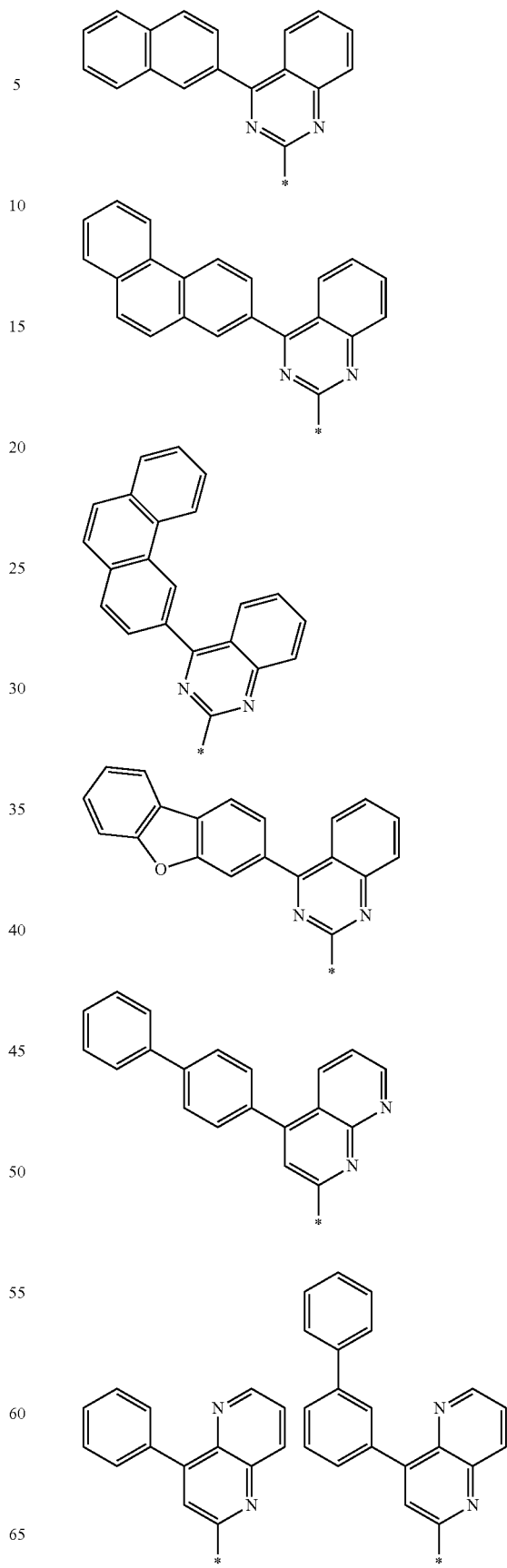

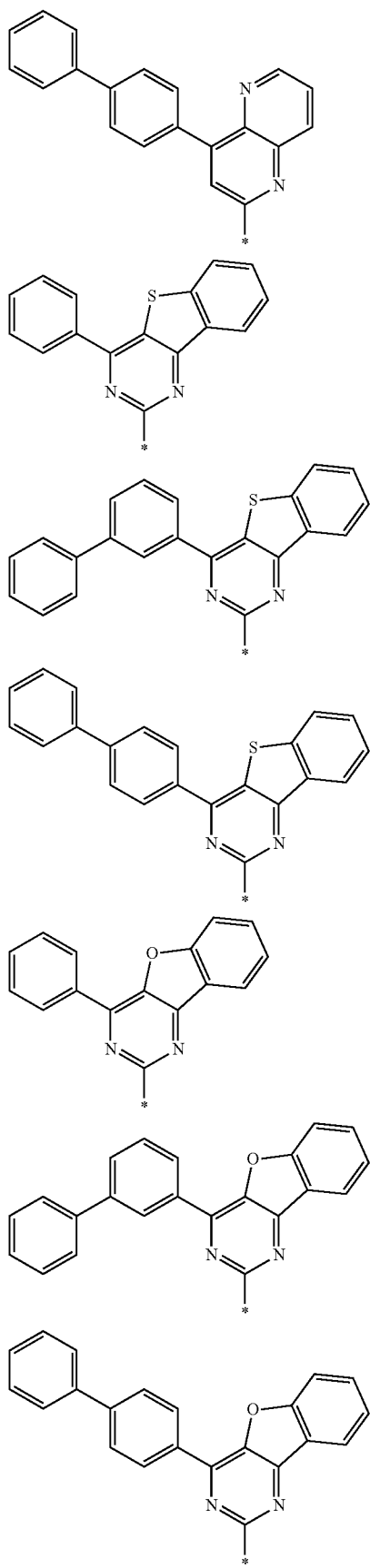
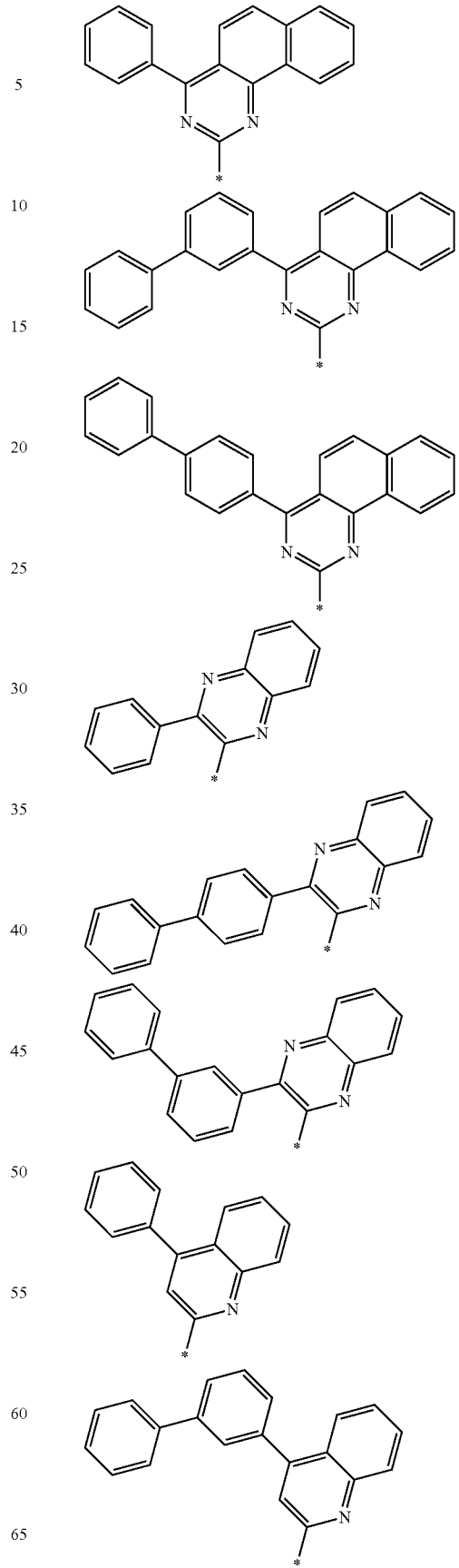

-continued

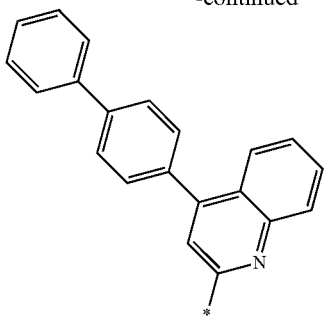

In Group I, * is a binding site with an adjacent atom.

In addition, in an example embodiment, L of Chemical Formula 1 may be a single bond, a substituted or unsubstituted phenylene group, a substituted or unsubstituted biphenylene group, a substituted or unsubstituted terphenylene group, a substituted or unsubstituted quinolinylene group, a substituted or unsubstituted isoquinolinylene group, a substituted or unsubstituted quinazolinylene group, a substituted or unsubstituted naphthyridinylene group, a substituted or unsubstituted benzofuranpyrimidinylene group, a substituted or unsubstituted benzothiophenepyrimidinylene group, or a substituted or unsubstituted phenanthrolinylene group, in a specific example embodiment, L of Chemical Formula 1 may be a single bond, a substituted or unsubstituted quinazolinylene group, a substituted or unsubstituted dibenzofuranpyrimidinylene group, or a substituted or unsubstituted dibenzothiophenepyrimidinylene group, and for example, it may be a single bond or one of linking groups of Group II.

[Group II]

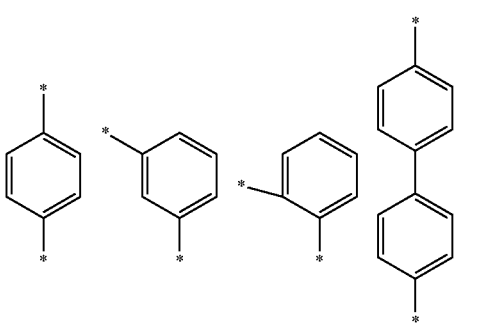

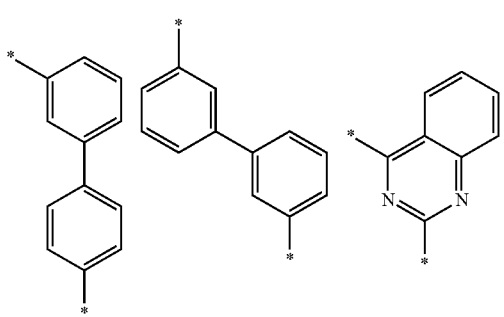

-continued

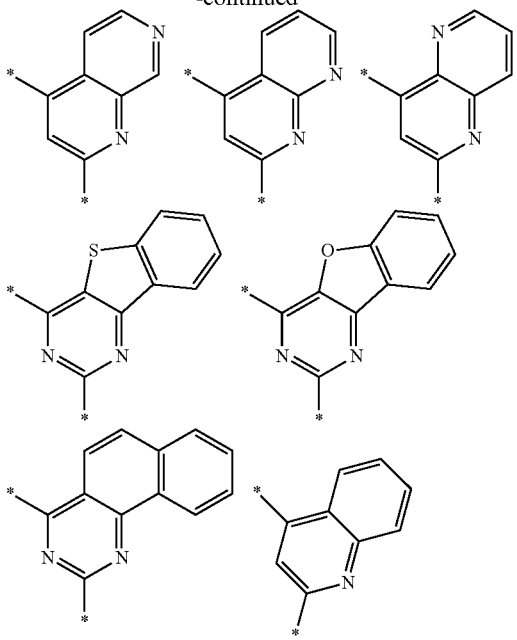

In Group II, * is a binding site with an adjacent atom.

In addition, in an example embodiment, X may be O or S.

In an example embodiment, $R^2$ to $R^5$ may independently be hydrogen, deuterium, a substituted or unsubstituted C1 to C10 alkyl group, a substituted or unsubstituted C6 to C20 aryl group, in a specific example embodiment, $R^2$ to $R^5$ may independently be hydrogen, deuterium, a substituted or unsubstituted C1 to C4 alkyl group, a substituted or unsubstituted C6 to C12 aryl group, and $R^2$ to $R^5$ may be for example all hydrogen.

In a most specific example embodiment, X may be O or S, $R^1$ may be a substituted or unsubstituted phenyl group, a substituted or unsubstituted biphenyl group, a substituted or unsubstituted terphenyl group, a substituted or unsubstituted phenanthrenyl group, a substituted or unsubstituted triphenylene group, a substituted or unsubstituted carbazolyl group, a substituted or unsubstituted dibenzofuranyl group, a substituted or unsubstituted dibenzothiophenyl group, a substituted or unsubstituted triazinyl group, a substituted or unsubstituted quinazolinyl group, a substituted or unsubstituted benzofuranpyrimidinyl group, or a substituted or unsubstituted benzothiophenepyrimidinyl group, L may be a single bond, a substituted or unsubstituted quinazolinylene group, a substituted or unsubstituted dibenzofuranpyrimidinylene group, or a substituted or unsubstituted dibenzothiophenepyrimidinylene group, and $R^2$ to $R^5$ may be all hydrogen.

Herein, the "substituted" refers to replacement of at least one hydrogen by deuterium, a C1 to C4 alkyl group, a phenyl group, a biphenyl group, a naphthyl group, a phenanthrenyl group, a triphenylene group, a fluoranthenyl group, a carbazolyl group, a dibenzofuranyl group, a dibenzothiophenyl group, a pyridinyl group, a pyrimidinyl group, or a triazinyl group.

Chemical Formula 1 may be for example represented by Chemical Formula 1A or Chemical Formula 1B.

[Chemical Formula 1A]

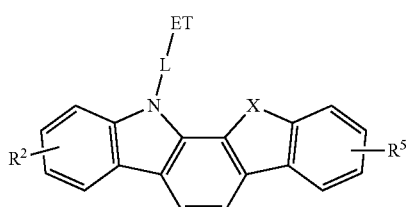

[Chemical Formula 1B]

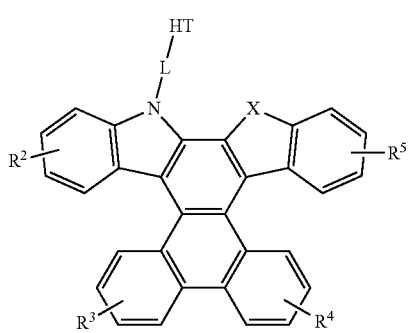

In Chemical Formula 1A and Chemical Formula 1B,

X is O, or S,

ET is a substituted or unsubstituted pyridinyl group, a substituted or unsubstituted pyrimidinyl group, a substituted or unsubstituted triazinyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzofuranpyrimidinyl group, a substituted or unsubstituted benzothiophenepyrimidinyl group, or a substituted or unsubstituted phenanthrolinyl group, HT is a substituted or unsubstituted phenyl group, a substituted or unsubstituted biphenyl group, a substituted or unsubstituted terphenyl group, a substituted or unsubstituted naphthyl group, a substituted or unsubstituted phenanthrenyl group, a substituted or unsubstituted triphenylene group, a substituted or unsubstituted fluorenyl group, a substituted or unsubstituted fluoranthenyl group, a substituted or unsubstituted carbazolyl group, a substituted or unsubstituted dibenzofuranyl group, or a substituted or unsubstituted dibenzothiophenyl group, $R^2$ to $R^9$ are independently hydrogen, deuterium, a substituted or unsubstituted C1 to C20 alkyl group, a substituted or unsubstituted C6 to C30 aryl group, a substituted or unsubstituted C2 to C30 heterocyclic group, or a combination thereof, and L is a single bond, a substituted or unsubstituted C6 to C30 arylene group, a substituted or unsubstituted C2 to C30 heteroarylene group, or a combination thereof.

In an example embodiment, Chemical Formula 1 may be represented by Chemical Formula 1A and ET may be specifically a substituted or unsubstituted pyrimidinyl group, a substituted or unsubstituted triazinyl group, a substituted or unsubstituted quinazolinyl group, a substituted or unsubstituted dibenzofuranpyrimidinyl group, or a substituted or unsubstituted dibenzothiophenepyrimidinyl group, and the "substituted" refers to replacement of at least one hydrogen by a phenyl group, a biphenyl group, a phenanthrene group, a triphenylene group, a dibenzofuranyl group, or a dibenzothiophenyl group.

More specifically, ET may be selected from Group I.

The compound for an organic optoelectric device represented by Chemical Formula 1 may be for example selected from compounds of Group 1, but is not limited thereto.

[Group 1]

1

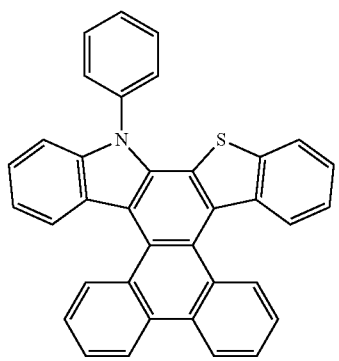

2

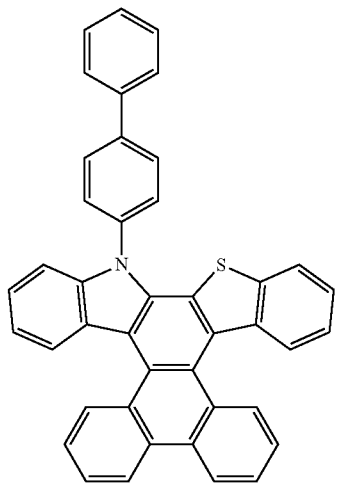

3

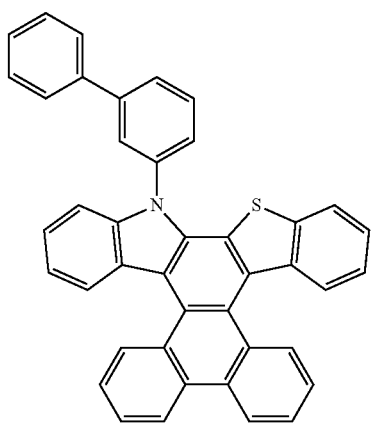

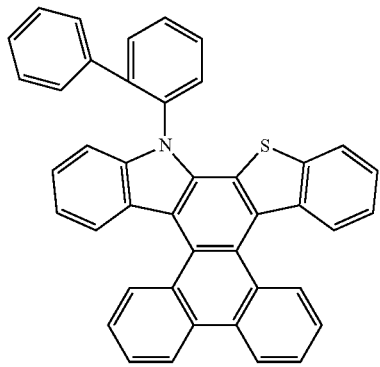
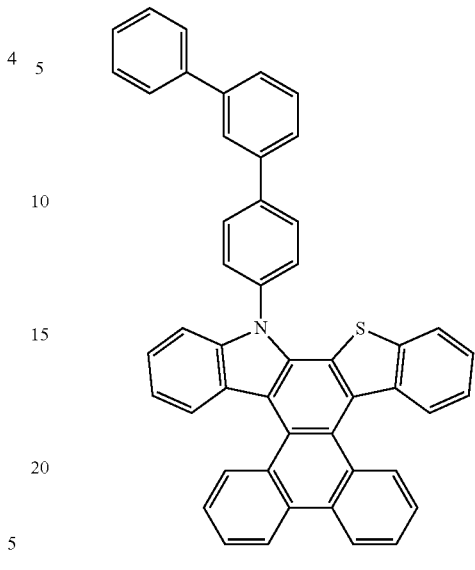
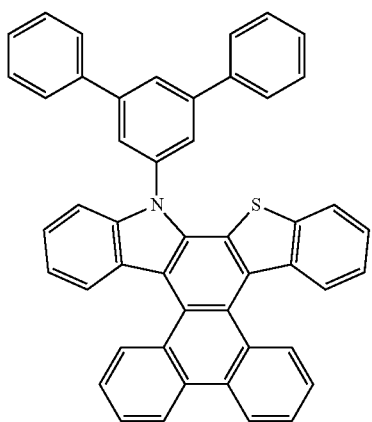
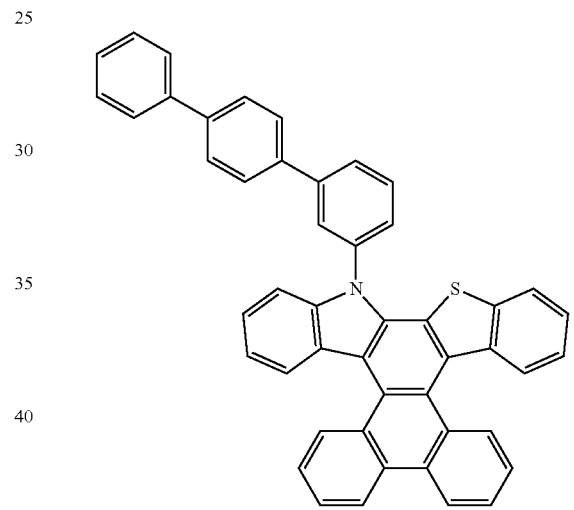
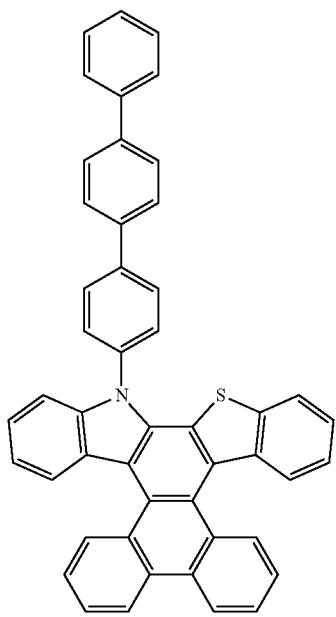
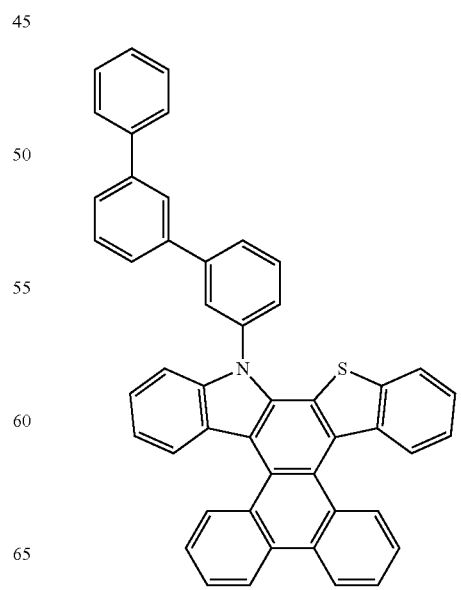

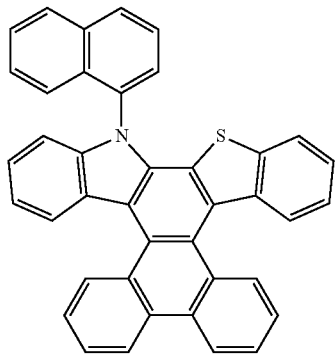
10
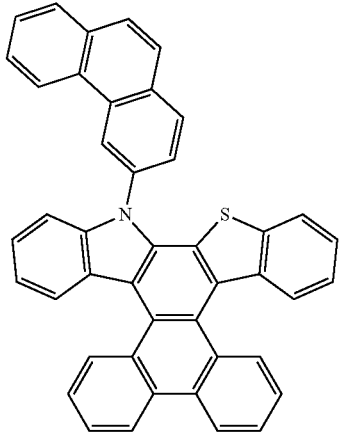
5
11
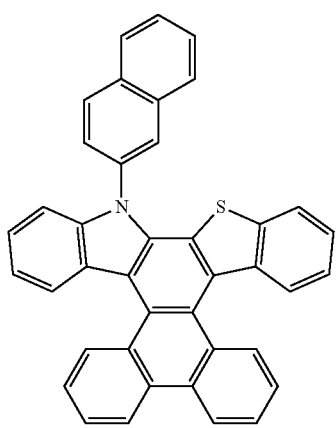
12
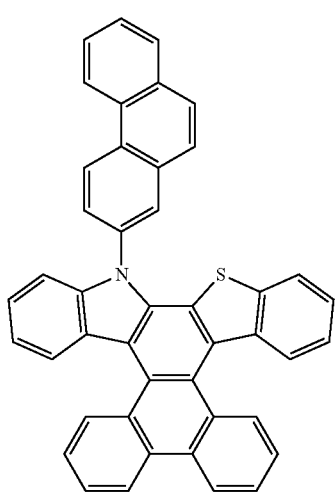
13
14
15
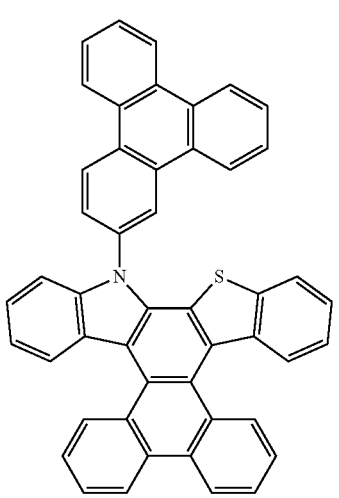

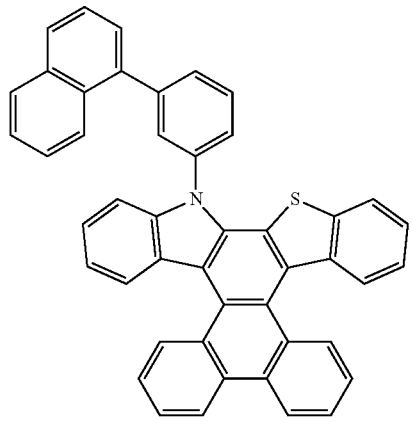
16
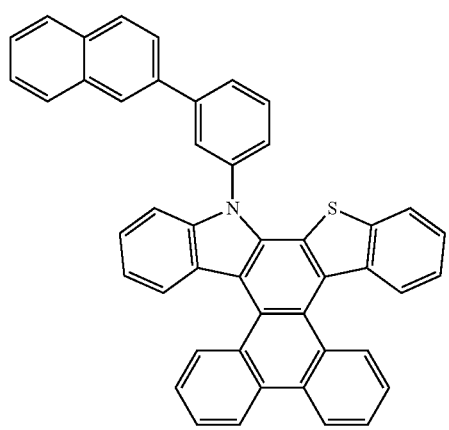
17
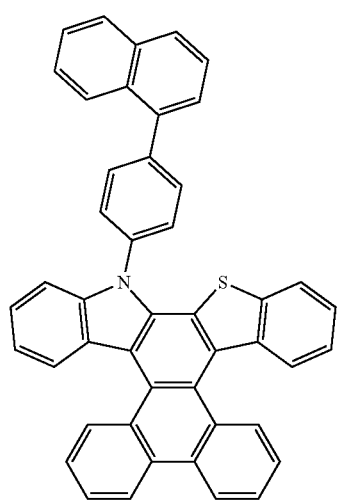
18
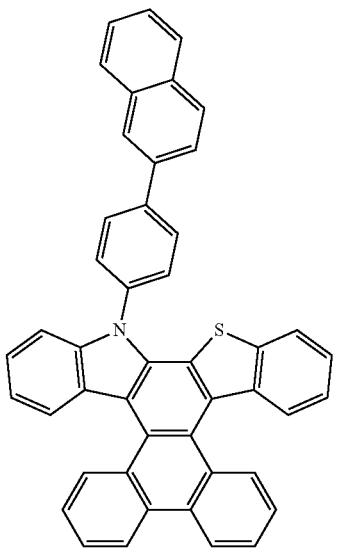
19
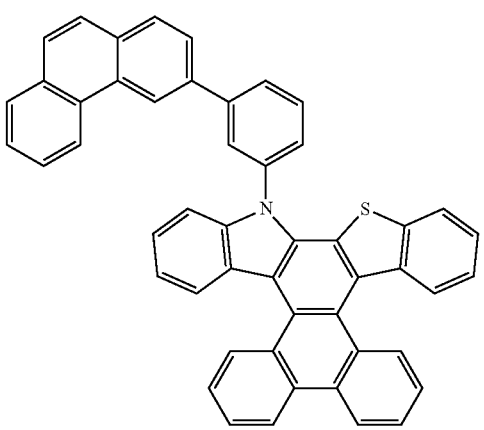
20
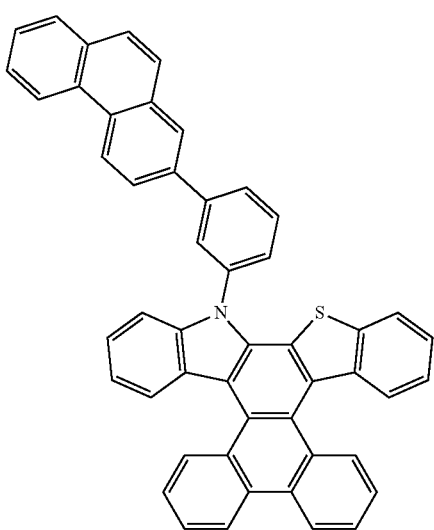
21

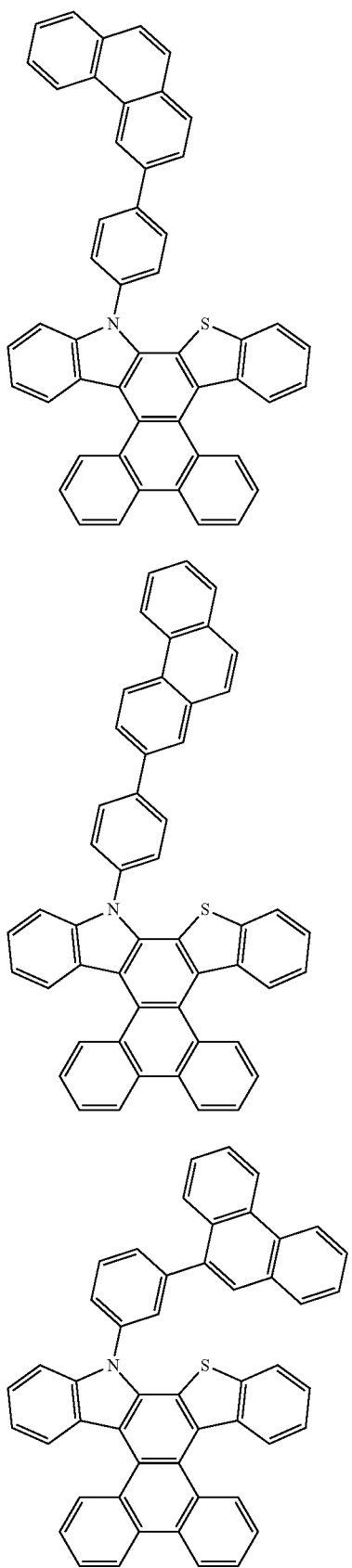
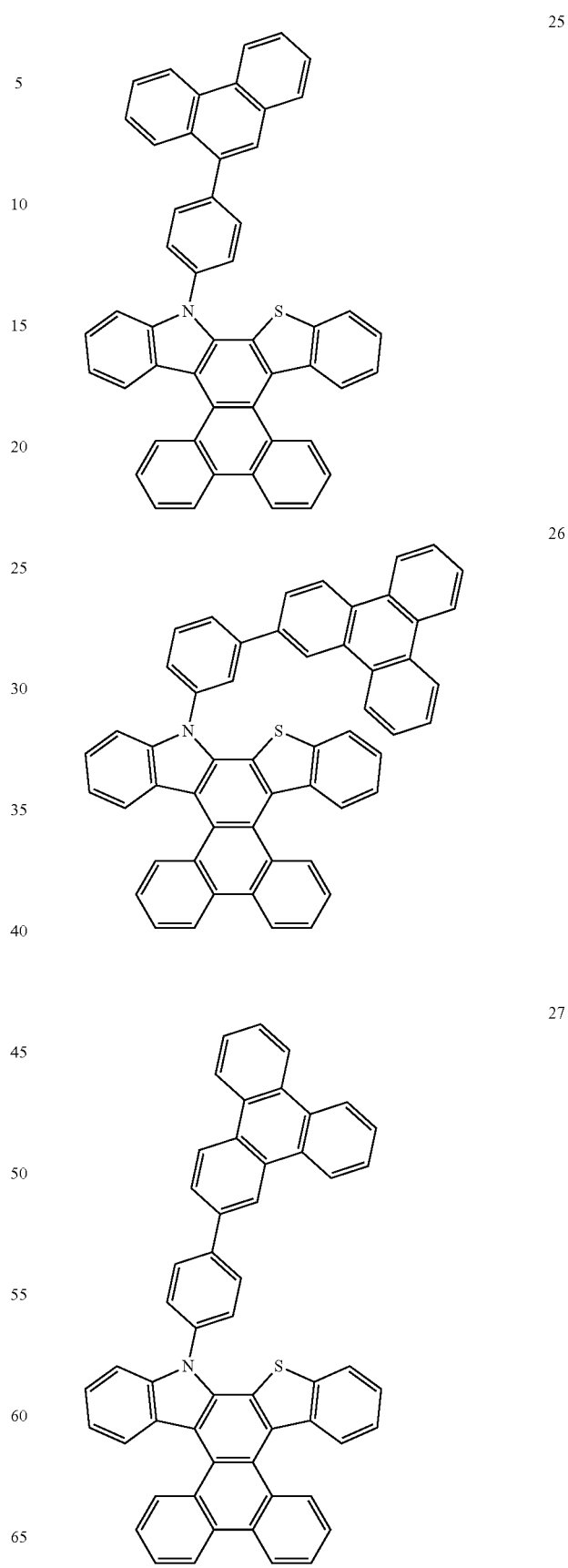

28
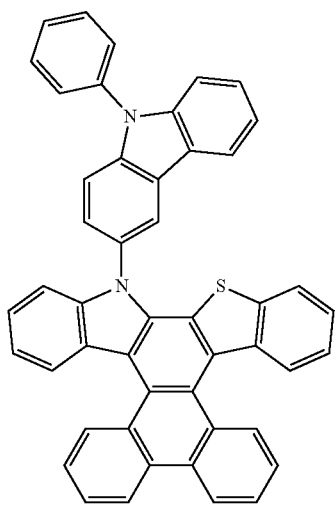
29
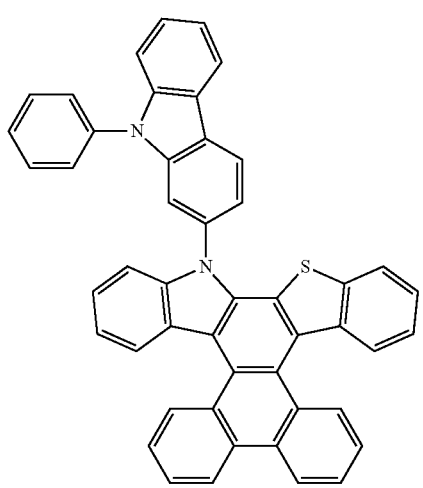
30
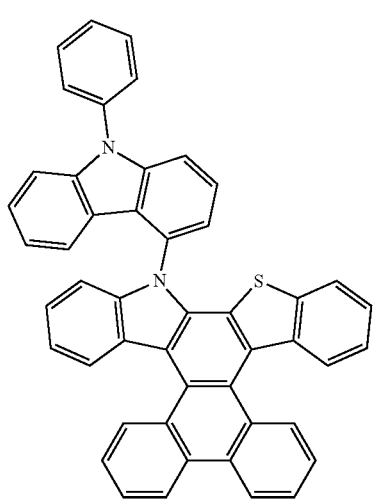
31
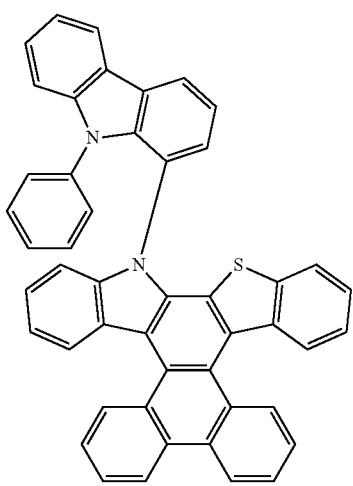
32
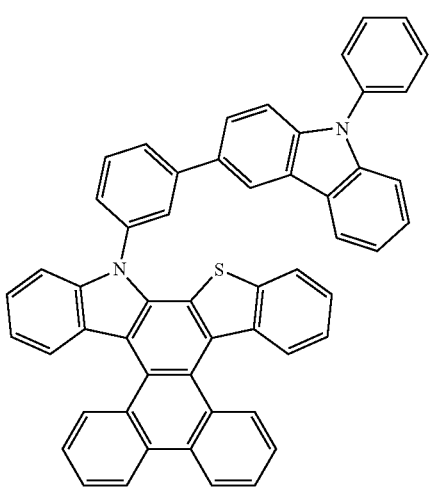
33
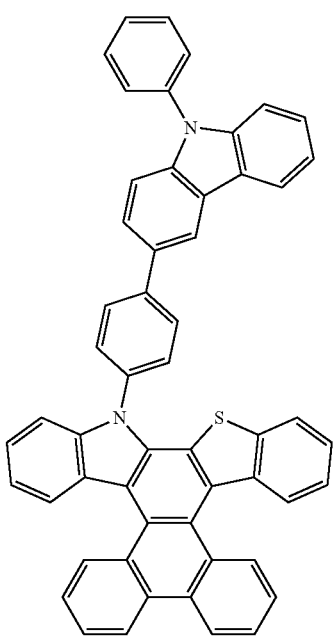

34
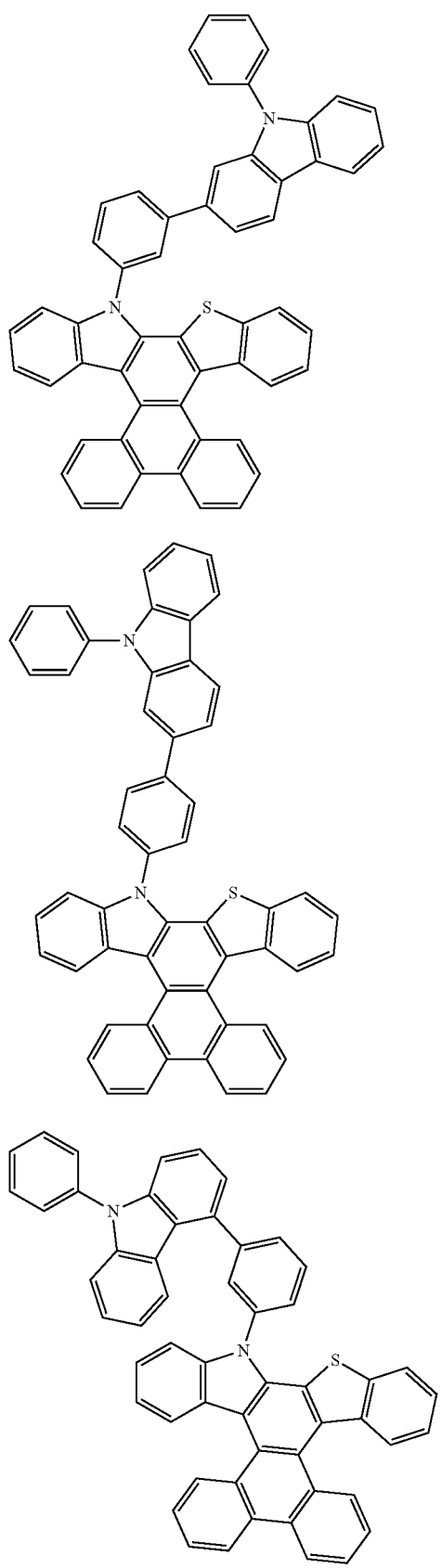
35
36
37
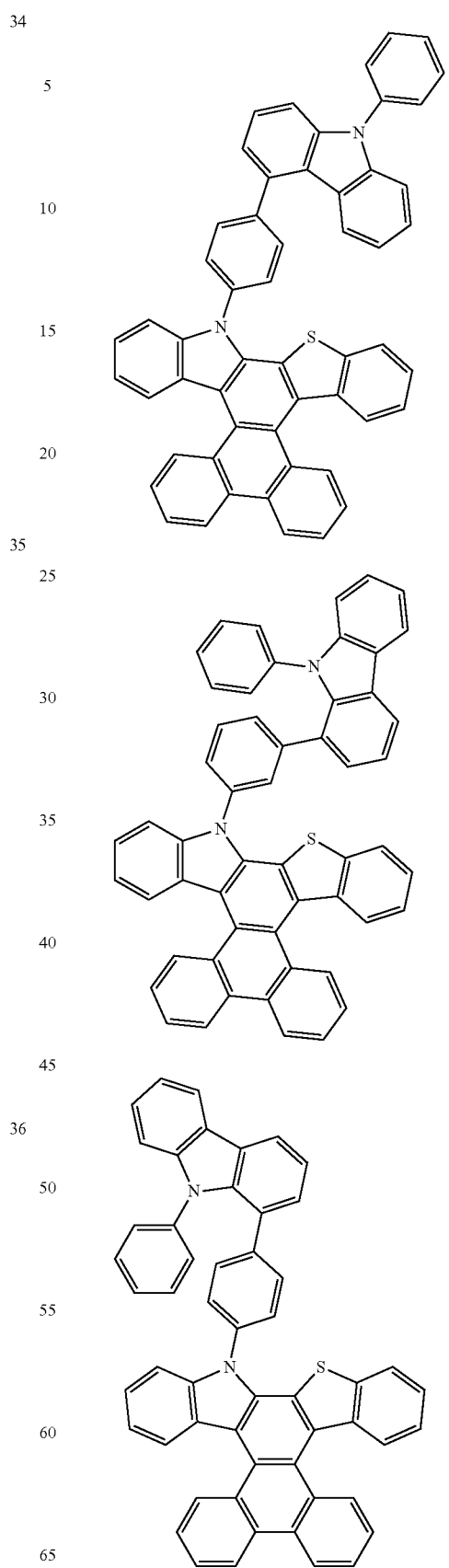
38
39

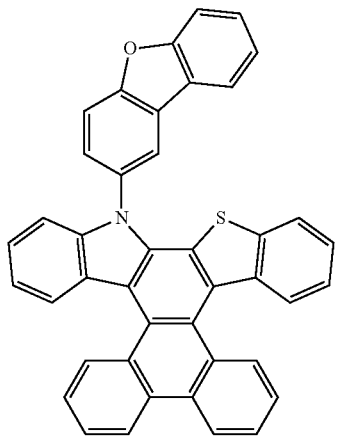
33
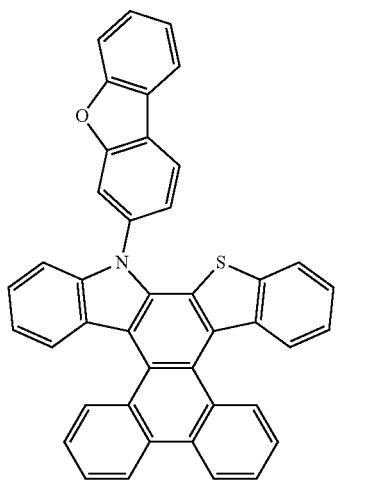
41
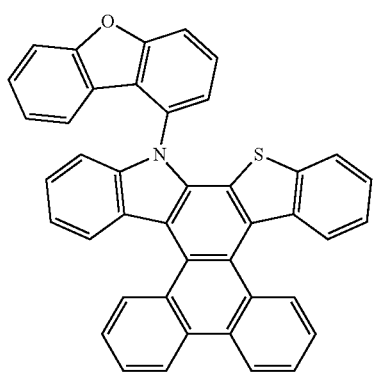
42
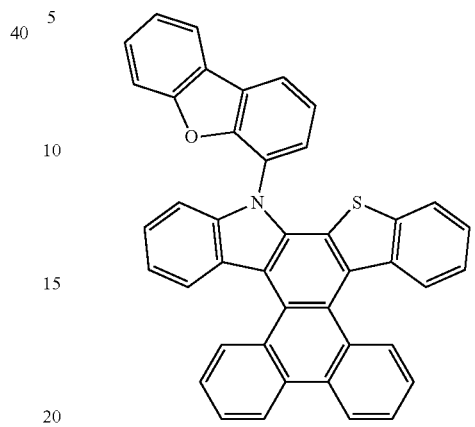
43
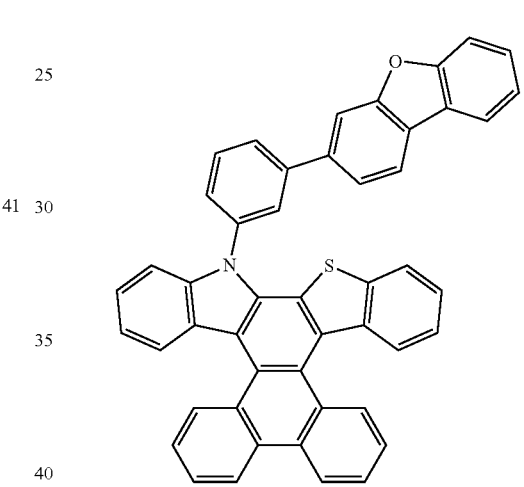
44
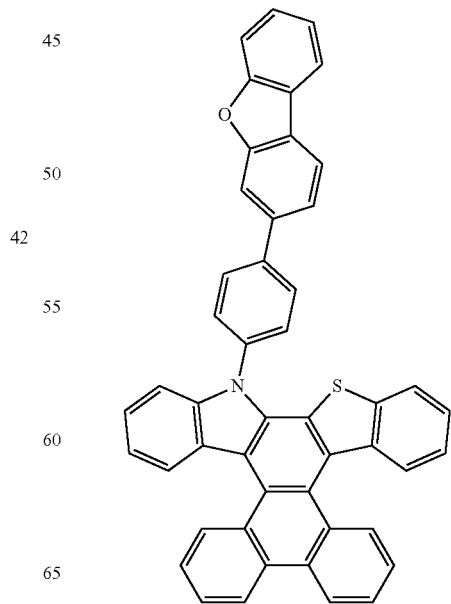
45

46
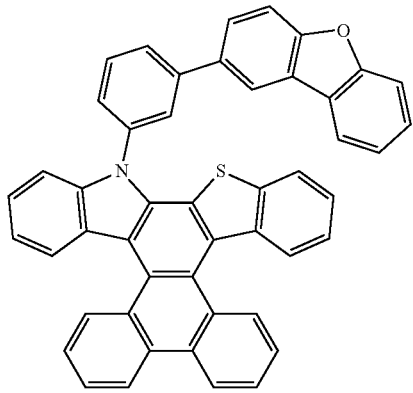
47
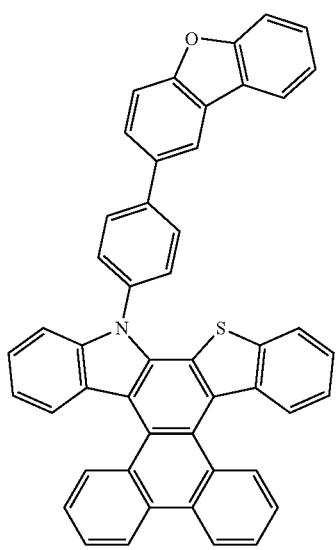
48
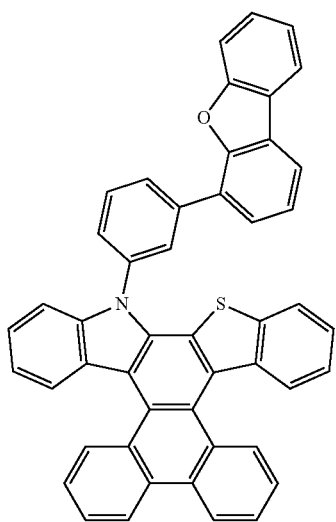
49
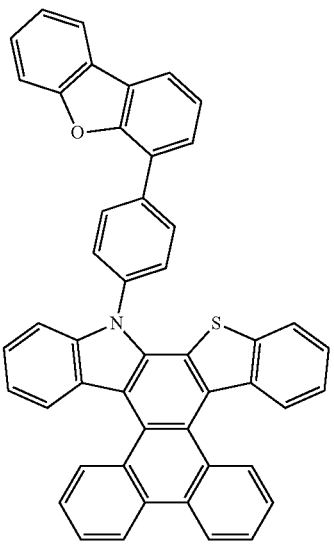
50
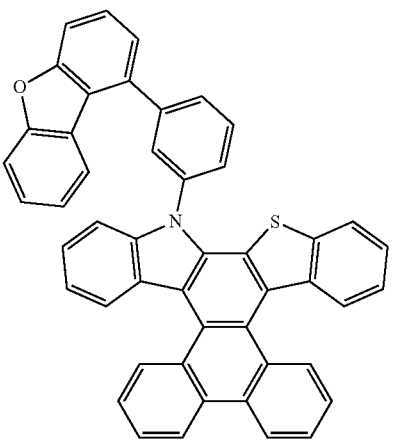
51
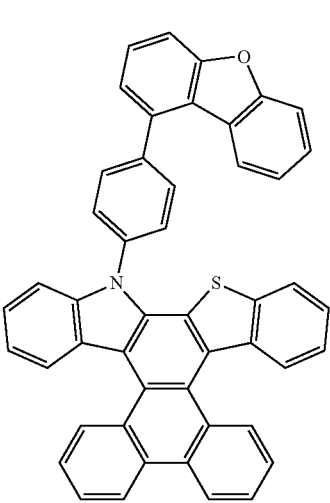

37
-continued
52
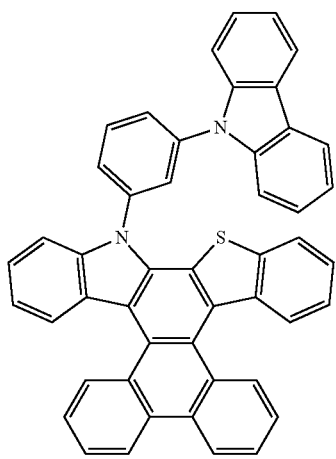
53
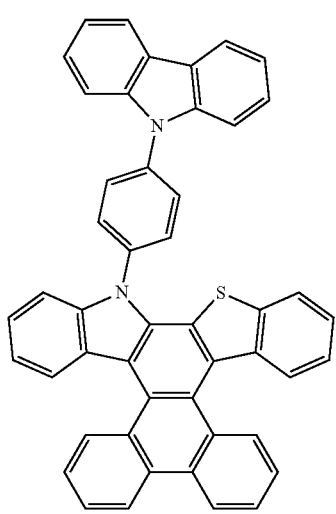
54
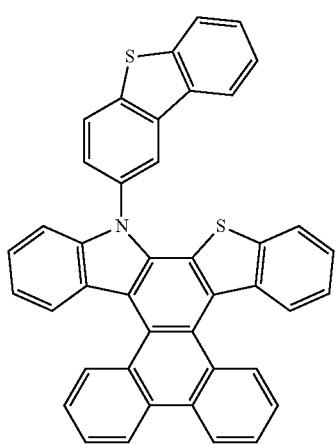
38
-continued
55
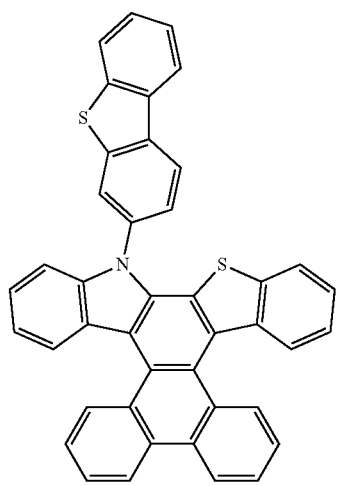
56
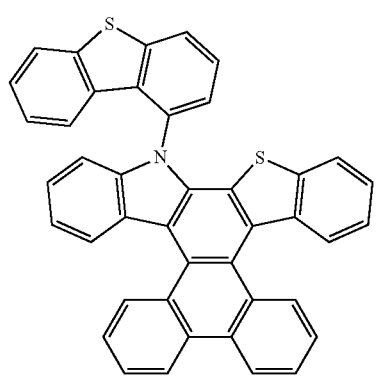
57
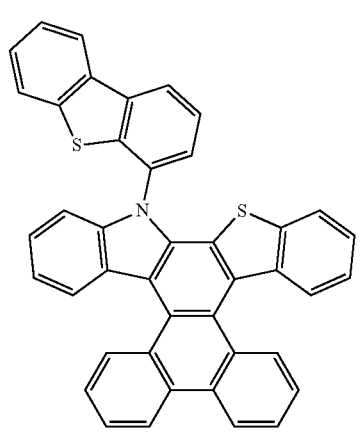

58 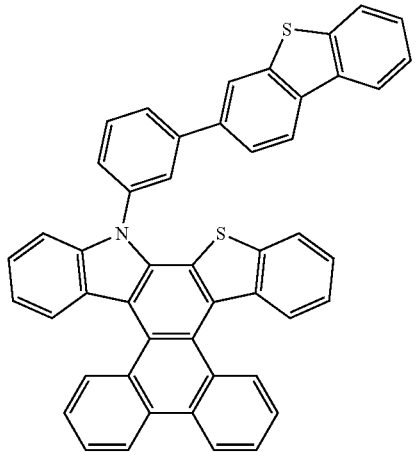
59 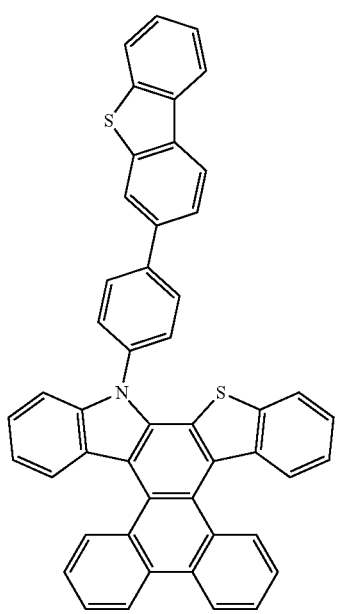
60 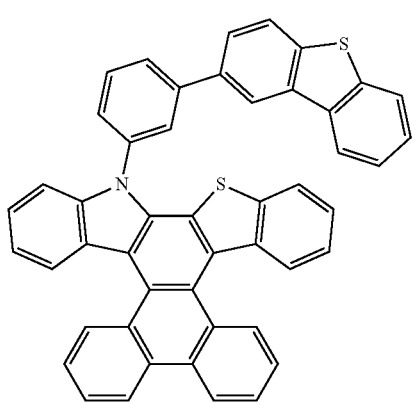
61 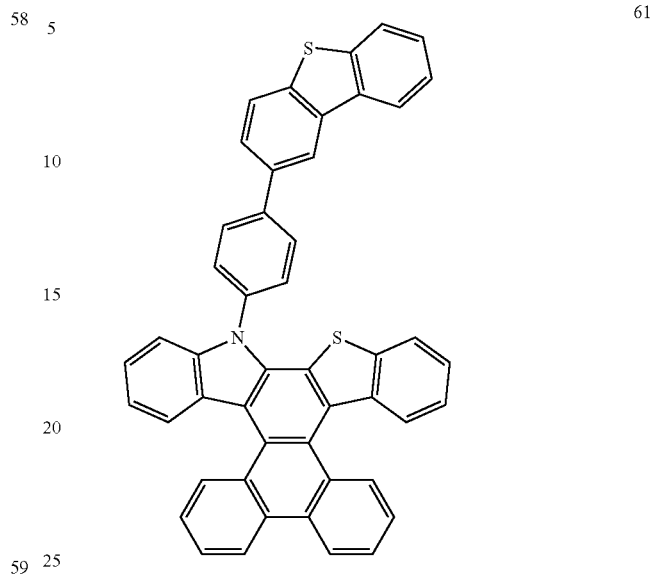
62 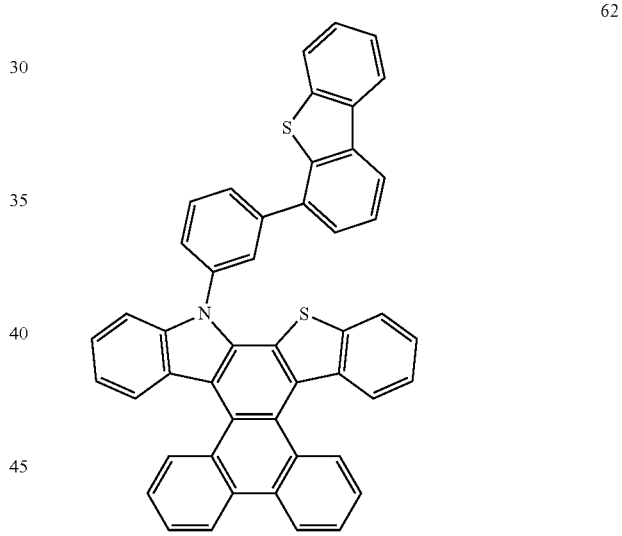
63 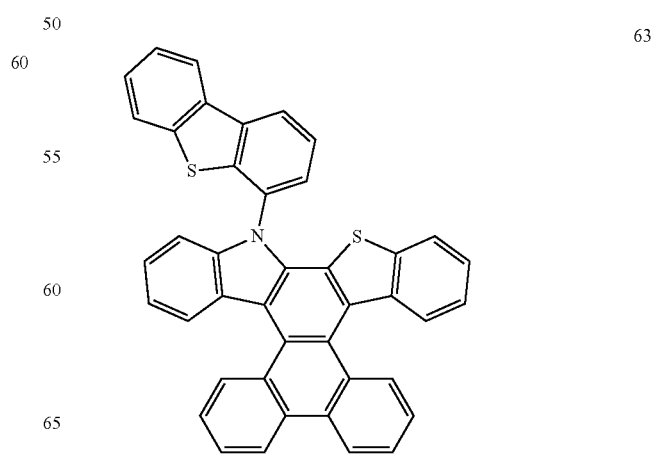

-continued
64
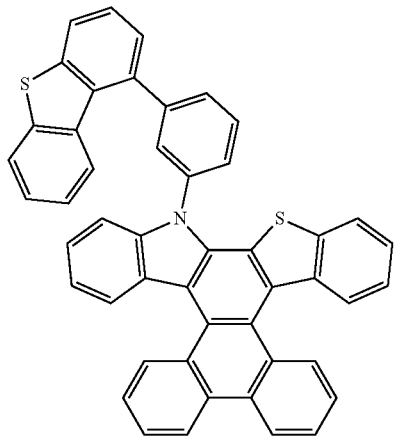
65
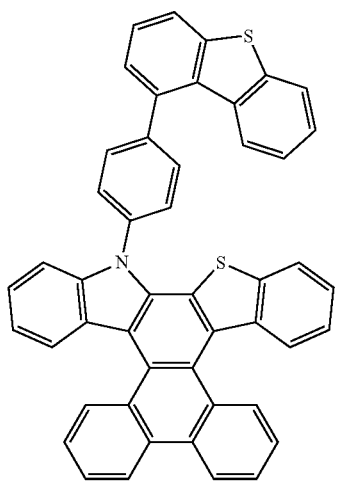
66
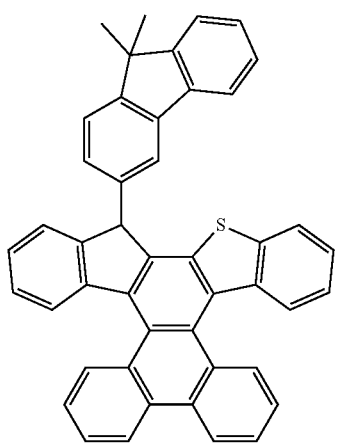
-continued
67
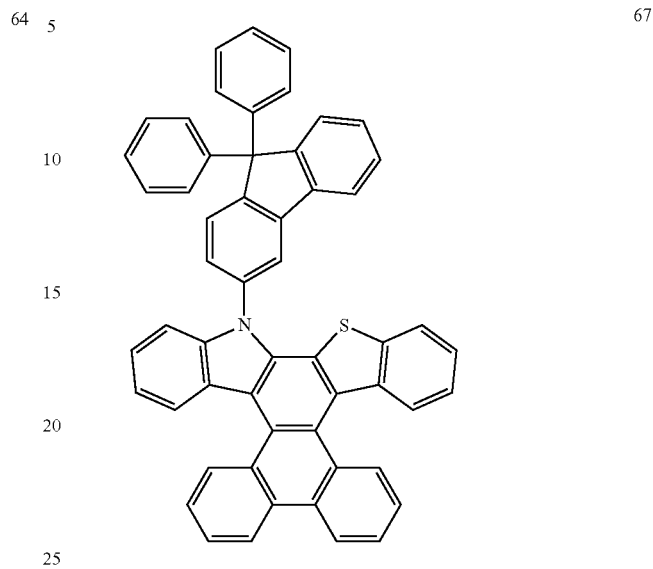
68
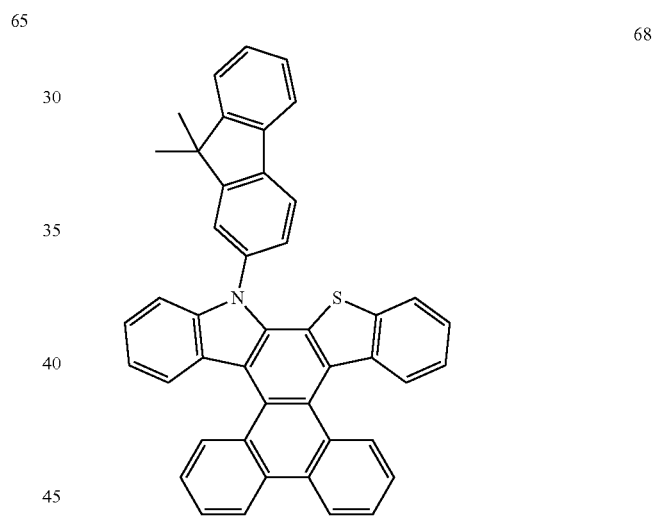
69
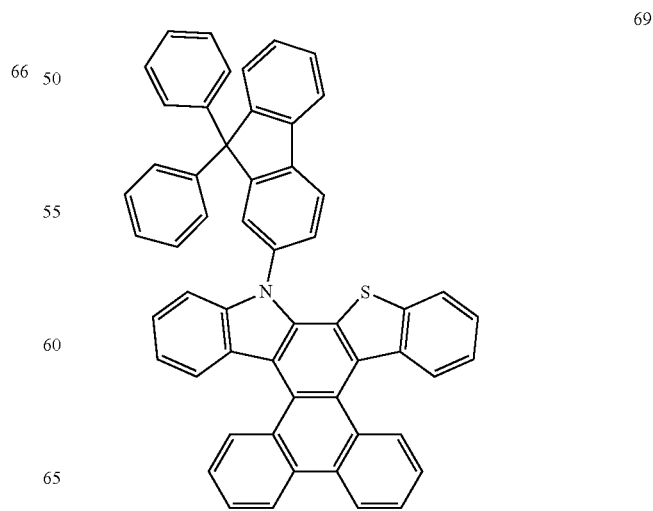

43
70
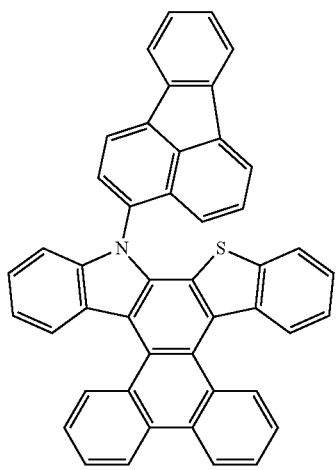
71
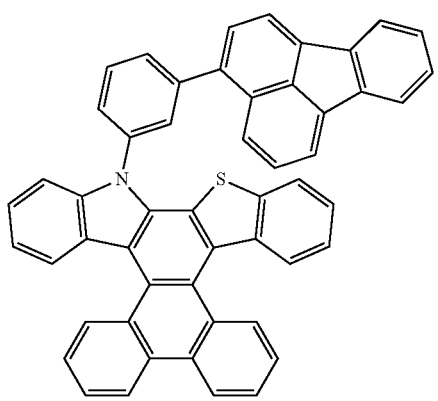
72
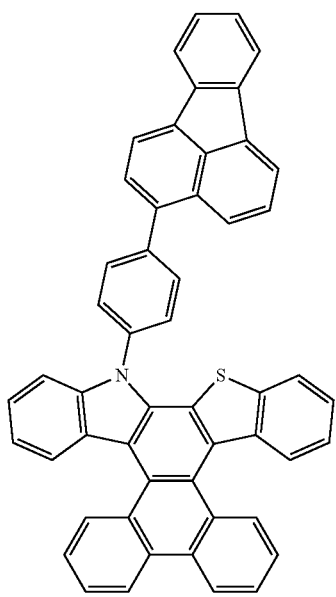
44
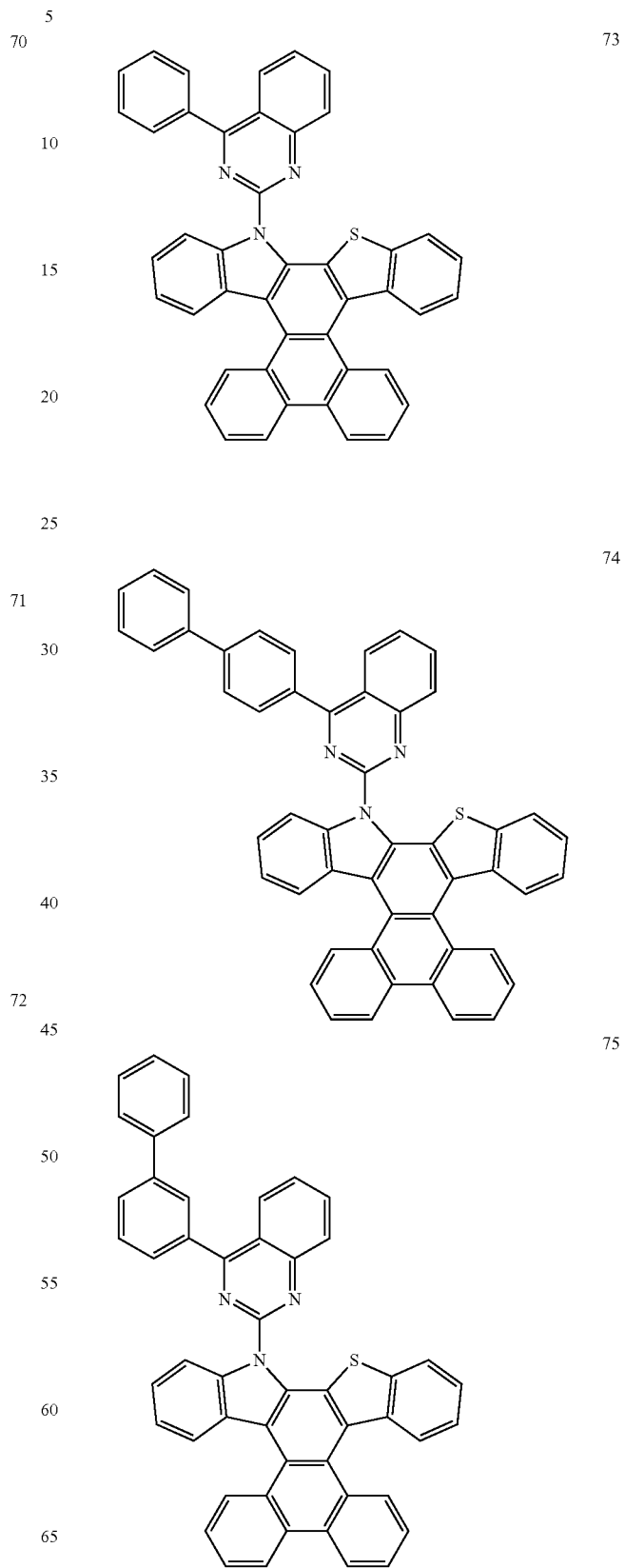

76
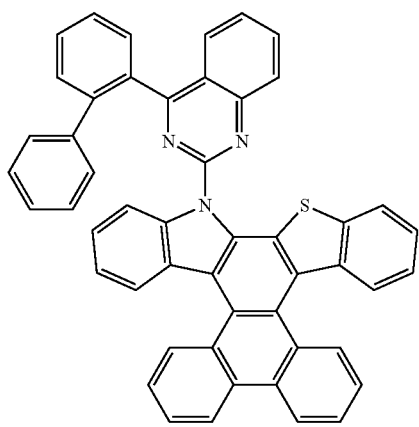
77
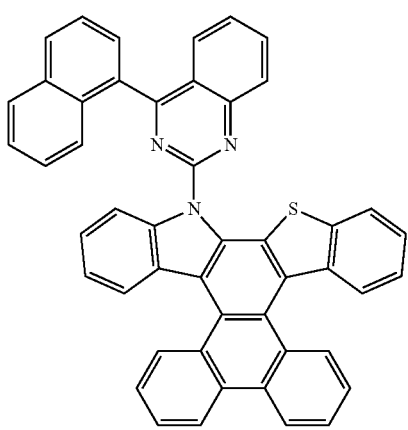
78
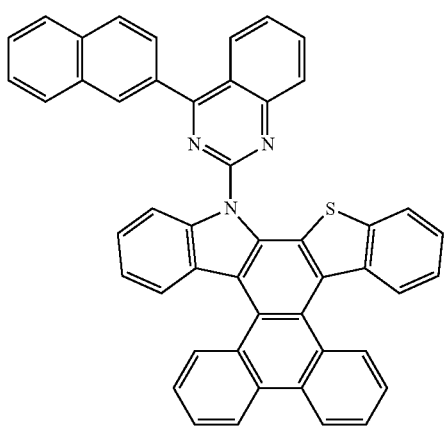
79
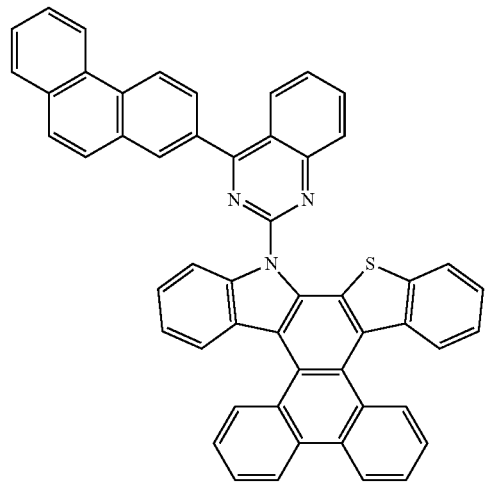
80
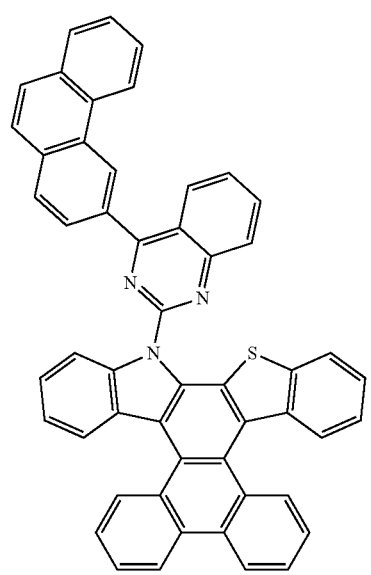
81
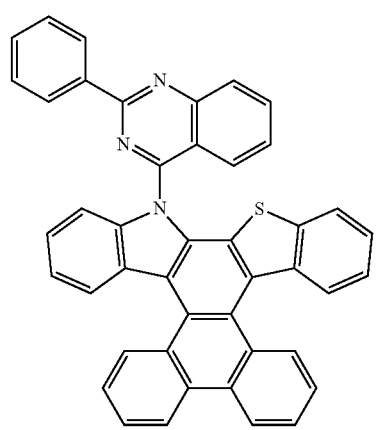

82
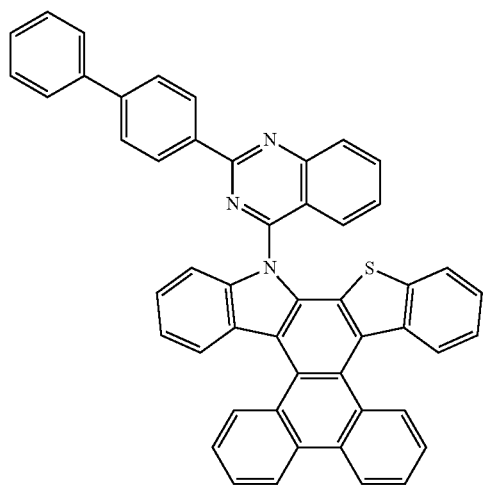
83
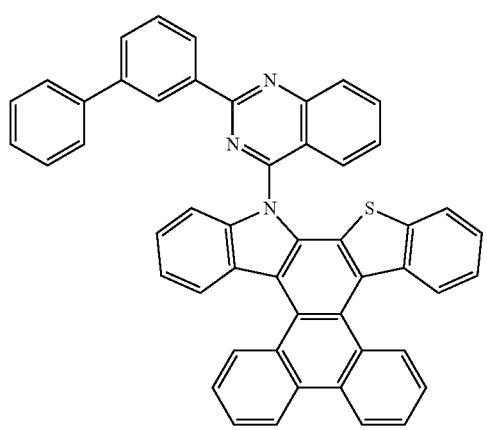
84
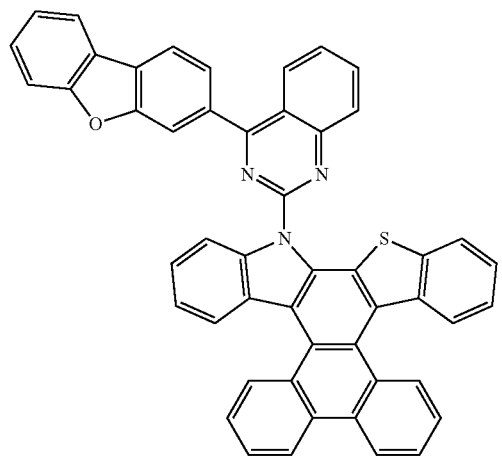
85
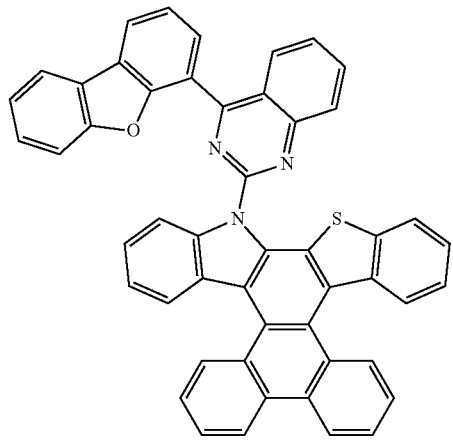
86
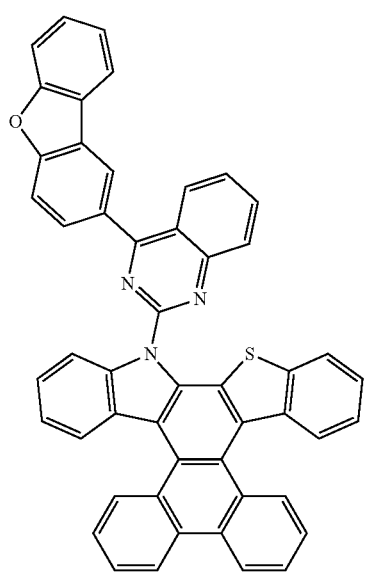
87
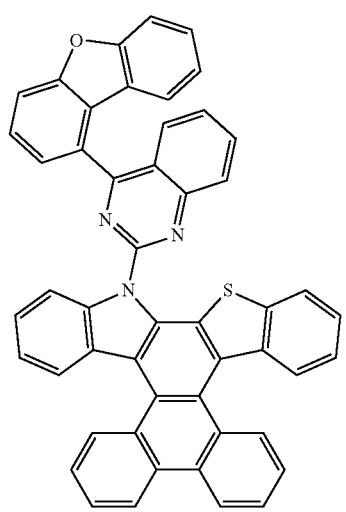

88
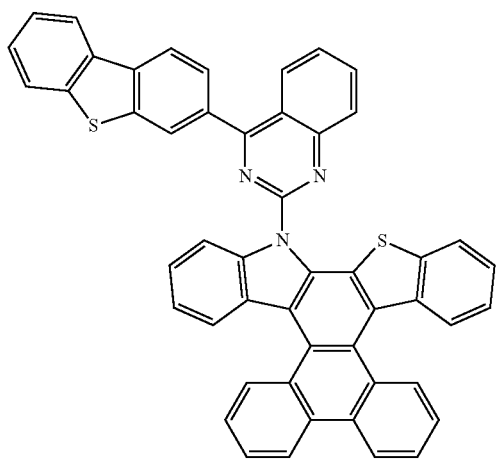
91
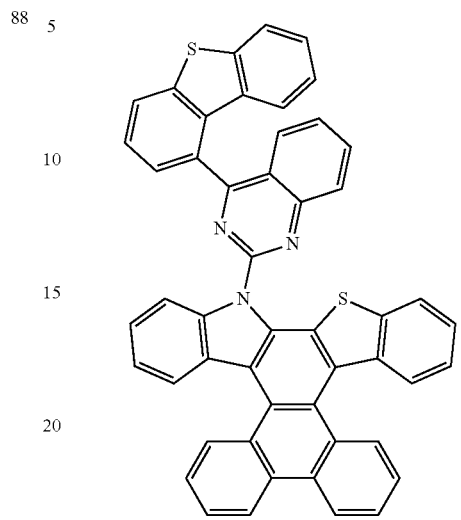
89
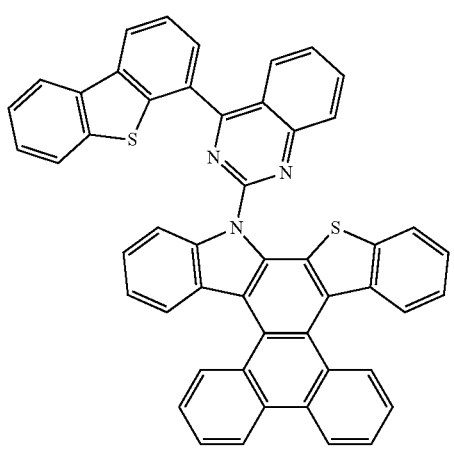
92
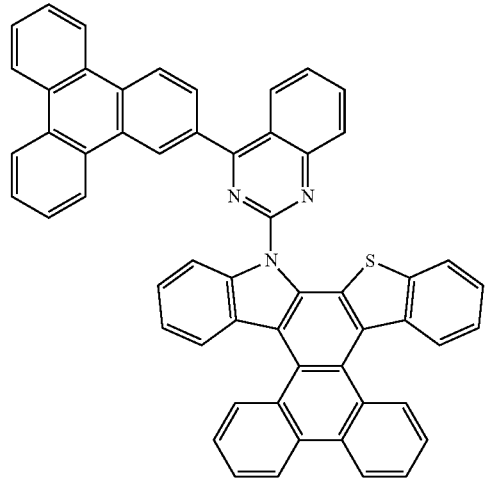
90
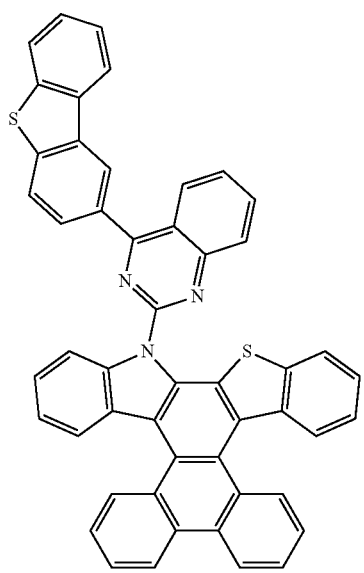
93
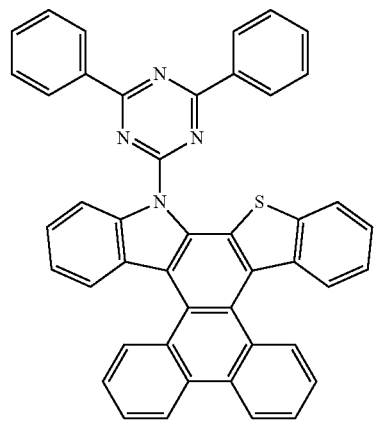

94
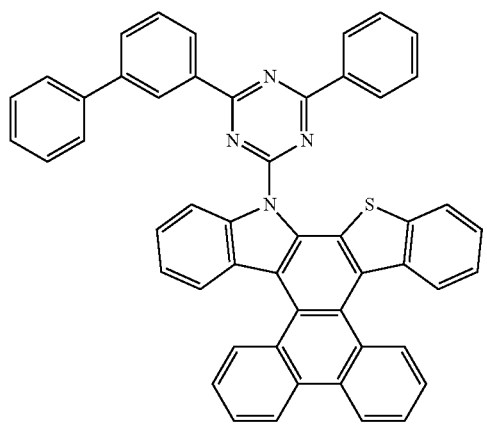
95
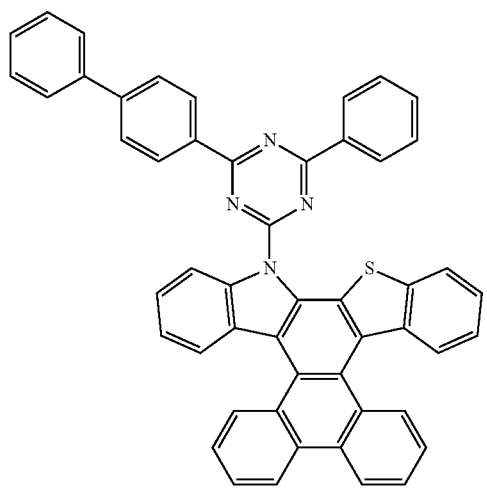
96
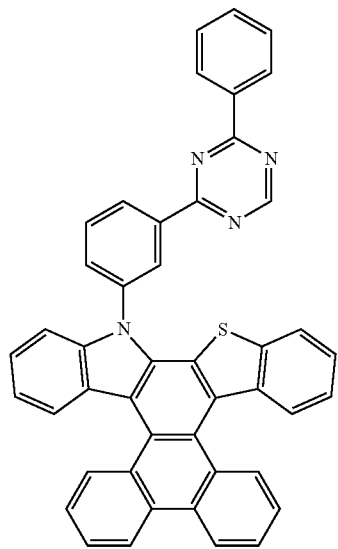
97
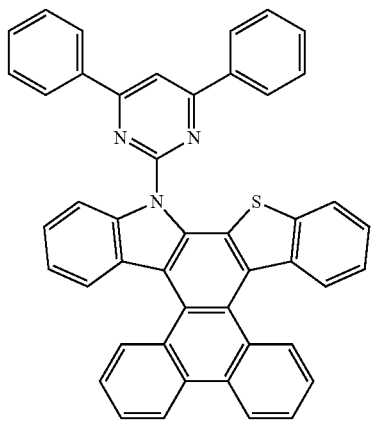
98
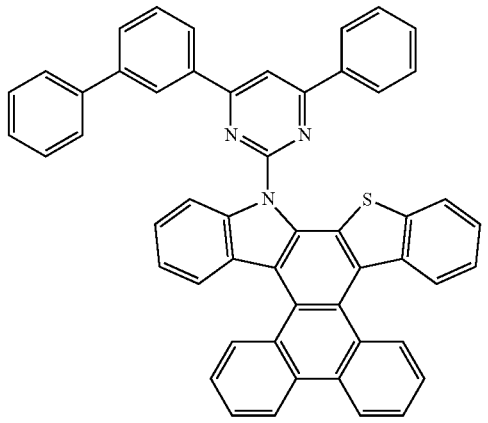
99
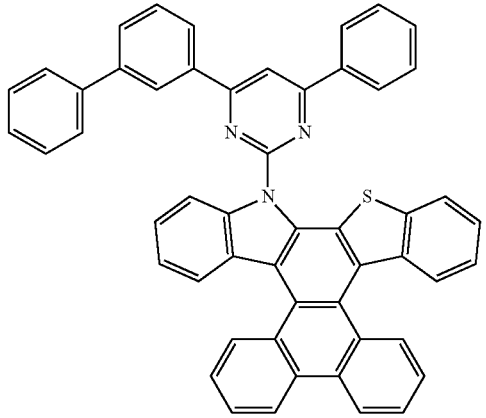

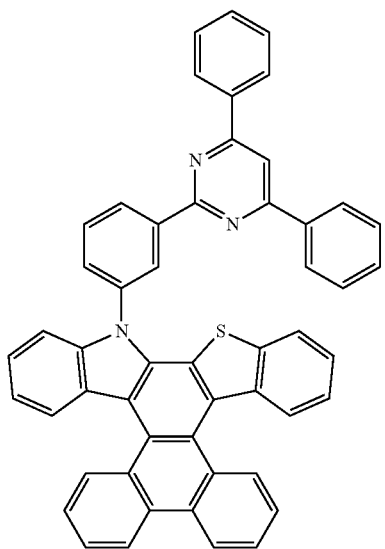
100
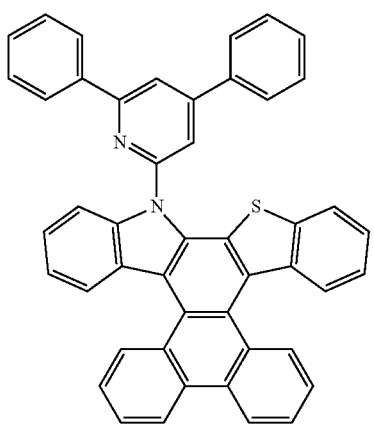
101
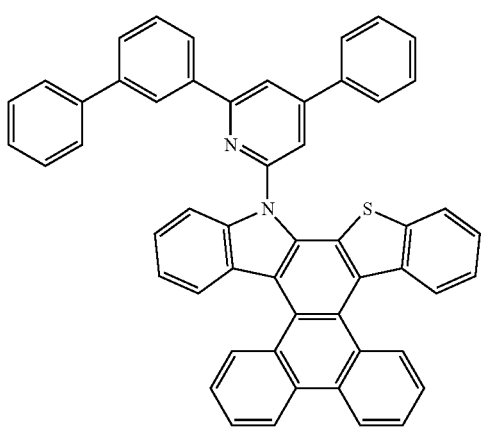
102
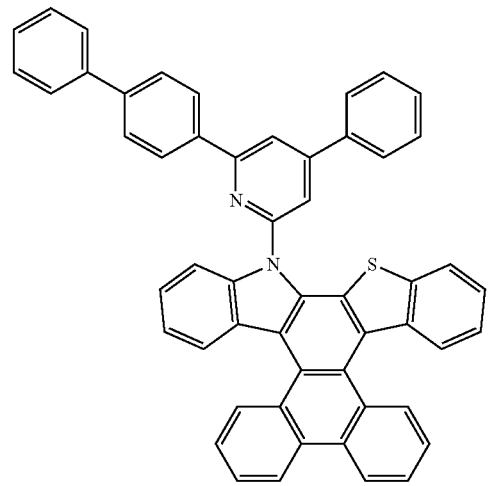
103
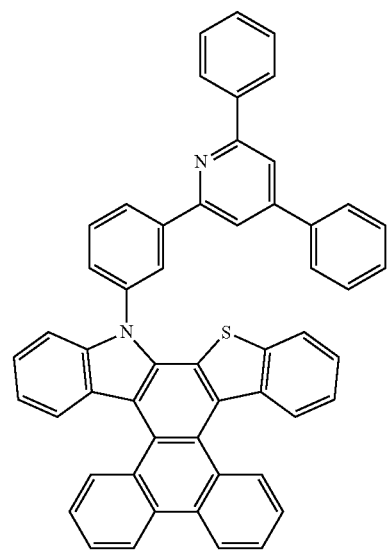
104
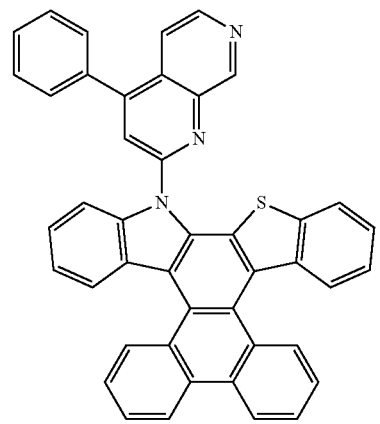
105

106 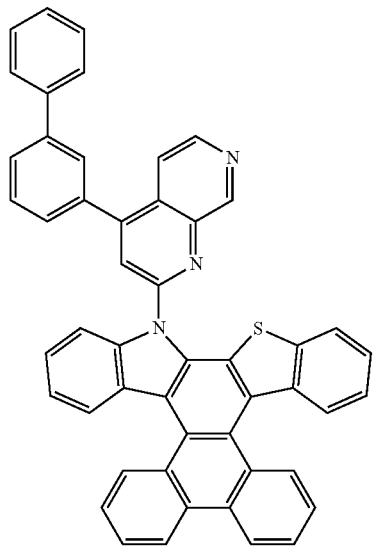
107 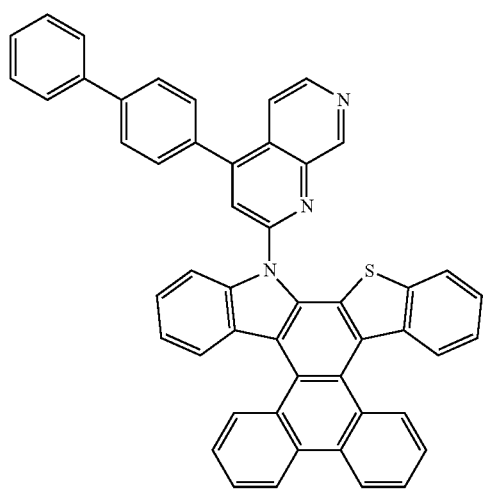
108 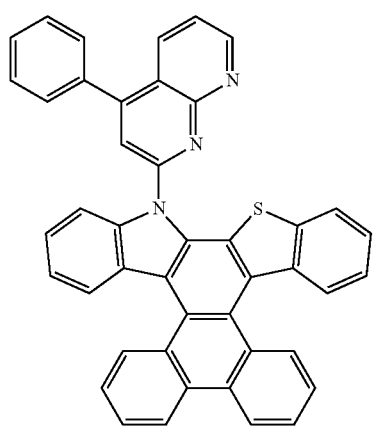
109 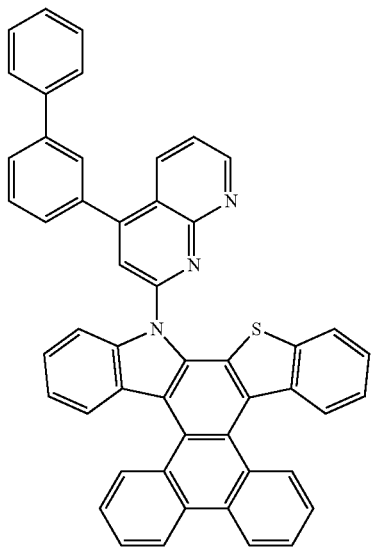
110 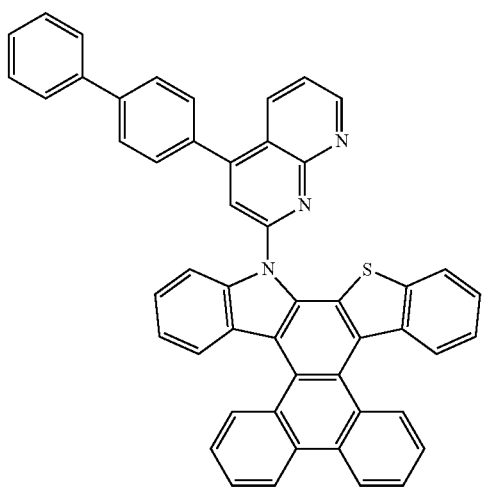
111 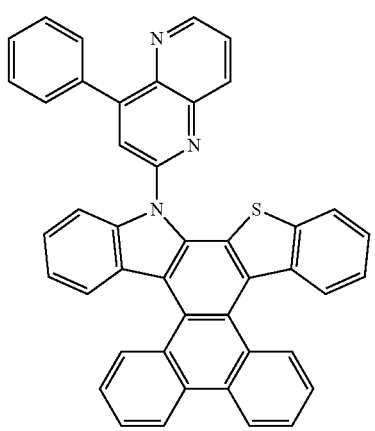

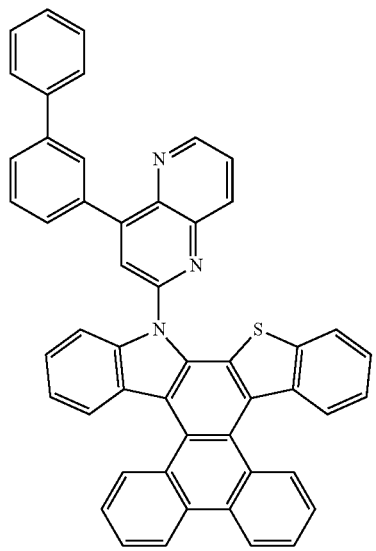
112
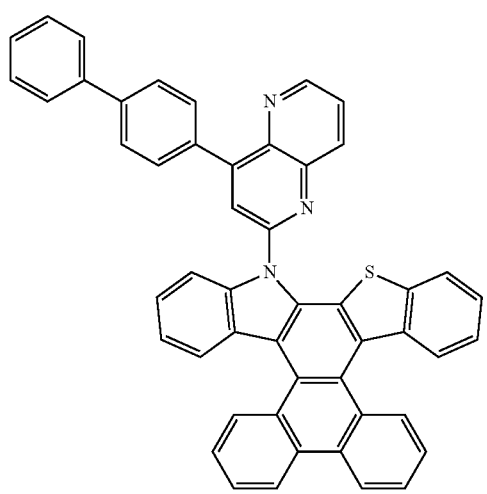
113
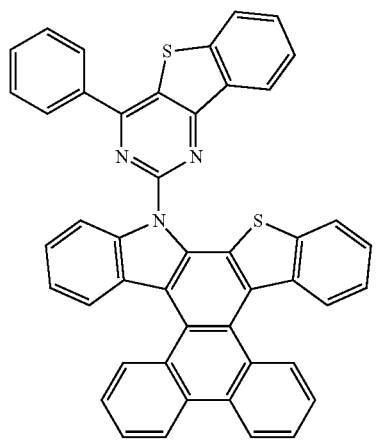
114
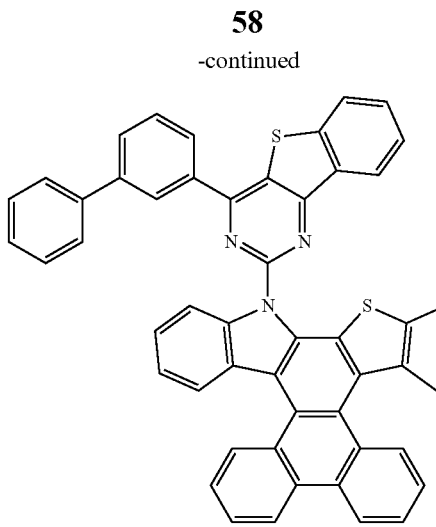
115
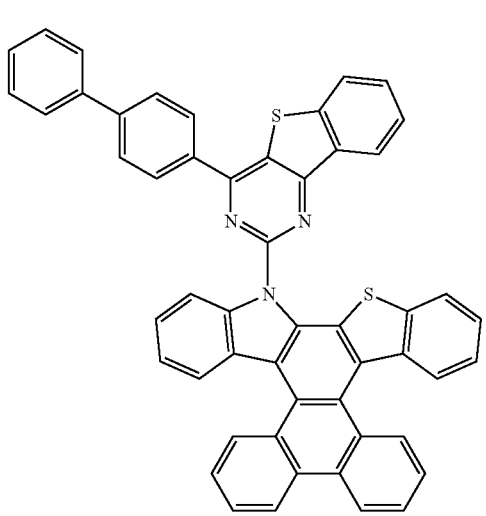
116
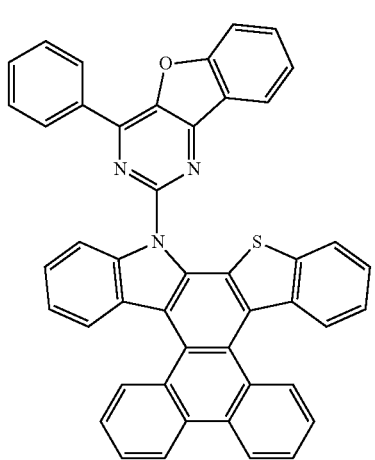
117

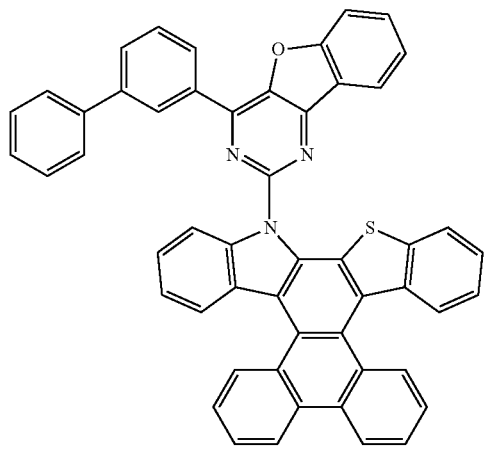
118
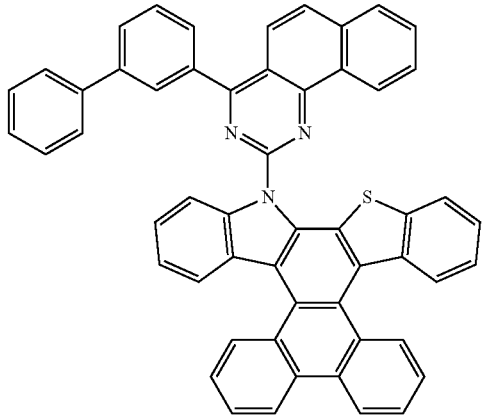
121
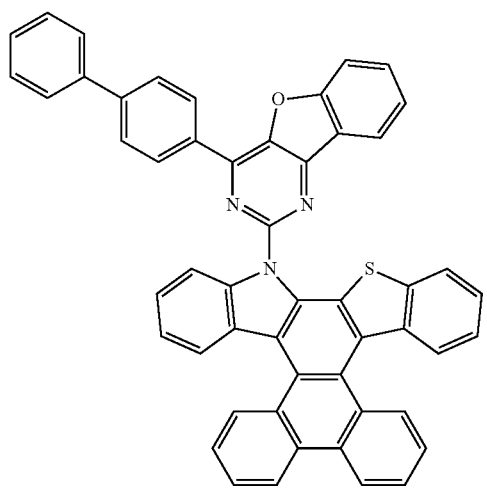
119
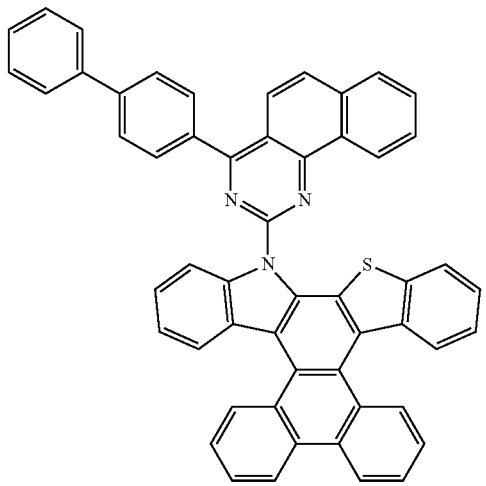
122
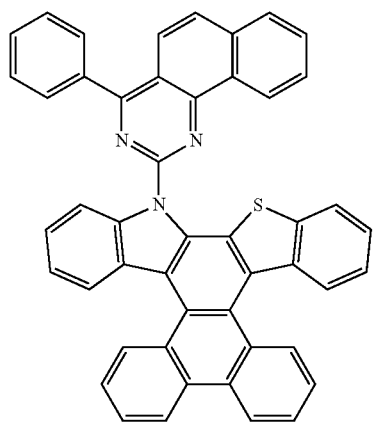
120
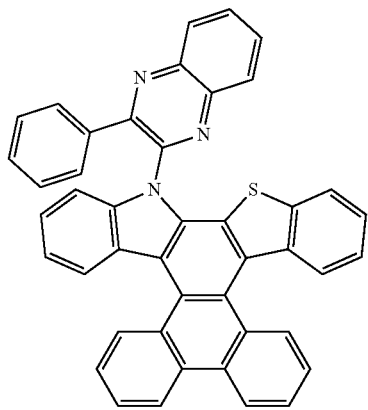
123

US 10,096,784 B2
61
-continued
62
-continued
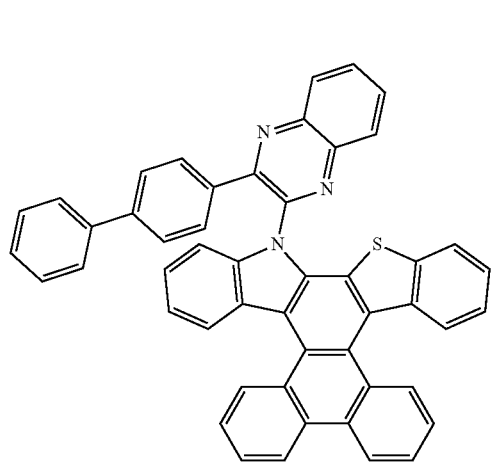
124
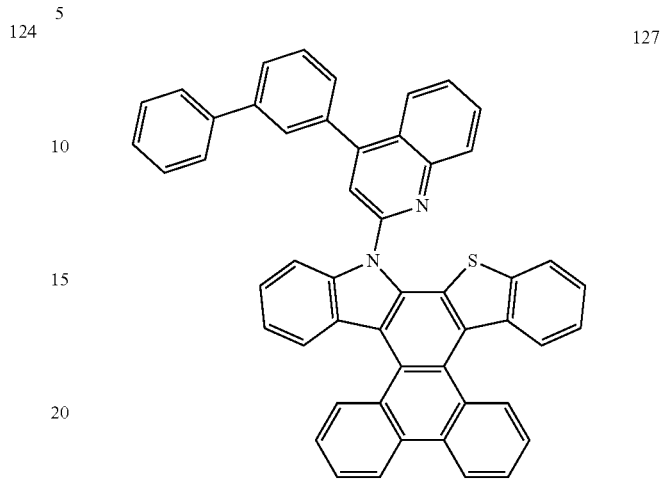
127
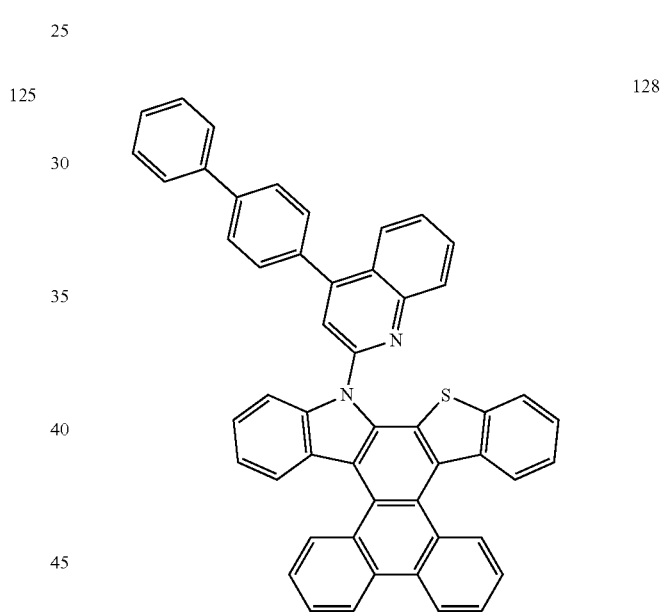
125
128
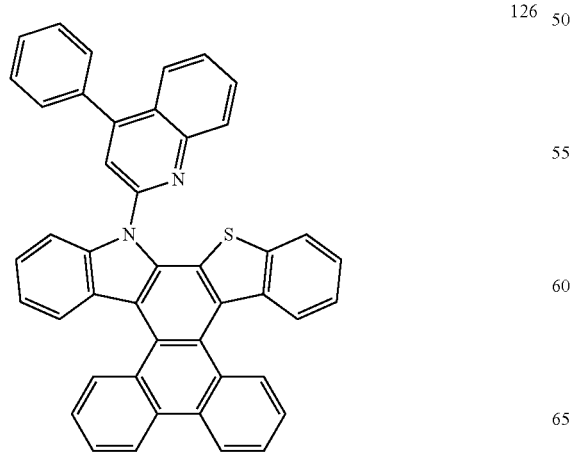
126
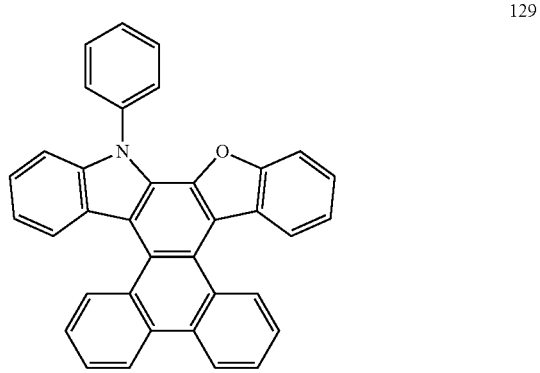
129

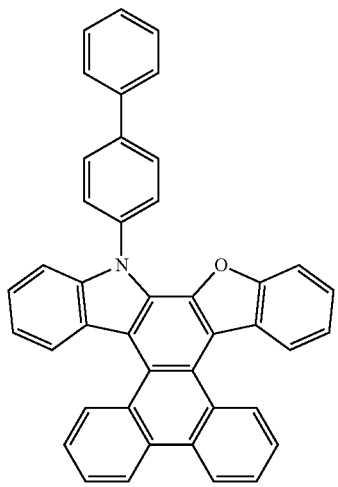
130
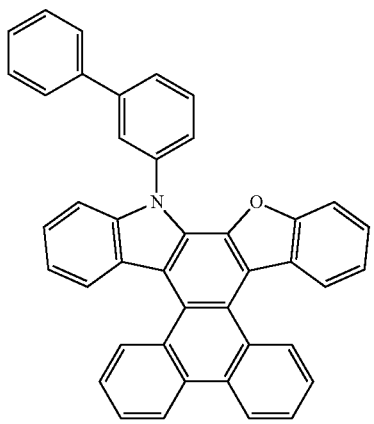
131
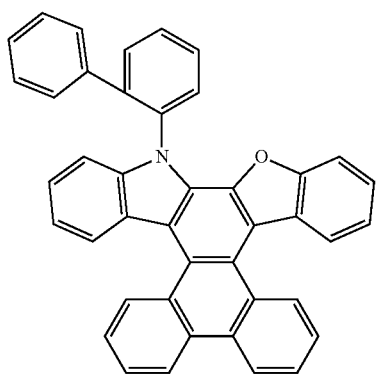
132
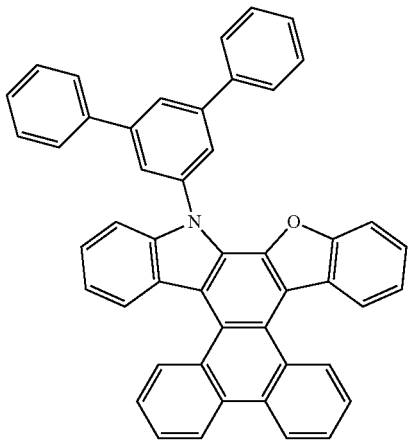
133
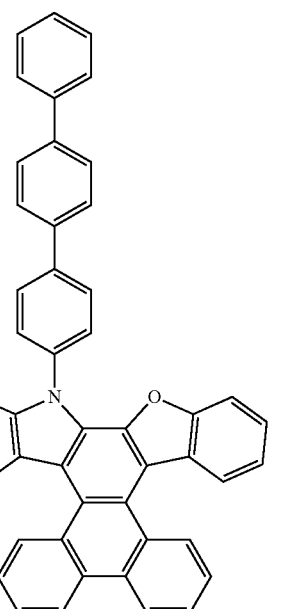
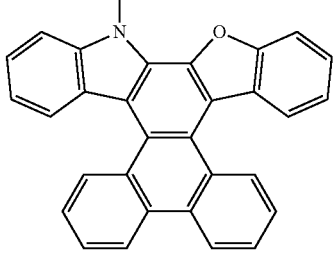
134
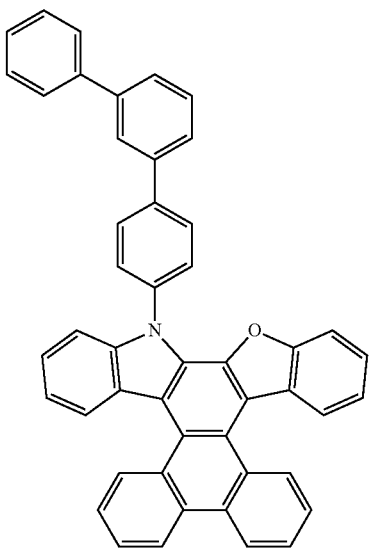
135

136
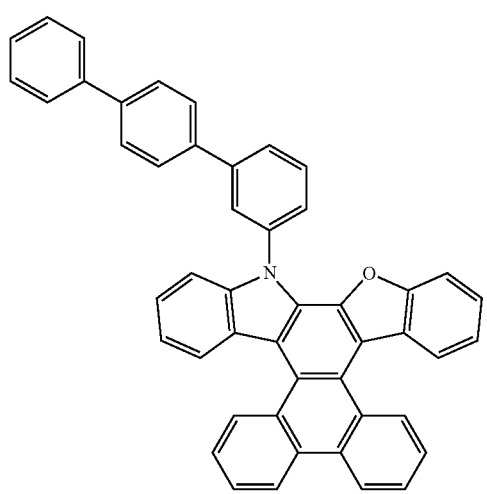
137
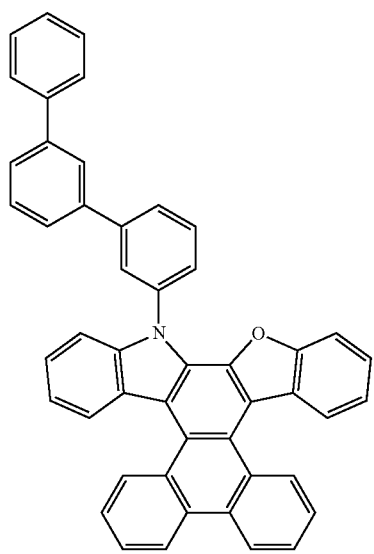
138
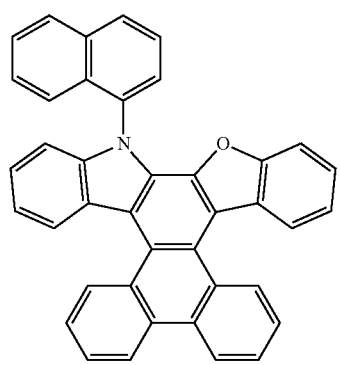
139
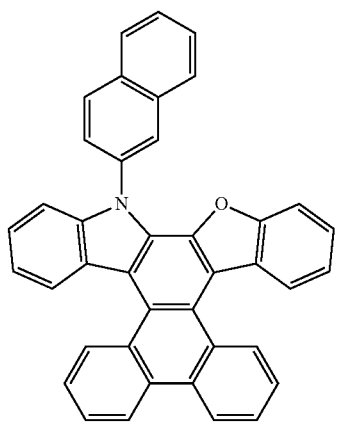
140
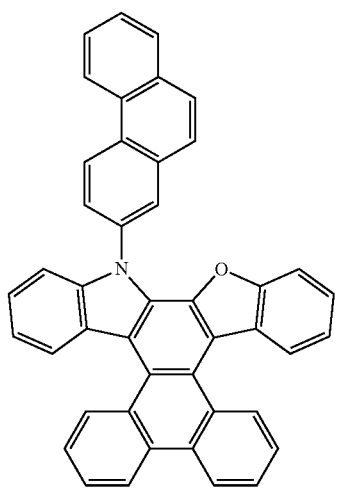
141
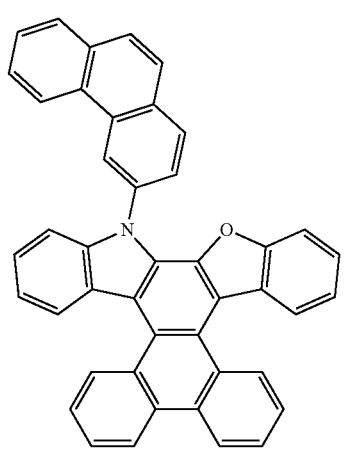

142
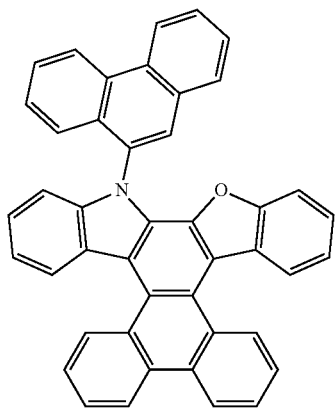
143
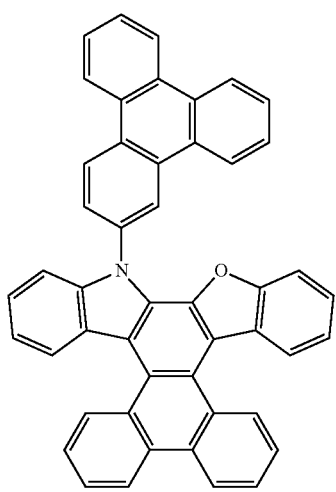
144
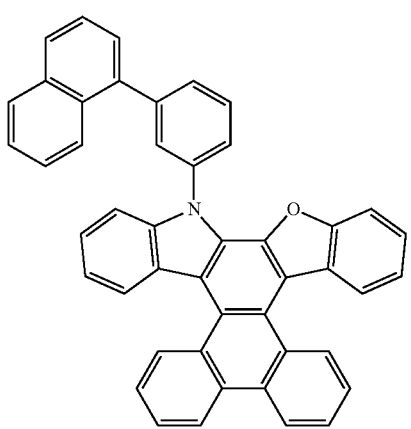
145
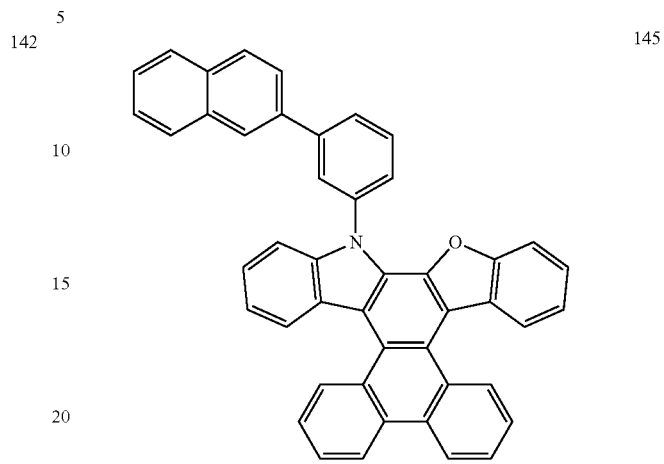
146
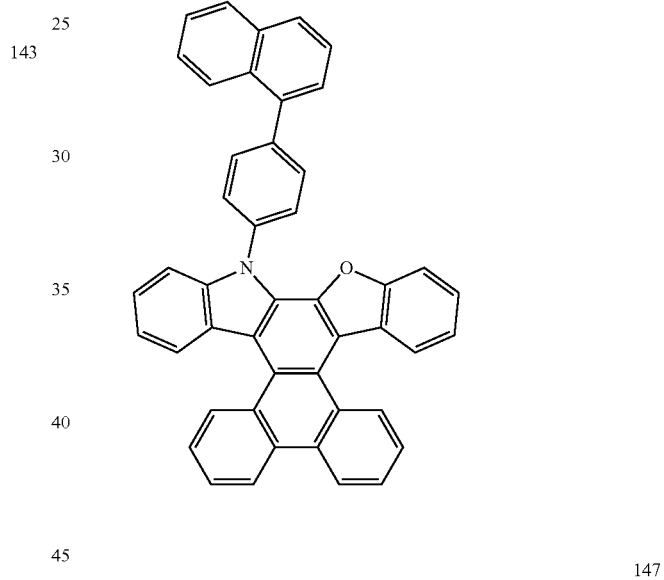
147
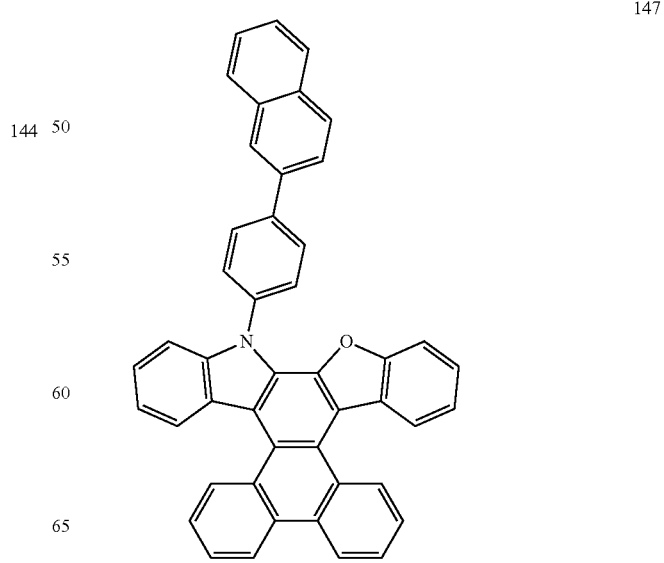

148
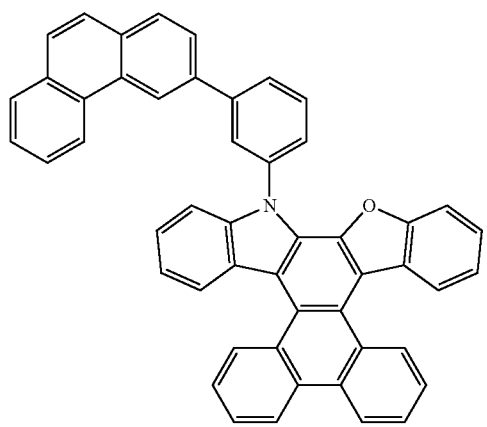
149
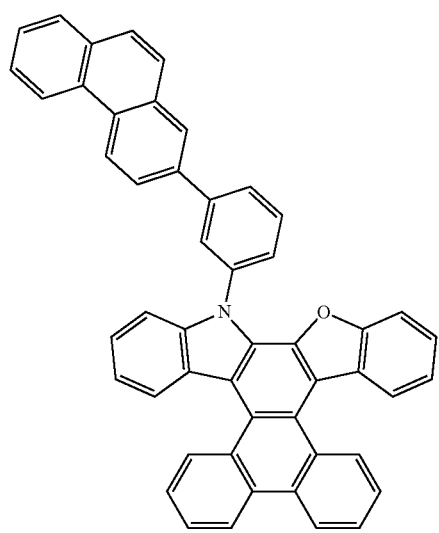
150
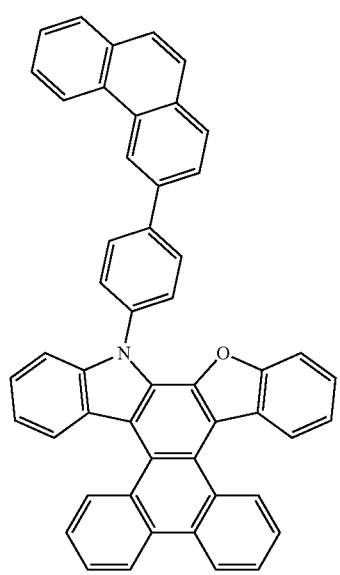
151
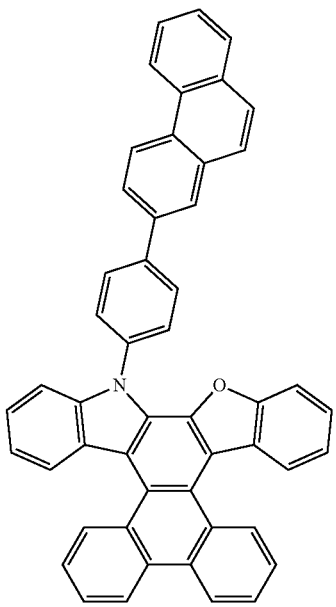
152
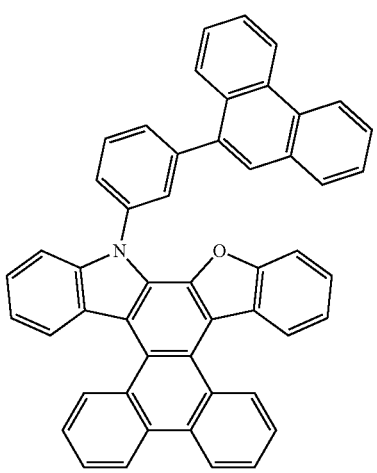
153
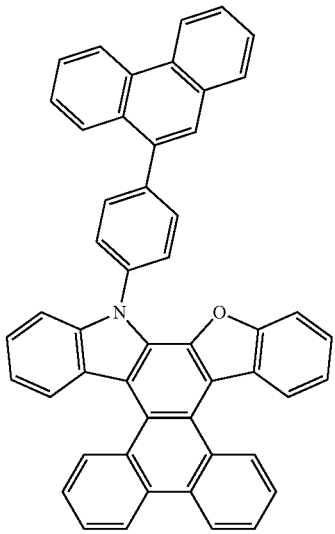

71
-continued
154
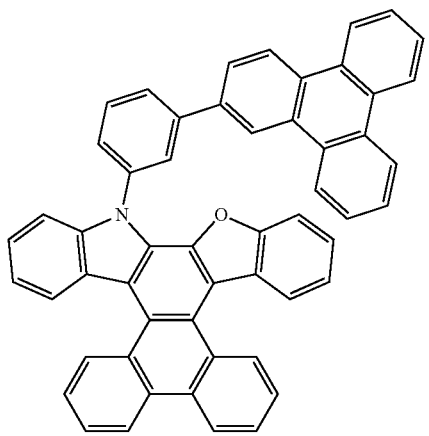
155
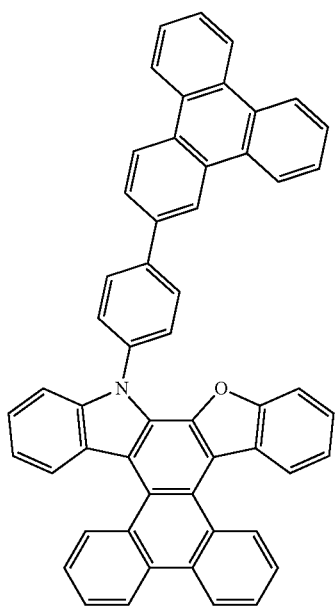
156
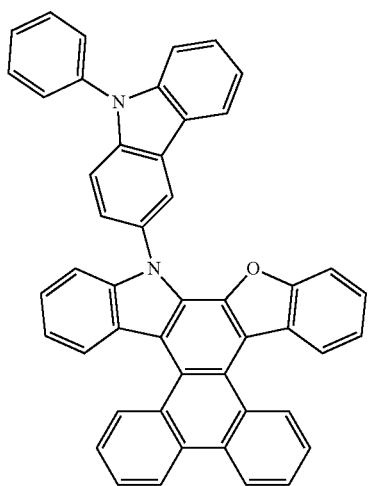
72
-continued
157
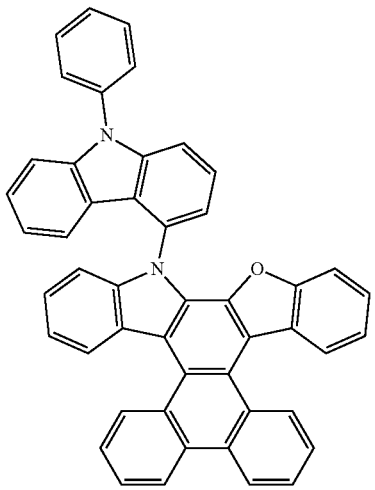
158
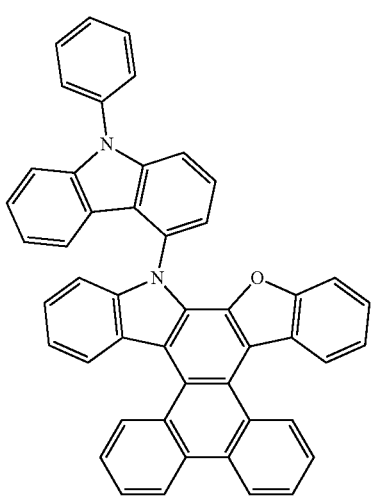
159
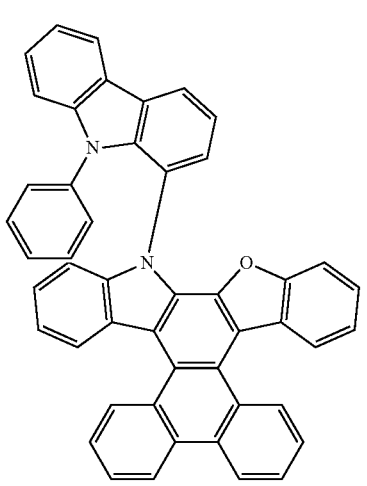

| 73 | 74 |
|---|---|
| -continued | -continued |
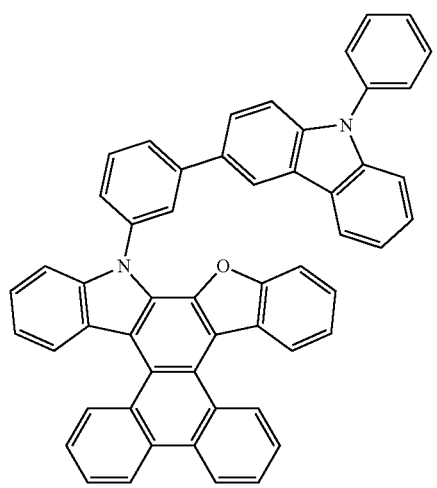
160
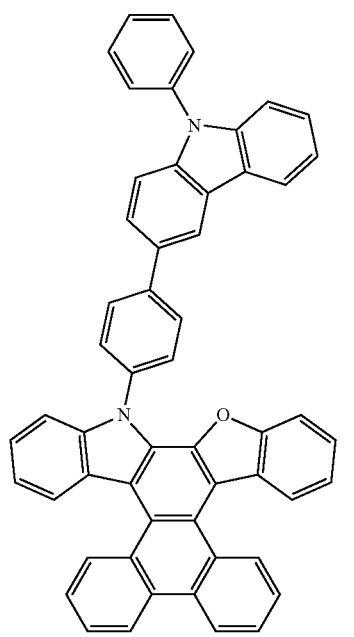
161
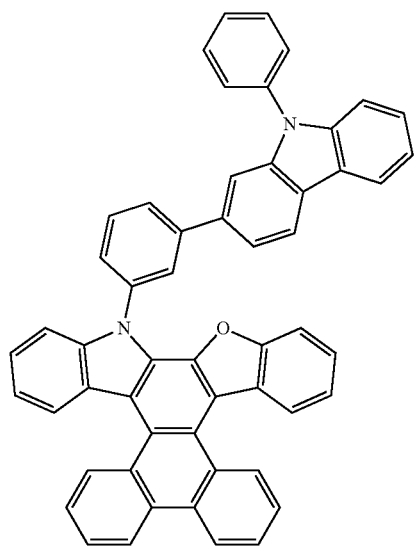
162
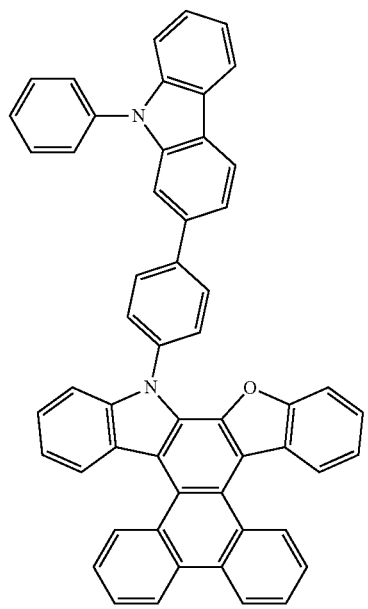
163
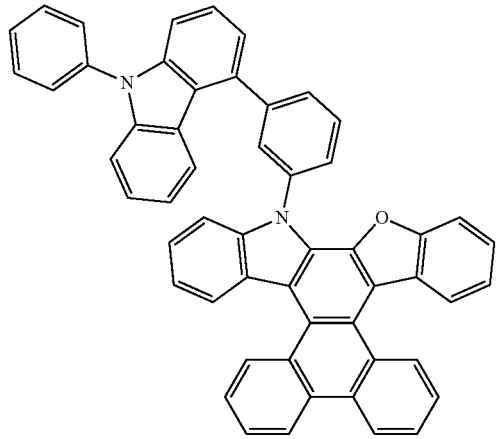
164
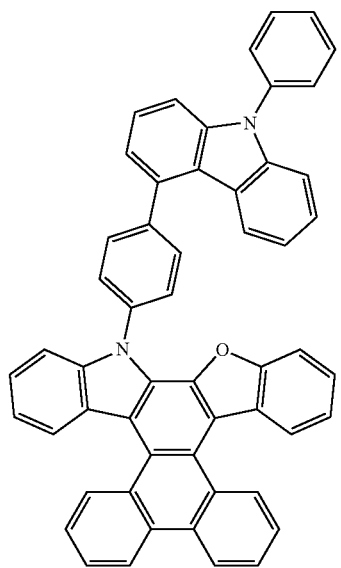
165

166
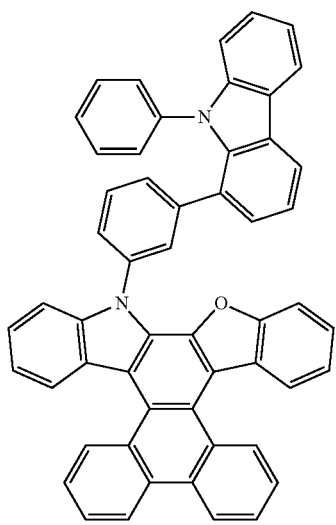
167
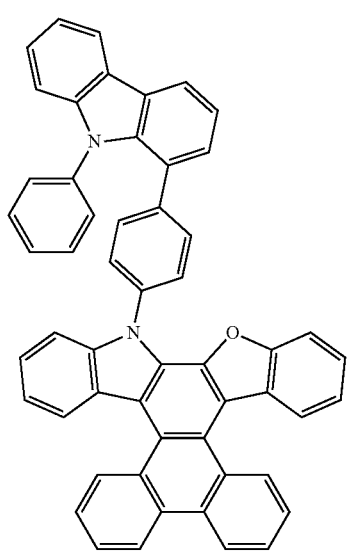
168
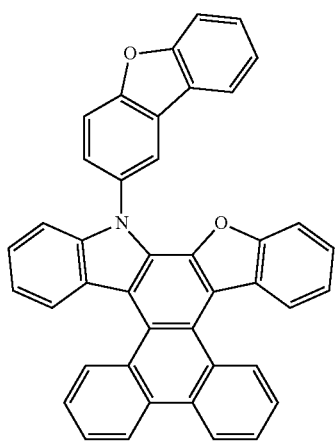
169
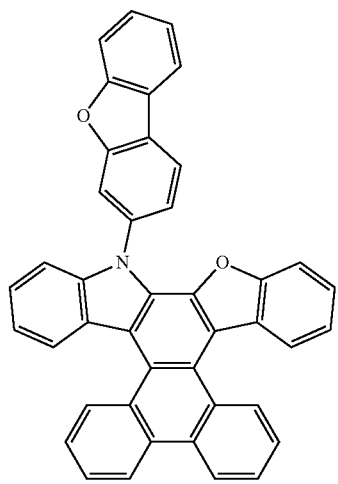
170
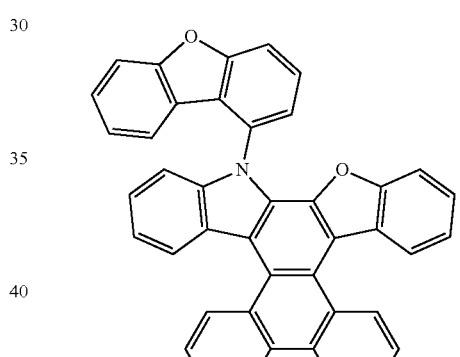
171
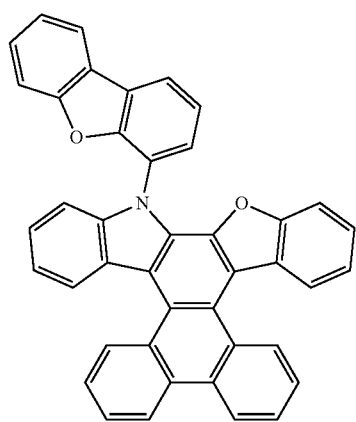

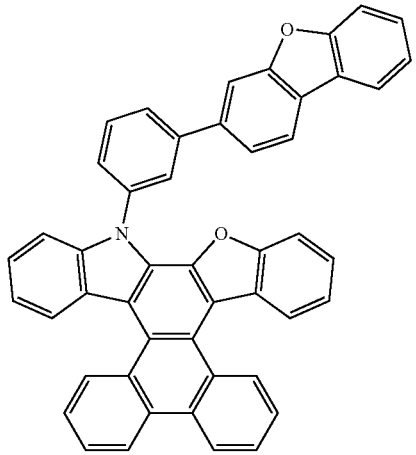
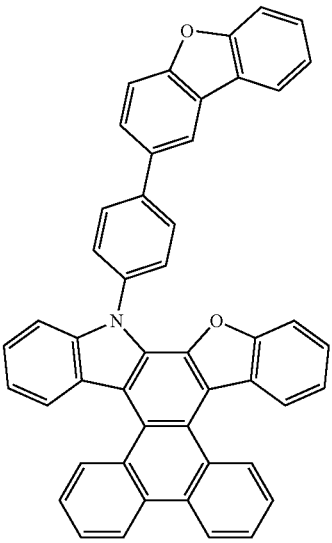
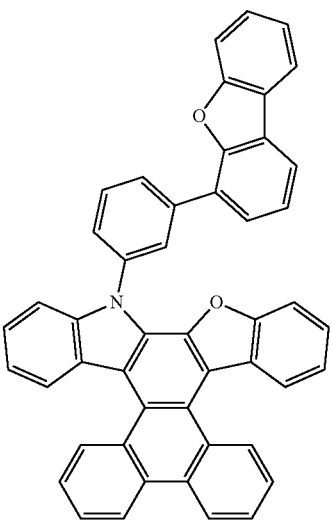
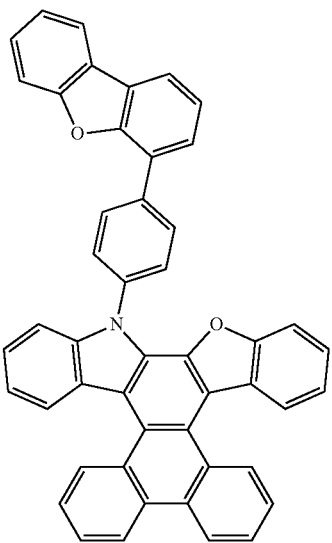

79
-continued
178
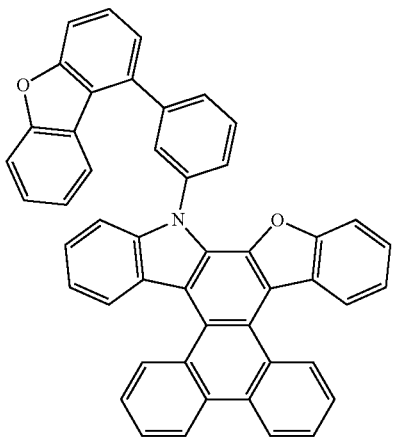
179
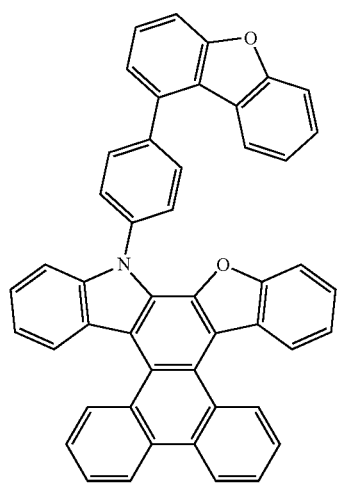
180
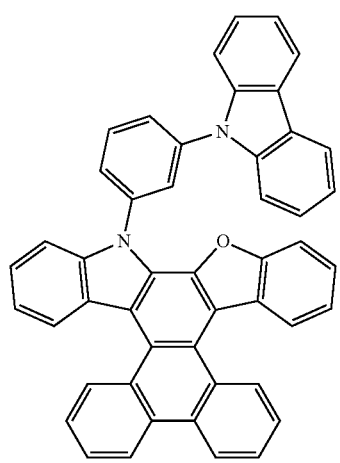
80
-continued
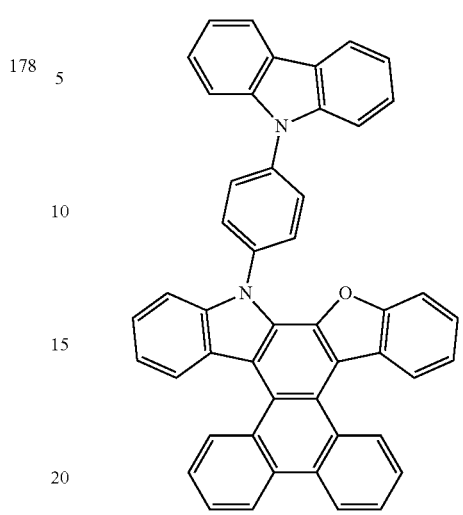
181
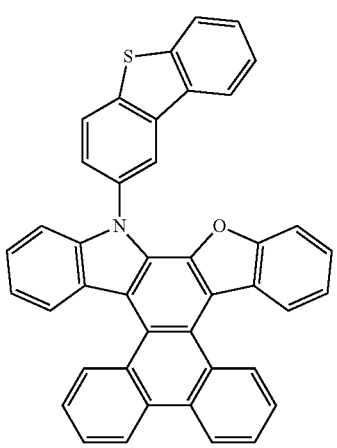
182
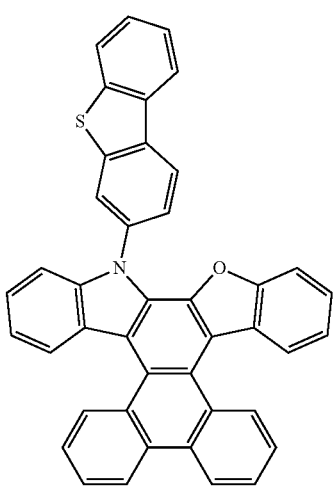
183

81
-continued
82
-continued
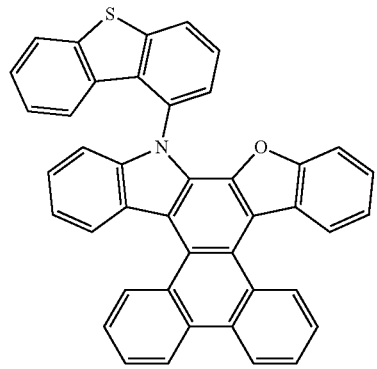
184
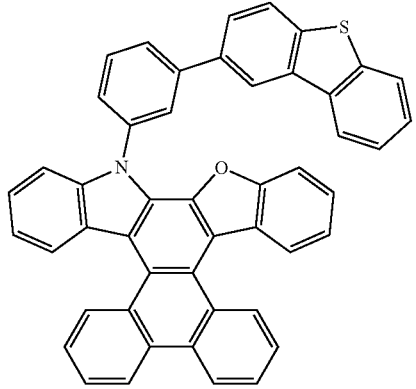
187
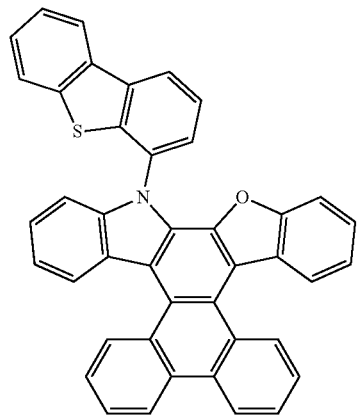
185
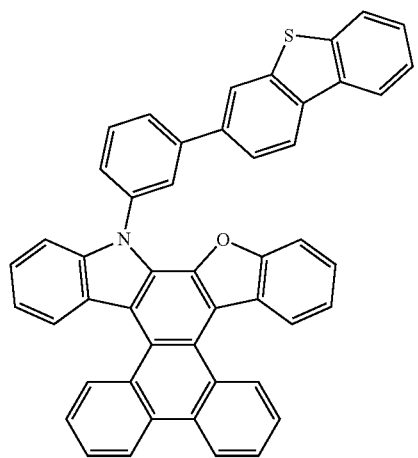
186
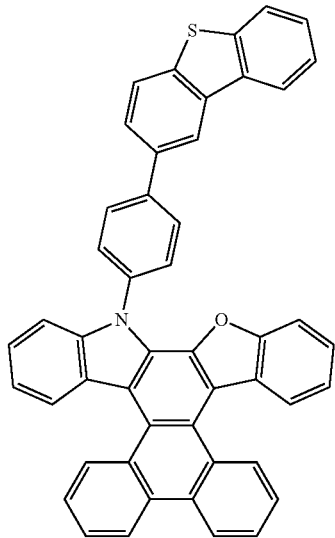
188
189

US 10,096,784 B2
83
-continued
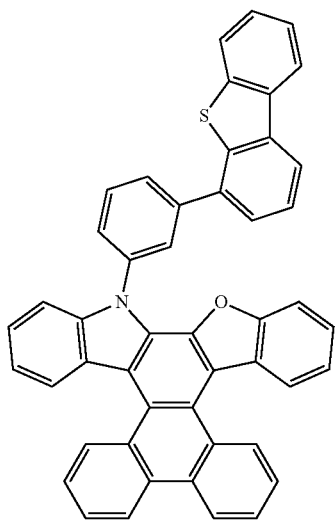
190
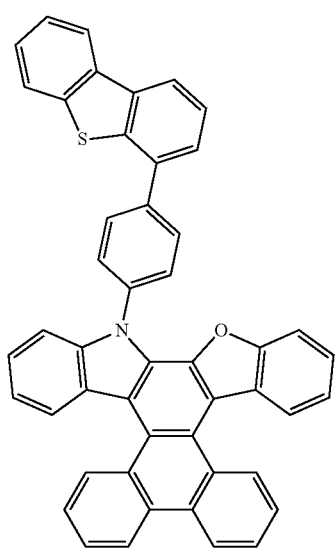
191
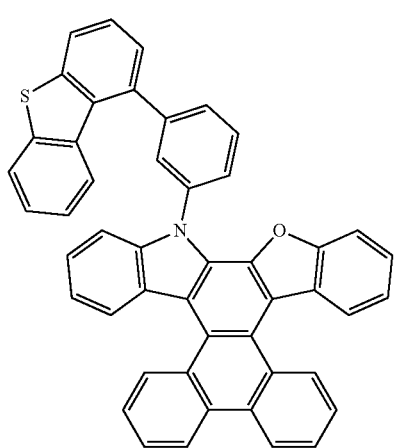
192
84
-continued
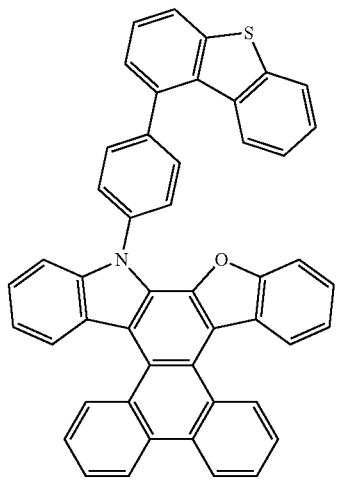
193
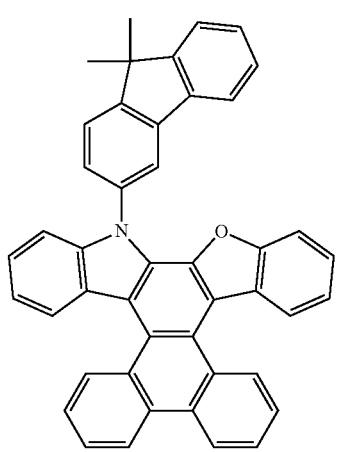
194
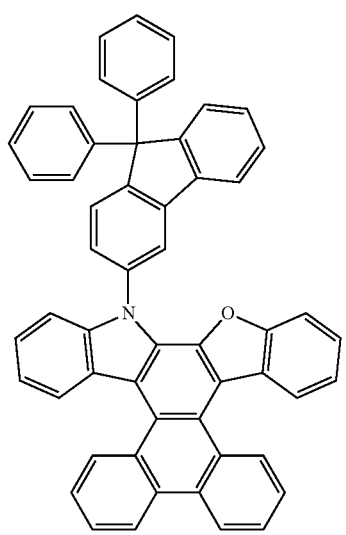
195

85
-continued
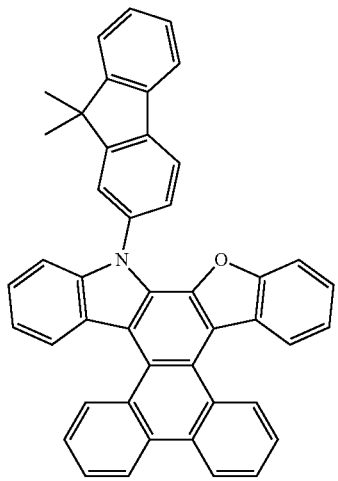
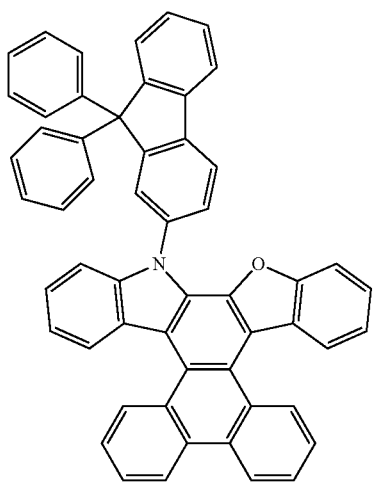
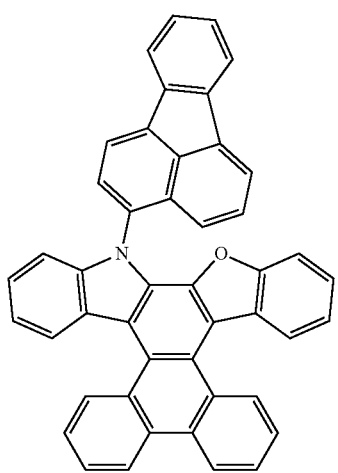
86
-continued
196 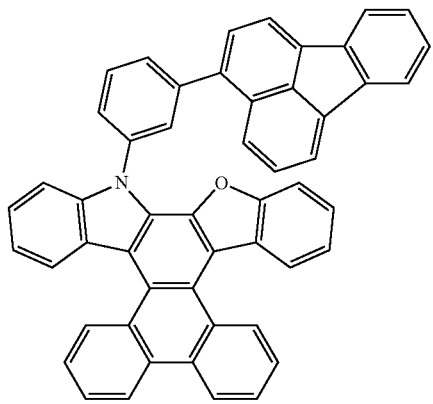
197 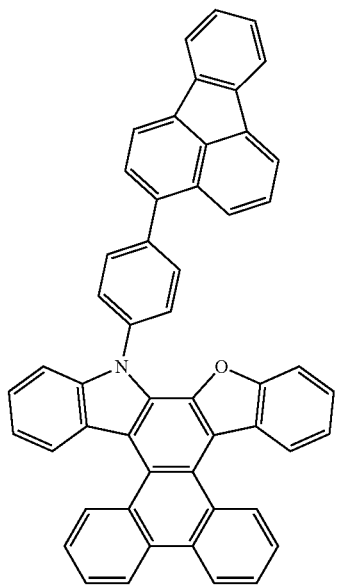
198
199
200
201 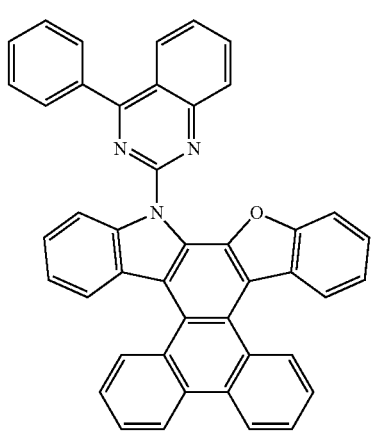

-continued
202
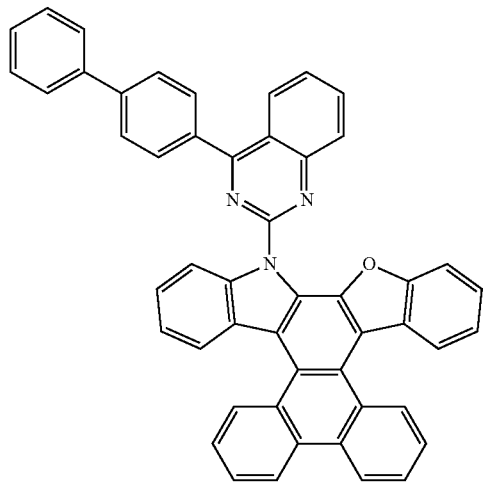
203
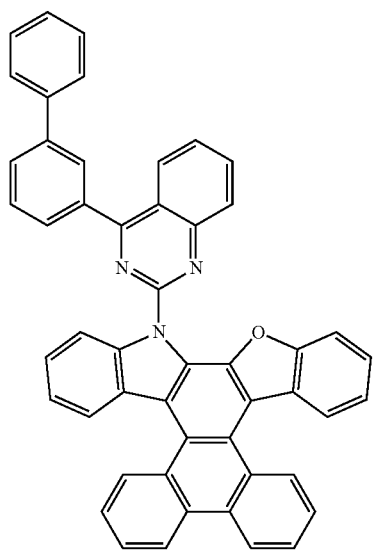
204
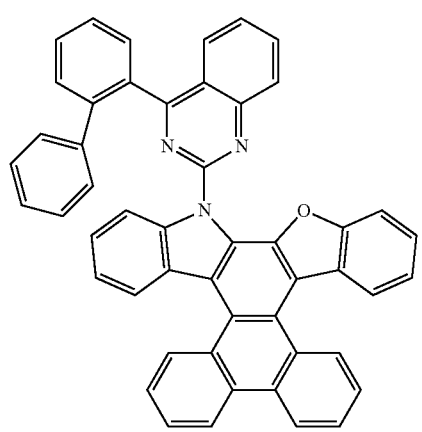
-continued
205
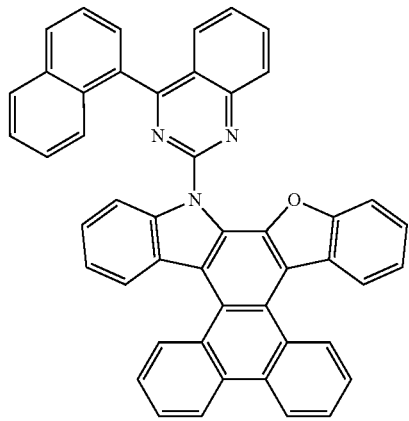
206
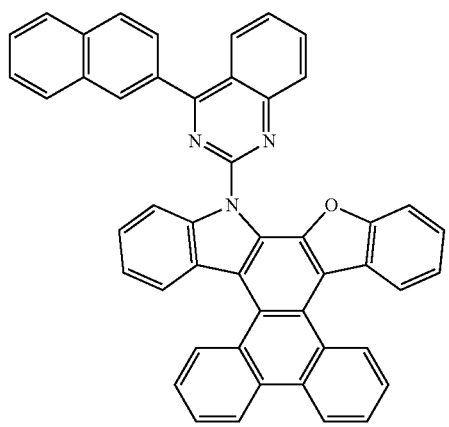
207
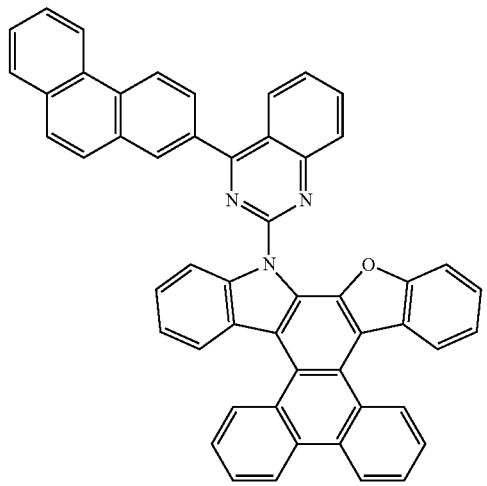

89
-continued
208
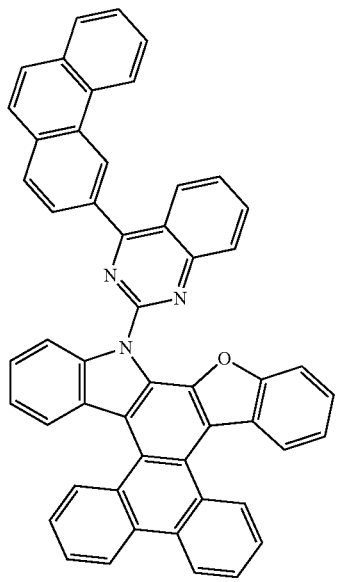
209
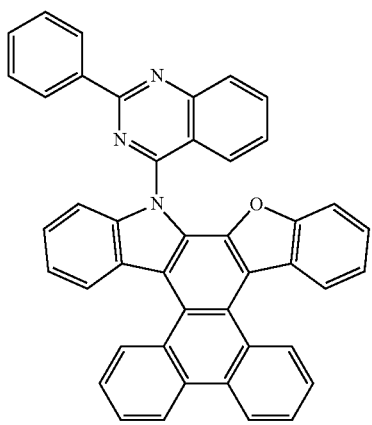
210
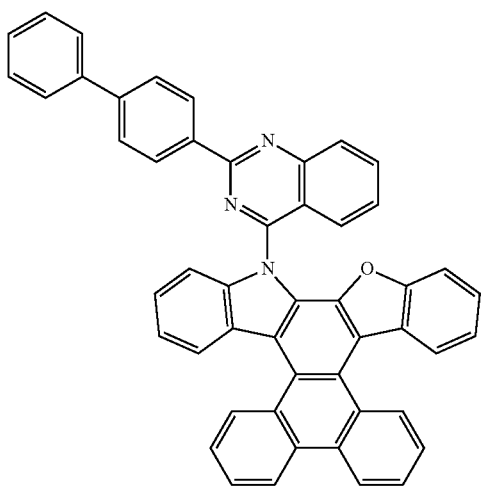
90
-continued
211
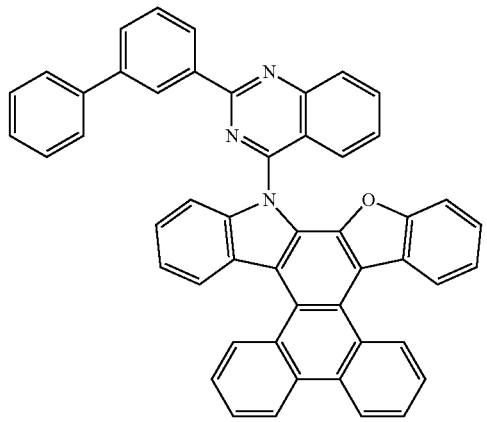
212
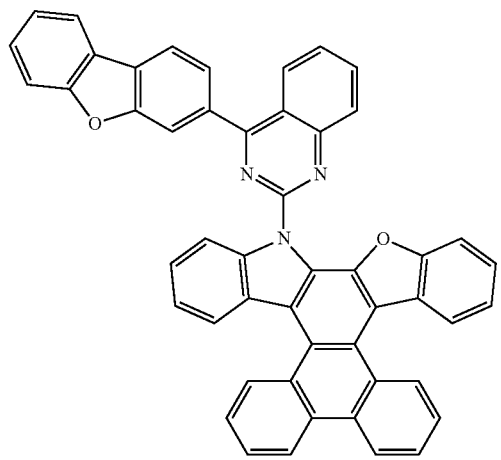
213
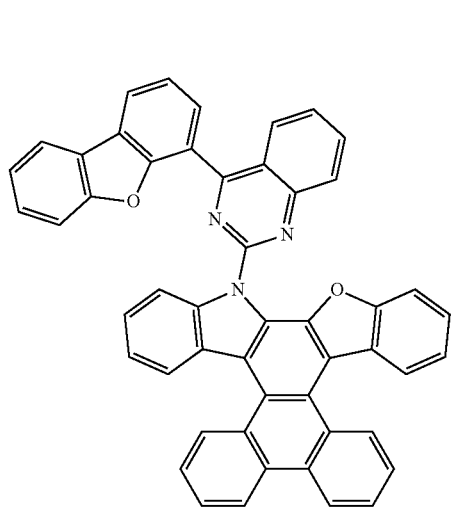

214
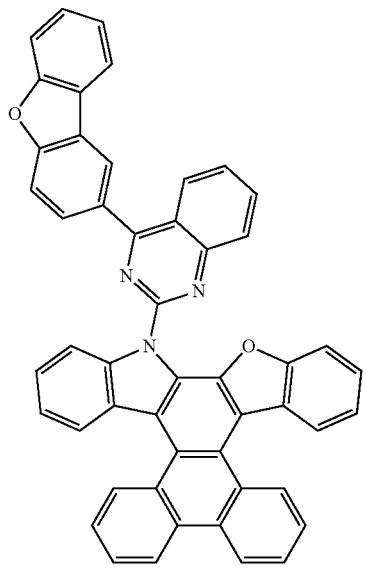
215
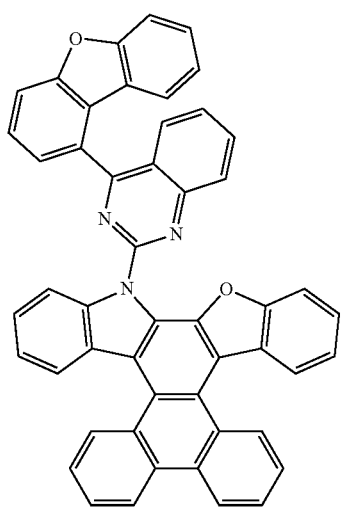
216
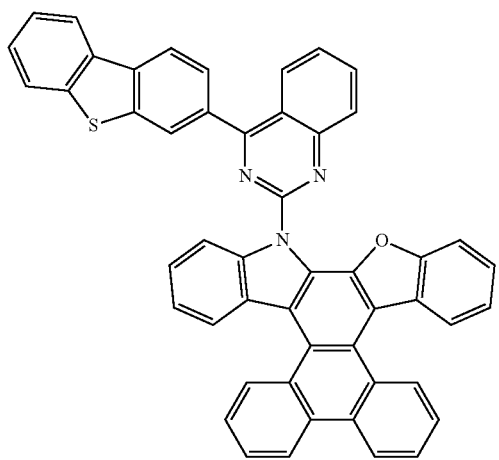
217
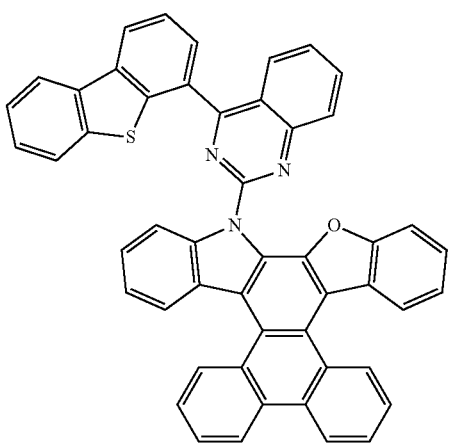
218
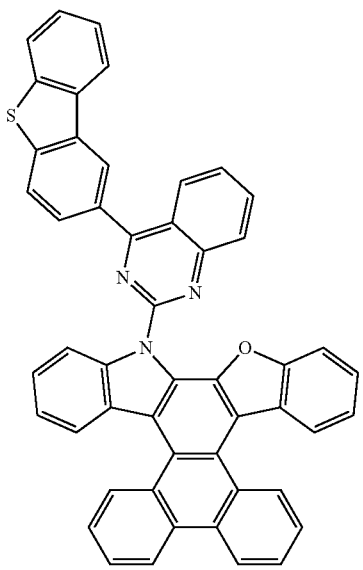
219
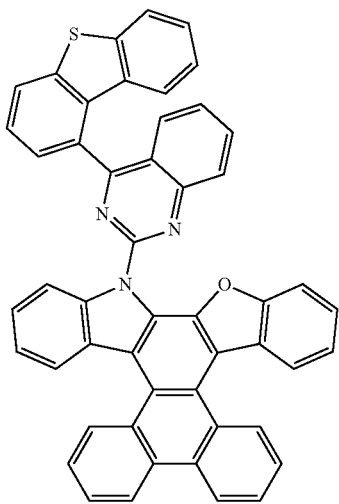

93
-continued
94
-continued
220
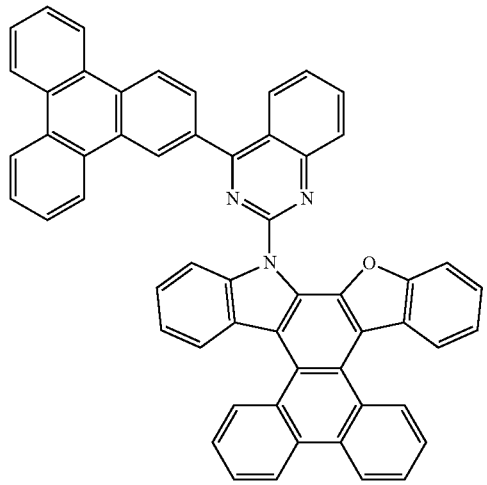
223
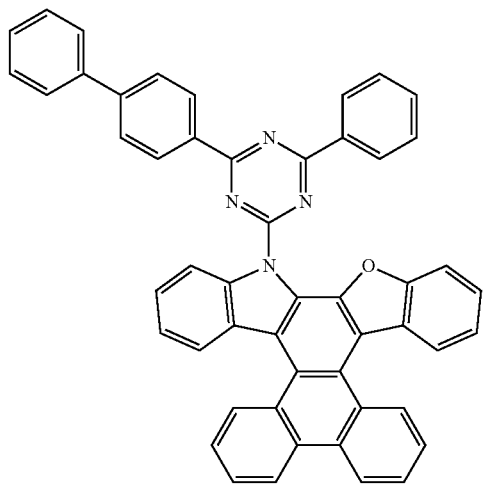
221
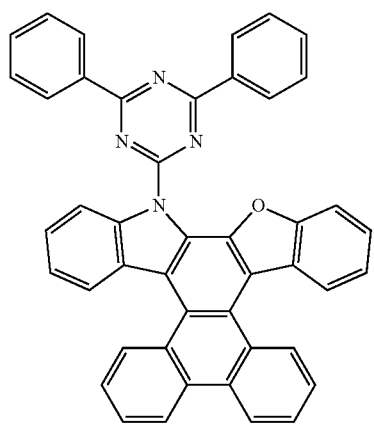
224
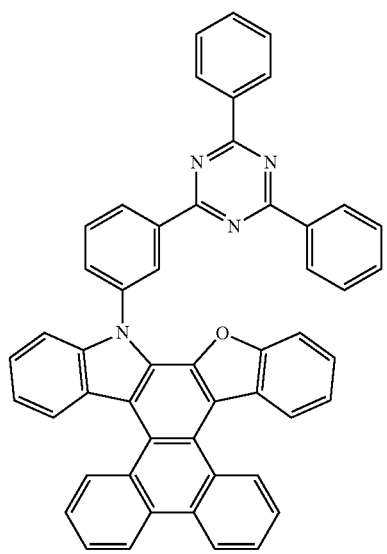
222
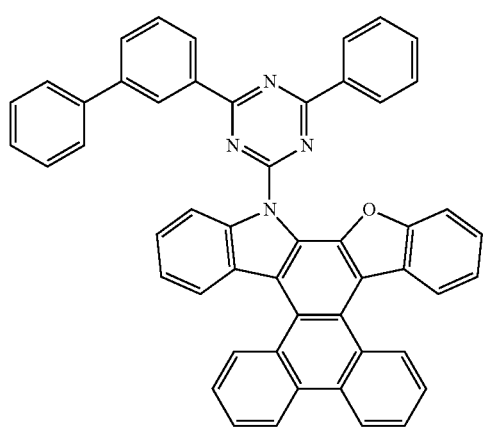
225
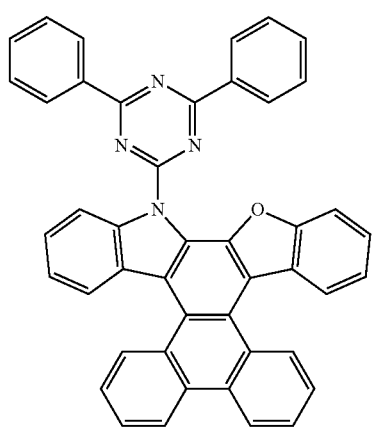

226
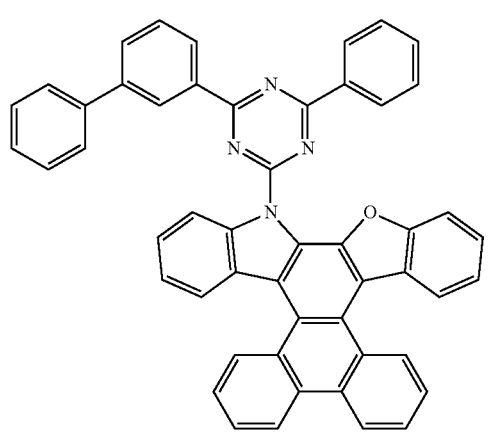
227
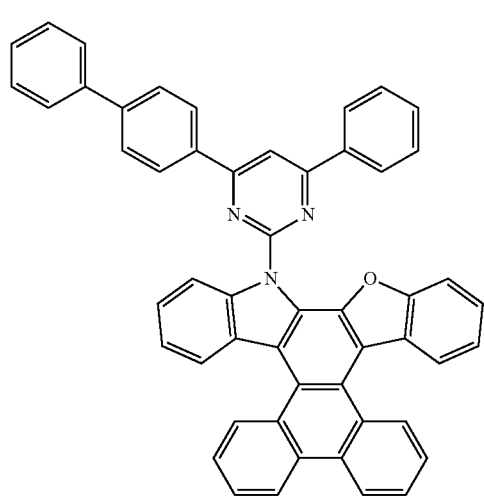
228
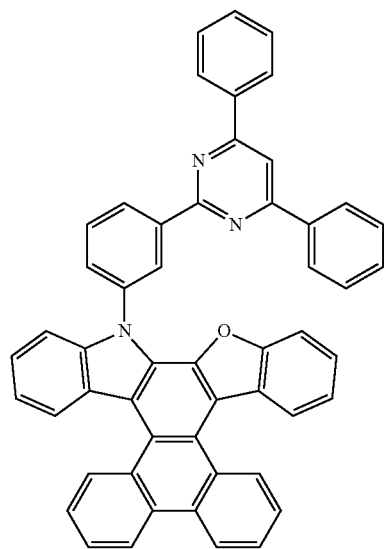
229
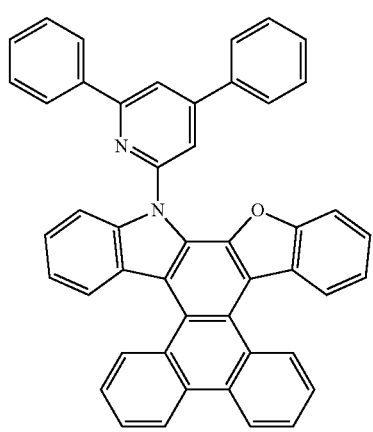
230
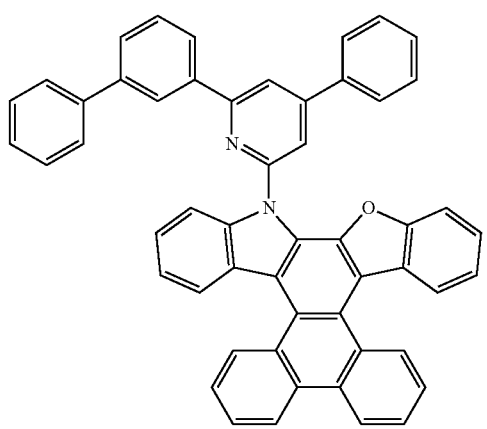
231
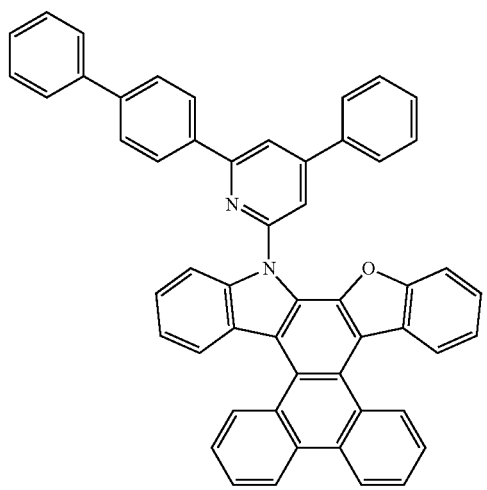

97
-continued
232
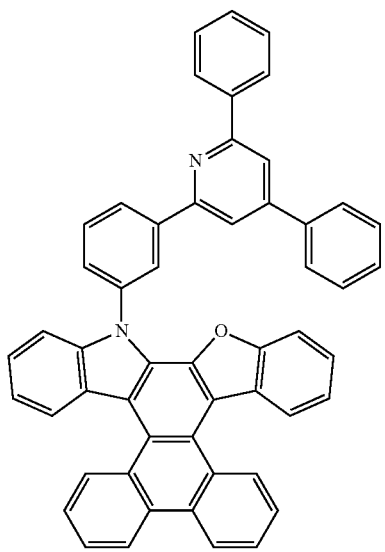
233
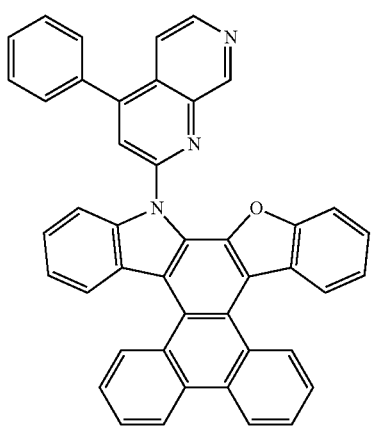
234
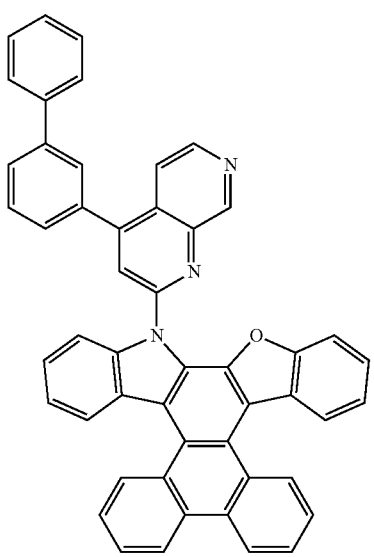
98
-continued
235
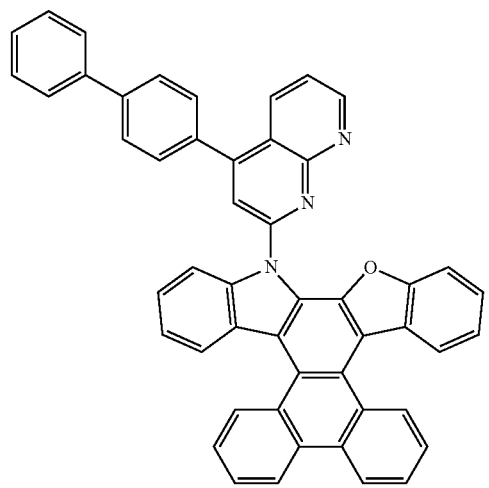
236
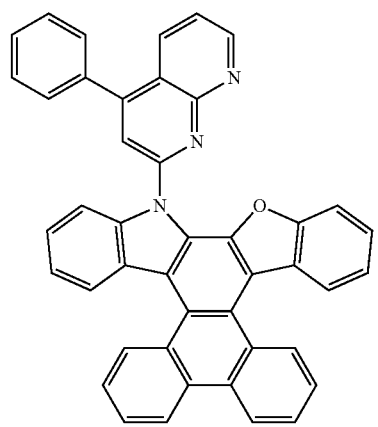
237
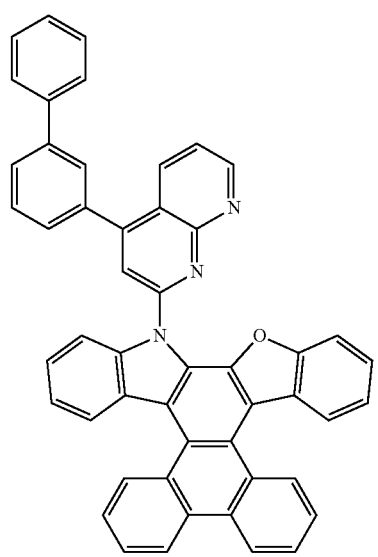

99
-continued
238
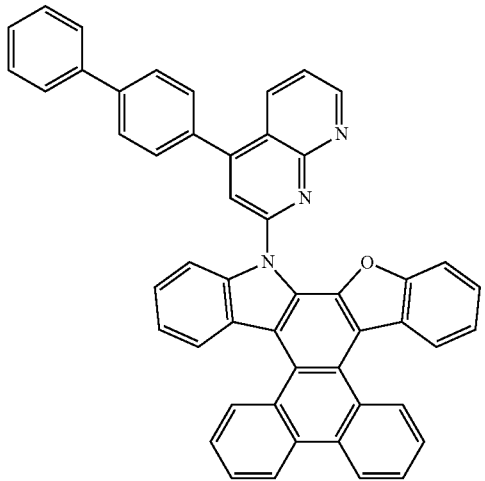
239
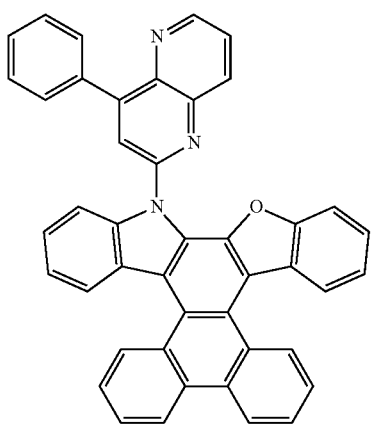
240
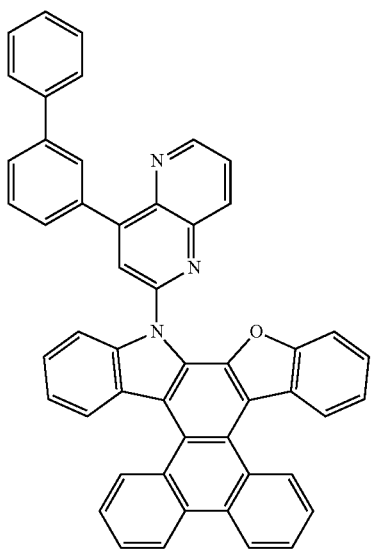
100
-continued
241
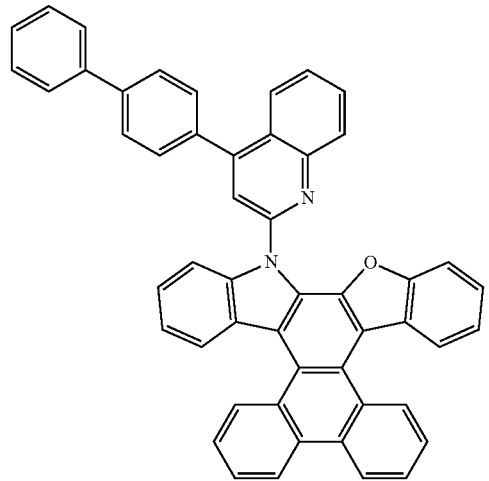
242
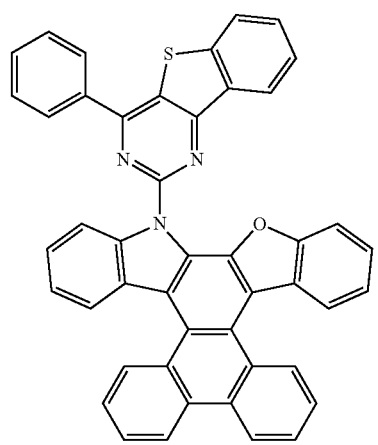
243
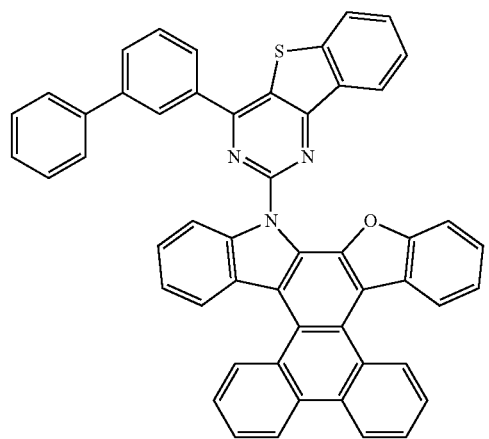

101
-continued
244
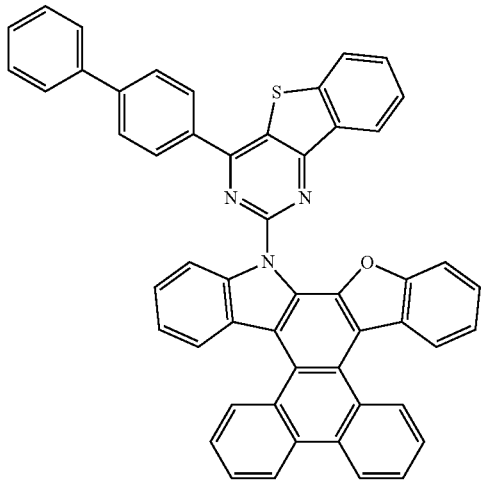
245
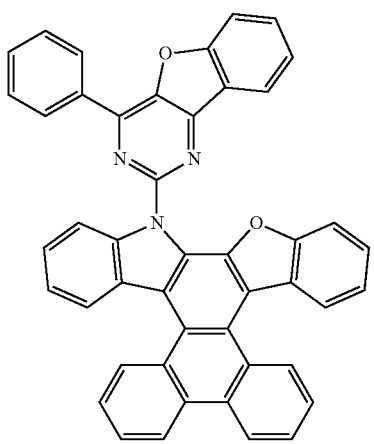
246
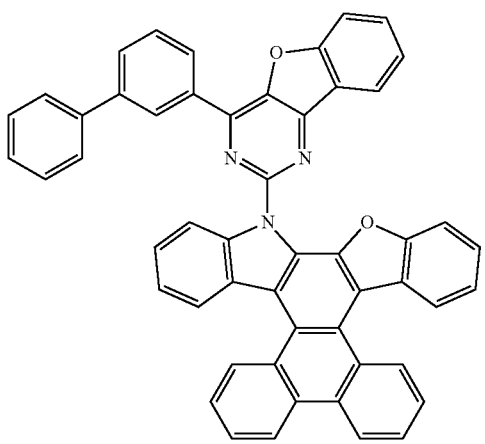
102
-continued
247
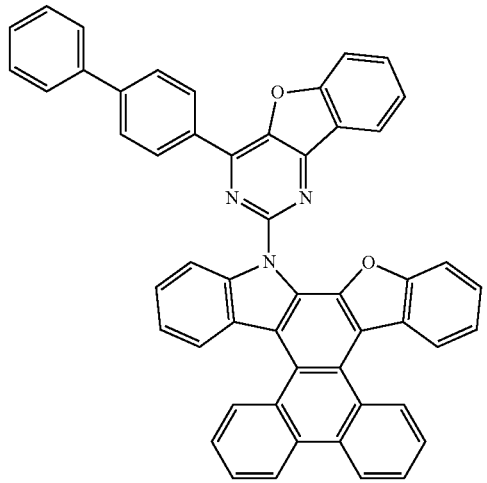
248
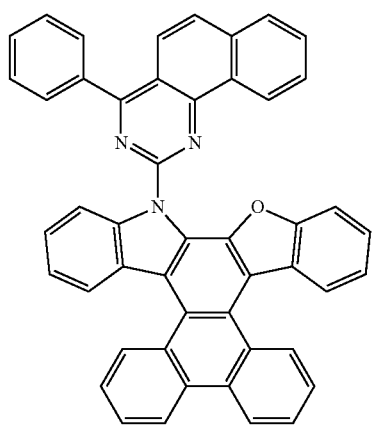
249
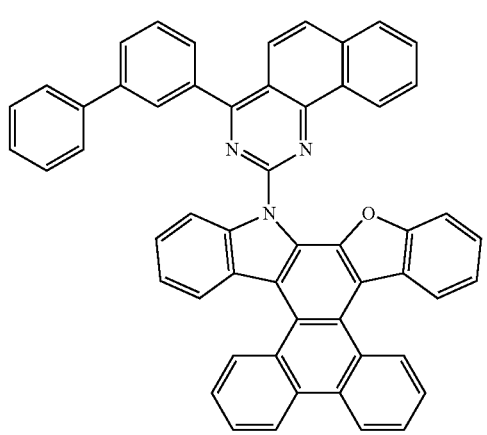

103
-continued
250
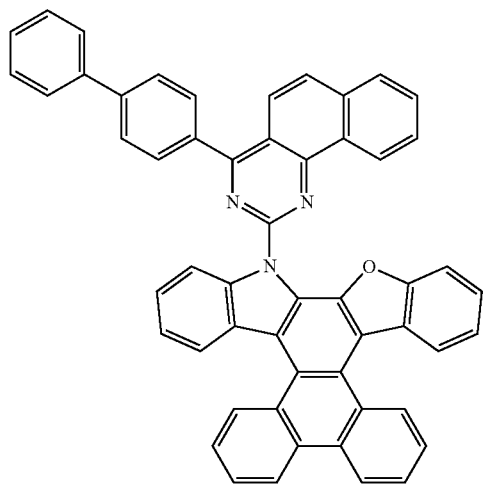
251
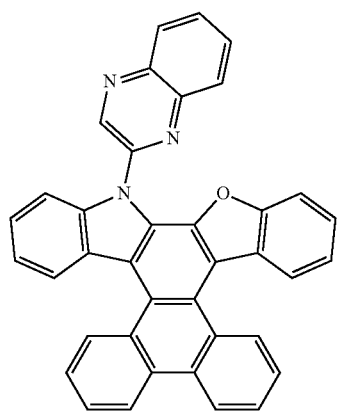
252
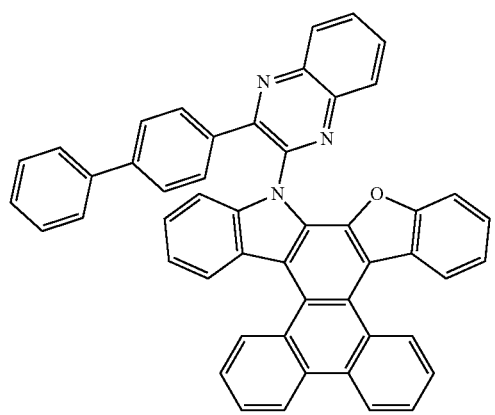
104
-continued
253
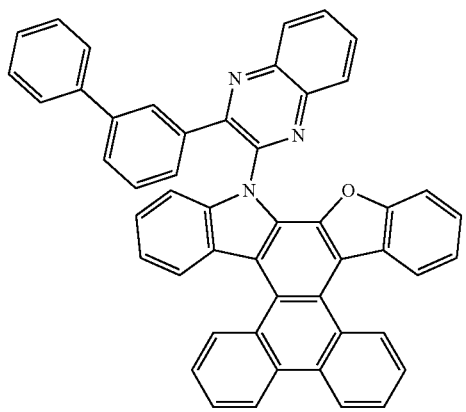
254
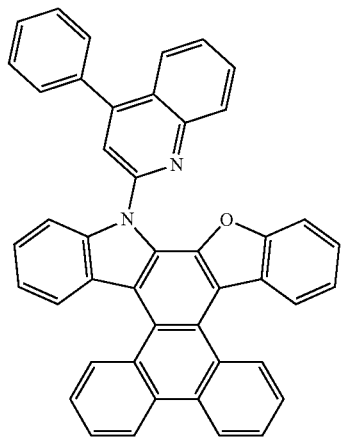
255
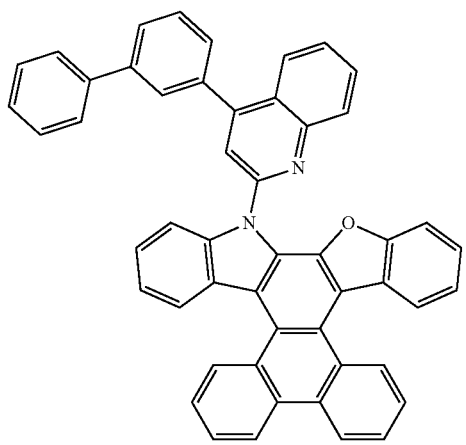

-continued

256

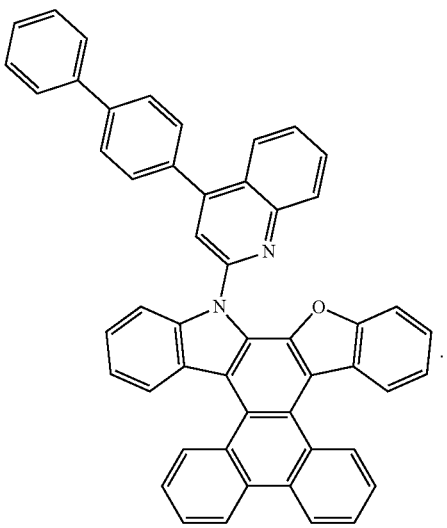

The compound for an organic optoelectric device may be applied to an organic optoelectric device and may be may be applied to an organic optoelectric device alone or with another compound for an organic optoelectric device. When the compound for an organic optoelectric device is applied with another compound for an organic optoelectric device, it may be applied in a form of a composition.

Hereinafter, one example of a composition for an organic optoelectric device including the compound for an organic optoelectric device is described.

A composition for an organic optoelectric device according to another embodiment includes a first compound for an organic optoelectric device represented by Chemical Formula 1A; and a second compound for an organic optoelectric device represented by Chemical Formula 1B.

In Chemical Formula 1A and Chemical Formula 1B, X may be O or S, ET may be a substituted or unsubstituted pyridinyl group, a substituted or unsubstituted pyrimidinyl group, a substituted or unsubstituted triazinyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzofuranpyrimidinyl group, a substituted or unsubstituted benzothiophenepyrimidinyl group, or a substituted or unsubstituted phenanthrolinyl group, HT may be a substituted or unsubstituted phenyl group, a substituted or unsubstituted biphenyl group, a substituted or unsubstituted terphenyl group, a substituted or unsubstituted naphthyl group, a substituted or unsubstituted phenanthrenyl group, a substituted or unsubstituted triphenylene group, a substituted or unsubstituted fluorenyl group, a substituted or unsubstituted fluoranthenyl group, a substituted or unsubstituted carbazolyl group, a substituted or unsubstituted dibenzofuranyl group, or a substituted or unsubstituted dibenzothiophenyl group, $R^2$ to $R^9$ may independently be hydrogen, deuterium, a substituted or unsubstituted C1 to C20 alkyl group, a substituted or unsubstituted C6 to C30 aryl group, a substituted or unsubstituted C2 to C30 heterocyclic group, or a combination thereof, and L may be a single bond, a substituted or unsubstituted C6 to C30 arylene group, a substituted or unsubstituted C2 to C30 heteroarylene group, or a combination thereof.

Specifically, ET may be a substituted or unsubstituted quinazolinyl group, HT may be a substituted or unsubstituted phenyl group, a substituted or unsubstituted biphenyl group, a substituted or unsubstituted terphenyl group, a substituted or unsubstituted phenanthrene group, a substituted or unsubstituted dibenzofuranyl group, or a substituted or unsubstituted dibenzothiophenyl group, $R^2$ to $R^9$ may be a hydrogen, and the "substituted" refers to replacement of at least one hydrogen by deuterium, a C1 to C4 alkyl group, a phenyl group, a biphenyl group, a naphthyl group, a phenanthrenyl group, a triphenylene group, a fluoranthenyl group, a carbazolyl group, a dibenzofuranyl group, a dibenzothiophenyl group, a pyridinyl group, a pyrimidinyl group, or a triazinyl group.

A composition for an organic optoelectric device according to another embodiment includes the first compound for an organic optoelectric device; and at least one second compound for an organic optoelectric device selected from a compound represented by Chemical Formula 2 and a compound consisting of a combination of a moiety represented by Chemical Formula 3 and a moiety represented by Chemical Formula 4.

[Chemical Formula 2]

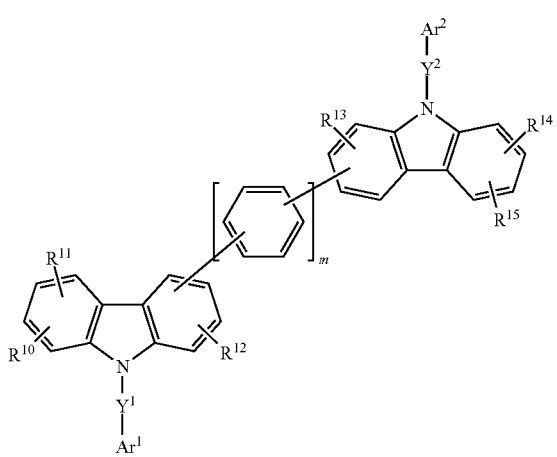

In Chemical Formula 2, $Y^1$ and $Y^2$ are independently a single bond, a substituted or unsubstituted C6 to C30 arylene group, a substituted or unsubstituted C2 to C30 heteroarylene group, or a combination thereof, $Ar^1$ and $Ar^2$ are independently a substituted or unsubstituted C6 to C30 aryl group, a substituted or unsubstituted C2 to C30 heterocyclic group, or a combination thereof, $R^{10}$ to $R^{15}$ are independently hydrogen, deuterium, a substituted or unsubstituted C1 to C20 alkyl group, a substituted or unsubstituted C6 to C30 aryl group, a substituted or unsubstituted C2 to C50 heterocyclic group, or a combination thereof, and m is an integer of 0 to 2;

[Chemical Formula 3]

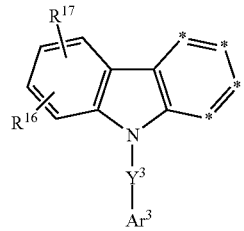

[Chemical Formula 4]

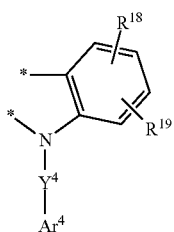

[Group III]

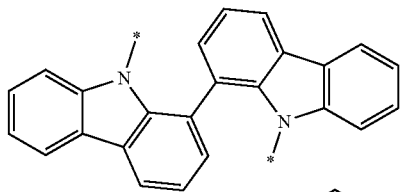

C-1

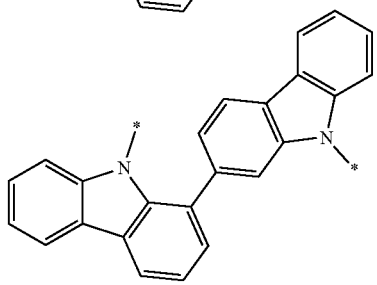

C-2

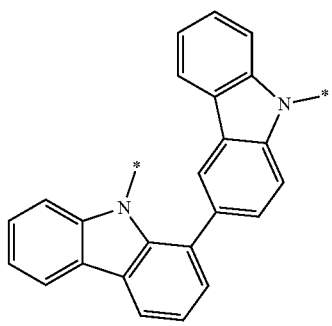

C-3

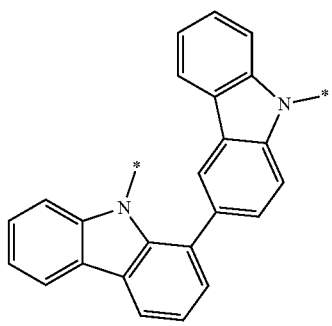

C-4

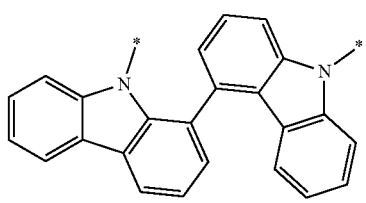

C-5

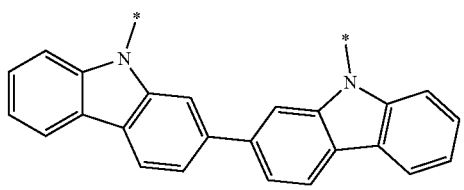

C-6

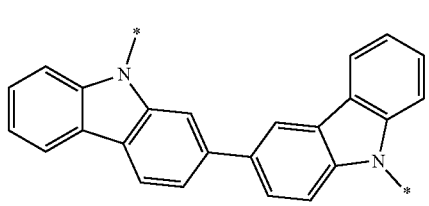

C-7

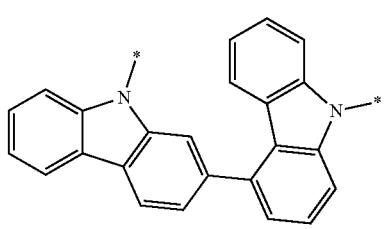

wherein, in Chemical Formulae 3 and 4, $Y^3$ and $Y^4$ are independently a single bond, a substituted or unsubstituted C6 to C30 arylene group, a substituted or unsubstituted C2 to C30 heteroarylene group, or a combination thereof, $Ar^3$ and $Ar^4$ are independently a substituted or unsubstituted C6 to C30 aryl group, a substituted or unsubstituted C2 to C30 heterocyclic group, or a combination thereof, $R^{16}$ to $R^{19}$ are independently hydrogen, deuterium, a substituted or unsubstituted C1 to C20 alkyl group, a substituted or unsubstituted C6 to C50 aryl group, a substituted or unsubstituted C2 to C50 heterocyclic group, or a combination thereof, two adjacent *'s of Chemical Formula 3 are bound to two adjacent *'s of Chemical Formula 4 to provide a fused ring and *'s of not providing the fused ring in Chemical Formula 3 are independently $CR^a$, and $R^a$ is hydrogen, deuterium, a substituted or unsubstituted C1 to C10 alkyl group, a substituted or unsubstituted C6 to C12 aryl group, a substituted or unsubstituted C2 to C12 heterocyclic group, or a combination thereof;

wherein the "substituted" refers to replacement of at least one hydrogen by deuterium, a C1 to C4 alkyl group, a C6 to C18 aryl group, or a C2 to C18 heteroaryl group.

In an example embodiment, $Y^1$ and $Y^2$ of Chemical Formula 2 may independently be a single bond, or a substituted or unsubstituted C6 to C18 arylene group.

In an example embodiment, $Ar^1$ and $Ar^2$ of Chemical Formula 2 may independently be a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted triphenylenyl group, a substituted or unsubstituted pyridinyl group, a substituted or unsubstituted pyrimidinyl group, a substituted or unsubstituted quinazolyl group, a substituted or unsubstituted isoquinazolyl group, a substituted or unsubstituted dibenzothiophenyl group, a substituted or unsubstituted dibenzofuranyl group, a substituted or unsubstituted carbazolyl group, a substituted or unsubstituted fluorenyl group, or a combination thereof.

In an example embodiment, $R^{10}$ to $R^{15}$ of Chemical Formula 2 may independently be hydrogen, deuterium, or a substituted or unsubstituted C6 to C12 aryl group.

In an example embodiment, m of Chemical Formula 2 may be 0 or 1.

In a specific example embodiment, Chemical Formula 2 may be one of structures of Group III and *—$Y^1$—$Ar^1$ and *—$Y^2$—$Ar^2$ may be one of substituents of Group IV.

C-8
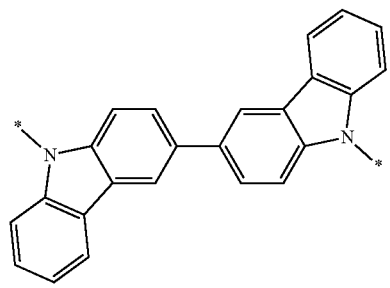
C-9
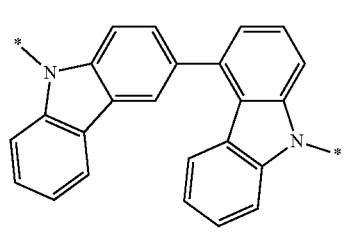
C-10
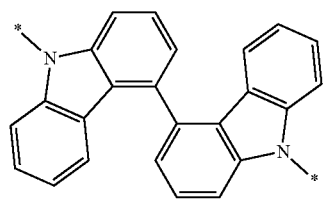
C-11
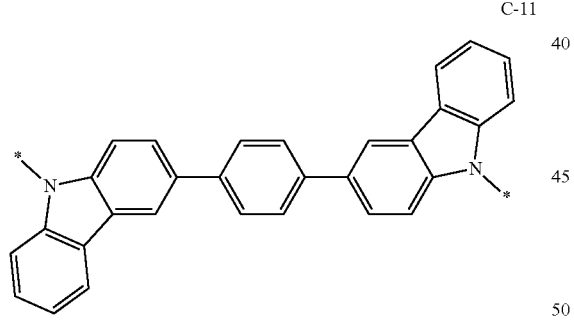
C-12
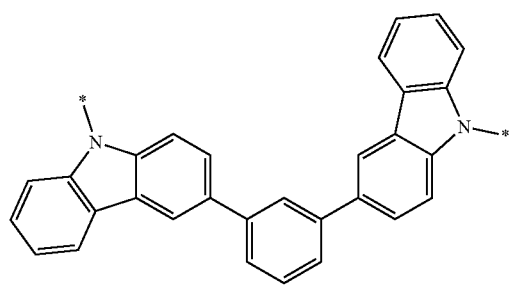
C-13
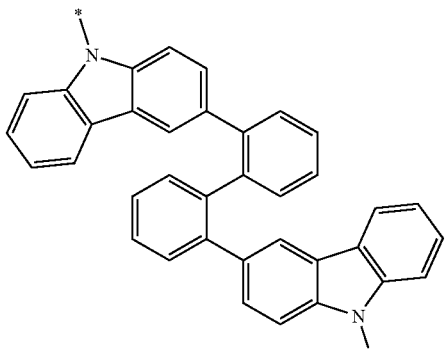
C-14
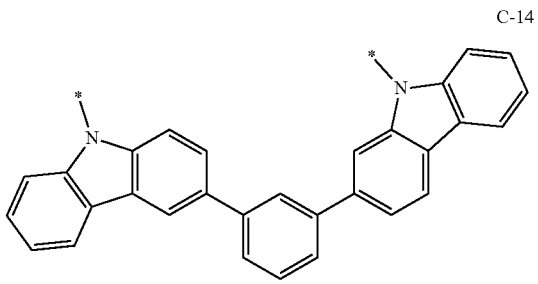
C-15
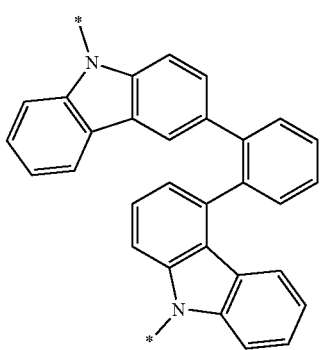
C-16
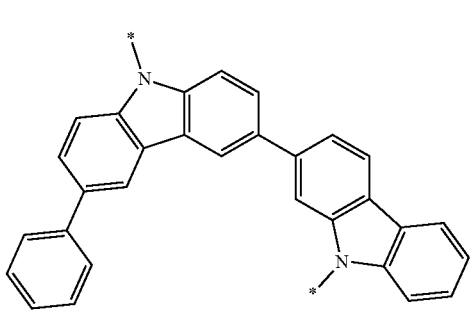
C-17
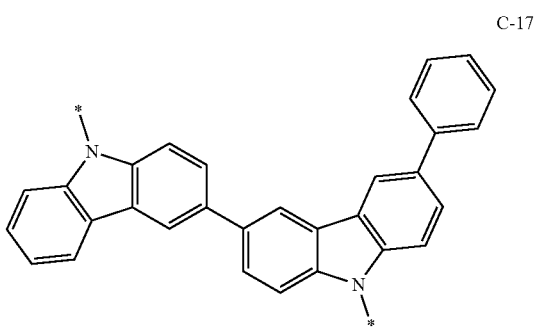

C-18
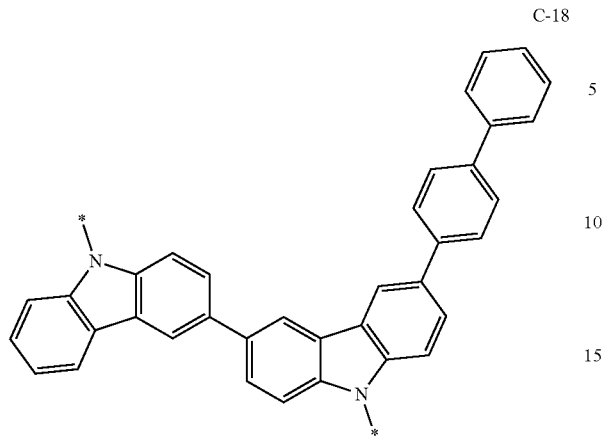
[Group IV]
B-1
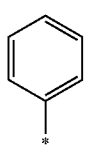
B-2
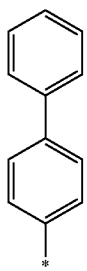
B-3
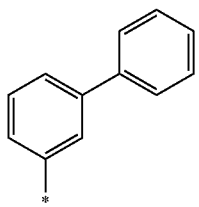
B-4
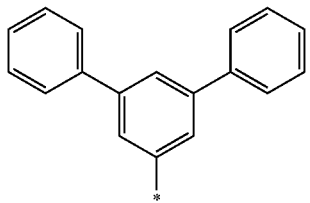
B-5
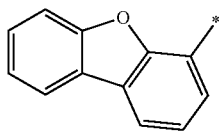
B-6
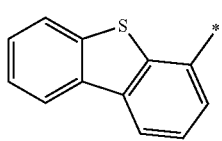
B-7
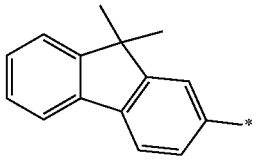
B-8
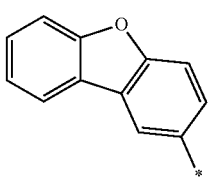
B-9
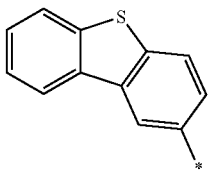
B-10
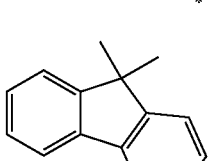
B-11
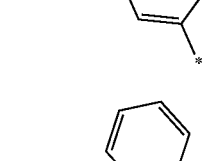
B-12
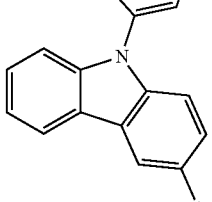
B-13
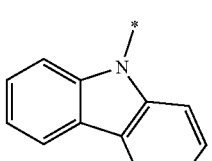
B-13
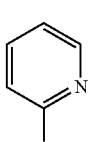
B-14
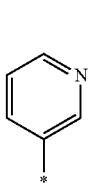

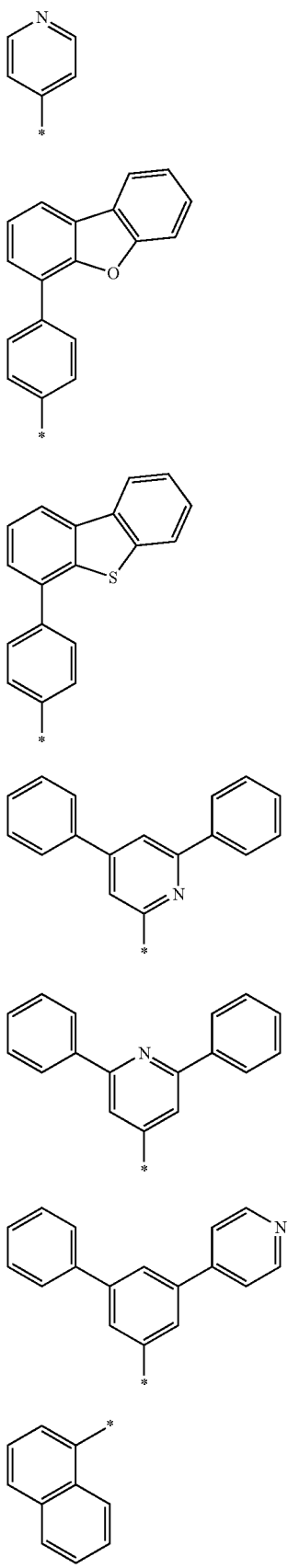

In Group III and Group IV, * is a linking point.

Specifically, Chemical Formula 2 may be represented by C-8 of Group III and *—Y$^1$—Ar$^1$ and *—Y$^2$—Ar$^2$ may be represented by one of B-1 to B-4 of Group IV.

More specifically, *—Y$^1$—Ar$^1$ and *—Y$^2$—Ar$^2$ may be selected from B-2 of Group IV, B-3 of Group IV, and a combination thereof.

The second compound for an organic optoelectric device represented by Chemical Formula 2 may be for example compounds of Group 2, but is not limited thereto.

[Group 2]

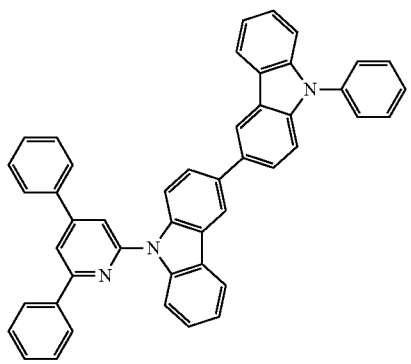

[B-1]

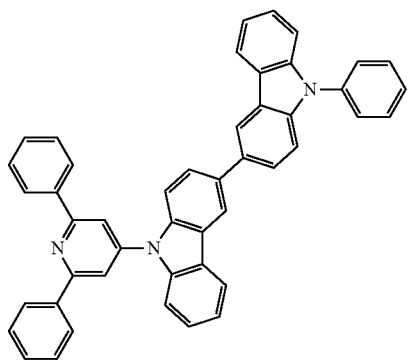

[B-2]

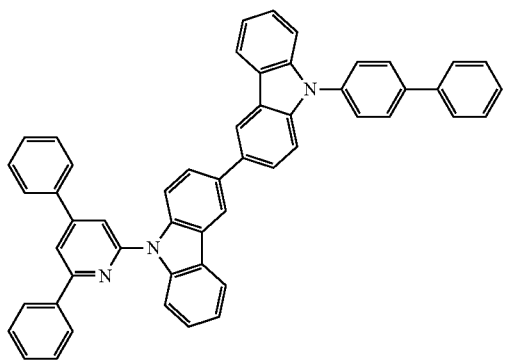

[B-3]

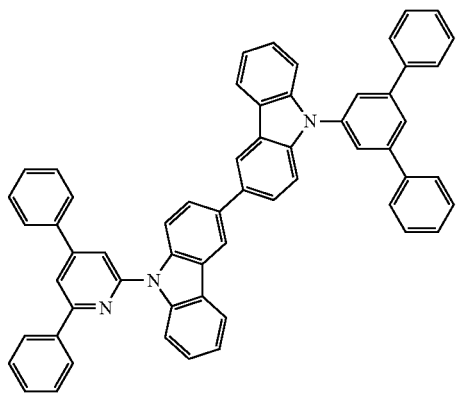

[B-4]

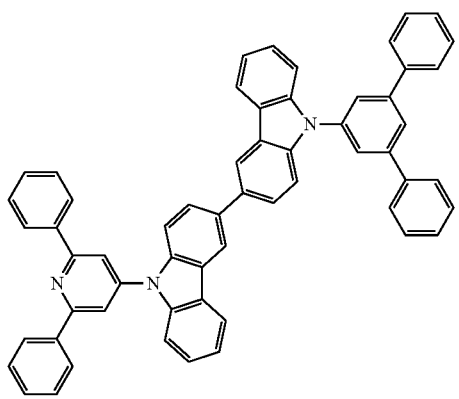

[B-5]

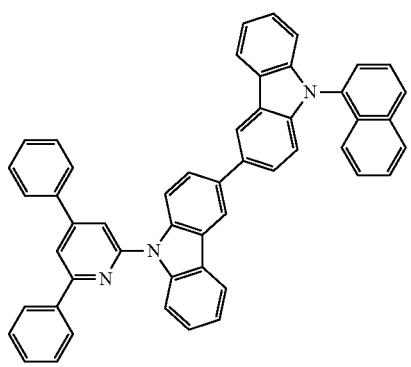

[B-6]

[B-7] 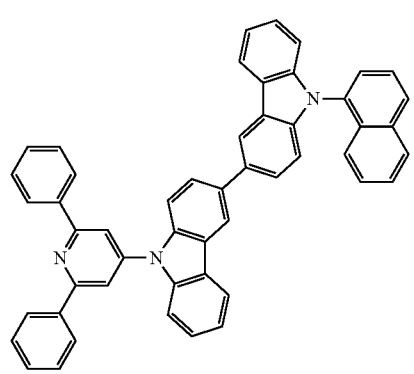
[B-8] 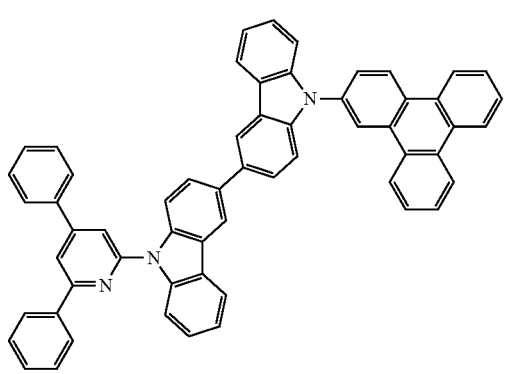
[B-9] 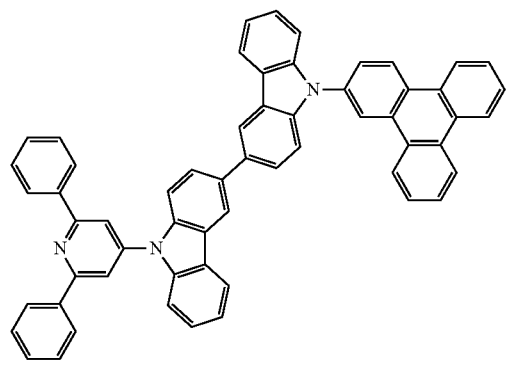
[B-10] 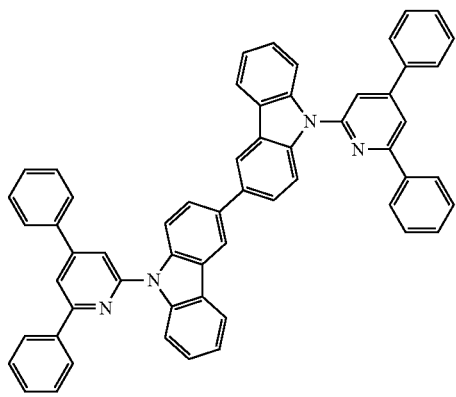
[B-11] 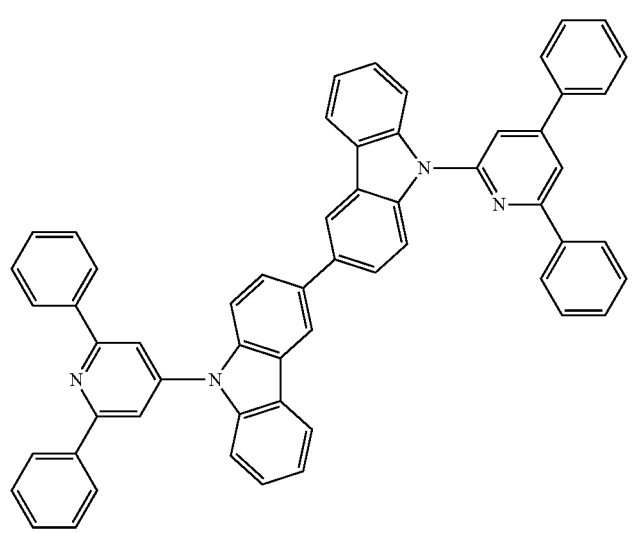

-continued
[B-12]
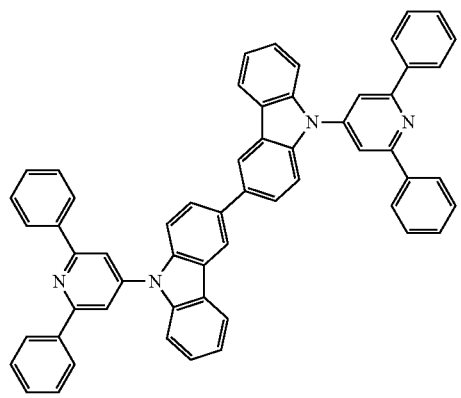
[B-13]
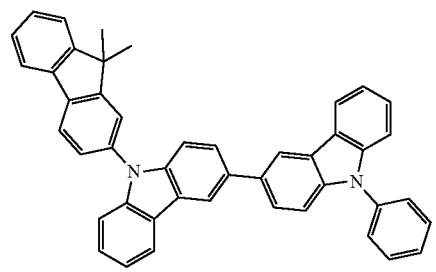
[B-14]
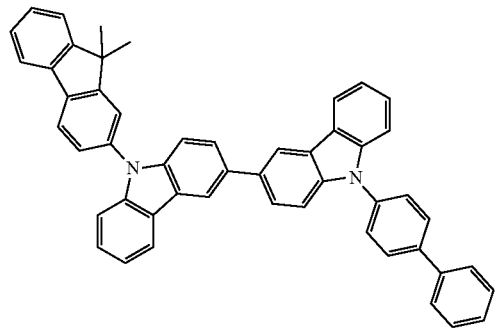
[B-15]
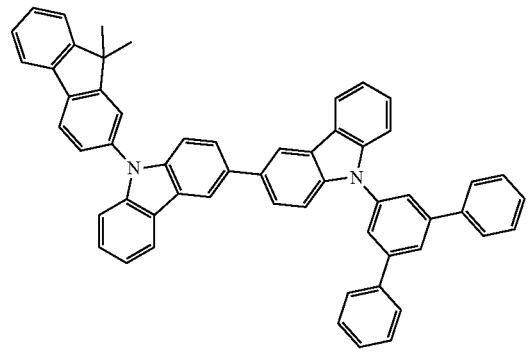
[B-16]
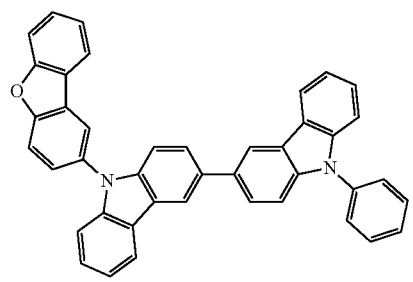
[B-17]
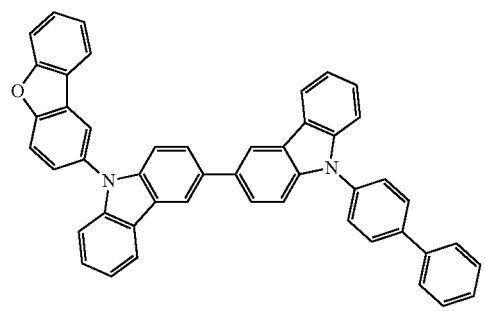
[B-18]
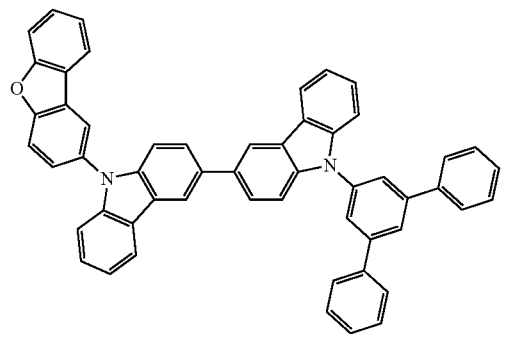
[B-19]
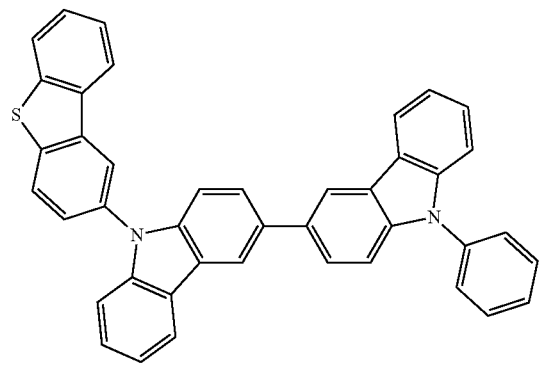

-continued
[B-20]
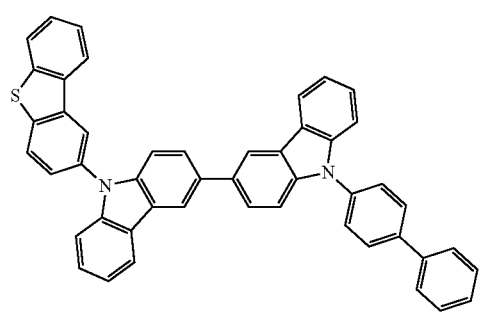
[B-21]
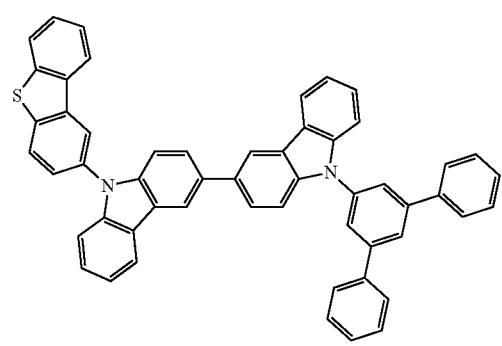
[B-22]
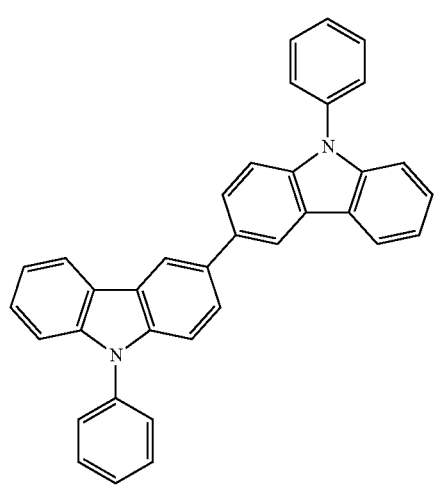
[B-23]
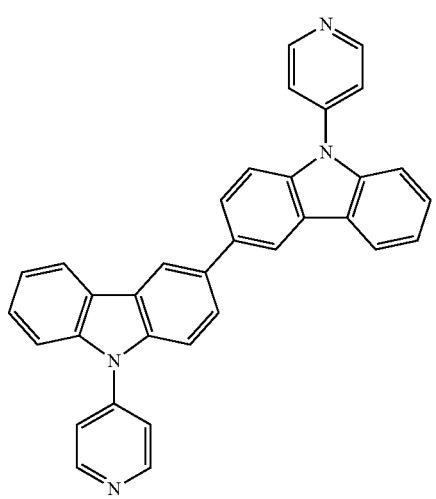
[B-24]
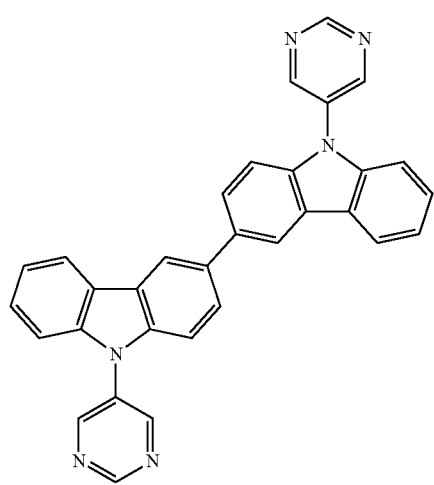
[B-25]
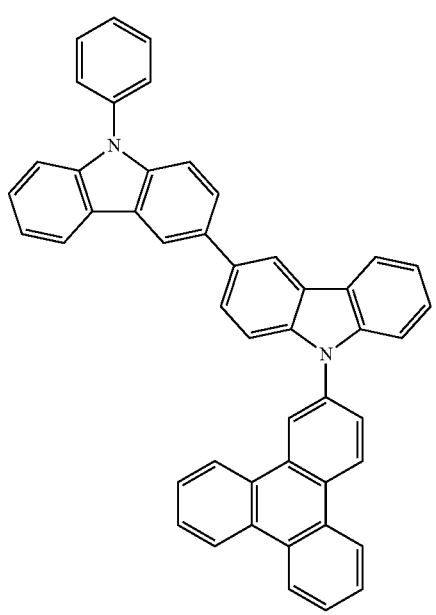

-continued
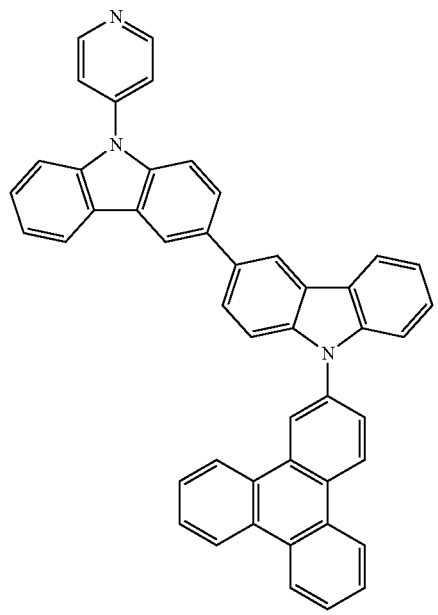
[B-26]
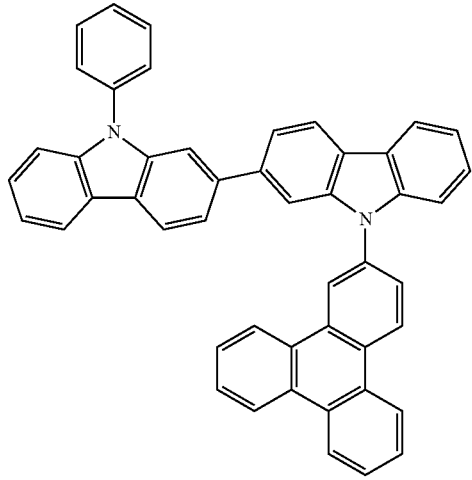
[B-27]
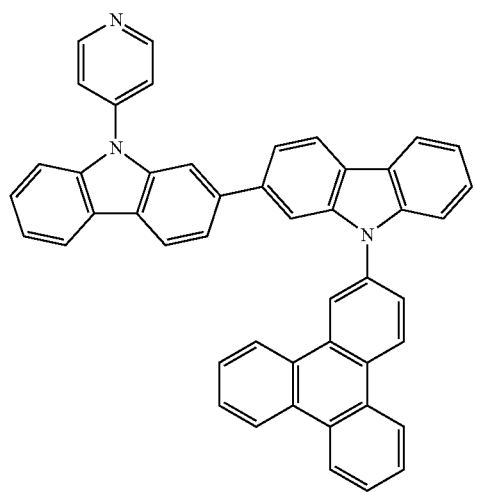
[B-28]
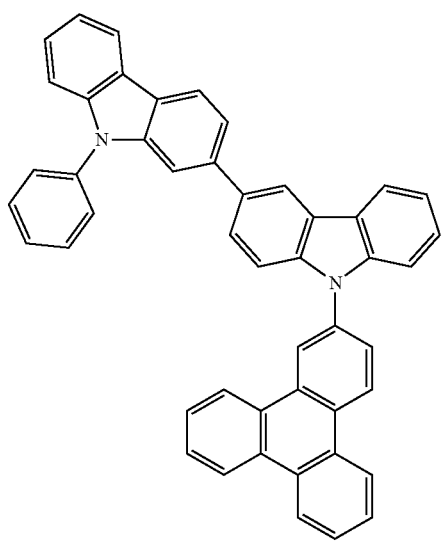
[B-29]

[B-30]
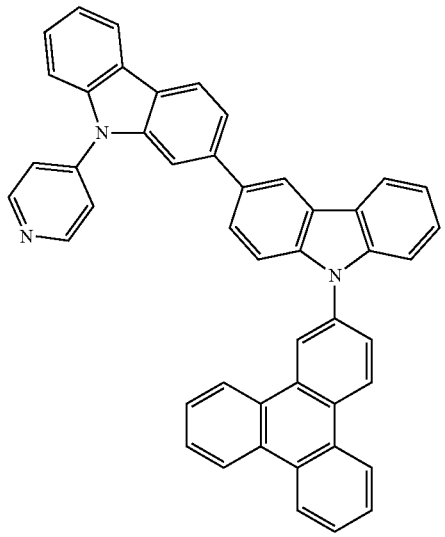
[B-31]
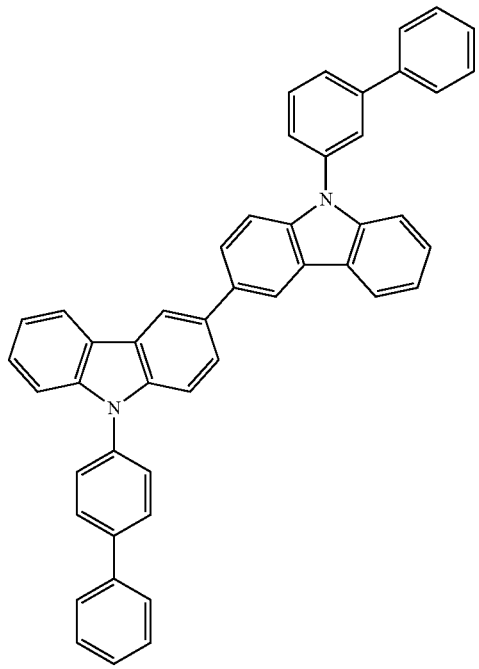
[B-32]
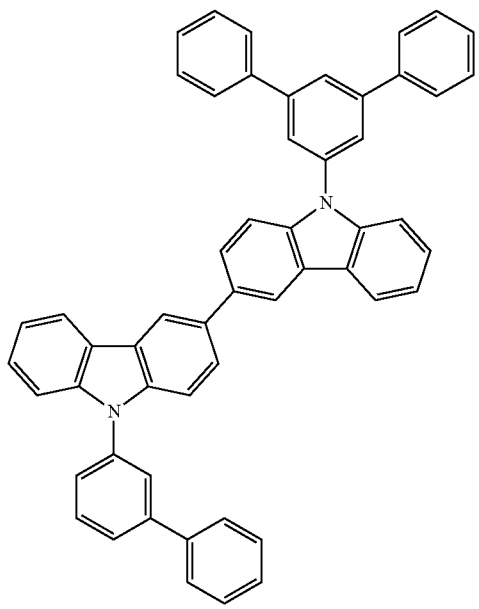
[B-33]
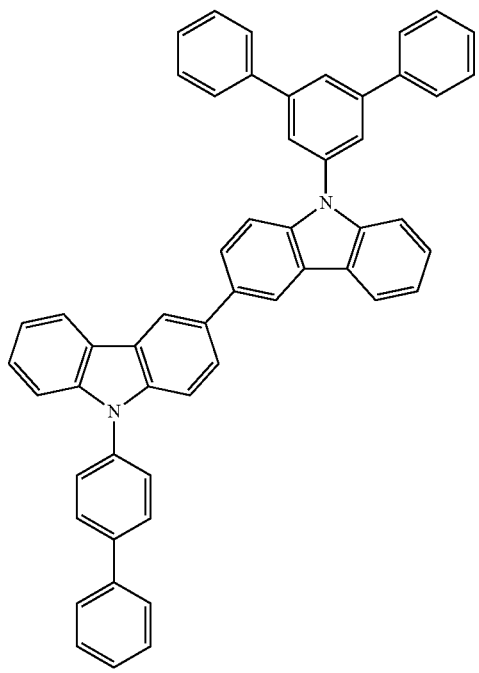

[B-34]
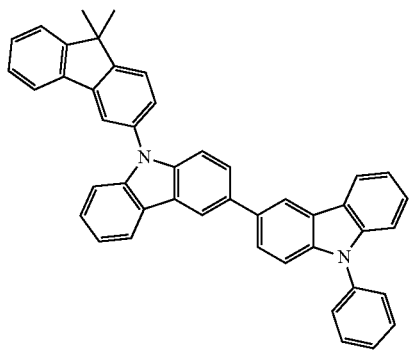
[B-35]
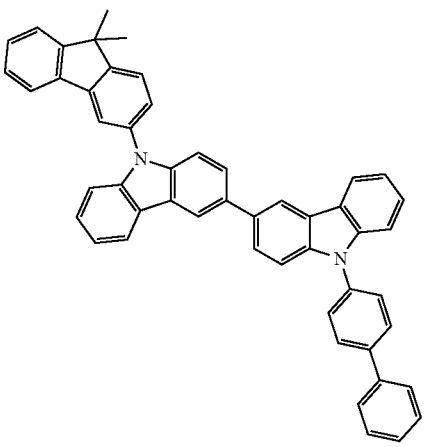
[B-36]
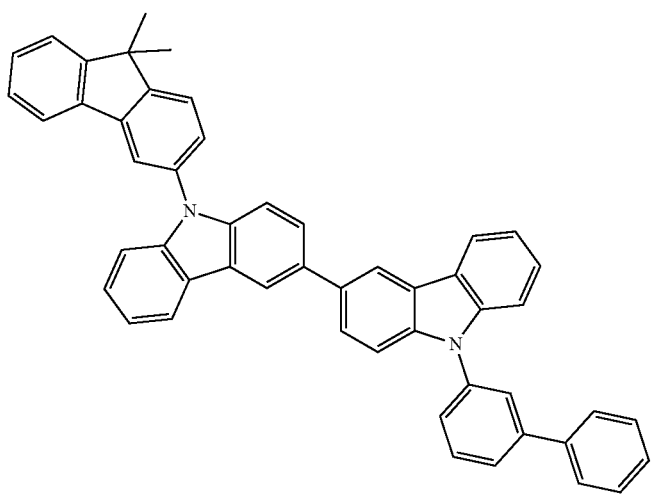
[B-37]
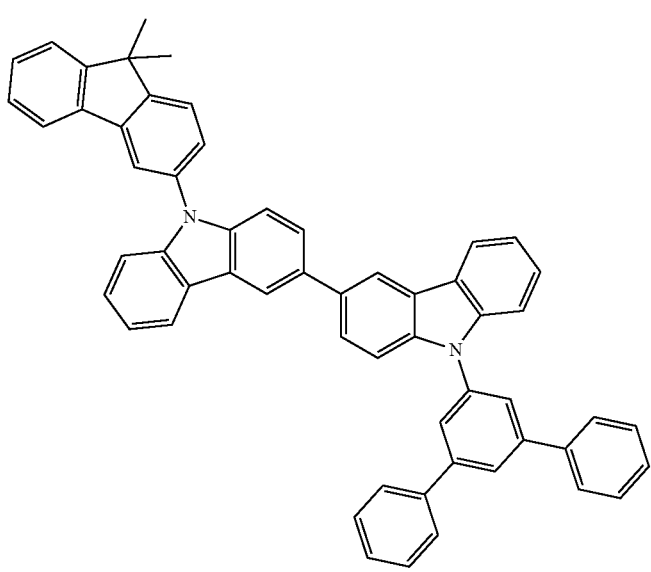

[B-38]
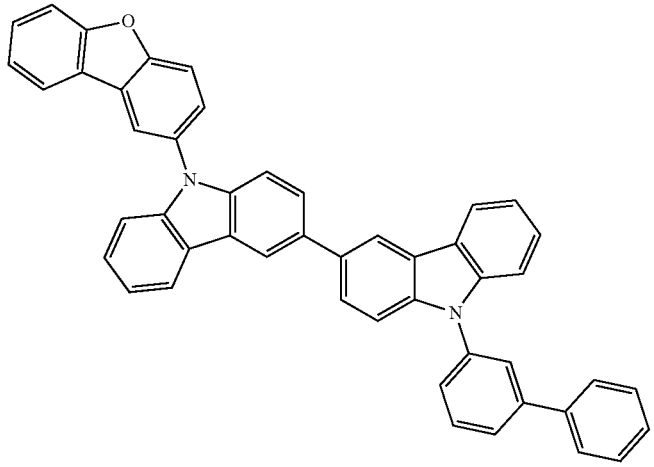
[B-39]
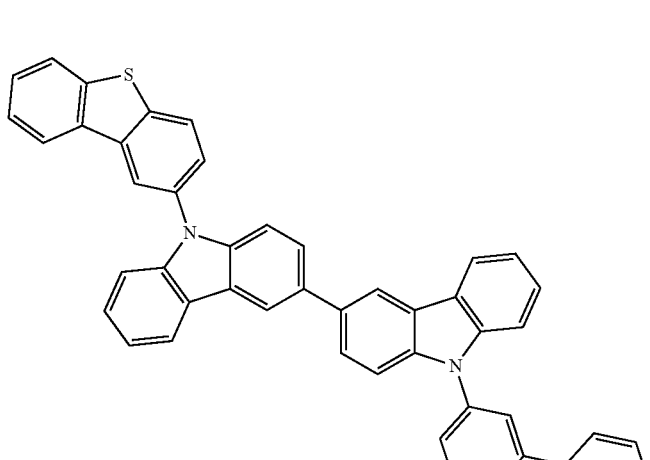
[B-40]
[B-41]

-continued
[B-42]
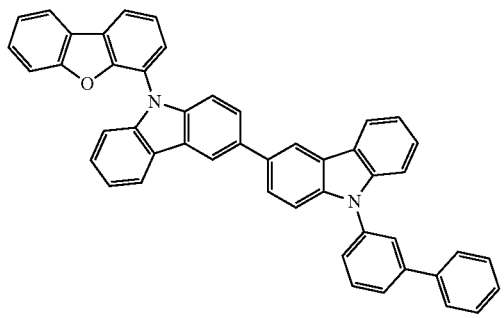
[B-43]
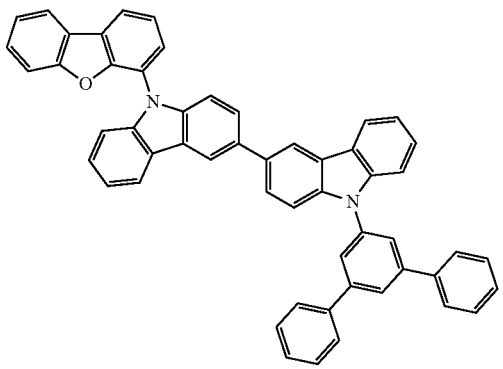
[B-44]
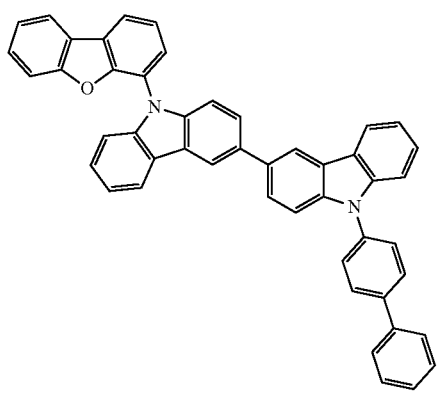
[B-45]
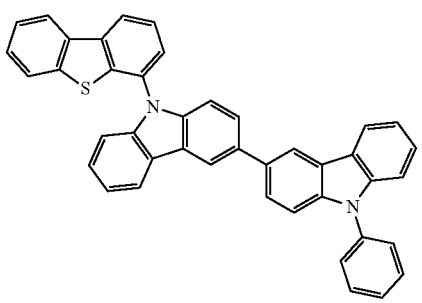
[B-46]
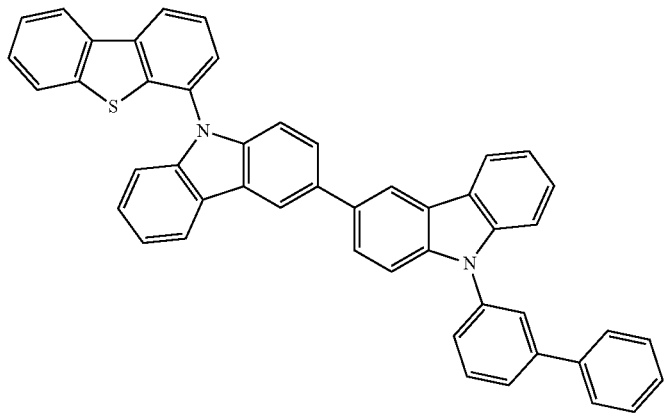
[B-47]
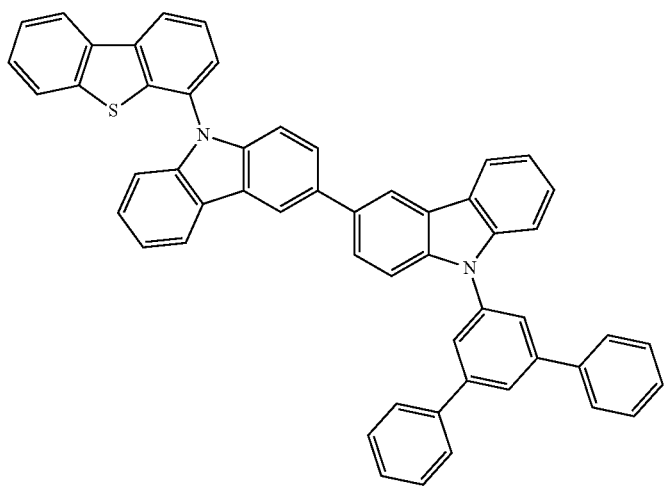

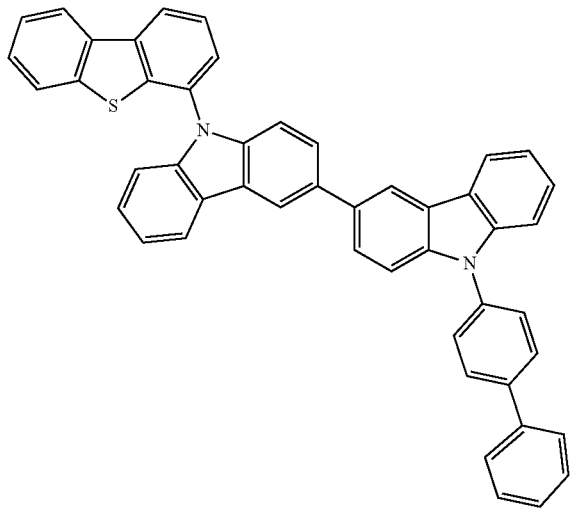
[B-48]
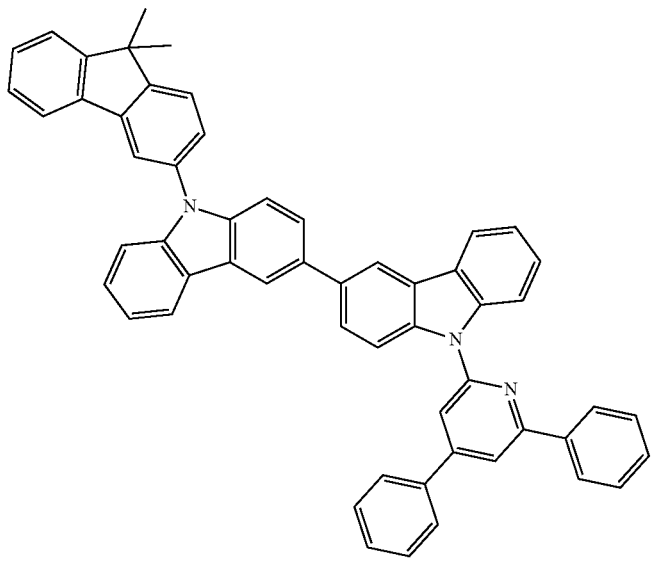
[B-49]
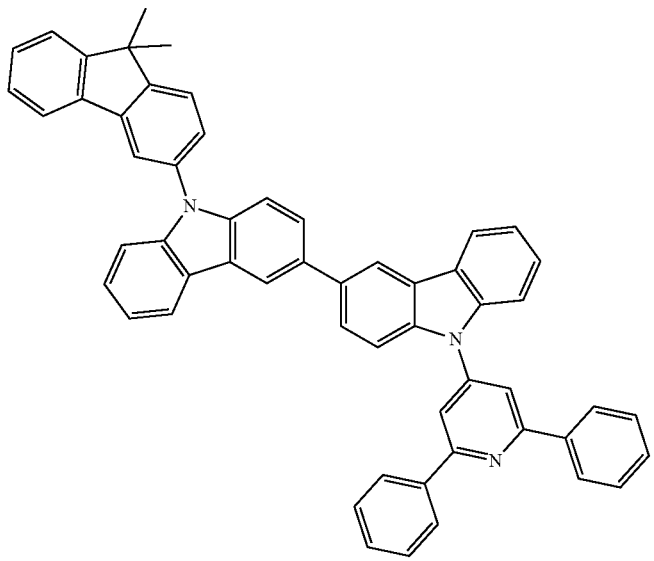
[B-50]

[B-51]
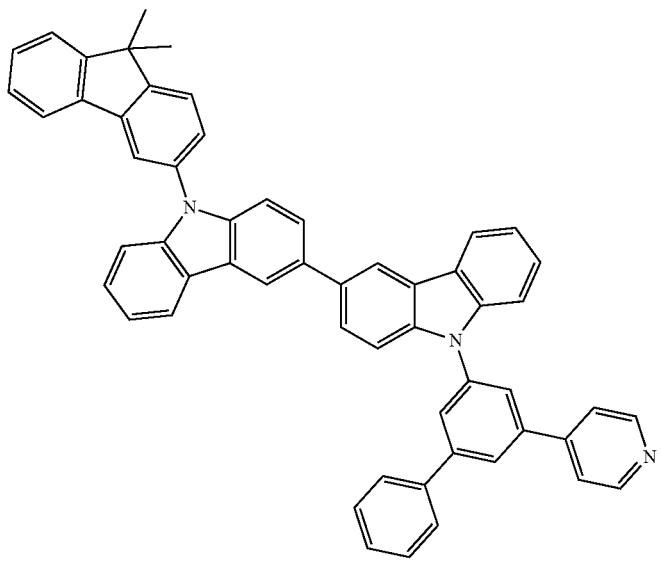
[B-52]
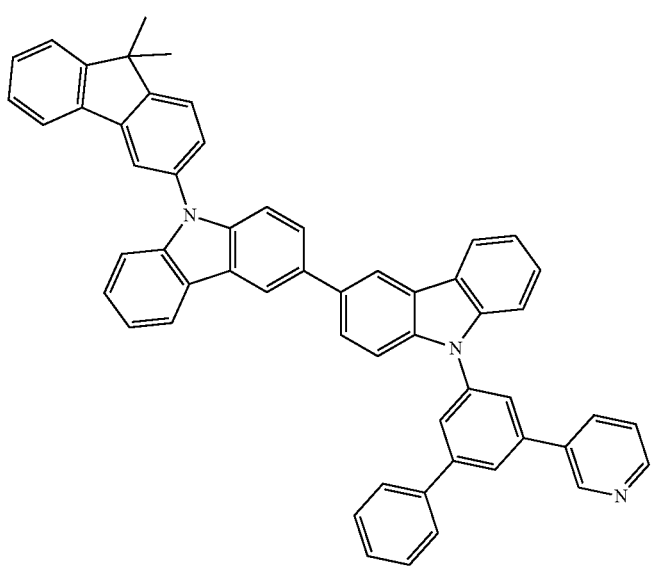
[B-53]
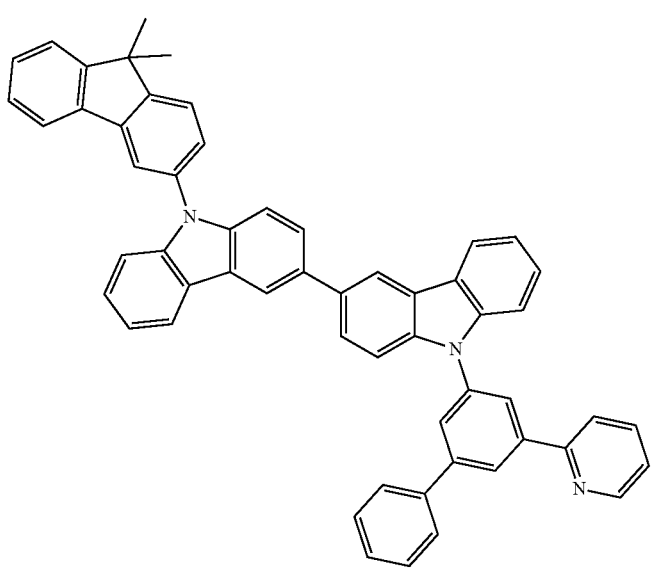

-continued
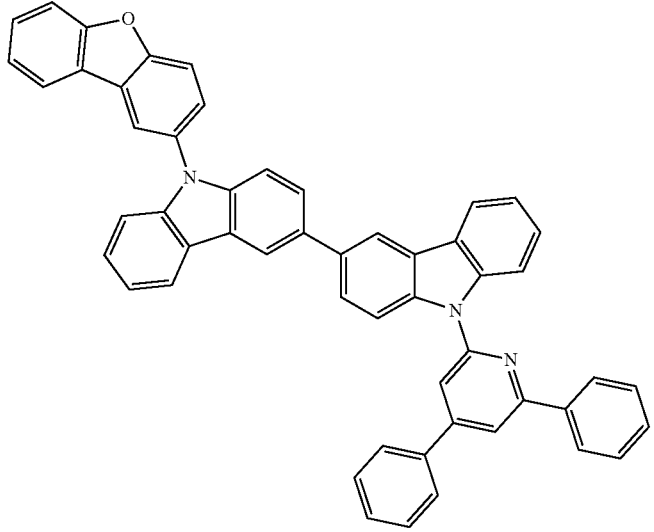
[B-54]
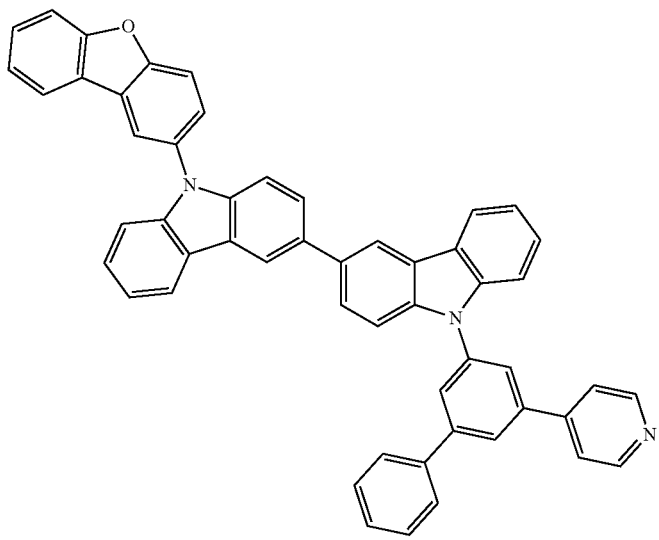
[B-55]
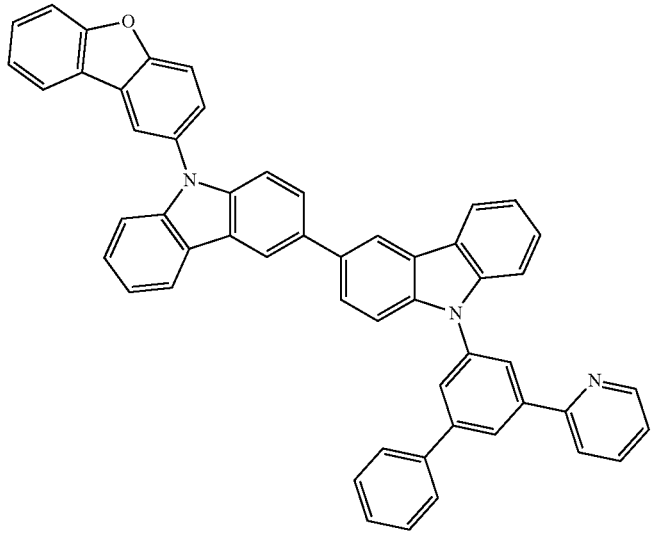
[B-56]

-continued
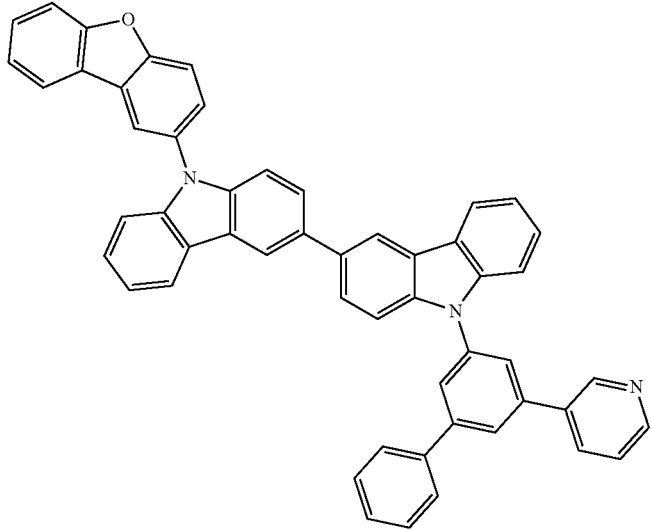
[B-57]
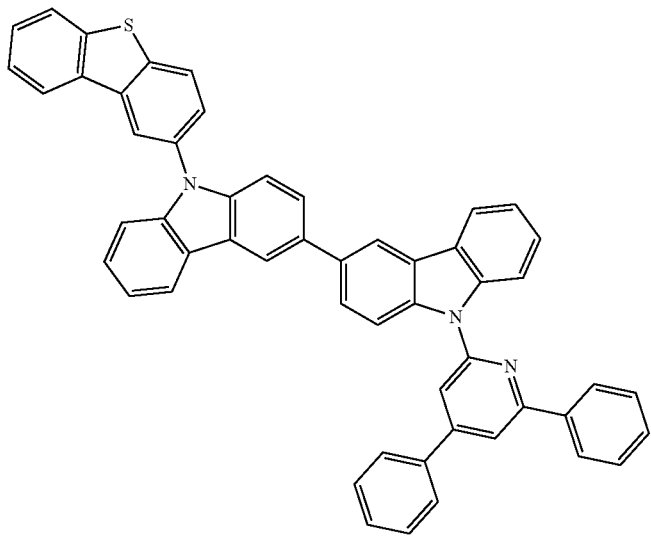
[B-58]
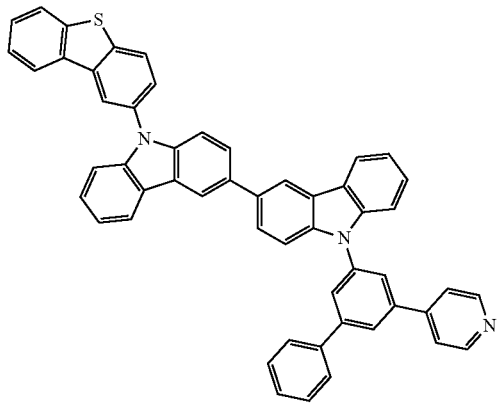
[B-59]
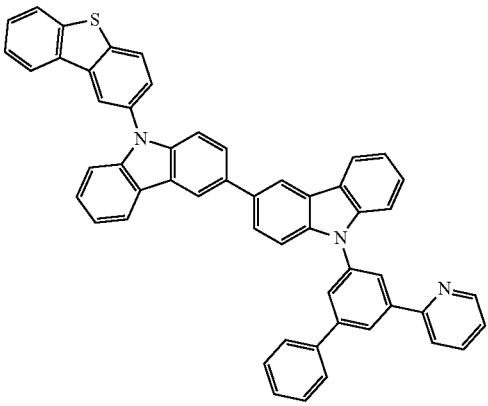
[B-60]

-continued
[B-61]
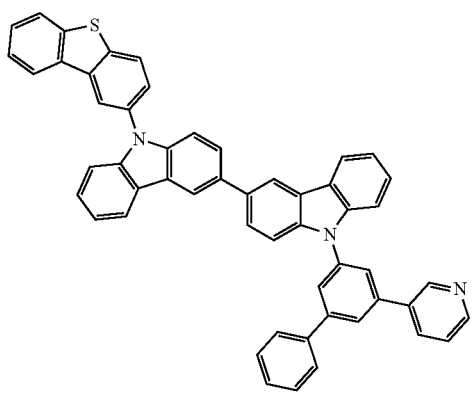
[B-62]
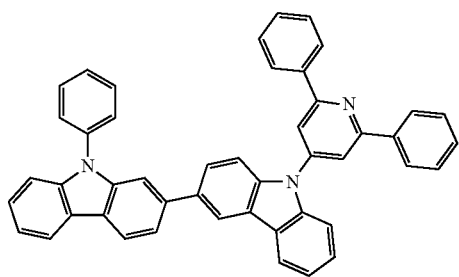
[B-63]
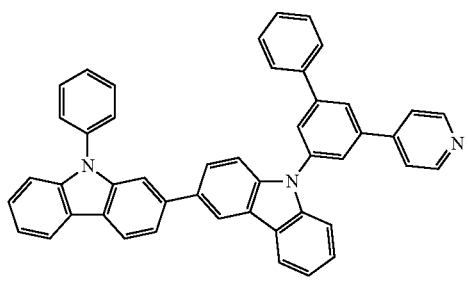
[B-64]
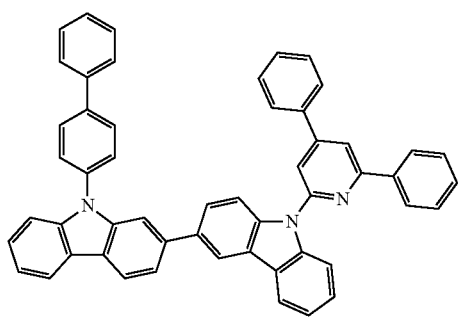
[B-65]
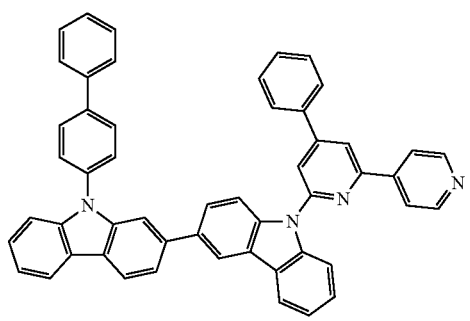
[B-66]
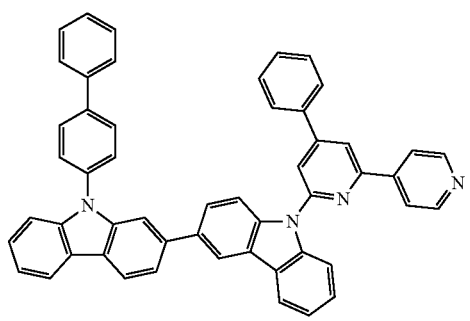
[B-67]
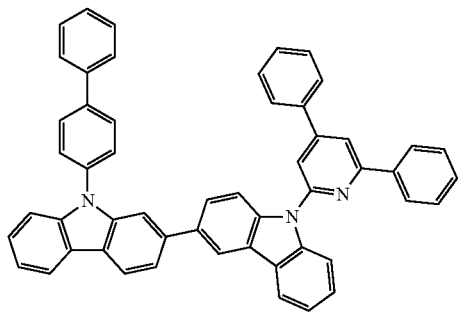
[B-68]
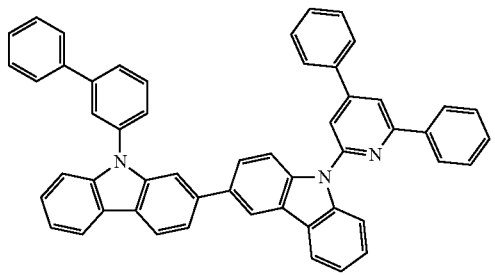
[B-69]
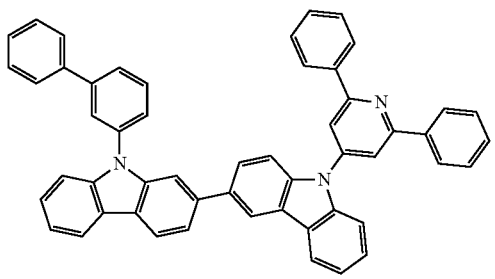
[B-70]
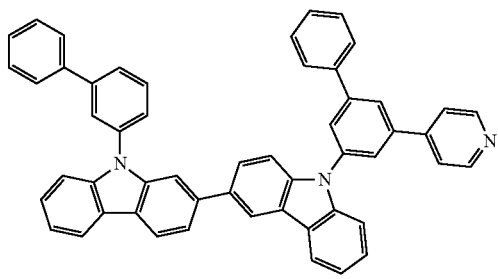

-continued
[B-71]
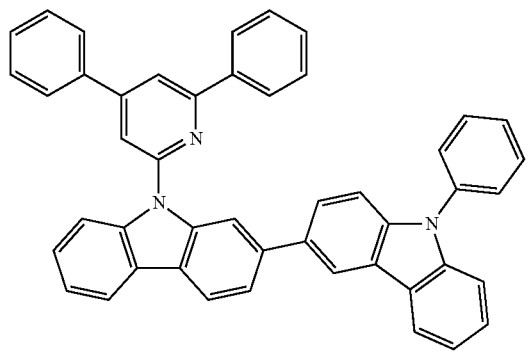
[B-72]
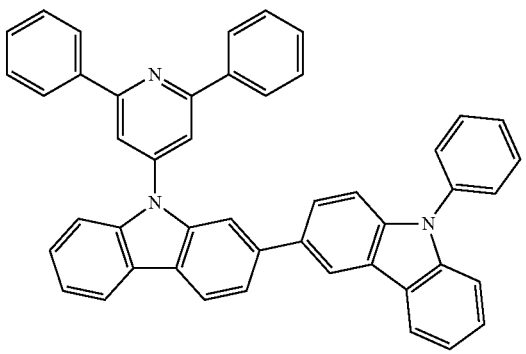
[B-73]
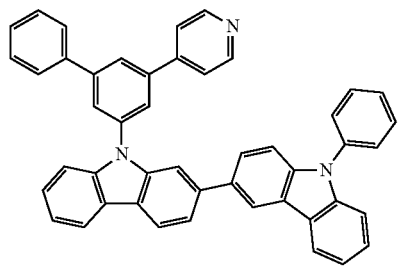
[B-74]
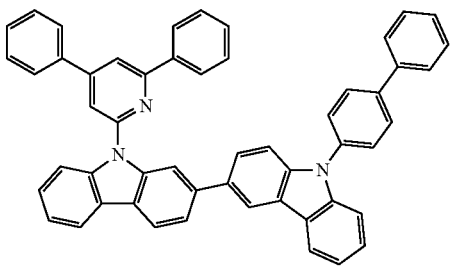
[B-75]
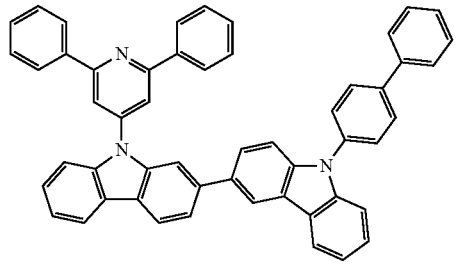
[B-76]
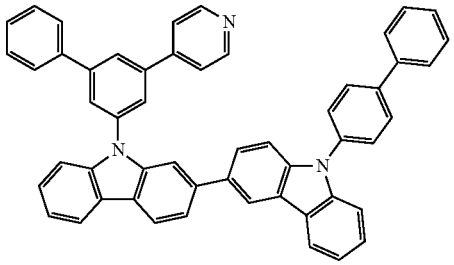
[B-77]
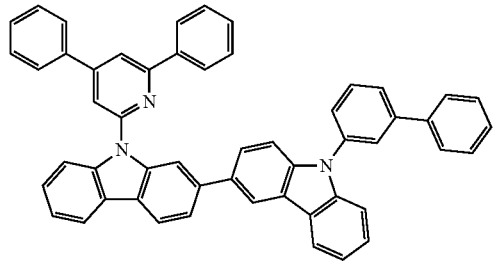
[B-78]
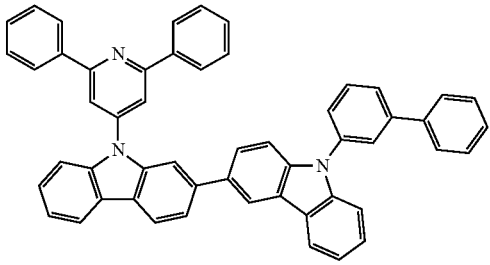
[B-79]
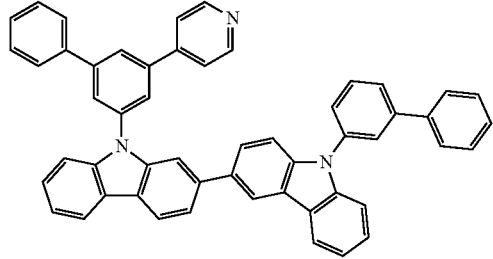
[B-80]
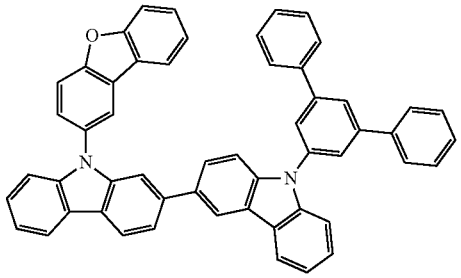

-continued
[B-81]
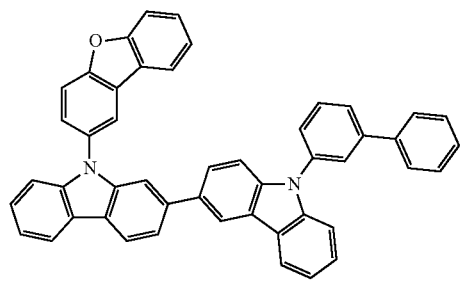
[B-82]
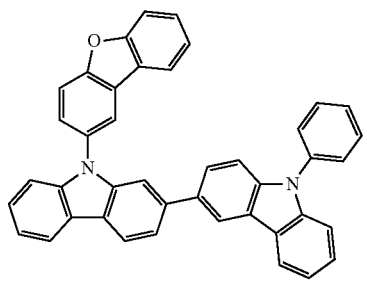
[B-83]
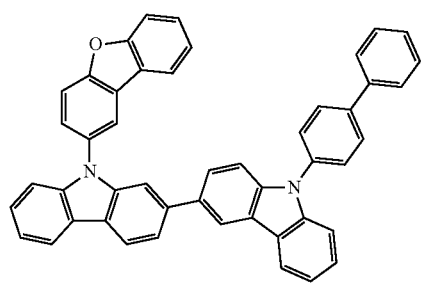
[B-84]
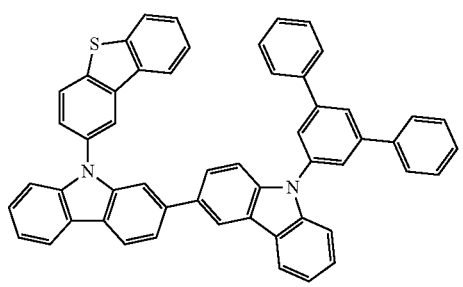
[B-85]
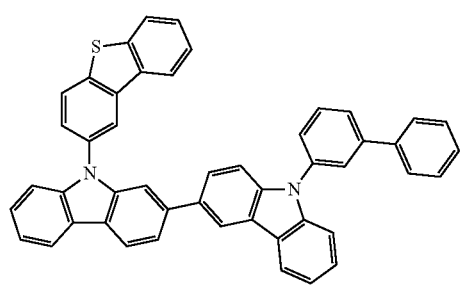
[B-86]
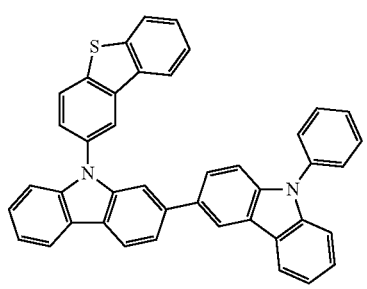
[B-87]
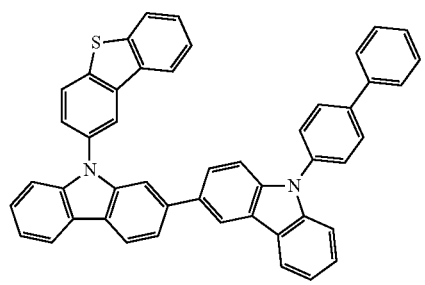
[B-88]
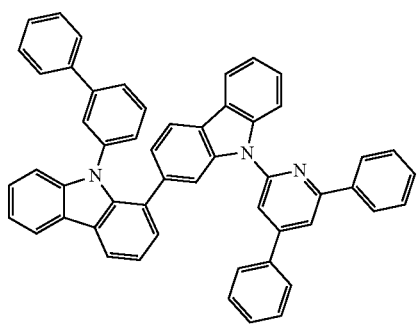
[B-89]
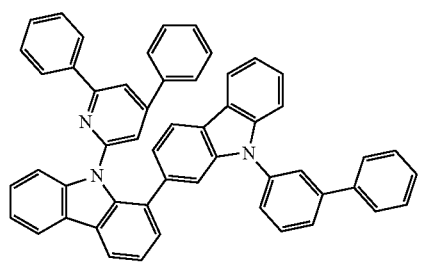
[B-90]
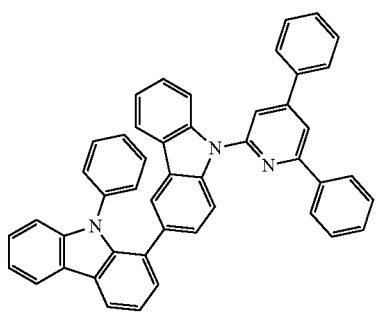

-continued
[B-91]
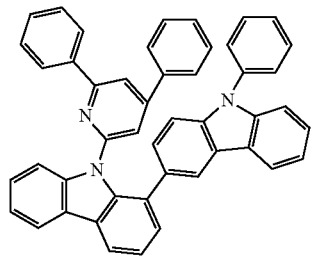
[B-92]
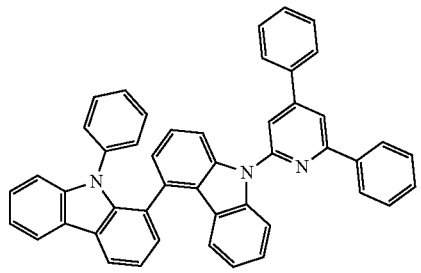
[B-93]
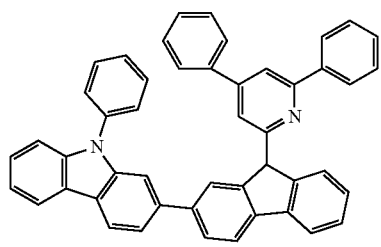
[B-94]
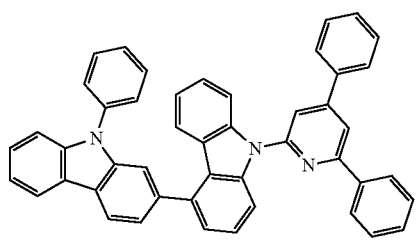
[B-95]
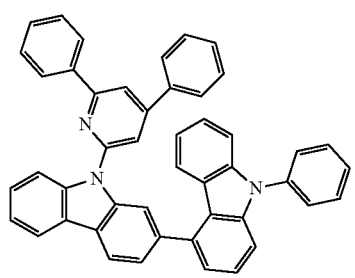
[B-96]
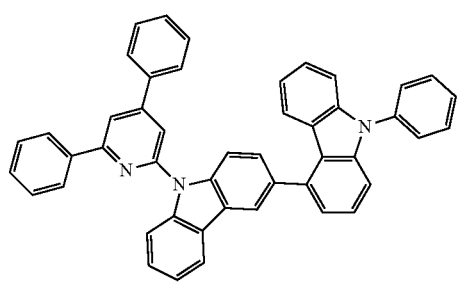
[B-97]
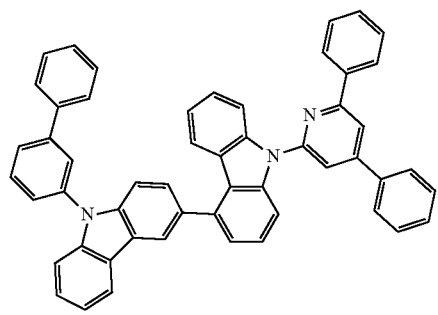
[B-98]
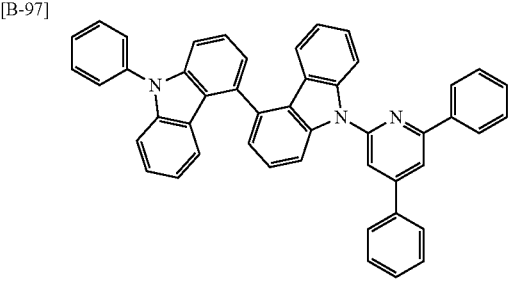

-continued
[B-99]
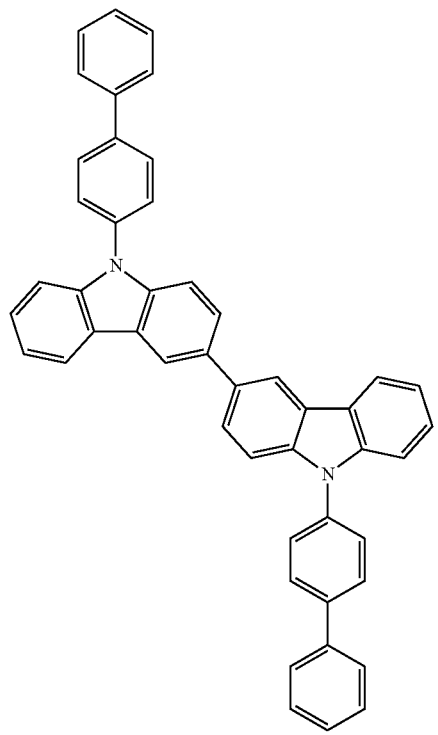
[B-100]
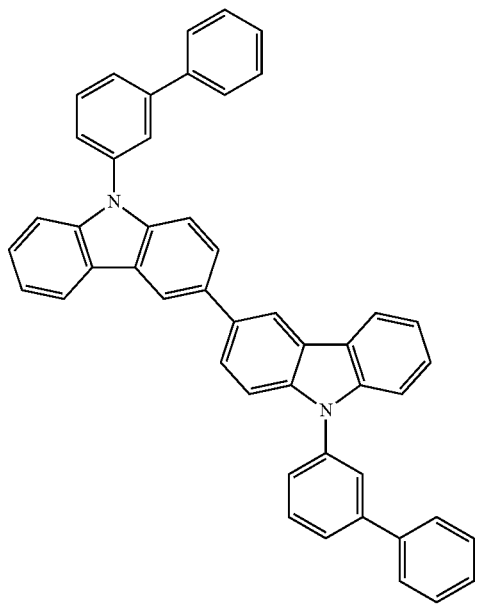
[B-101]
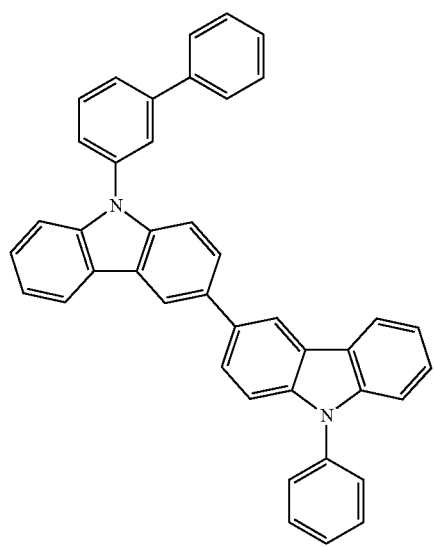
[B-102]
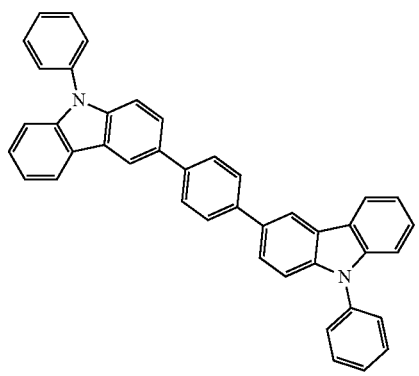

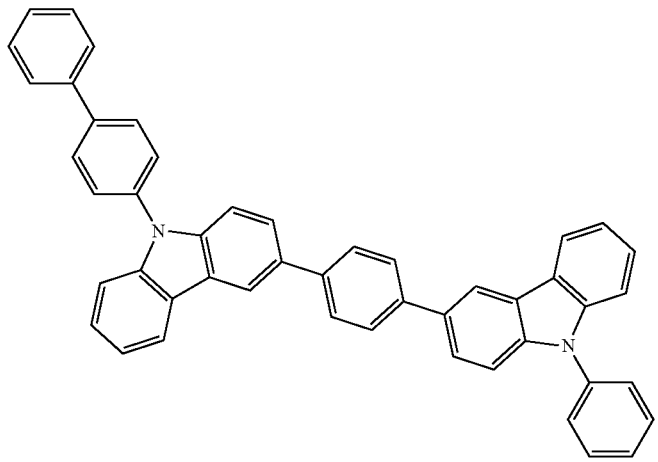
[B-103]
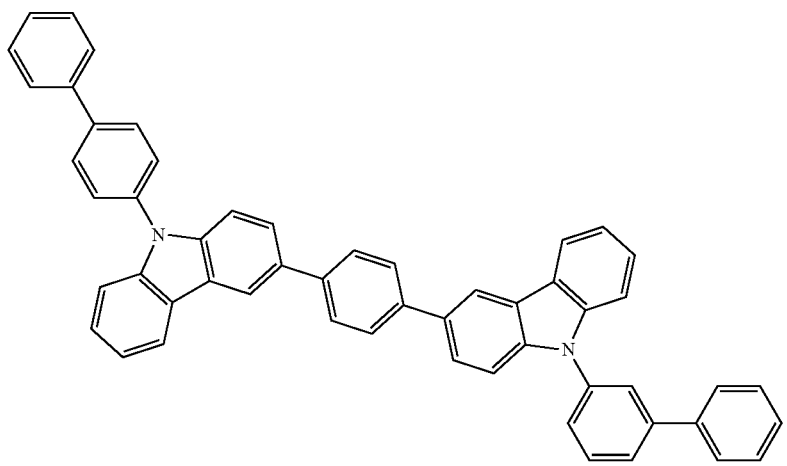
[B-104]
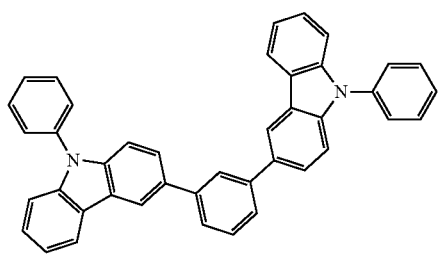
[B-105]
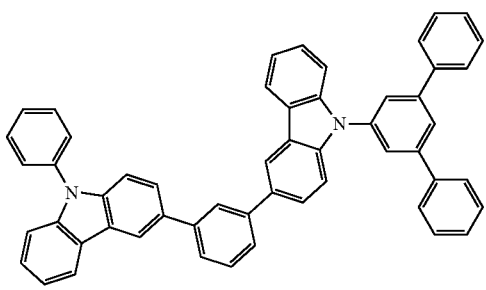
[B-106]
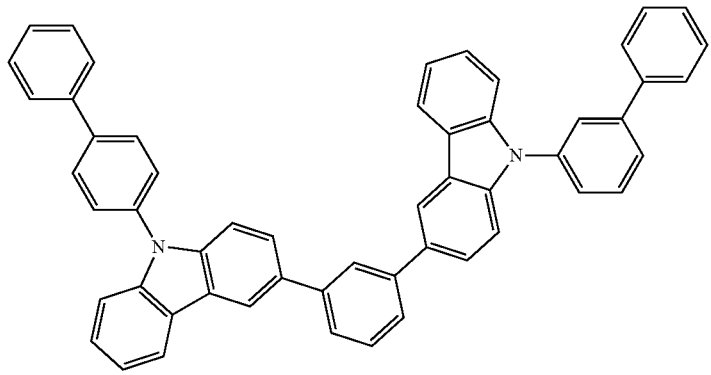
[B-107]

-continued
[B-108]
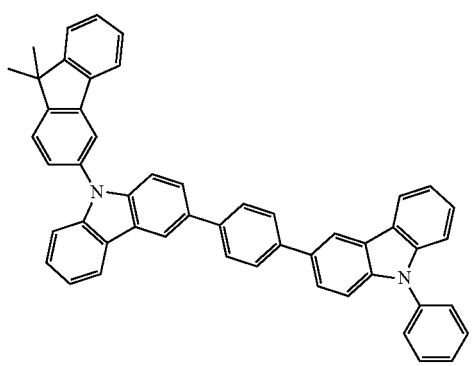
[B-109]
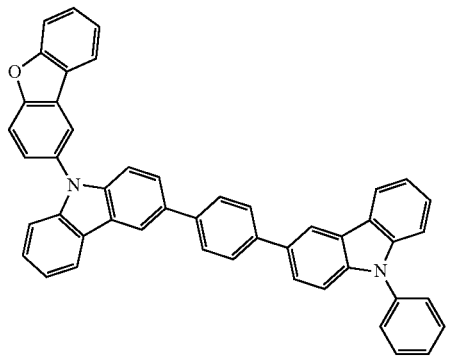
[B-110]
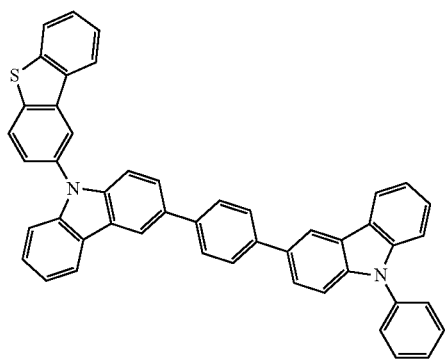
[B-111]
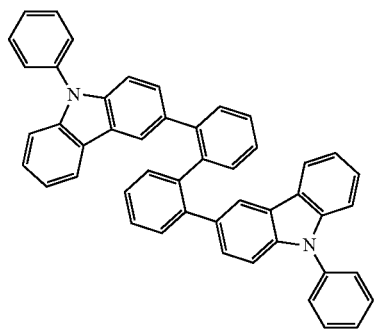
[B-112]
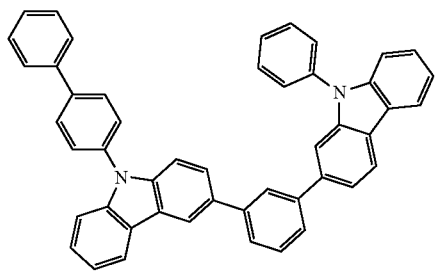
[B-113]
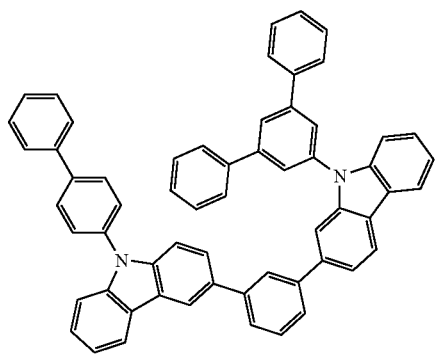
[B-114]
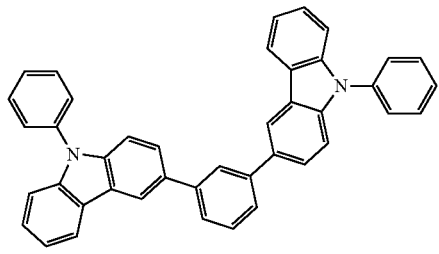
[B-115]
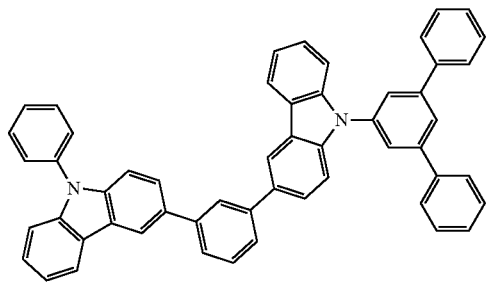

-continued
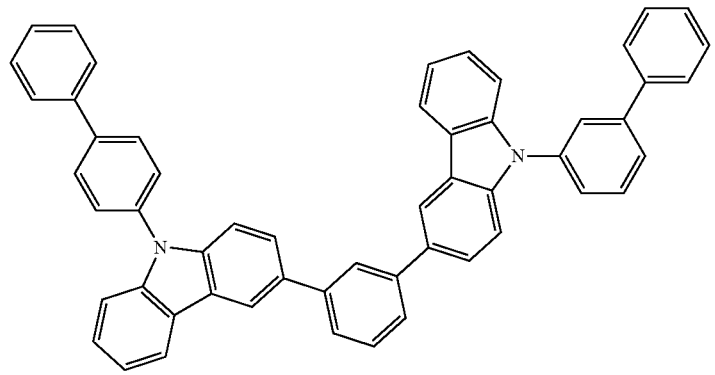
[B-116]
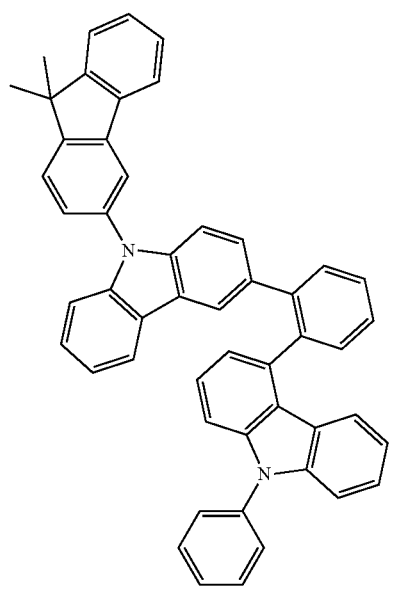
[B-117]
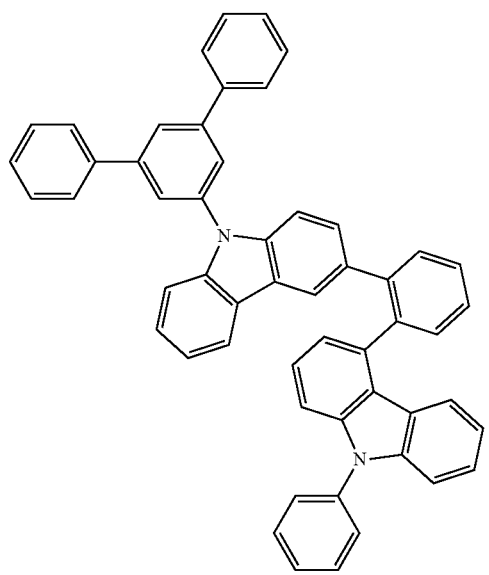
[B-118]
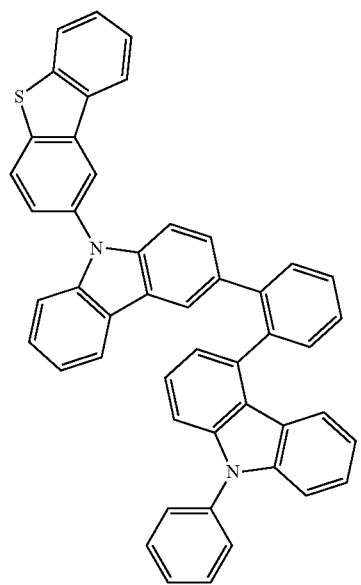
[B-119]
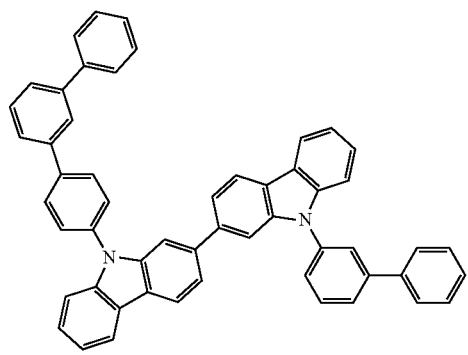
[B-120]

-continued
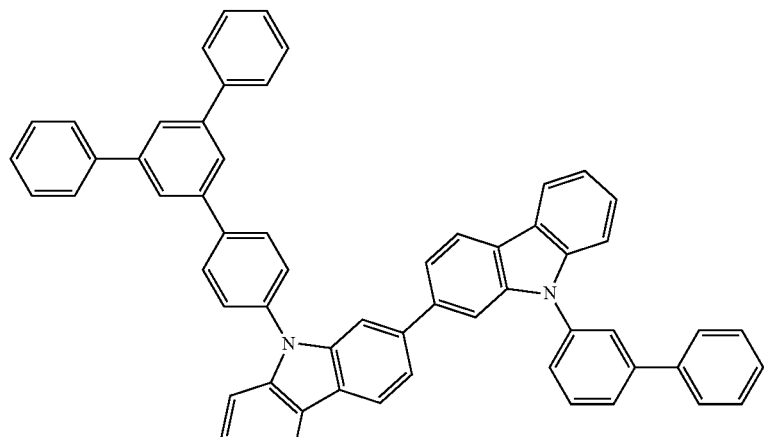
[B-121]
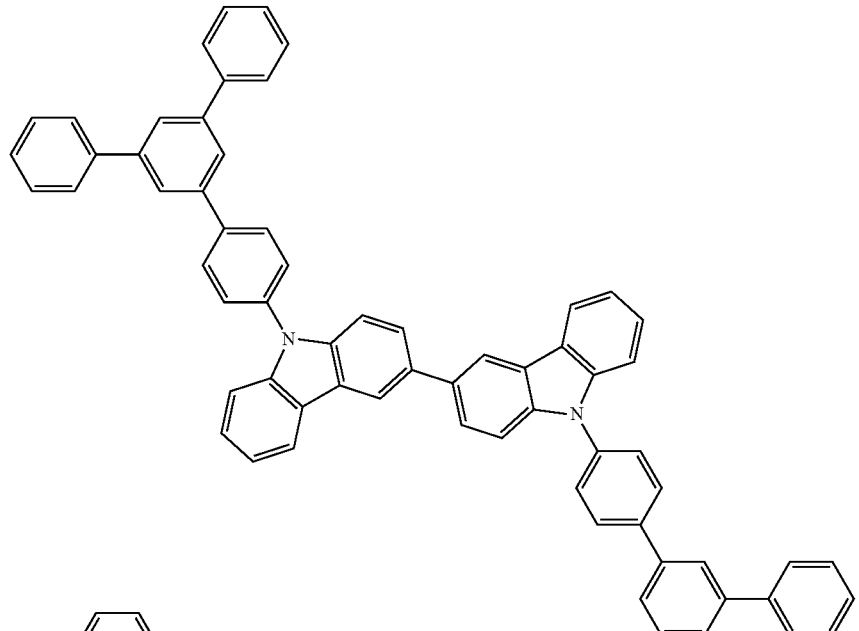
[B-122]
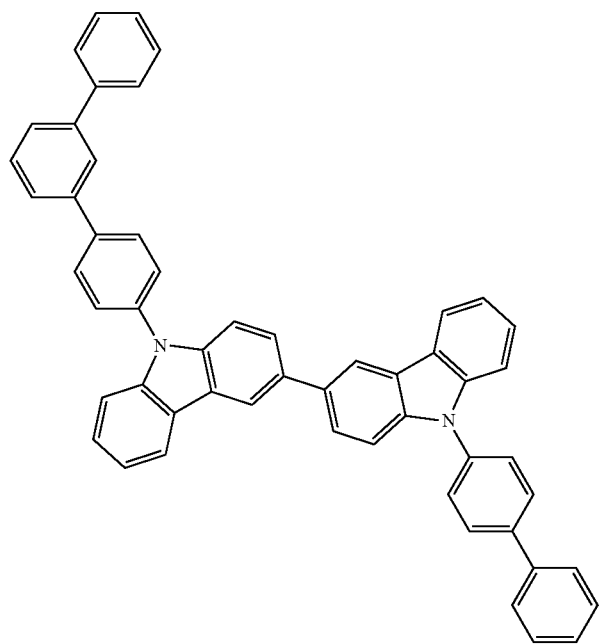
[B-123]

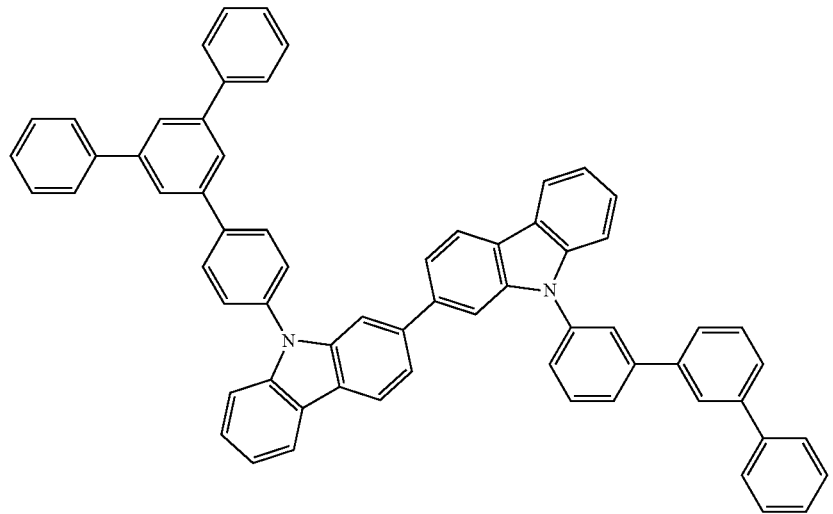
[B-124]
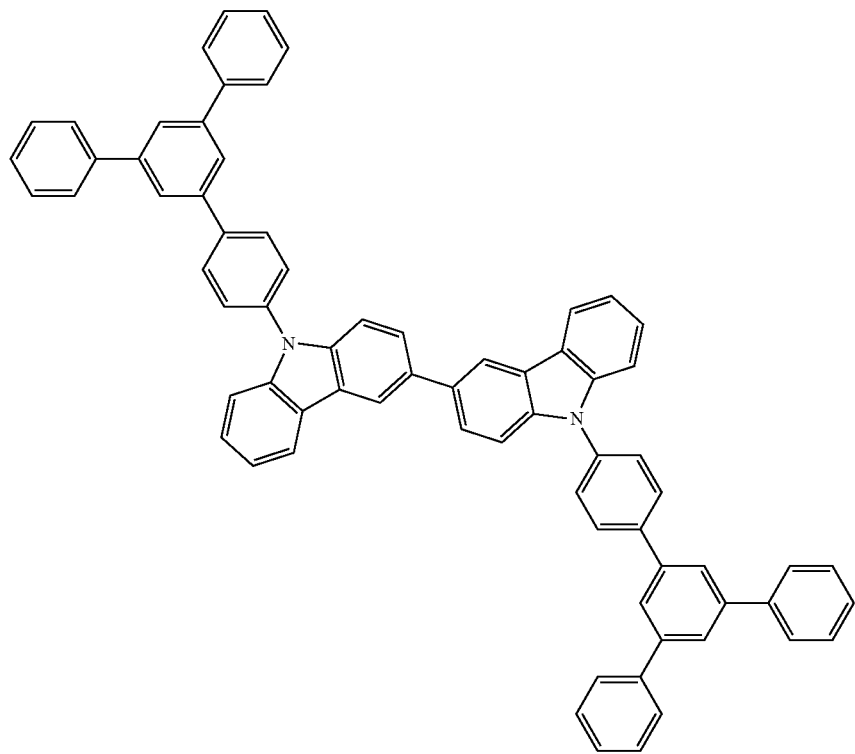
[B-125]

[B-126]
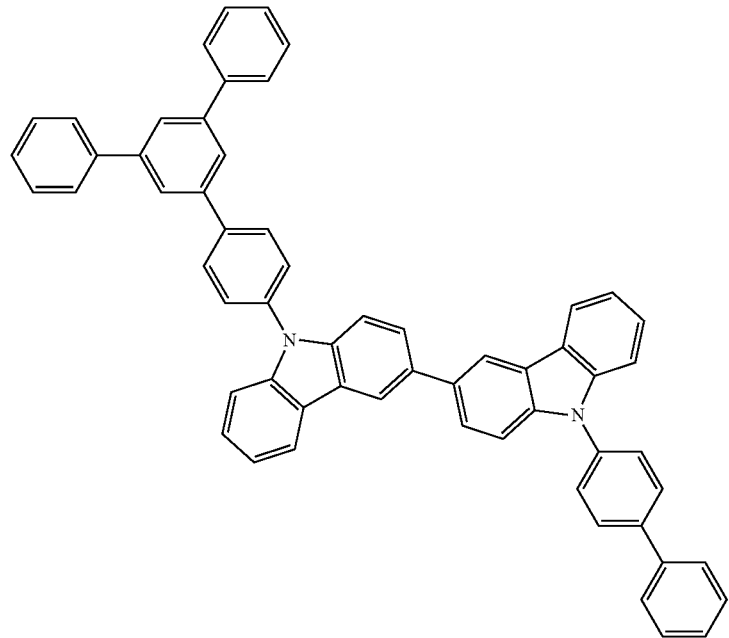
[B-127]
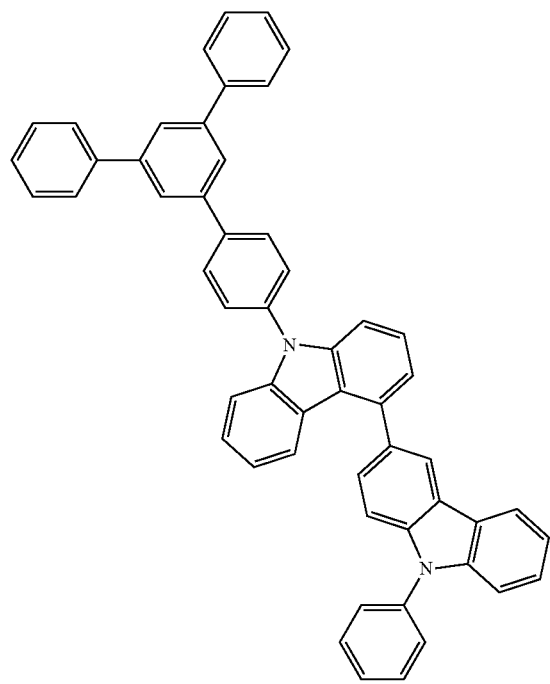
[B-128]
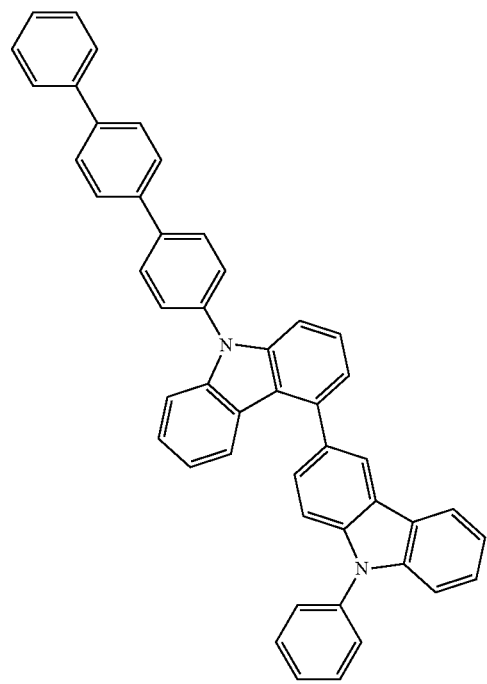

-continued
[B-129]
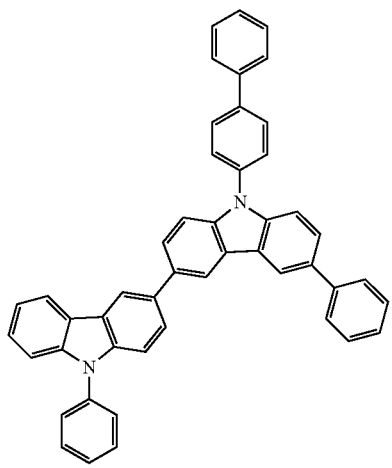
[B-130]
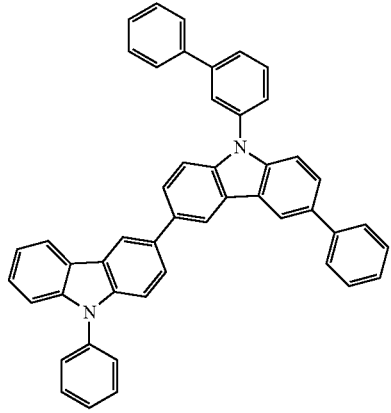
[B-131]
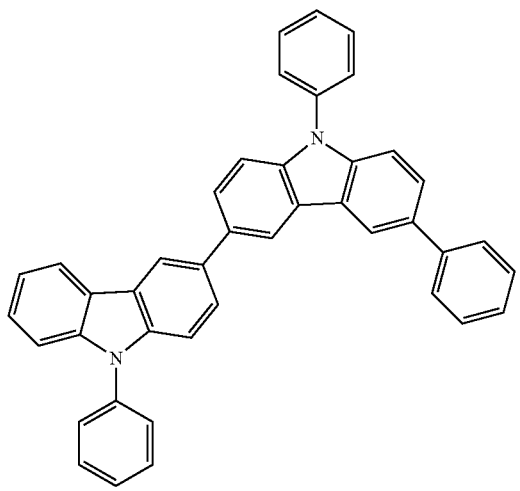
[B-132]
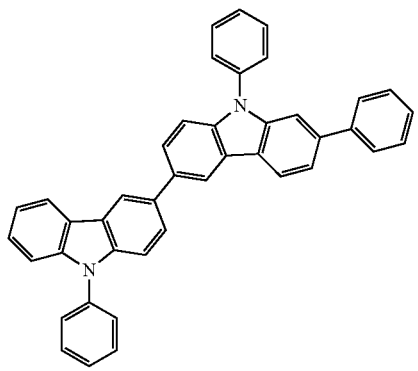
[B-133]
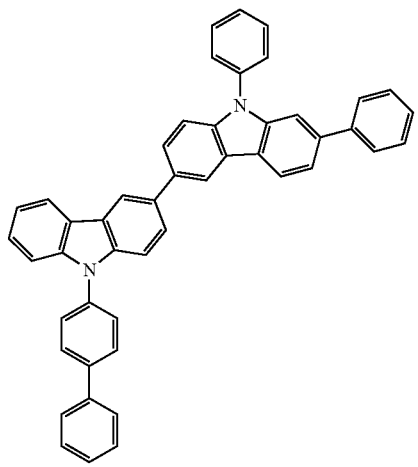

[B-134]
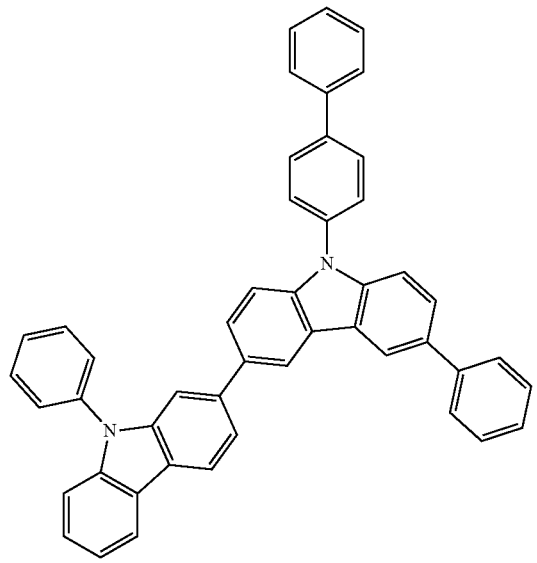
[B-135]
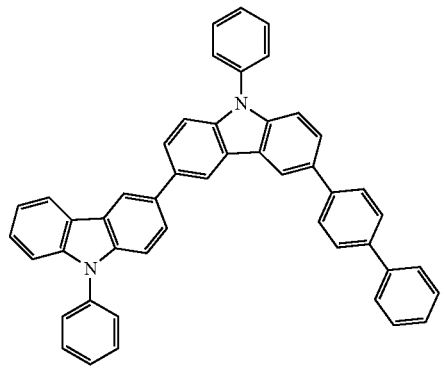
[B-136]
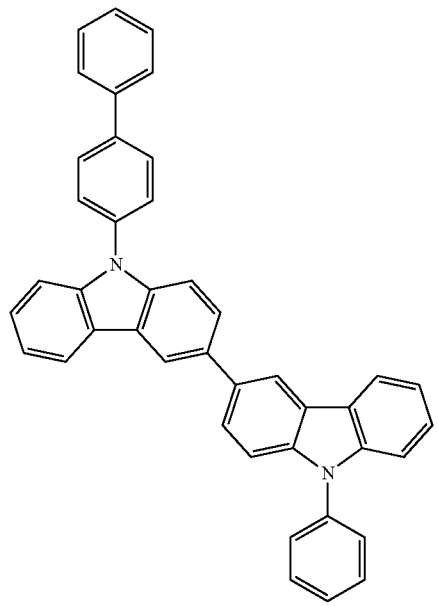
[B-137]
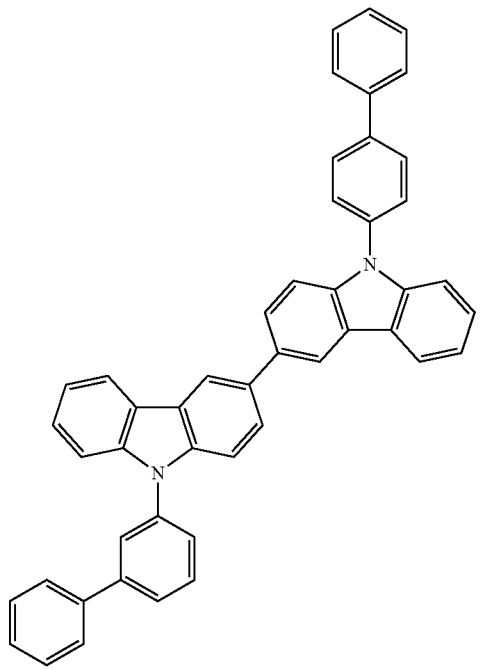

[B-138]
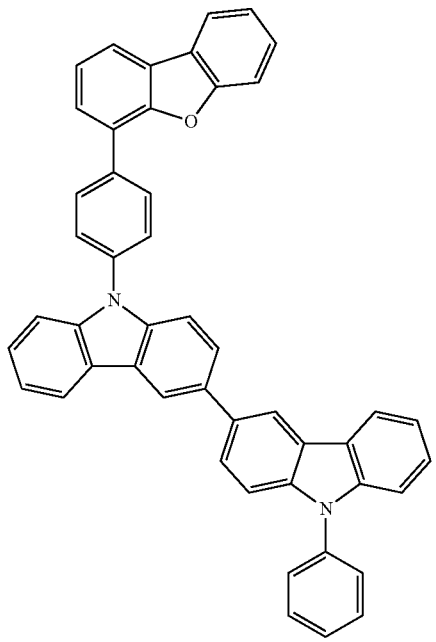
[B-139]
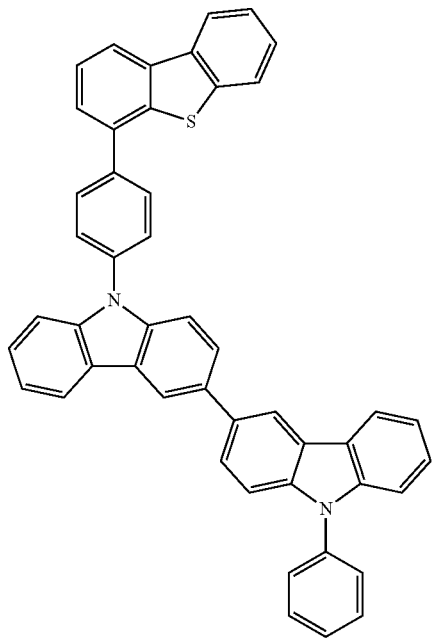
In an example embodiment, the second compound for an organic optoelectric device consisting of a moiety represented by Chemical Formula 3 and a moiety represented by Chemical Formula 4 may be represented by at least one of Chemical Formulas 3-I to 3-V.
[Chemical Formula 3-I]
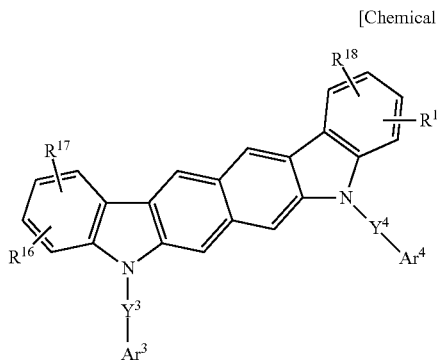
[Chemical Formula 3-II]
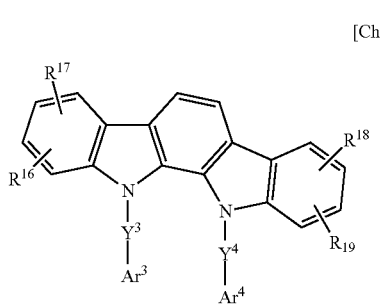
[Chemical Formula 3-III]
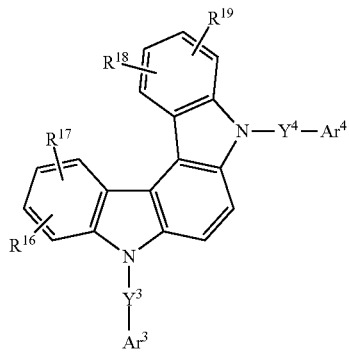
[Chemical Formula 3-IV]
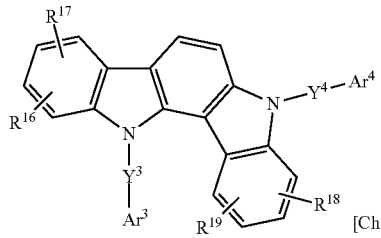
[Chemical Formula 3-V]
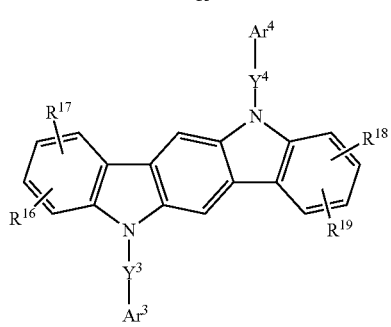

In Chemical Formula 3-I to 3-V, $Y^3$, $Y^4$, $Ar^a$, $Ar^4$, and $R^{16}$ to $R^{19}$ are the same as described above.

In an example embodiment, $Y^3$ and $Y^4$ of Chemical Formulae 3-I to 3-V may be a single bond, a phenylene group, a biphenylene group, a pyridylene group, or a pyrimidinylene group.

In an example embodiment, $Ar^3$ and $Ar^4$ of Chemical Formulae 3-I to 3-V may be a substituted or unsubstituted phenyl group, a substituted or unsubstituted biphenyl group, a substituted or unsubstituted pyridyl group, a substituted or unsubstituted pyrimidinyl group, or a substituted or unsubstituted triazinyl group.

In an example embodiment, $R^{16}$ to $R^{19}$ of Chemical Formulae 3-I to 3-V may be hydrogen.

The second compound for an organic optoelectric device consisting of the combination of the moiety represented by Chemical Formula 3 and the moiety represented by Chemical Formula 4 may be for example compounds of Group 3, but is not limited thereto.

[Group 3]

[E-1]
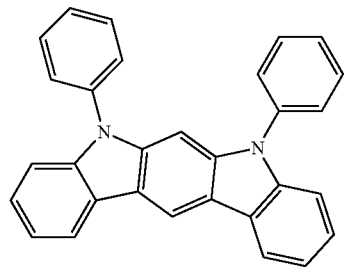

[E-2]
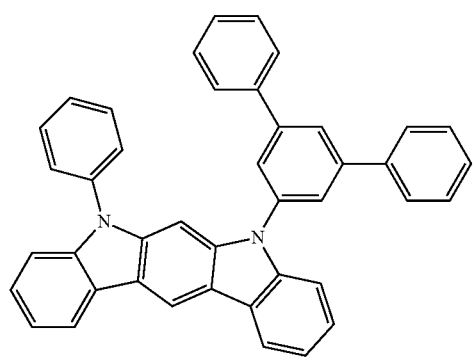

[E-3]
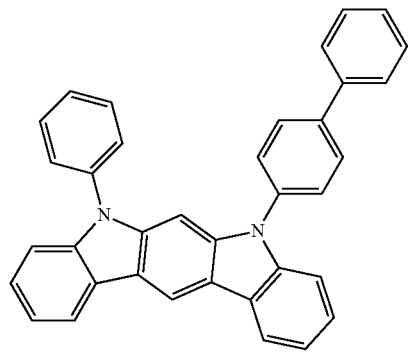

[E-4]
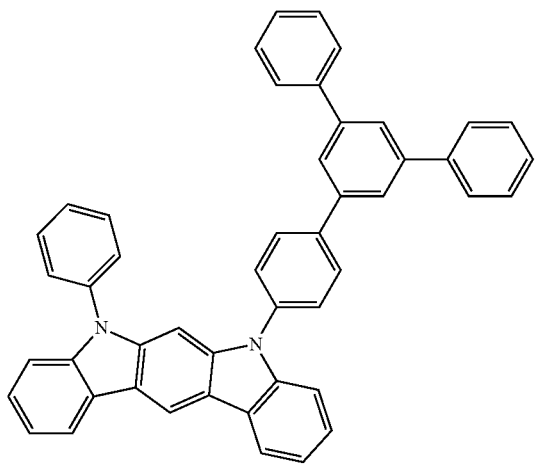

[E-5]
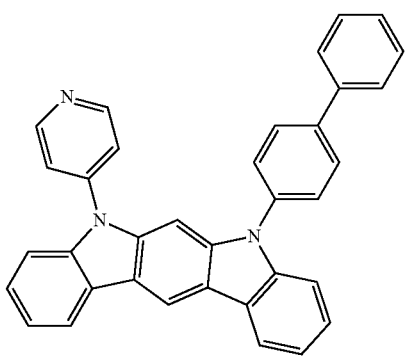

[E-6]
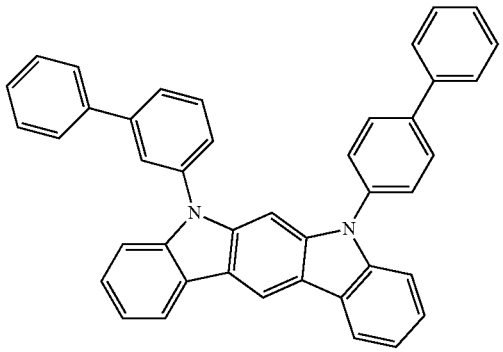

[E-7]
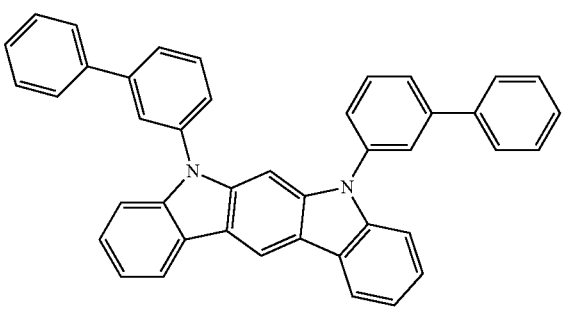

[E-8]
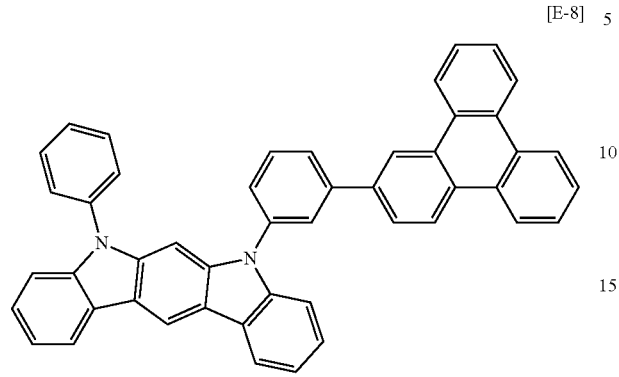
[E-9]
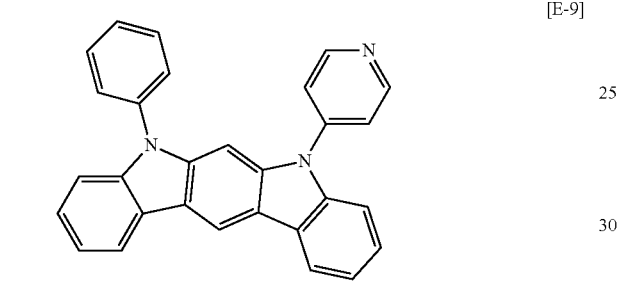
[E-10]
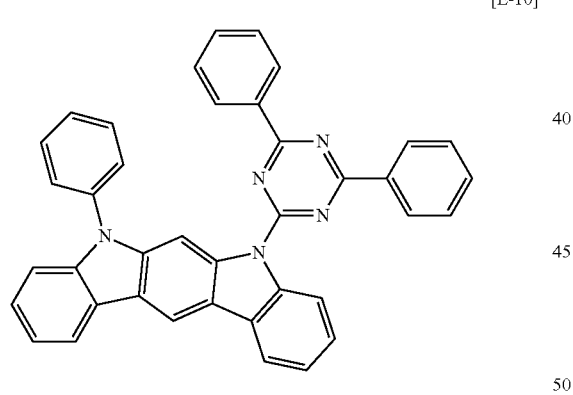
[E-11]
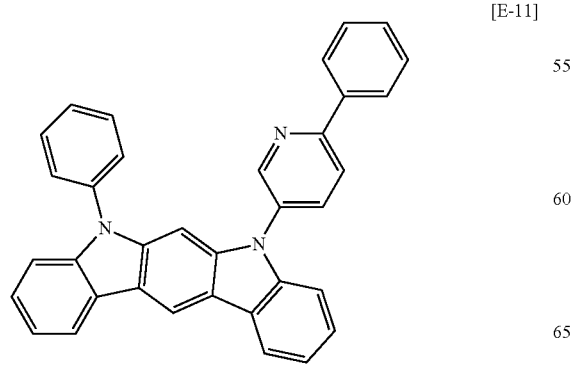
[E-12]
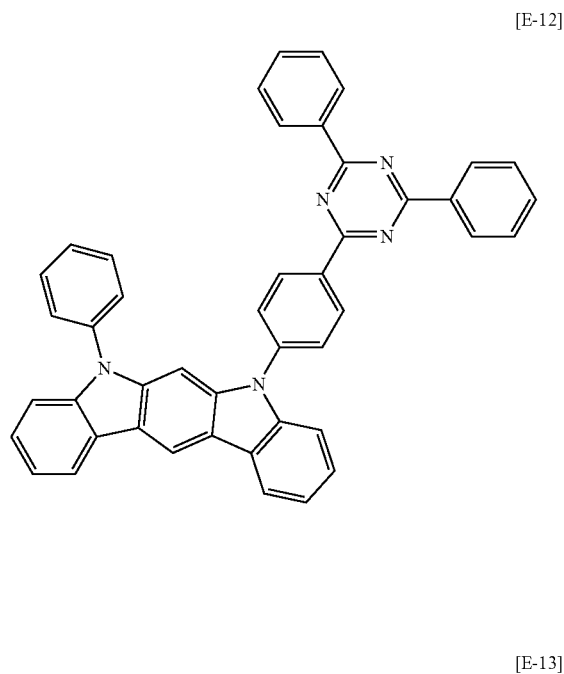
[E-13]
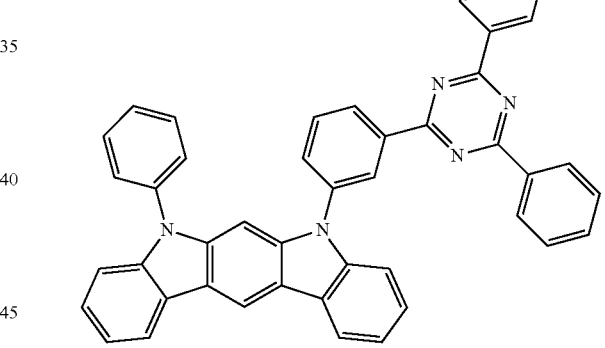
[E-14]
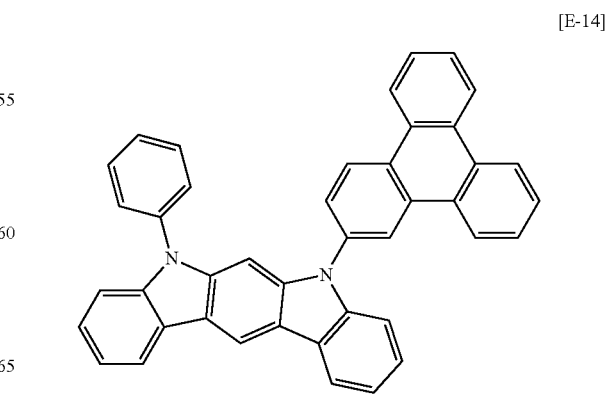

-continued
[E-15]
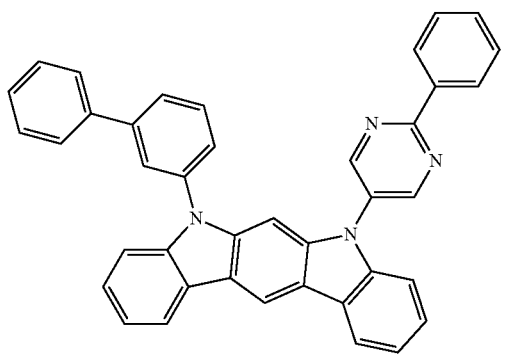
[E-16]
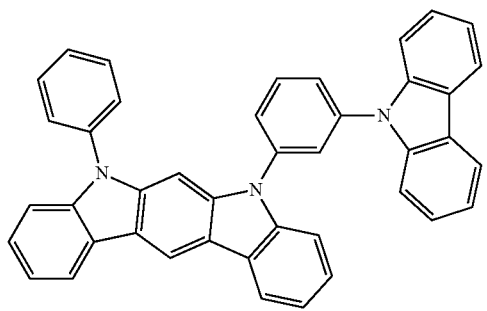
[E-17]
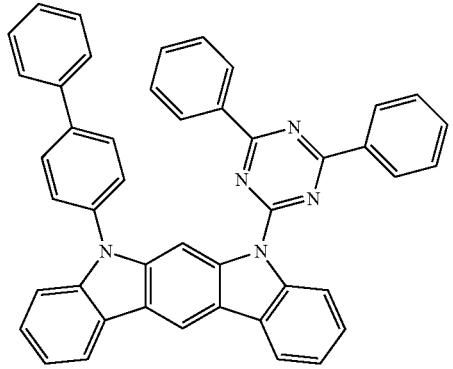
[E-18]
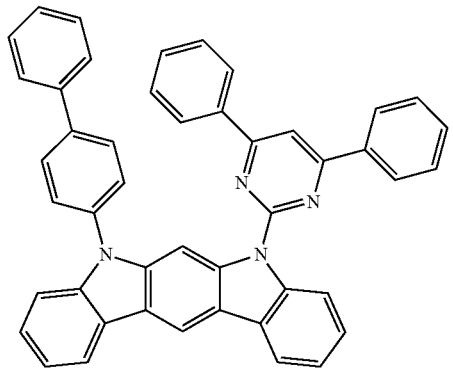
-continued
[E-19]
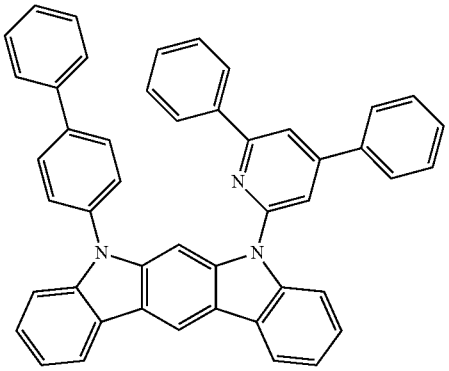
[E-20]
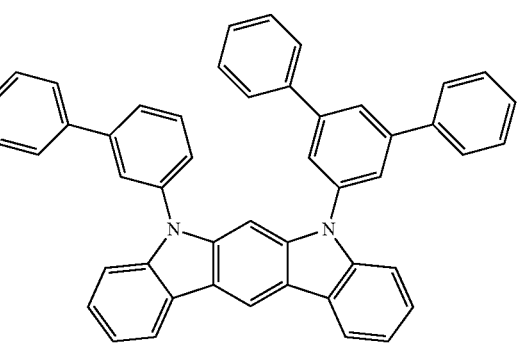
[E-21]
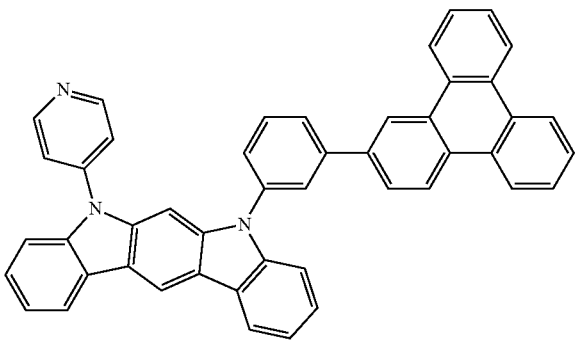
[E-22]
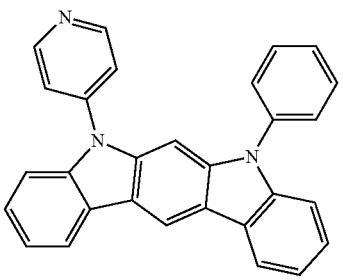

[E-23]
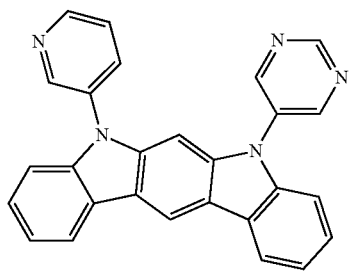
[E-24]
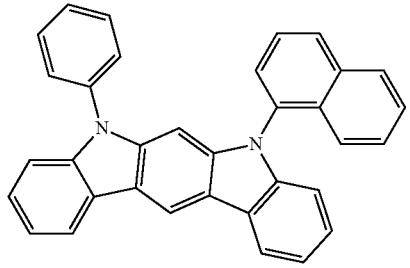
[E-25]
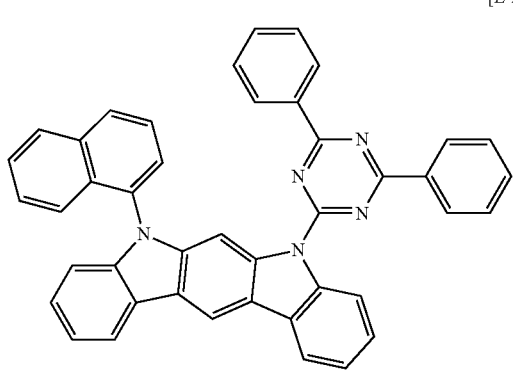
[E-26]
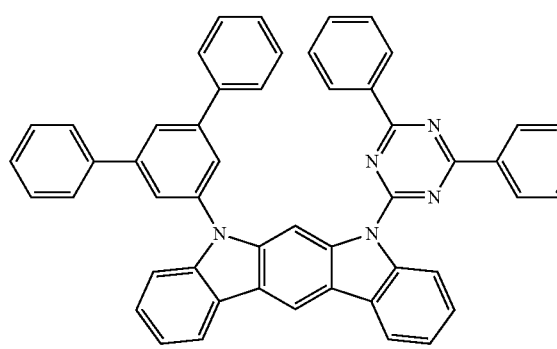
[E-27]
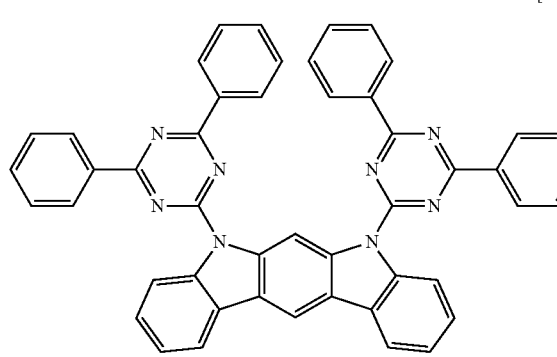
[E-28]
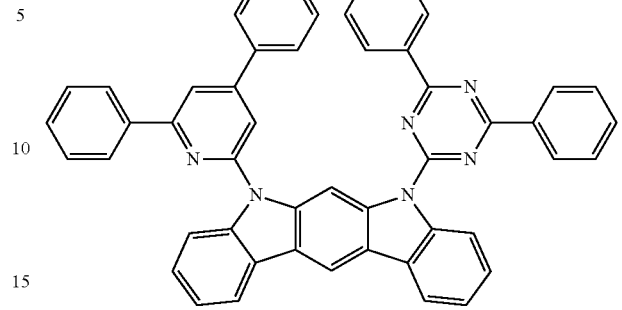
[E-29]
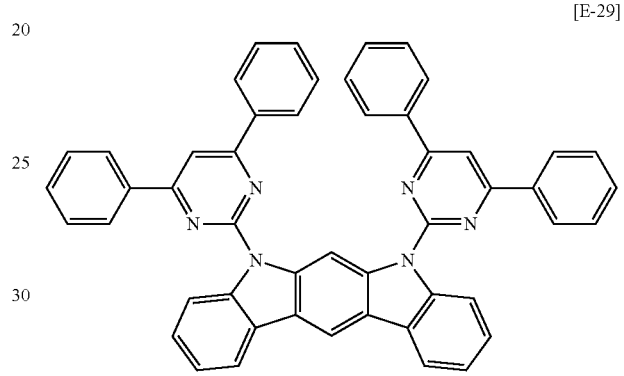
[E-30]
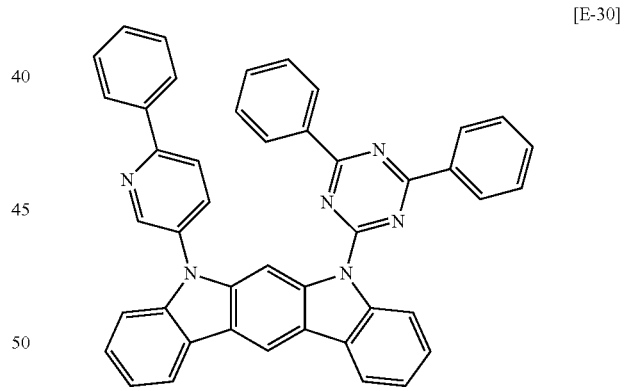
[E-31]
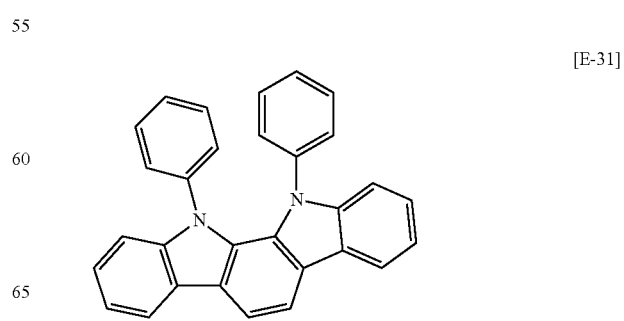

[E-32]
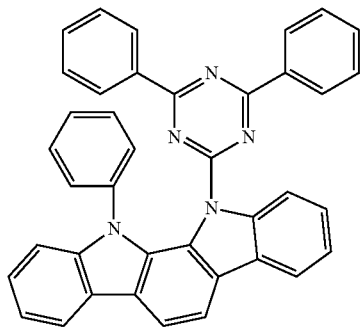
[E-33]
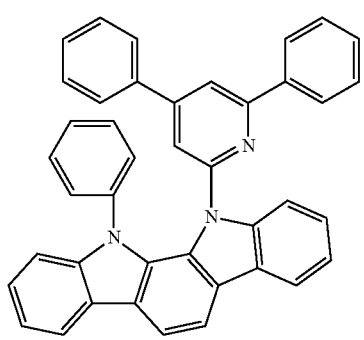
[E-34]
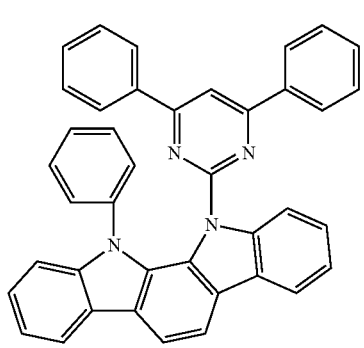
[E-35]
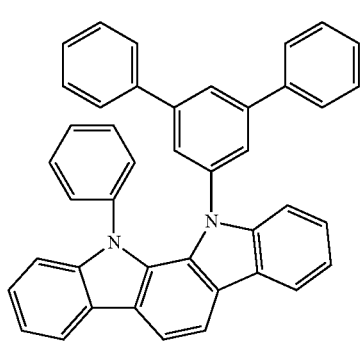
[E-36]
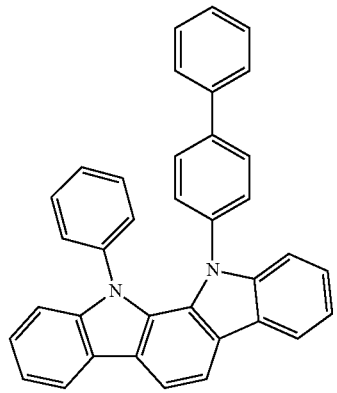
[E-37]
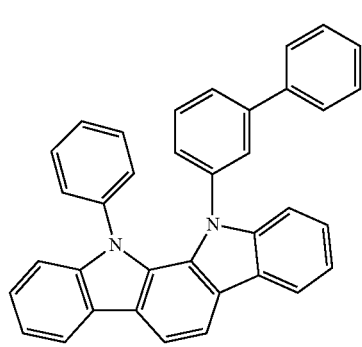
[E-38]
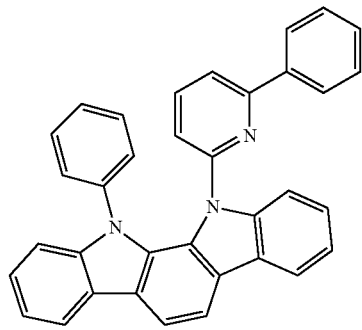
[E-39]
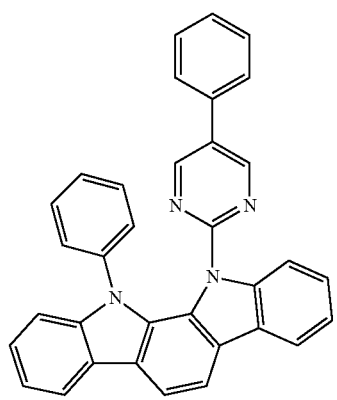

[E-40]

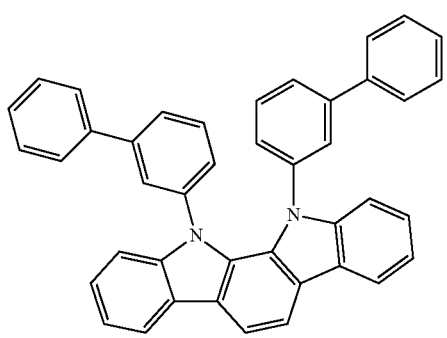

The second compound for an organic optoelectric device is used with the first compound for an organic optoelectric device in the light emitting layer and increases charge mobility and stability, and thereby luminous efficiency and life-span characteristics may be improved. In addition, a ratio of the second compound for an organic optoelectric device and the first compound for an organic optoelectric device may be adjusted and thereby charge mobility may be controlled.

In addition, the first compound for an organic optoelectric device and the second compound for an organic optoelectric device may be for example included in a weight ratio of about 1:9 to 9:1, about 2:8 to 8:2, about 3:7 to 7:3, about 4:6 to 6:4, or about 5:5, specifically about 1:9 to 8:2, about 1:9 to 7:3, about 1:9 to 6:4, or about 1:9 to 5:5, and more specifically, about 2:8 to 7:3, about 2:8 to 6:4 or about 2:8 to 5:5. In addition, they may be included in a weight ratio of about 3:7 to 6:4 or about 3:7 to 5:5, and more specifically about 5:5.

Within the ranges, efficiency and life-span may be simultaneously improved.

The composition may further include one or more organic compounds in addition to the first compound for an organic optoelectric device and the second compound for an organic optoelectric device.

The compound for an organic optoelectric device may further include a dopant. The dopant may be a red, green, or blue dopant.

The dopant is mixed in a small amount to cause light emission, and may be generally a material such as a metal complex that emits light by multiple excitation into a triplet or more. The dopant may be, for example an inorganic, organic, or organic/inorganic compound, and one or more kinds thereof may be used.

The dopant may be for example a phosphorescent dopant and examples of the phosphorescent dopant may be an organometallic compound including Ir, Pt, Os, Ti, Zr, Hf, Eu, Tb, Tm, Fe, Co, Ni, Ru, Rh, Pd, or a combination thereof. The phosphorescent dopant may be for example a compound represented by Chemical Formula Z, but is not limited thereto.

L$_2$MX [Chemical Formula Z]

In Chemical Formula Z, M is a metal, and L and X are the same or different, and are a ligand to form a complex compound with M.

The M may be for example Ir, Pt, Os, Ti, Zr, Hf, Eu, Tb, Tm, Fe, Co, Ni, Ru, Rh, Pd, or a combination thereof and the L and X may be for example a bidendate ligand.

Hereinafter, an organic optoelectric device including the compound for an organic optoelectric device or the composition for an organic optoelectric device is described.

An organic optoelectric device according to another embodiment includes an anode and a cathode facing each other and at least one organic layer disposed between the anode and the cathode, wherein the organic layer includes the compound for an organic optoelectric device or the composition for an organic optoelectric device.

For example, the organic layer may include a light emitting layer and the light emitting layer may include the compound for an organic optoelectric device or the composition for an organic optoelectric device.

Specifically, the compound for an organic optoelectric device or the composition for an organic optoelectric device may be included as a host, for example a red host of the light emitting layer.

In addition, the organic layer may include a light emitting layer and at least one auxiliary layer selected from a hole injection layer, a hole transport layer, an electron blocking layer, an electron transport layer, an electron injection layer, and a hole blocking layer and the auxiliary layer may include the compound for an organic optoelectric device or the composition for an organic optoelectric device.

The auxiliary layer may further include a hole transport auxiliary layer that is adjacent to the light emitting layer and the hole transport auxiliary layer may include the compound for an organic optoelectric device or the composition for an organic optoelectric device.

The organic optoelectric device may be any device to convert electrical energy into photoenergy and vice versa without particular limitation, and may be, for example an organic photoelectric device, an organic light emitting diode, an organic solar cell, and an organic photo conductor drum.

Herein, an organic light emitting diode as one example of an organic optoelectric device is described referring to drawings.

Figure 2:
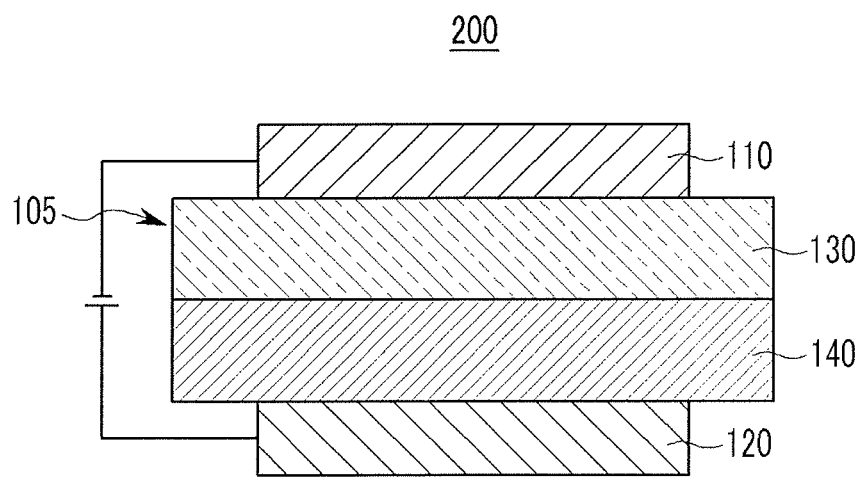

FIGS. 1 and 2 are cross-sectional views showing an organic light emitting diode according to embodiments.

Referring to FIG. 1, an organic light emitting diode 100 according to an embodiment includes an anode 120 and a cathode 110 and an organic layer 105 disposed between the anode 120 and the cathode 110.

The anode 120 may be made of a conductor having a large work function to help hole injection and may be for example made of a metal, a metal oxide and/or a conductive polymer. The anode 120 may be, for example a metal such as nickel, platinum, vanadium, chromium, copper, zinc, gold, and the like, or an alloy thereof; metal oxide such as zinc oxide, indium oxide, indium tin oxide (ITO), indium zinc oxide (IZO), and the like; a combination of metal and oxide such as ZnO and Al or SnO$_2$ and Sb; a conductive polymer such as poly(3-methylthiophene), poly(3,4-(ethylene-1,2-dioxy)thiophene) (PEDT), polypyrrole, and polyaniline, but is not limited thereto.

The cathode 110 may be made of a conductor having a small work function to help electron injection, and may be for example made of a metal, a metal oxide, and/or a conductive polymer. The cathode 110 may be for example a metal such as magnesium, calcium, sodium, potassium, titanium, indium, yttrium, lithium, gadolinium, aluminum silver, tin, lead, cesium, barium, and the like, or an alloy thereof; a multi-layer structure material such as LiF/Al, LiO$_2$/Al, LiF/Ca, LiF/Al and BaF$_2$/Ca, but is not limited thereto.

The organic layer 105 includes a light emitting layer 130 including the compound or the composition for an organic optoelectric device.

FIG. 2 is a cross-sectional view showing an organic light emitting diode according to another embodiment.

Referring to FIG. 2, an organic light emitting diode 200 further includes a hole auxiliary layer 140 in addition to the light emitting layer 130. The hole auxiliary layer 140 may further increase hole injection and/or hole mobility and block electrons between the anode 120 and the light emitting layer 130. The hole auxiliary layer 140 may be, for example a hole transport layer, a hole injection layer, and/or an electron blocking layer, and may include at least one layer.

The organic layer 105 of FIG. 1 or 2 may further include an electron injection layer, an electron transport layer, an electron transport auxiliary layer, a hole transport layer, a hole transport auxiliary layer, a hole injection layer, or a combination thereof even if they are not shown. The compound or the composition for an organic optoelectric device according to an embodiment may be included in these organic layers. The organic light emitting diodes 100 and 200 may be manufactured by forming an anode or a cathode on a substrate, forming an organic layer using a dry film formation method such as a vacuum deposition method (evaporation), sputtering, plasma plating, and ion plating or a wet coating method such as spin coating, dipping, and flow coating, and forming a cathode or an anode thereon.

The organic light emitting diode may be applied to an organic light emitting diode display.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Hereinafter, starting materials and reactants used in Examples and Synthesis Examples were purchased from Sigma-Aldrich Co., Ltd. or TCI Inc. as far as there in no particular comment or were synthesized by known methods.

(Preparation of Compound for Organic Optoelectric Device)

The compound as one specific examples of the present disclosure was synthesized through the following steps.

(Synthesis of First Compound for Organic Optoelectric Device)

Synthesis Example 1: Synthesis of Intermediate A

[Reaction Scheme 1]

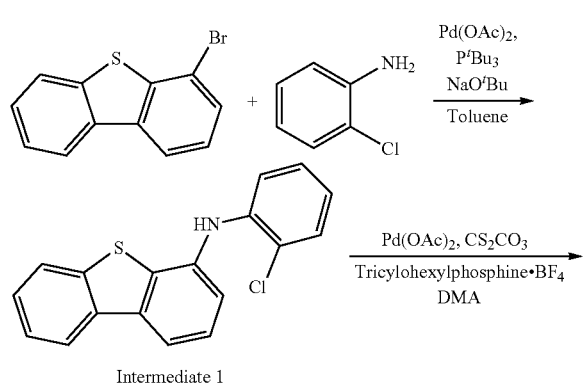

Intermediate 1

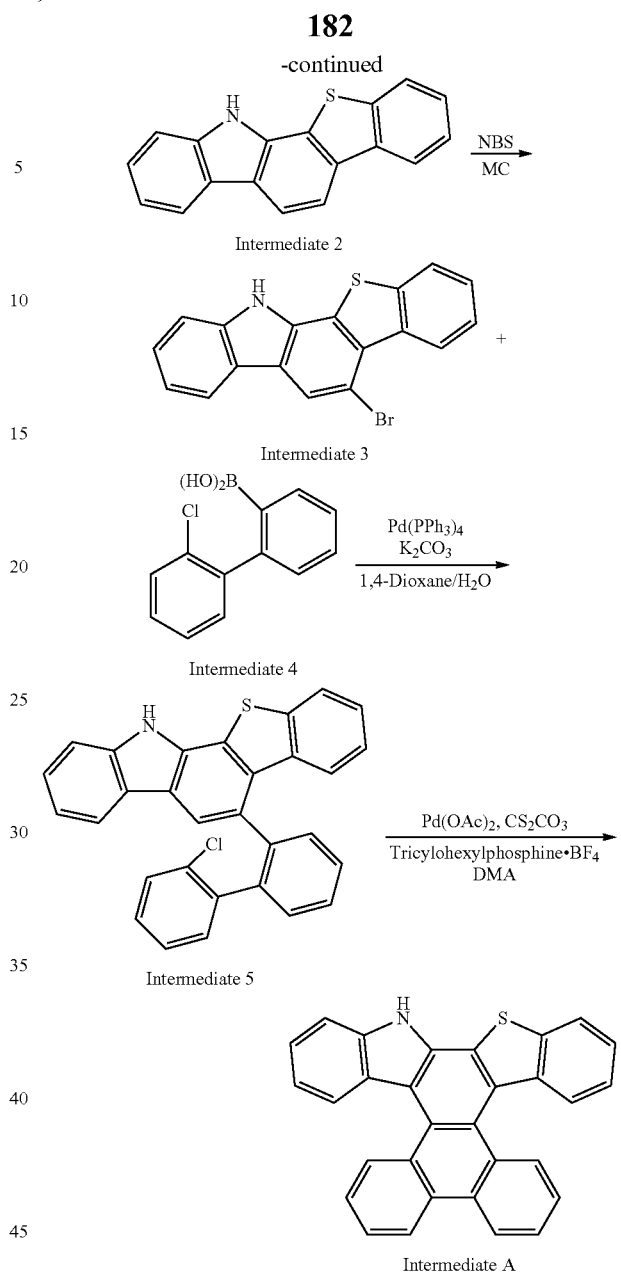

First Step: Synthesis of Intermediate 1

127.4 g (0.48 mol) of 4-bromodibenzothiophene, 75.9 ml (0.73 mol) of 2-chloroaniline, 140.0 g (1.45 mol) of sodium t-butoxide, 10.9 g (48.4 mmol) of palladium acetate, and 47 g (50% in toluene) of tri t-butylphosphine were mixed with 3 L of xylene in a 5 L flask, and the mixture was heated and refluxed under a nitrogen flow for 15 hours. After volatilizing and removing a solvent therein when a reaction was complete, a resultant therefrom is added to 2 L of methanol, and a solid crystallized therein is filtered, dissolved in dichlorobenzene, filtered with silica gel/Celite, and after removing an appropriate amount of an organic solvent, recrystallized with methanol to obtain Intermediate 1 (105.0 g, a yield of 70%).

Second Step: Synthesis of Intermediate 2

104.0 g (0.33 mol) of Intermediate 1, 7.54 g (33.6 mmol) of palladium acetate, 328.26 g (1.0 mol) of cesium carbonate, and 24.7 g (67.17 mol) of tricyclohexylphosphine-tetrafluoro borate were mixed with 1.1 L of N,N-dimethylacetamide in a 3 L flask, and the mixture was heated and refluxed under a nitrogen flow for 12 hours. After volatilizing and removing a solvent when a reaction was complete, the resultant is added to 2 L of methanol, and a solid crystallized therein was filtered, dissolved in dichlorobenzene, filtered with silica gel/Celite, and after removing an appropriate amount of an organic solvent, recrystallized with methanol to obtain Intermediate 2 (81.0 g, a yield of 88%).

Third Step: Synthesis of Intermediate 3

80.0 g (0.23 mol) of Intermediate 2 was mixed with 2.0 L of methylene dichloride in a 3 L flask, and an internal temperature of the mixture was decreased down to −10° C. The internal temperature is maintained at −10° C., while 45.7 g (0.26 mol) of N-bromosuccinimide was slowly added thereto. After removing a solvent therefrom when a reaction was complete, the resultant was treated through column chromatography to obtain Intermediate 3 (51.0 g, a yield of 62%).

Fourth Step: Synthesis of Intermediate 5

Intermediate 3 (51.0 g, 144.8 mmol), Intermediate 4 (40.4 g, 173.7 mmol), potassium carbonate (50.0 g, 362.0 mmol), and tetrakis(triphenylphosphine) palladium (0) (5.0 g, 4.3 mmol) were added to 480 mL of 1,4-dioxane and 240 mL of water in a 2 L flask, and the mixture was heated at 70° C. under a nitrogen flow for 24 hours. An organic layer was separated and volatilized and then, added to 1000 L of methanol, and a solid crystallized therein was filtered, dissolved in monochlorobenzene, filtered with silica gel/Celite, and after removing an appropriate amount of an organic solvent, recrystallized with monochlorobenzene to obtain Intermediate 5 (42.0 g, a yield of 63%).

Fifth Step: Synthesis of Intermediate A 41.9 g (91.14 mmol) of Intermediate 5, 2.05 g (9.11 mmol) of palladium acetate, 89.08 g (273.42 mmol) of cesium carbonate, and 6.71 g (18.23 mmol) of tricyclohexylphosphine-tetrafluoro borate were mixed with 300 mL of N,N-dimethylacetamide in a 1 L flask, and the mixture was heated and refluxed under a nitrogen flow for 12 hours. After volatilizing and removing a solvent therefrom when a reaction was complete, the resultant was added to 500 mL of methanol, and a solid crystallized therein was filtered, dissolved in dichlorobenzene, filtered with silica gel/Celite, and after removing an appropriate amount of an organic solvent, recrystallized with methanol to obtain Intermediate A (33.5 g, a yield of 87%).

calcd. C30H17NS: C, 85.08; H, 4.05; N, 3.31; S, 7.57; found: C, 85.08; H, 4.04; N, 3.31; S, 7.56.

Synthesis Example 2: Synthesis of Intermediate B

[Reaction Scheme 2]

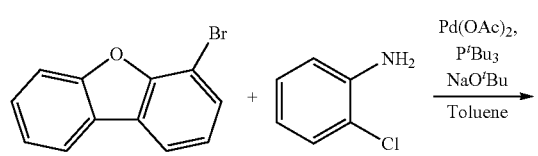

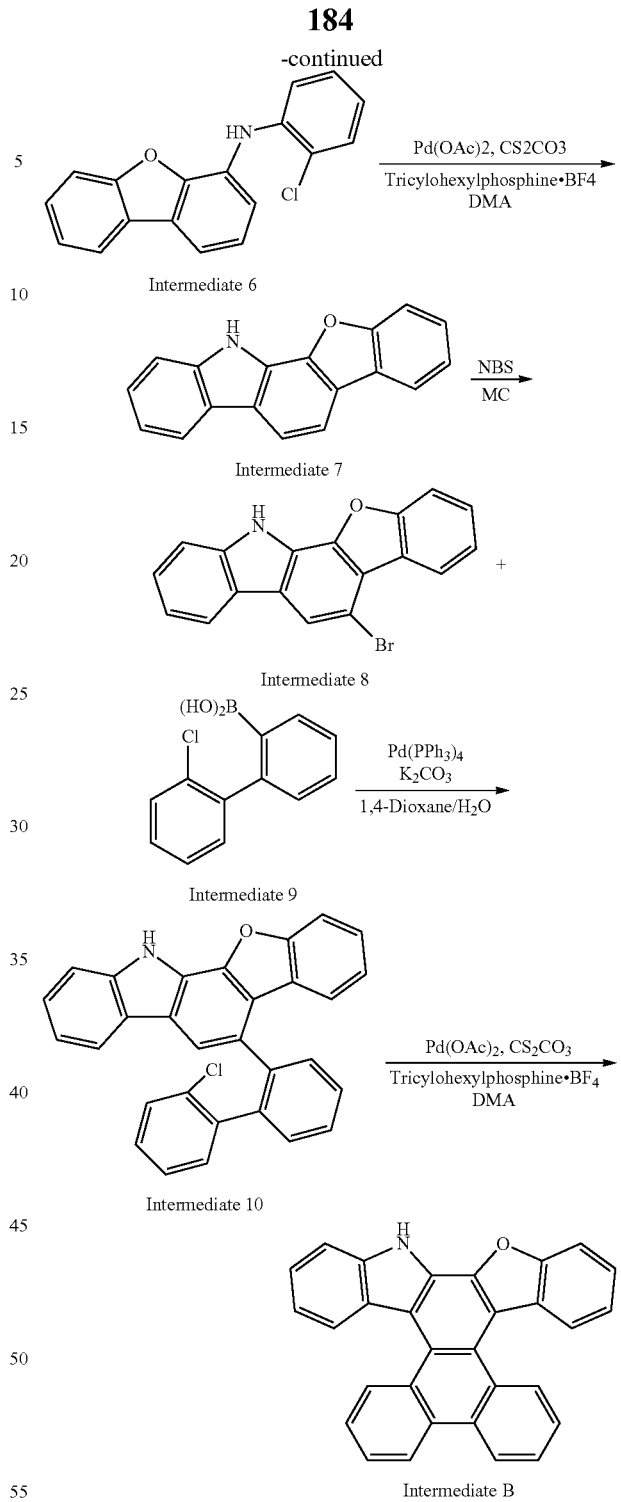

First Step: Synthesis of Intermediate 6

130.0 g (0.53 mol) of 4-bromodibenzofuran, 82.5 ml (0.79 mol) of 2-chloroaniline, 151.7 g (1.58 mol) of sodium t-butoxide, 11.8 g (52.6 mmol) of palladium acetate, and 51.1 g (50% in toluene) of tri t-butylphosphine were mixed with 2.5 L of xylene in a 5 L flask, and the mixture was heated and refluxed under a nitrogen flow for 15 hours. After volatilizing and removing a solvent when a reaction was complete, 2 L of methanol was added thereto, and a solid crystallized therein was filtered, dissolved in dichlorobenzene, filtered with silica gel/Celite, and after removing an appropriate amount of an organic solvent, recrystallized with methanol to obtain Intermediate 6 (115.0 g, a yield of 74%).

Second Step: Synthesis of Intermediate 7

114.2 g (0.39 mol) of Intermediate 6, 8.7 g (38.9 mmol) of palladium acetate, 379.9 g (1.2 mol) of cesium carbonate, and 28.6 g (77.73 mol) of tricyclohexylphosphine-tetrafluoro borate were mixed with 1.3 L of N,N-dimethylacetamide in a 3 L flask, and the mixture was heated and refluxed under a nitrogen flow for 12 hours. After volatilizing and removing a solvent therefrom when a reaction was complete, 2 L of methanol was added thereto, and a solid crystallized therein was filtered, dissolved in dichlorobenzene, filtered with silica gel/Celite, and after removing an appropriate amount of an organic solvent, recrystallized with methanol to obtain Intermediate 7 (87.0 g, a yield of 87%).

Third Step: Synthesis of Intermediate 8

87.0 g (0.34 mol) of Intermediate 7 was mixed with 3.0 L of methylenedichloride in a 3 L flask, and an internal temperature of the flask was decreased down to −10° C. The internal temperature was maintained at −10° C., while 66.2 g (0.37 mol) of N-bromosuccinimide was slowly added thereto. After removing a solvent therefrom when a reaction was complete, the resultant was treated through column chromatography to obtain Intermediate 8 (66.0 g, a yield of 58%).

Fourth Step: Synthesis of Intermediate 10

Intermediate 8 (65.0 g, 193.3 mmol), Intermediate 9 (53.9 g, 232.0 mmol), potassium carbonate (66.8 g, 483.4 mmol), and tetrakis(triphenylphosphine) palladium (0) (6.7 g, 5.8 mmol) were added to 600 mL of 1,4-dioxane and 300 mL of water in a 2 L flask, and the mixture was heated at 70° C. under a nitrogen flow for 24 hours. An organic layer was separated and volatilized and then, added to 1000 L of methanol, and a solid crystallized therein was filtered, dissolved in monochlorobenzene, filtered with silica gel/Celite, and after removing an appropriate amount of an organic solvent, recrystallized with monochlorobenzene to obtain Intermediate 10 (51.0 g, a yield of 59%).

Fifth Step: Synthesis of Intermediate B 50.0 g (112.65 mmol) of Intermediate 10, 2.52 g (11.26 mmol) of palladium acetate, 110.11 g (337.95 mmol) of cesium carbonate, and 8.29 g (22.53 mmol) of tricyclohexylphosphine-tetrafluoro borate were mixed with 400 mL of N,N-dimethylacetamide in a 1 L flask, and the mixture was heated and refluxed under a nitrogen flow for 12 hours. After volatilizing and removing a solvent therefrom when a reaction was complete, the resultant was added to 700 mL of methanol, and a solid crystallized therein was filtered, dissolved in dichlorobenzene, filtered with silica gel/Celite, and after removing an appropriate amount of an organic solvent, recrystallized with methanol to obtain Intermediate B (41.2 g, a yield of 90%).
calcd. C30H17NO: C, 88.43; H, 4.21; N, 3.44; O, 3.93; found: C, 88.42; H, 4.21; N, 3.44; O, 3.93.

Synthesis Example 3: Synthesis of Compound 73

3.37 g (7.96 mmol) of Intermediate A, 2.3 g (9.56 mmol) of 2-chloro-4-phenyl-quinazoline, 1.53 g (15.93 mmol) of sodium t-butoxide, 0.46 g (0.8 mmol) of tris(dibenzylideneacetone) dipalladium, and 0.65 g (50% in toluene) of tri t-butylphosphine were mixed with 53 mL of xylene, and the mixture was heated and refluxed under a nitrogen flow for 15 hours. The obtained mixture was added to 300 mL of methanol, and a solid crystallized therein was filtered, dissolved in monochlorobenzene, filtered with silica gel/Celite, and after removing an appropriate amount of an organic solvent, recrystallized with methanol to obtain Compound 73 (3.6 g, a yield of 72%).
calcd. C44H25N3S: C, 84.18; H, 4.01; N, 6.69; S, 5.11; found: C, 84.17; H, 4.00; N, 6.69; S, 5.11.

Synthesis Example 4: Synthesis of Compound 74

Compound 74 (3.8 g, a yield of 76%) was obtained according to the same method as Synthesis Example 3 except for mixing 3.0 g (7.1 mmol) of Intermediate A, 2.7 g (8.5 mmol) of 4-(biphenyl-4-yl)-2-chloroquinazoline, 1.36 g (14.2 mmol) of sodium t-butoxide, 0.41 g (0.71 mmol) of tris(dibenzylideneacetone)dipalladium, and tri t-butylphosphine 0.57 g (50% in toluene) with 45 mL of xylene.
calcd. C50H29N3S: C, 85.32; H, 4.15; N, 5.97; S, 4.56; found: C, 85.32; H, 4.15; N, 5.96; S, 4.55.

Synthesis Example 5: Synthesis of Compound 75

Compound 75 (3.6 g, a yield of 72%) was obtained according to the same method as Synthesis Example 3 except for mixing 3.0 g (7.1 mmol) of Intermediate A, 2.7 g (8.5 mmol) of 4-(biphenyl-3-yl)-2-chloroquinazoline, 1.36 g (14.2 mmol) of sodium t-butoxide, 0.41 g (0.71 mmol) of tris(dibenzylideneacetone)dipalladium, and 0.57 g (50% in toluene) of tri t-butylphosphine with 45 mL of xylene.
calcd. C50H29N3S: C, 85.32; H, 4.15; N, 5.97; S, 4.56; found: C, 85.31; H, 4.15; N, 5.97; S, 4.55.

Synthesis Example 6: Synthesis of Compound 79

Compound 79 (3.26 g, a yield of 65%) was obtained according to the same method as Synthesis Example 3 except for mixing 2.91 g (6.87 mmol) of Intermediate A, 2.81 g (8.24 mmol) of 2-chloro-4-(phenanthren-2-yl)quinazoline, 1.32 g (13.7 mmol) of sodium t-butoxide, 0.39 g (0.69 mmol) of tris(dibenzylideneacetone) dipalladium, and 0.56 g (50% in toluene) of tri t-butylphosphine with 45 mL of xylene.
calcd. C52H29N3S: C, 85.81; H, 4.02; N, 5.77; S, 4.41; found: C, 85.81; H, 4.02; N, 5.76; S, 4.41.

Synthesis Example 7: Synthesis of Compound 84

Compound 84 (3.51 g, a yield of 70%) was obtained according to the same method as Synthesis Example 3 except for mixing 2.95 g (6.96 mmol) of Intermediate A, 2.77 g (8.36 mmol) of 2-chloro-4-(dibenzofuran-3-yl)quinazoline, 1.34 g (13.93 mmol) of sodium t-butoxide, 0.40 g (0.70 mmol) of tris(dibenzylideneacetone) dipalladium, and 0.56 g (50% in toluene) of tri t-butylphosphine with 45 mL of xylene.
calcd. C50H27N3OS: C, 83.66; H, 3.79; N, 5.85; O, 2.23; S, 4.47; found: C, 83.66; H, 3.78; N, 5.85; O, 2.22; S, 4.47.

Synthesis Example 8: Synthesis of Compound 88

Compound 88 (3.80 g, a yield of 76%) was obtained according to the same method as Synthesis Example 3 except for mixing 2.88 g (6.81 mmol) of Intermediate A, 2.84 g (8.18 mmol) of 2-chloro-4-(dibenzothiophene-3-yl) quinazoline, 1.31 g (13.63 mmol) of sodium t-butoxide, 0.39 g (0.68 mmol) of tris(dibenzylideneacetone) dipalladium, and 0.55 g (50% in toluene) of tri t-butylphosphine with 45 mL of xylene.

calcd. C50H27N3S2: C, 81.83; H, 3.71; N, 5.73; S, 8.74; found: C, 81.83; H, 3.71; N, 5.73; S, 8.74.

Synthesis Example 9: Synthesis of Compound 93

Compound 93 (3.96 g, a yield of 79%) was obtained according to the same method as Synthesis Example 3 except for mixing 3.23 g (7.64 mmol) of Intermediate A, 2.45 g (9.16 mmol) of 2,4-diphenyl-6-chlorotriazine, 1.47 g (15.27 mmol) of sodium t-butoxide, 0.44 g (0.76 mmol) of tris(dibenzylideneacetone) dipalladium, and 0.62 g (50% in toluene) of tri t-butylphosphine with 50 mL of xylene.

calcd. C45H26N4S: C, 82.54; H, 4.00; N, 8.56; S, 4.90; found: C, 82.54; H, 4.00; N, 8.55; S, 4.89.

Synthesis Example 10: Synthesis of Compound 114

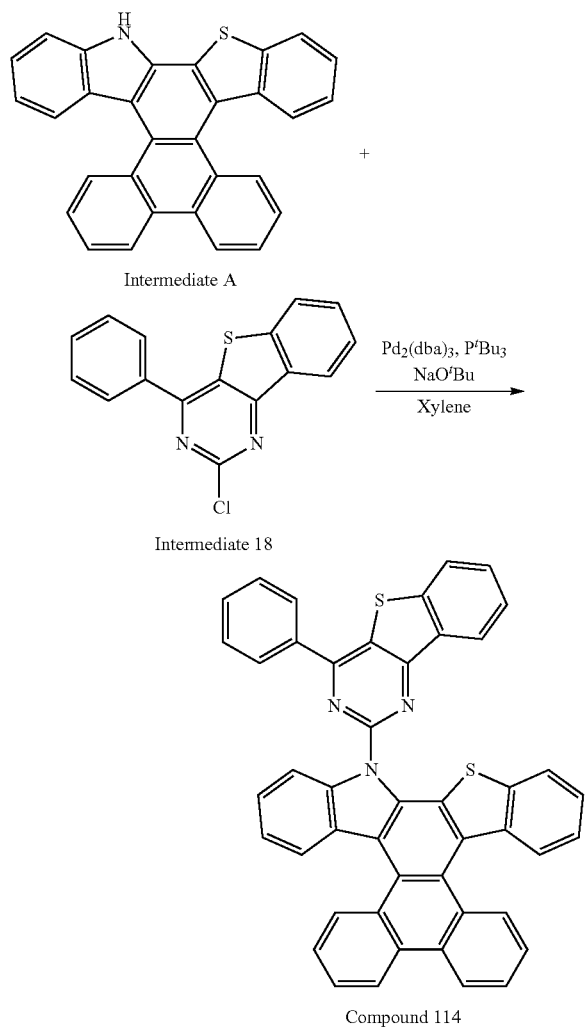

[Reaction Scheme 3]

Intermediate A

Intermediate 18

Compound 114

Compound 114 (3.82 g, a yield of 76%) was obtained according to the same method as Synthesis Example 3 except for mixing 3.10 g (7.31 mmol) of Intermediate A, 2.60 g (8.77 mmol) of Intermediate 18, 1.41 g (14.62 mmol) of sodium t-butoxide, 0.42 g (0.73 mmol) of tris(dibenzylideneacetone) dipalladium, and 0.59 g (50% in toluene) of tri t-butylphosphine with 50 mL of xylene.

calcd. C46H25N3S2: C, 80.79; H, 3.68; N, 6.14; S, 9.38; found: C, 80.79; H, 3.68; N, 6.14; S, 9.38.

Synthesis Example 11: Synthesis of Compound 201

Compound 201 (3.46 g, a yield of 70%) was obtained according to the same method as Compound 73 of Synthesis Example 3 except for using Intermediate B instead of Intermediate A.

calcd. C44H25N3O: C, 86.40; H, 4.12; N, 6.87; O, 2.62; found: C, 86.40; H, 4.12; N, 6.87; O, 2.62.

Synthesis Example 12: Synthesis of Compound 202

Compound 202 (3.89 g, a yield of 71%) was obtained according to the same method as Compound 74 of Synthesis Example 4 except for using Intermediate B instead of Intermediate A.

calcd. C50H29N3O: C, 87.31; H, 4.25; N, 6.11; O, 2.33; found: C, 87.31; H, 4.25; N, 6.11; O, 2.32.

Synthesis Example 13: Synthesis of Compound 203

Compound 203 (4.02 g, a yield of 68%) was obtained according to the same method as Compound 75 of Synthesis Example 5 except for using Intermediate B instead of Intermediate A.

calcd. C50H29N3O: C, 87.31; H, 4.25; N, 6.11; O, 2.33; found: C, 87.31; H, 4.23; N, 6.11; O, 2.33.

Synthesis Example 14: Synthesis of Compound 207

Compound 207 (3.55 g, a yield of 64%) was obtained according to the same method as Compound 79 of Synthesis Example 6 except for using Intermediate B instead of Intermediate A.

calcd. C52H29N3O: C, 87.74; H, 4.11; N, 5.90; O, 2.25; found: C, 87.74; H, 4.11; N, 5.89; O, 2.25.

Synthesis Example 15: Synthesis of Compound 212

Compound 212 (3.73 g, a yield of 67%) was obtained according to the same method as Compound 84 of Synthesis Example 7 except for using Intermediate B instead of Intermediate A.

calcd. C50H27N3O2: C, 85.57; H, 3.88; N, 5.99; O, 4.56; found: C, 85.56; H, 3.88; N, 5.98; O, 4.56.

Synthesis Example 16: Synthesis of Compound 216

Compound 216 (3.32 g, a yield of 63%) was obtained according to the same method as Compound 88 of Synthesis Example 8 except for using Intermediate B instead of Intermediate A.

calcd. C50H27N3OS: C, 83.66; H, 3.79; N, 5.85; O, 2.23; S, 4.47; found: C, 83.66; H, 3.78; N, 5.85; O, 2.23; S, 4.46.

Synthesis Example 17: Synthesis of Compound 221

Compound 221 (3.58 g, a yield of 69%) was obtained according to the same method as Compound 93 of Synthesis Example 9 except for using Intermediate B instead of Intermediate A.

calcd. C45H26N4O: C, 84.62; H, 4.10; N, 8.77; O, 2.50; found: C, 84.61; H, 4.09; N, 8.77; O, 2.50.

Synthesis Example 18: Synthesis of Compound 242

Compound 242 (4.29 g, a yield of 68%) was obtained according to the same method as Compound 114 of Synthesis Example 10 except for using Intermediate B instead of Intermediate A.
calcd. C46H25N3OS: C, 82.74; H, 3.77; N, 6.29; O, 2.40; S, 4.80; found: C, 82.74; H, 3.76; N, 6.29; O, 2.40; S, 4.79.

Synthesis of Second Compound for Organic Optoelectric Device

Synthesis Example 19: Synthesis of Compound 1

Compound 1 (5.04 g, a yield of 74%) was obtained according to the same method as Compound 73 of Synthesis Example 3 except for using bromobenzene instead of 2-chloro-4-phenyl-quinazoline.
calcd. C36H21NS: C, 86.54; H, 4.24; N, 2.80; S, 6.42; found: C, 86.53; H, 4.24; N, 2.80; S, 6.41.

Synthesis Example 20: Synthesis of Compound 2

Compound 2 (4.66 g, a yield of 73%) was obtained according to the same method as Compound 73 of Synthesis Example 3 except for using 4-bromobiphenyl instead of 2-chloro-4-phenyl-quinazoline.
calcd. C42H25NS: C, 87.62; H, 4.38; N, 2.43; S, 5.57; found: C, 87.62; H, 4.38; N, 2.43; S, 5.57.

Synthesis Example 21: Synthesis of Compound 3

Compound 3 (4.82 g, a yield of 77%) was obtained according to the same method as Compound 73 of Synthesis Example 3 except for using 3-bromobiphenyl instead of 2-chloro-4-phenyl-quinazoline.
calcd. C42H25NS: C, 87.62; H, 4.38; N, 2.43; S, 5.57; found: C, 87.62; H, 4.37; N, 2.43; S, 5.57.

Synthesis Example 22: Synthesis of Compound 5

Compound 5 (4.17 g, a yield of 70%) was obtained according to the same method as Compound 73 of Synthesis Example 3 except for using 5-bromo-3-phenyl-biphenyl instead of 2-chloro-4-phenyl-quinazoline.
calcd. C48H29NS: C, 88.45; H, 4.48; N, 2.15; S, 4.92; found: C, 88.45; H, 4.48; N, 2.14; S, 4.92.

Synthesis Example 23: Synthesis of Compound 6

Compound 6 (3.85 g, a yield of 68%) was obtained according to the same method as Compound 73 of Synthesis Example 3 except for using 4-bromo-p-terphenyl instead of 2-chloro-4-phenyl-quinazoline.
calcd. C48H29NS: C, 88.45; H, 4.48; N, 2.15; S, 4.92; found: C, 88.45; H, 4.48; N, 2.15; S, 4.92.

Synthesis Example 24: Synthesis of Compound 15

Compound 15 (4.09 g, a yield of 75%) was obtained according to the same method as Compound 73 of Synthesis Example 3 except for using 2-bromotriphenylene instead of 2-chloro-4-phenyl-quinazoline.
calcd. C48H27NS: C, 88.72; H, 4.19; N, 2.16; S, 4.93; found: C, 88.71; H, 4.19; N, 2.16; S, 4.93.

Synthesis Example 25: Synthesis of Compound 28

Compound 28 (4.55 g, a yield of 72%) was obtained according to the same method as Compound 73 of Synthesis Example 3 except for using 3-bromo-9-phenyl-9H-carbazole instead of 2-chloro-4-phenyl-quinazoline.
calcd. C48H28N2S: C, 86.72; H, 4.25; N, 4.21; S, 4.82; found: C, 86.72; H, 4.25; N, 4.21; S, 4.81.

Synthesis Example 26: Synthesis of Compound 41

Compound 41 (4.82 g, a yield of 72%) was obtained according to the same method as Compound 73 of Synthesis Example 3 except for using 3-bromodibenzofuran instead of 2-chloro-4-phenyl-quinazoline.
calcd. C42H23NOS: C, 85.54; H, 3.93; N, 2.38; O, 2.71; S, 5.44; found: C, 85.53; H, 3.92; N, 2.38; O, 2.71; S, 5.44.

Synthesis Example 27: Synthesis of Compound 55

Compound 55 (4.11 g, a yield of 70%) was obtained according to the same method as Compound 73 of Synthesis Example 3 except for using 3-bromodibenzothiophene of Intermediate 27 instead of 2-chloro-4-phenyl-quinazoline.
calcd. C42H23NS2: C, 83.27; H, 3.83; N, 2.31; S, 10.59; found: C, 83.27; H, 3.83; N, 2.30; S, 10.59.

Synthesis Example 28: Synthesis of Compound 129

Compound 129 (4.35 g, a yield of 68%) was obtained according to the same method as Compound 1 of Synthesis Example 19 except for using intermediate B instead of intermediate A.
calcd. C36H21NO: C, 89.42; H, 4.38; N, 2.90; O, 3.31; found: C, 89.42; H, 4.38; N, 2.90; O, 3.31.

Synthesis Example 29: Synthesis of Compound 130

Compound 130 (4.41 g, a yield of 71%) was obtained according to the same method as Compound 2 of Synthesis Example 20 except for using intermediate B instead of intermediate A.
calcd. C42H25NO: C, 90.14; H, 4.50; N, 2.50; O, 2.86; found: C, 90.14; H, 4.49; N, 2.50; O, 2.86.

Synthesis Example 30: Synthesis of Compound 131

Compound 131 (4.77 g, a yield of 66%) was obtained according to the same method as Compound 3 of Synthesis Example 21 except for using intermediate B instead of intermediate A.
calcd. C42H25NO: C, 90.14; H, 4.50; N, 2.50; O, 2.86; found: C, 90.14; H, 4.50; N, 2.50; O, 2.85.

Synthesis Example 31: Synthesis of Compound 133

Compound 133 (4.60 g, a yield of 63%) was obtained according to the same method as Compound 5 of Synthesis Example 22 except for using intermediate B instead of intermediate A.
calcd. C48H29NO: C, 90.68; H, 4.60; N, 2.20; O, 2.52; found: C, 90.67; H, 4.60; N, 2.20; O, 2.51.

Synthesis Example 32: Synthesis of Compound 134

Compound 134 (4.16 g, a yield of 65%) was obtained according to the same method as Compound 6 of Synthesis Example 23 except for using intermediate B instead of intermediate A.
calcd. C48H29NO: C, 90.68; H, 4.60; N, 2.20; O, 2.52; found: C, 90.68; H, 4.60; N, 2.20; O, 2.52.

Synthesis Example 33: Synthesis of Compound 143

Compound 143 (4.33 g, a yield of 68%) was obtained according to the same method as Compound 15 of Synthesis Example 24 except for using intermediate B instead of intermediate A.
calcd. C48H27NO: C, 90.97; H, 4.29; N, 2.21; O, 2.52; found: C, 90.96; H, 4.28; N, 2.21; O, 2.52.

Synthesis Example 34: Synthesis of Compound 156

Compound 156 (4.92 g, a yield of 69%) was obtained according to the same method as Compound 28 of Synthesis Example 25 except for using intermediate B instead of intermediate A.
calcd. C48H28N2O: C, 88.87; H, 4.35; N, 4.32; O, 2.47; found: C, 88.87; H, 4.35; N, 4.32; O, 2.46.

Synthesis Example 35: Synthesis of Compound 169

Compound 169 (3.47 g, a yield of 63%) was obtained according to the same method as Compound 26 of Synthesis Example 41 except for using intermediate B instead of intermediate A.
calcd. C42H23NO2: C, 87.94; H, 4.04; N, 2.44; O, 5.58; found: C, 87.94; H, 4.03; N, 2.44; O, 5.58.

Synthesis Example 36: Synthesis of Compound 183

Compound 183 (3.81 g, a yield of 67%) was obtained according to the same method as Compound 55 of Synthesis Example 27 except for using intermediate B instead of intermediate A.
calcd. C42H23NOS: C, 85.54; H, 3.93; N, 2.38; O, 2.71; S, 5.44; found: C, 85.54; H, 3.93; N, 2.38; O, 2.70; S, 5.43.

Synthesis Example 37: Synthesis of Compound B-130

[Reaction Scheme 4]

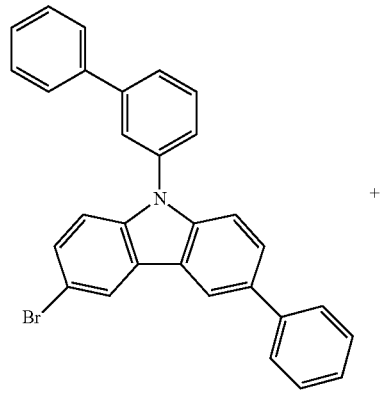

+

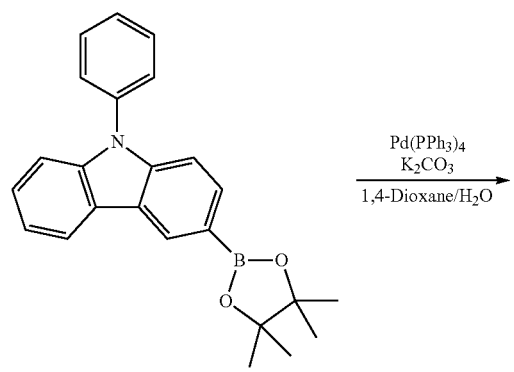

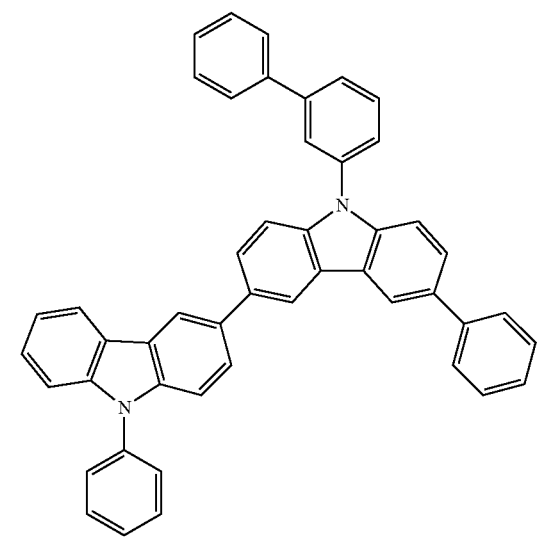

Compound B-130

20.00 g (42.16 mmol) of 3-bromo-6-phenyl-N-metabiphenylcarbazole, 17.12 g (46.38 mmol) of N-phenylcarbazole-3-boronic ester, and 175 mL of tetrahydrofuran and toluene (1:1) and 75 mL of a 2M-potassium carbonate aqueous solution under a nitrogen atmosphere in a 500 mL round-bottomed flask equipped with a stirrer, 1.46 g (1.26 mmol) of tetrakistriphenyl phosphine palladium (0) was added thereto, and the mixture was heated and refluxed under a nitrogen flow for 12 hours. When a reaction was complete, the reactant was poured into methanol, and a solid produced therein was filtered and then, sufficiently washed with water and methanol and dried. The obtained resulting material was heated with 700 mL of chlorobenzene and dissolved therein, and the solution was filtered with silica gel, and after completely removing the solvent, a solid obtained therefrom was heated with 400 mL of chlorobenzene and dissolved therein and then, recrystallized to obtain 18.52 g of Compound B-130 (a yield of 69%).
calcd. C42H32N2: C, 90.54; H, 5.07; N, 4.40; found: C, 90.54; H, 5.07; N, 4.40.

Manufacture of Organic Light Emitting Diode (Light Emitting Layer Device-Single Host)

Example 1

An organic light emitting diode was manufactured by using Compound 73 obtained in Synthesis Example 3 as a host and (piq)$_2$Ir(acac) as a dopant.

As for an anode, 1000 Å-thick ITO was used, and as for a cathode, 1000 Å-thick aluminum was used. Specifically, illustrating a method of manufacturing the organic light emitting diode, the anode was manufactured by cutting an ITO glass substrate having 15 Ω/cm$^2$ of a sheet resistance into a size of 50 mm×50 mm×0.7 mm, ultrasonic wave-cleaning them in each acetone, isopropyl alcohol, and pure water for 15 minutes respectively, and UV ozone cleaning them for 30 minutes.

On the substrate, an 800 Å-thick hole transport layer was formed by depositing N4,N4'-di(naphthalen-1-yl)-N,N4'-diphenylbiphenyl-4,4'-diamine (NPB) (80 nm) under a vacuum degree of 650×10$^{-7}$ Pa at a deposition rate of 0.1 to 0.3 nm/s. Subsequently, a 300 Å-thick light emitting layer was formed by using Compound 73 of Synthesis Example 3 under the same vacuum deposition condition, and a phosphorescent dopant of (piq)$_2$Ir(acac) was simultaneously deposited. Herein, the phosphorescent dopant was deposited to be 3 wt % based on 100 wt % of a total weight of the light emitting layer by adjusting the deposition rate.

On the light emitting layer, a 50 Å-thick hole blocking layer was formed by depositing bis(2-methyl-8-quinolinolate)-4-(phenylphenolato)aluminum (BAlq) under the same vacuum deposition condition. Subsequently, a 200 Å-thick electron transport layer was formed by depositing Alq3 under the same vacuum deposition condition. On the electron transport layer, a cathode was formed by sequentially depositing LiF and Al to manufacture an organic light emitting diode.

A structure of the organic light emitting diode was ITO/NPB (80 nm)/EML (Compound 73 (97 wt %)+(piq)$_2$Ir(acac) (3 wt %), 30 nm)/Balq (5 nm)/Alq$_3$ (20 nm)/LiF (1 nm)/Al (100 nm).

Examples 2 to 16

Organic light emitting diodes according to Examples 2 to 16 were respectively manufactured according to the same method as Example 1 except for using each of Compound 74, Compound 75, Compound 79, Compound 84, Compound 88, Compound 93, Compound 114, Compound 201, Compound 202, Compound 203, Compound 207, Compound 212, Compound 216, Compound 221, and Compound 242 instead of Compound 73 as a host for forming a light emitting layer.

Comparative Example 1

An organic light emitting diode according to Comparative Example 1 was manufactured according to the same method as Example 1 except for using a compound of Comparative Structure Example 1 instead of Compound 41 as a host for forming a light emitting layer. Simulation data of Compound 73 of Example 1 and Comparative Structure Example 1 of Comparative Example 1 were shown in Table 1.

Comparative Structure Example 1

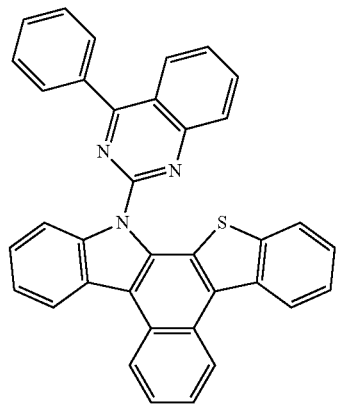 [SMILES: c1ccc(-c2nc(-n3c4ccccc4c4c5ccccc5c5c6ccccc6sc5c43)nc3ccccc23)cc1]

TABLE 1

| | HOMO (eV) | LUMO (eV) | T1 (eV) | S1 (eV) |
|---|---|---|---|---|
| Comparative Structure Example 1 | −5.17 | −2.11 | 2.347 | 2.595 |
| Compound 73 | −5.075 | −2.105 | 2.272 | 2.49 |

Referring to Table 1, Compound 73 showed a more shallow HOMO Level than that of Comparative Structure Example 1. The reason is that the HOMO level of Compound 73 is closer to that of a dopant than that of Comparative Structure Example 1, and thus holes may be more injected. Accordingly, Compound 49 may have a better balance between holes and electrons and thus have a fast driving voltage and show high efficiency, long life-span device characteristics.

Evaluation Example 1: Characteristics Evaluation (I) of Organic Light Emitting Diode Luminous efficiency and life-span characteristics of each organic light emitting diode according to Examples 1 to 16 and Comparative Example 1 were evaluated.

Specific measurement methods are as follows, and the results are shown in Table 2.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by area to provide the results.

(2) Measurement of Luminance Change Depending on Voltage Change

Luminance was measured by using a luminance meter (Minolta Cs-1000A), while the voltages of the organic light emitting diodes were increased from 0 V to 10 V.

(3) Measurement of Luminous Efficiency

Current efficiency (cd/A) at the same current density (10 mA/cm$^2$) were calculated by using the luminance, current density, and voltages (V) from the items (1) and (2).

(4) Measurement of Driving Voltage

A driving voltage of each diode was measured using a current-voltage meter (Keithley 2400) at 15 mA/cm$^2$.

TABLE 2

| Nos. | Compound | Driving voltage (V) | Current efficiency (cd/A) | Color (EL color) |
|---|---|---|---|---|
| Example 1 | 73 | 4.3 | 20.3 | Red |
| Example 2 | 74 | 4.1 | 20.5 | Red |
| Example 3 | 75 | 4.1 | 20.5 | Red |
| Example 4 | 79 | 4.3 | 20.1 | Red |
| Example 5 | 84 | 4.4 | 20.4 | Red |
| Example 6 | 88 | 4.2 | 20.3 | Red |
| Example 7 | 93 | 4.3 | 20.0 | Red |
| Example 8 | 114 | 4.5 | 20.7 | Red |
| Example 9 | 201 | 4.5 | 20.2 | Red |
| Example 10 | 202 | 4.3 | 20.3 | Red |
| Example 11 | 203 | 4.3 | 20.6 | red |
| Example 12 | 207 | 4.4 | 20.0 | Red |
| Example 13 | 212 | 4.5 | 20.4 | Red |
| Example 14 | 216 | 4.4 | 20.3 | Red |
| Example 15 | 221 | 4.6 | 20.1 | Red |
| Example 16 | 242 | 4.5 | 20.4 | Red |
| Comparative Example 1 | Comparative Structure Example 1 | 5.3 | 17.1 | Red |

Referring to Table 2, the organic light emitting diodes of Examples 1 to 16 of the present disclosure showed a low driving voltage and high efficiency compared with that of Comparative Example 1.

Accordingly, the compound according to the present invention have excellent charge the characteristics and well overlapping with an absorption spectrum of the dopant as a phosphorescent host material and thus may improve performance such as an efficiency increase and a driving voltage decrease and exhibit maximized capability as an OLED material.

Manufacture of Organic Light Emitting Diode (II) (Light Emitting Layer Device-Mixed Host)

Example 17

An organic light emitting diode was manufactured according to the same method as Example 1 except for forming a 400 Å-thick light emitting layer by codepositing (piq)$_2$Ir(acac) (a dopant), Compound 73 (a first host), and Compound B-137 (a second host) in a weight ratio of 3:48.5:48.5 on a hole transport layer.

Examples 18 to 23

Organic light emitting diodes according to Examples 18 to 23 were respectively manufactured according to the same method as Example 17 except for using each of Compound 74, Compound 75, Compound 88, Compound 202, Compound 203, and Compound 216 instead of Compound 73 as the first host to form the light emitting layer.

Example 24

An organic light emitting diode was manufactured according to the same method as Example 17 except for codepositing (piq)$_2$Ir(acac) (dopant), Compound 75 (a first host), and Compound 2 (a second host) in a weight ratio of 3:48.5:48.5 to form a 400 Å-thick light emitting layer on a hole transport layer.

Examples 25 to 30

Organic light emitting diodes according to Examples 25 to 30 were manufactured according to the same method as Example 24 except for using each of Compound 3, Compound 23, Compound 25, Compound 55, Compound 134, and Compound 156 as the second host instead of Compound 2 to form a light emitting layer.

Evaluation Example 2: Characteristics Evaluation (II) of Organic Light Emitting Diode A driving voltage, efficiency, luminance, and a life-span of each organic light emitting diode according to Examples 17 to 30 and Comparative Example 1 were measured by supplying power from a current voltage meter (Kethley SMU 236) and using a luminance meter, PR650 Spectroscan Source Measurement Unit (Photo Research Inc.) according to the same method as Evaluation Example 1. The results are shown in Table 3.

TABLE 3

| Examples | First host | Second host | Driving Voltage (V) | Current efficiency (cd/A) | Color (EL color) |
|---|---|---|---|---|---|
| 17 | 73 | B-137 | 4.0 | 21.4 | red |
| 18 | 74 | B-137 | 3.9 | 21.2 | red |
| 19 | 75 | B-137 | 3.8 | 21.2 | red |
| 20 | 88 | B-137 | 4.0 | 20.8 | red |
| 21 | 202 | B-137 | 4.2 | 21.0 | red |
| 22 | 203 | B-137 | 4.1 | 21.2 | red |
| 23 | 216 | B-137 | 4.4 | 20.3 | red |
| 24 | 75 | 2 | 4.1 | 20.9 | red |
| 25 | 75 | 3 | 4.2 | 20.8 | red |
| 26 | 75 | 23 | 4.5 | 20.6 | red |
| 27 | 75 | 25 | 4.4 | 20.3 | red |
| 28 | 75 | 55 | 3.9 | 21.5 | red |
| 29 | 75 | 134 | 4.0 | 20.5 | red |
| 30 | 75 | 156 | 4.0 | 21.0 | red |
| Comparative Example 1 | Comparative Structure Example 1 | | 5.3 | 17.1 | red |

Referring to Table 3, the organic light emitting diodes of Examples 17 to 30 using both first and second host materials which were the compounds of the present disclosure showed low driving voltages or high efficiency.

DESCRIPTION OF SYMBOLS

100, 200: organic light emitting diode
105: organic layer
110: cathode
120: anode
130: light emitting layer
140: hole auxiliary layer Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A compound for an organic optoelectric device represented by Chemical Formula 1:

[Chemical Formula 1]

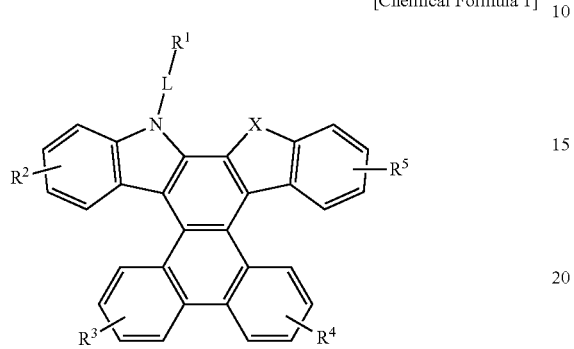

wherein, in Chemical Formula 1,

X is O, S, $CR^6R^7$, or $SiR^8R^9$, $R^1$ is a substituted or unsubstituted C6 to C30 aryl group, a substituted or unsubstituted C2 to C30 heterocyclic group, or a combination thereof, $R^2$ to $R^9$ are independently hydrogen, deuterium, a substituted or unsubstituted C1 to C20 alkyl group, a substituted or unsubstituted C6 to C30 aryl group, a substituted or unsubstituted C2 to C30 heterocyclic group, or a combination thereof, L is a single bond, a substituted or unsubstituted C6 to C30 arylene group, a substituted or unsubstituted C2 to C30 heteroarylene group, or a combination thereof, and the "substituted" refers to replacement of at least one hydrogen by deuterium, a C1 to C4 alkyl group, a C6 to C18 aryl group, or a C2 to C18 heteroaryl group.

2. The compound for an organic optoelectric device of claim 1, wherein $R^1$ is a substituted or unsubstituted phenyl group, a substituted or unsubstituted biphenyl group, a substituted or unsubstituted terphenyl group, a substituted or unsubstituted naphthyl group, a substituted or unsubstituted phenanthrenyl group, a substituted or unsubstituted triphenylene group, a substituted or unsubstituted fluorenyl group, a substituted or unsubstituted fluoranthenyl group, a substituted or unsubstituted carbazolyl group, a substituted or unsubstituted dibenzofuranyl group, a substituted or unsubstituted dibenzothiophenyl group, a substituted or unsubstituted pyridinyl group, a substituted or unsubstituted pyrimidinyl group, a substituted or unsubstituted triazinyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzofuranpyrimidinyl group, a substituted or unsubstituted benzothiophenepyrimidinyl group, or a substituted or unsubstituted phenanthrolinyl group.

3. The compound for an organic optoelectric device of claim 1, wherein $R^1$ is selected from substituents of Group I:

[Group I]

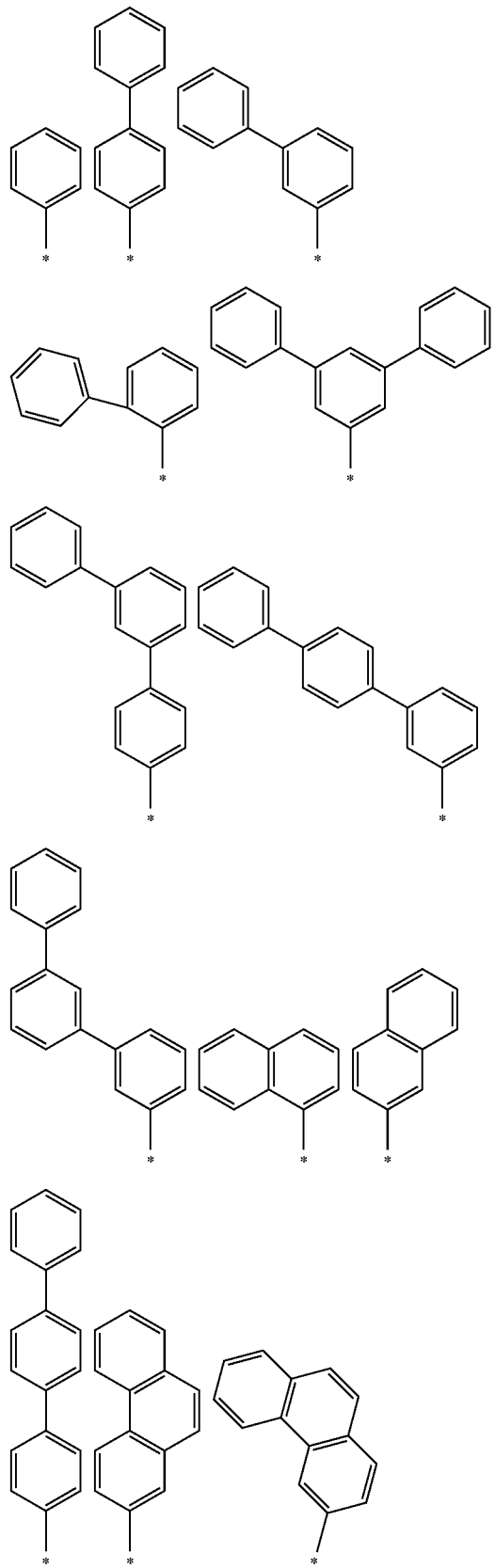

-continued
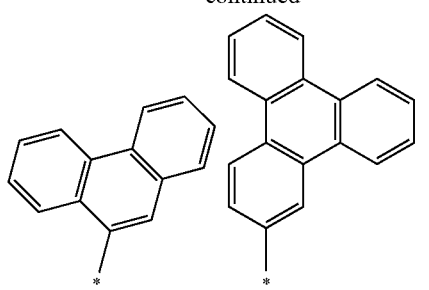
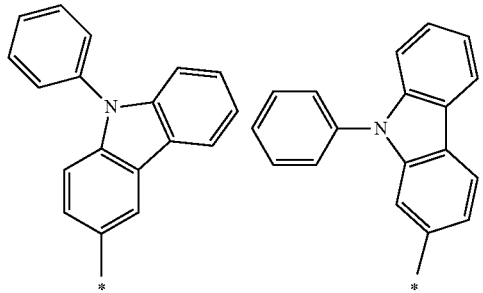
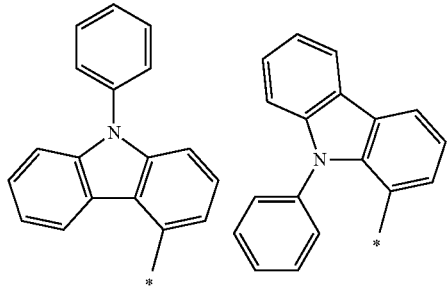
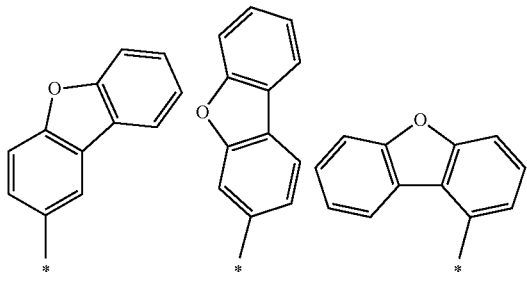
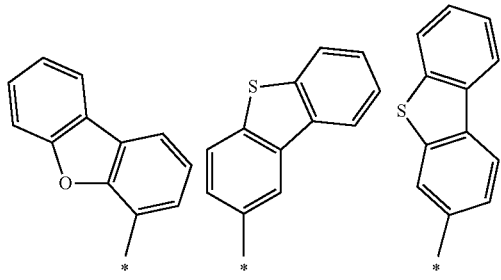
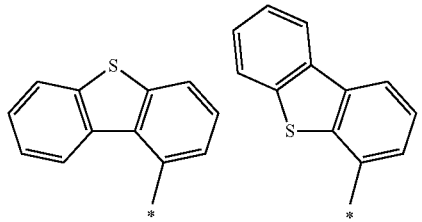
-continued
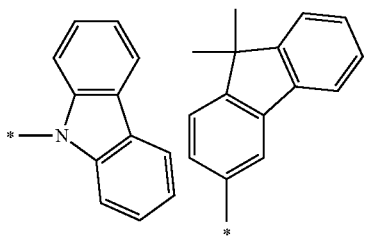
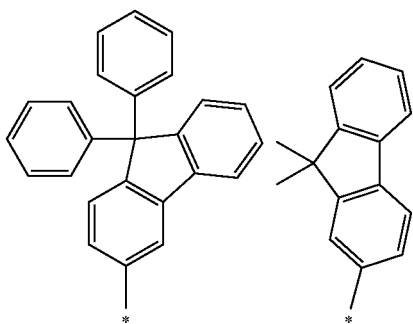
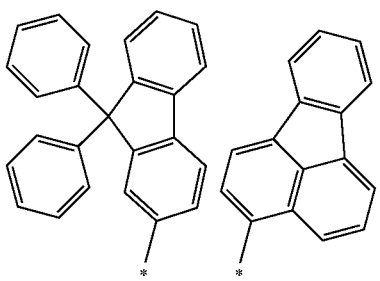
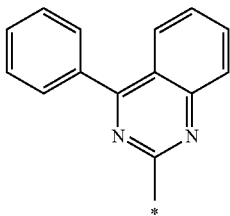
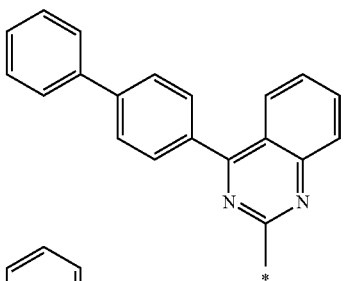
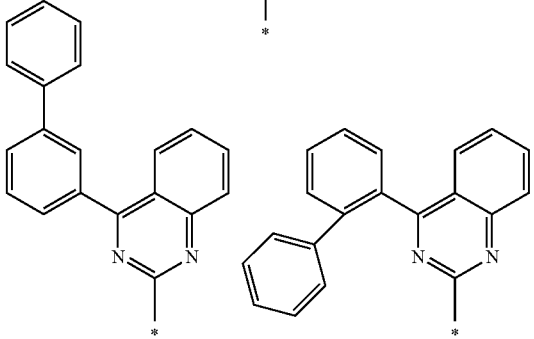

201
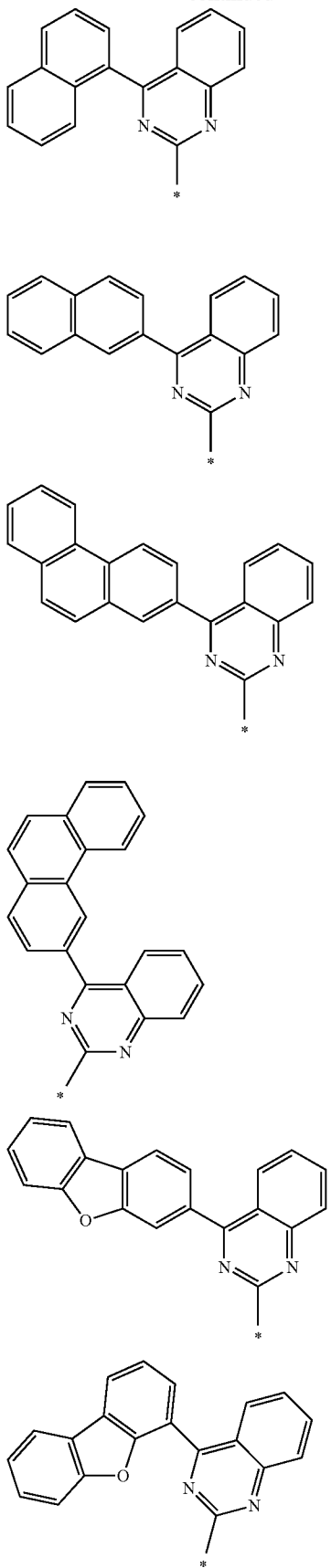
202
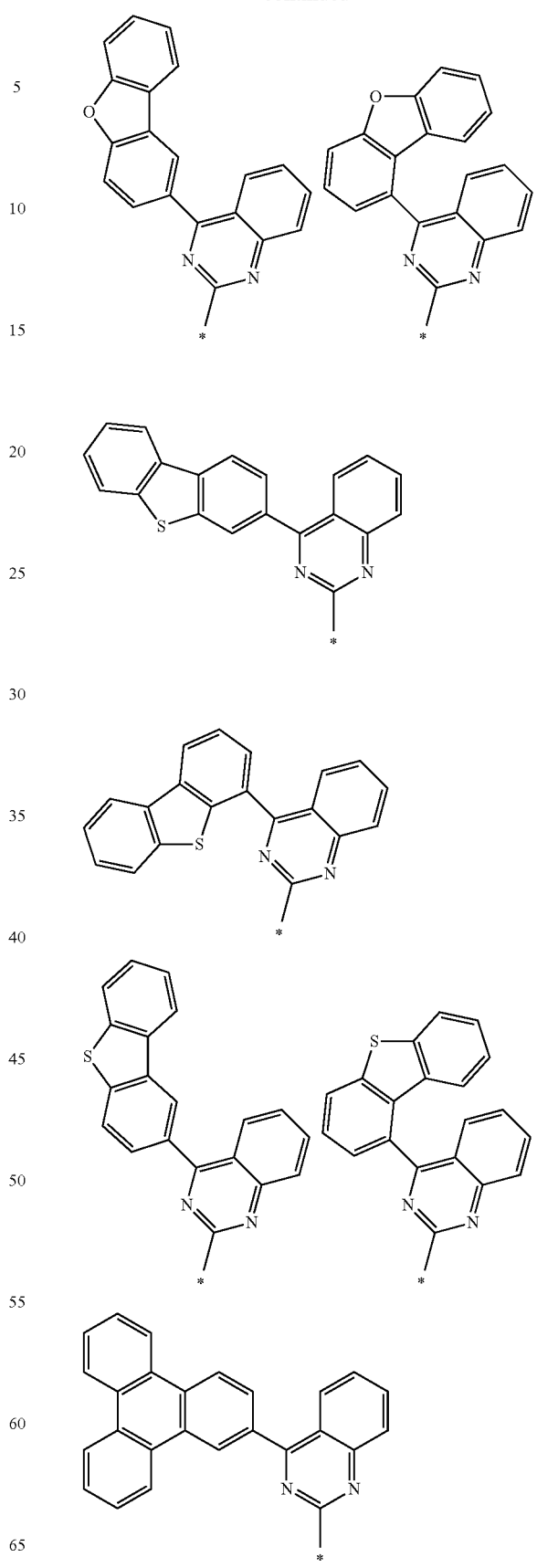

-continued
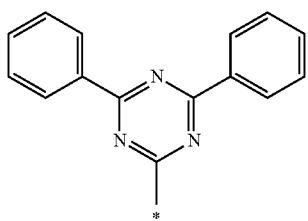
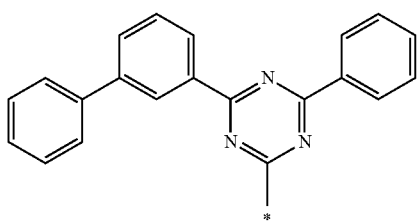
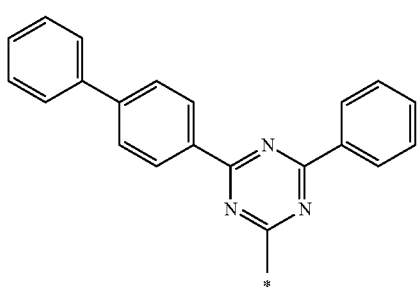
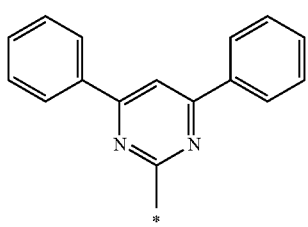
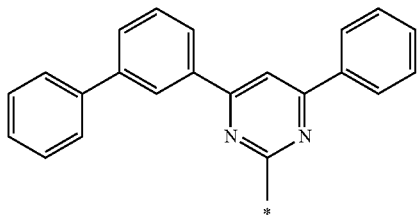
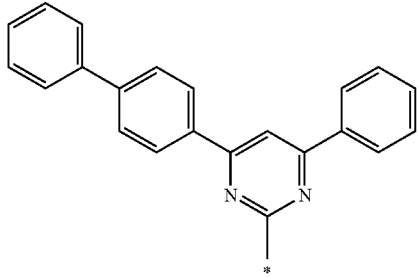
-continued
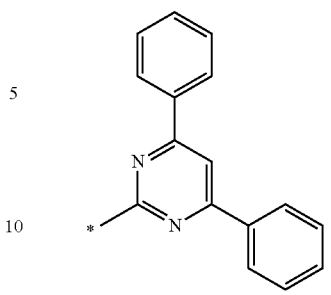
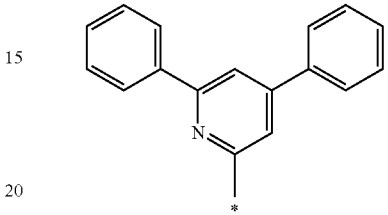
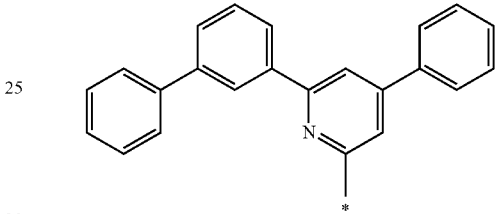
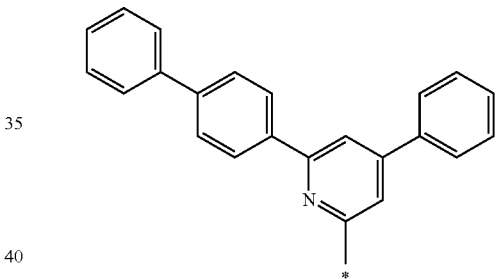
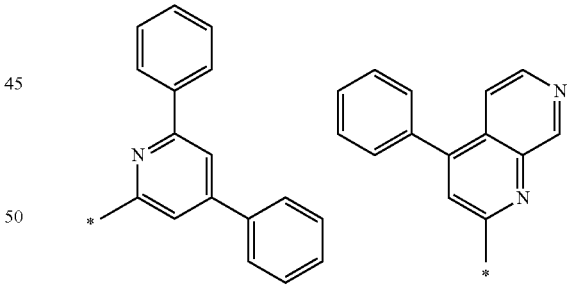
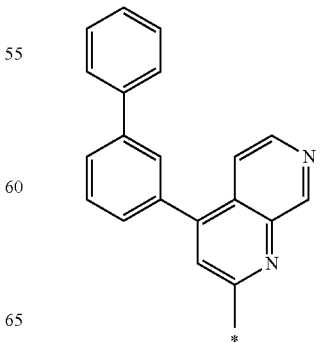

205
-continued
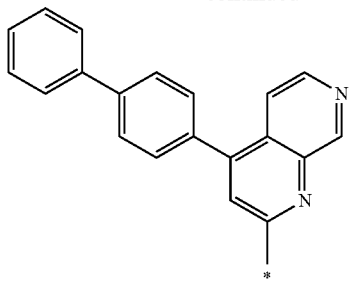
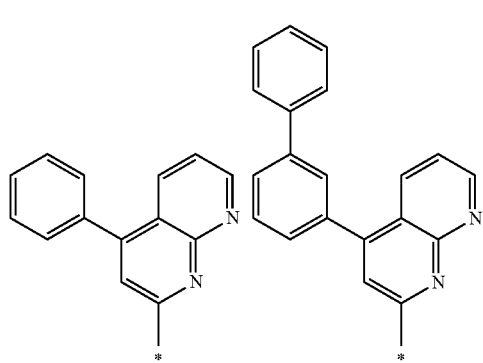
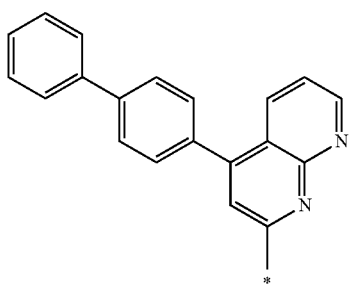
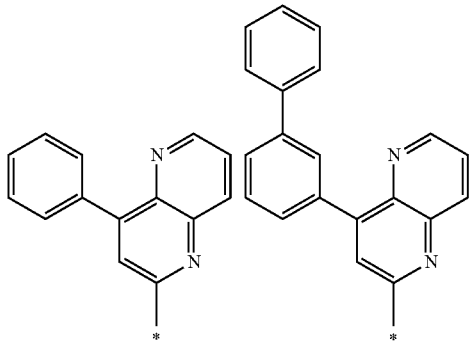
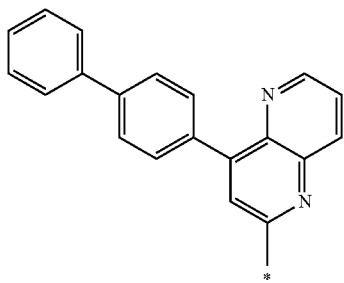
206
-continued
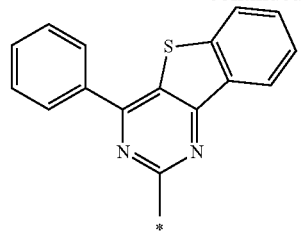
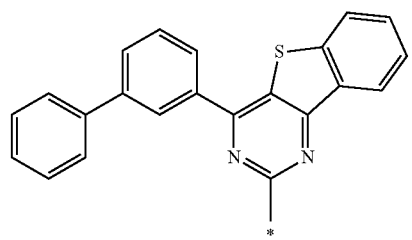
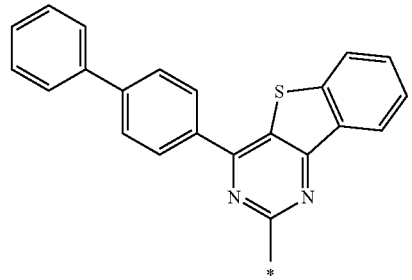
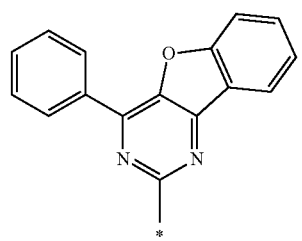
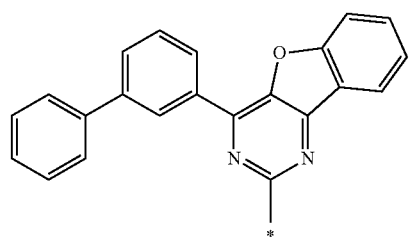
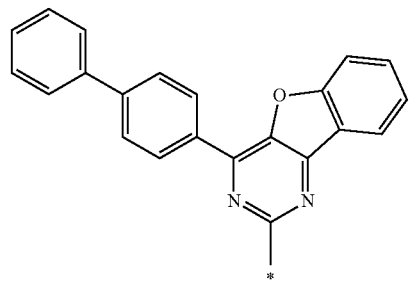

-continued

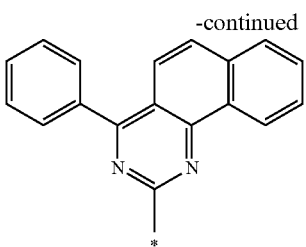
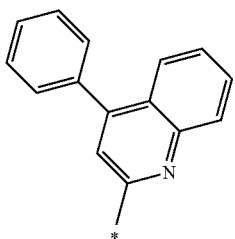
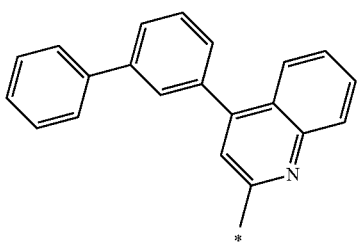
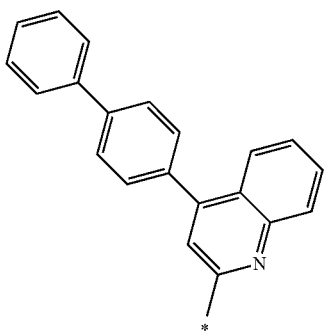
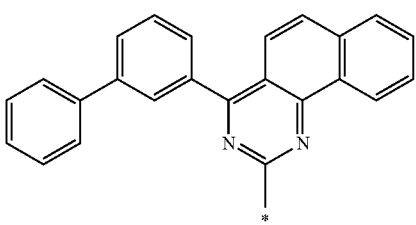
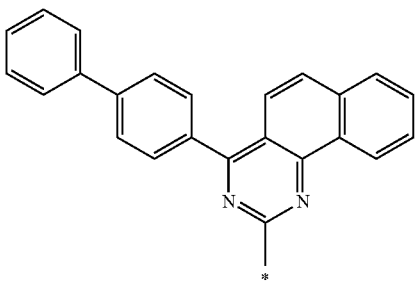

-continued

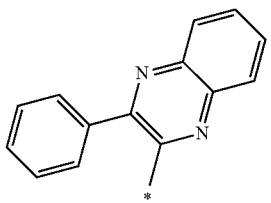
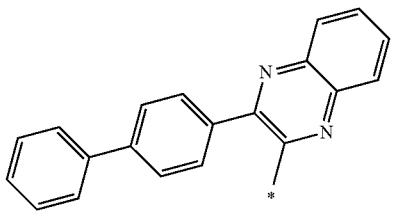
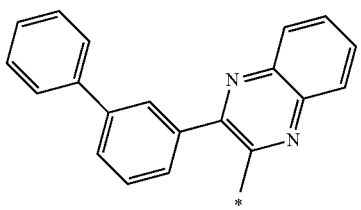

wherein, in Group I, * is a binding site with an adjacent atom.

4. The compound for an organic optoelectric device of claim 1, wherein X is O or S, $R^1$ is a substituted or unsubstituted phenyl group, a substituted or unsubstituted biphenyl group, a substituted or unsubstituted terphenyl group, a substituted or unsubstituted phenanthrenyl group, a substituted or unsubstituted triphenylene group, a substituted or unsubstituted carbazolyl group, a substituted or unsubstituted dibenzofuranyl group, a substituted or unsubstituted dibenzothiophenyl group, a substituted or unsubstituted triazinyl group, a substituted or unsubstituted quinazolinyl group, a substituted or unsubstituted benzofuranpyrimidinyl group, or a substituted or unsubstituted benzothiophenepyrimidinyl group, L is a single bond, a substituted or unsubstituted quinazolinylene group, a substituted or unsubstituted dibenzofuranpyrimidinylene group, or a substituted or unsubstituted dibenzothiophenepyrimidinylene group, $R^2$ to $R^5$ are hydrogen, and the "substituted" refers to replacement of at least one hydrogen by deuterium, a C1 to C4 alkyl group, a phenyl group, a biphenyl group, a naphthyl group, a phenanthrenyl group, a triphenylene group, a fluoranthenyl group, a carbazolyl group, a dibenzofuranyl group, a dibenzothiophenyl group, a pyridinyl group, a pyrimidinyl group, or triazinyl group.

5. The compound for an organic optoelectric device of claim 1, wherein the compound is represented by Chemical Formula 1A or Chemical Formula 1B:

[Chemical Formula 1A]

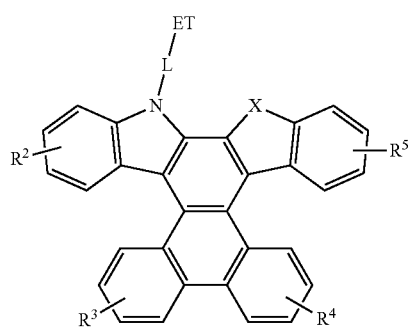

[Chemical Formula 1B]

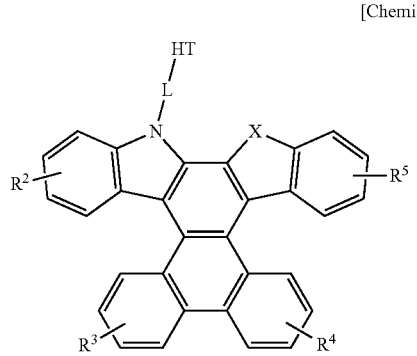

wherein, in Chemical Formula 1A and Chemical Formula 1B,

X is O, or S,

ET is a substituted or unsubstituted pyridinyl group, a substituted or unsubstituted pyrimidinyl group, a substituted or unsubstituted triazinyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzofuranpyrimidinyl group, a substituted or unsubstituted benzothiophenepyrimidinyl group, or a substituted or unsubstituted phenanthrolinyl group, HT is a substituted or unsubstituted phenyl group, a substituted or unsubstituted biphenyl group, a substituted or unsubstituted terphenyl group, a substituted or unsubstituted naphthyl group, a substituted or unsubstituted phenanthrenyl group, a substituted or unsubstituted triphenylene group, a substituted or unsubstituted fluorenyl group, a substituted or unsubstituted fluoranthenyl group, a substituted or unsubstituted carbazolyl group, a substituted or unsubstituted dibenzofuranyl group, or a substituted or unsubstituted dibenzothiophenyl group, $R^2$ to $R^9$ are independently hydrogen, deuterium, a substituted or unsubstituted C1 to C20 alkyl group, a substituted or unsubstituted C6 to C30 aryl group, a substituted or unsubstituted C2 to C30 heterocyclic group, or a combination thereof, and L is a single bond, a substituted or unsubstituted C6 to C30 arylene group, a substituted or unsubstituted C2 to C30 heteroarylene group, or a combination thereof.

6. The compound for an organic optoelectric device of claim 1, wherein the compound is selected from compounds of Group 1:

[Group 1]

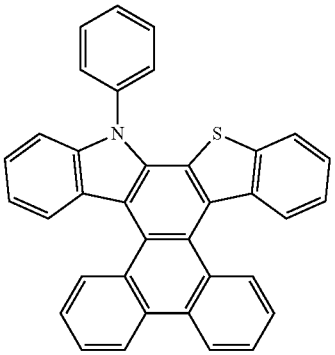

1

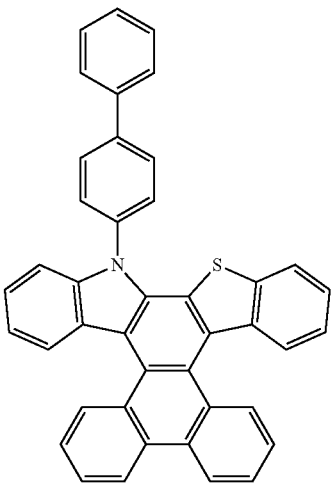

2

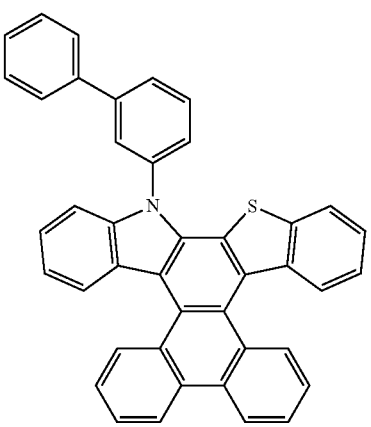

3

211
-continued
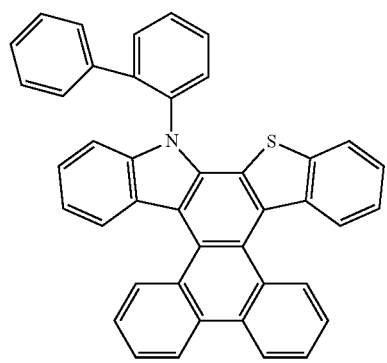
4
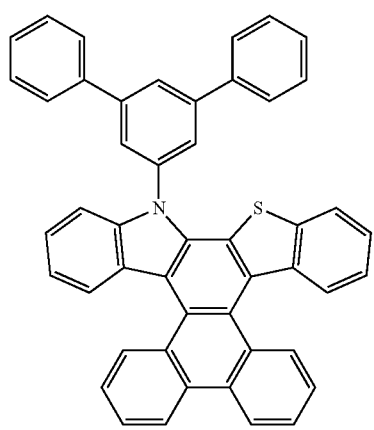
5
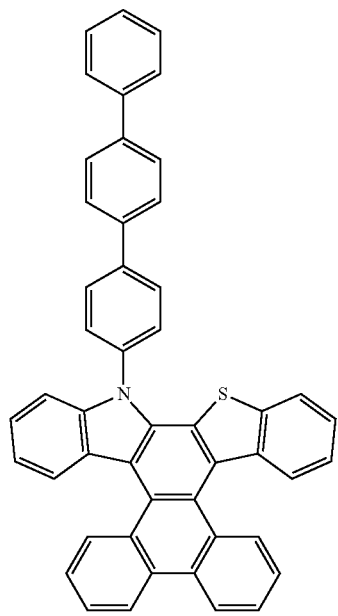
6
212
-continued
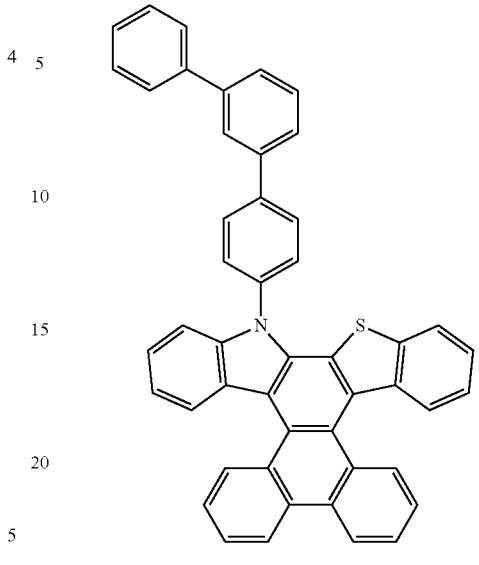
7
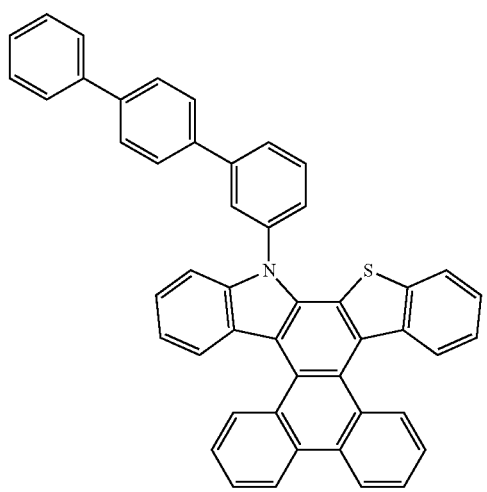
8
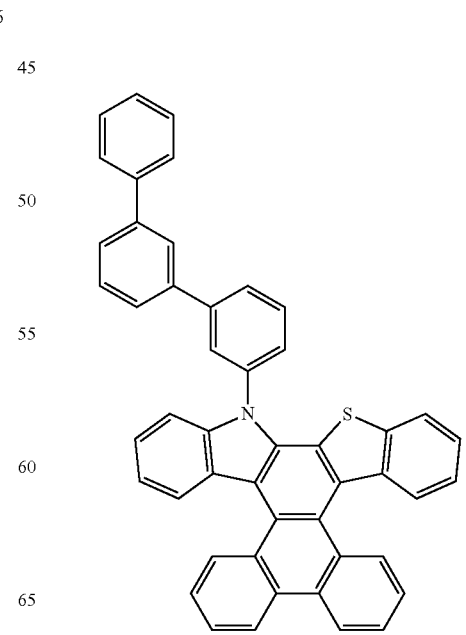
9

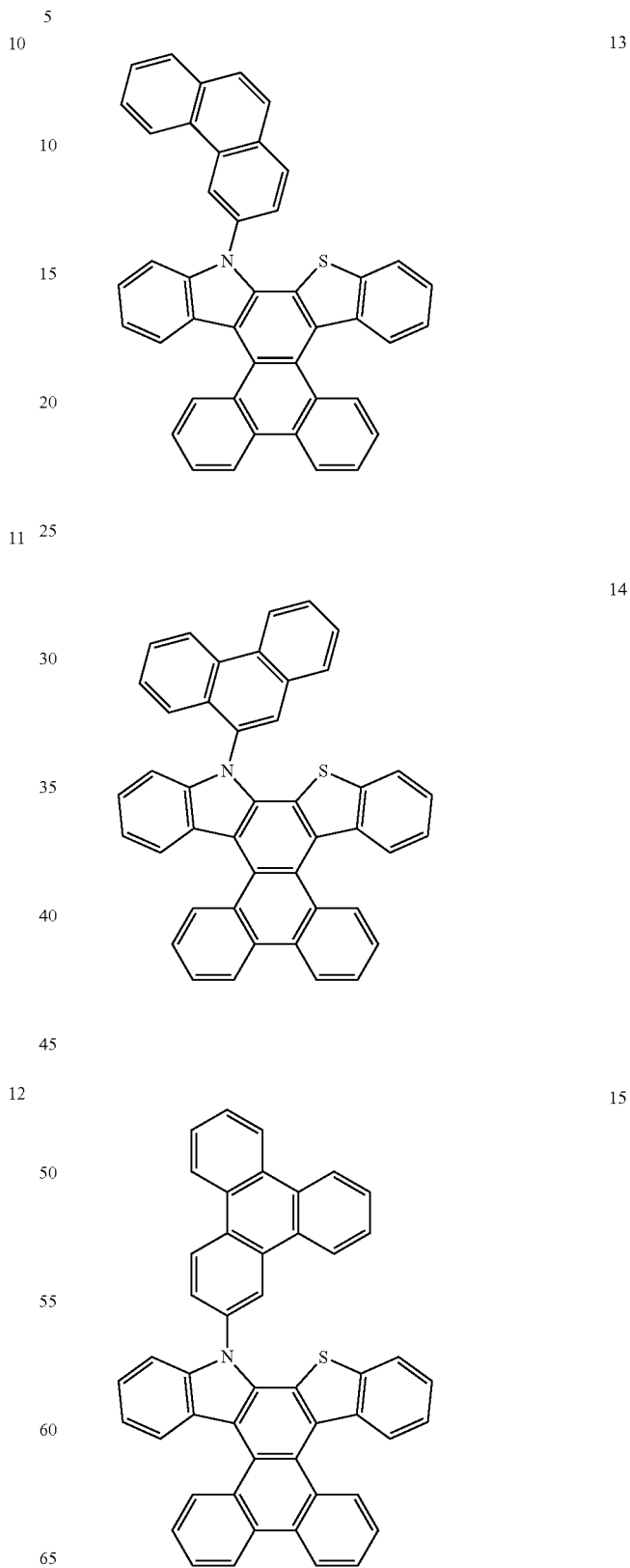

215
-continued
216
-continued
16
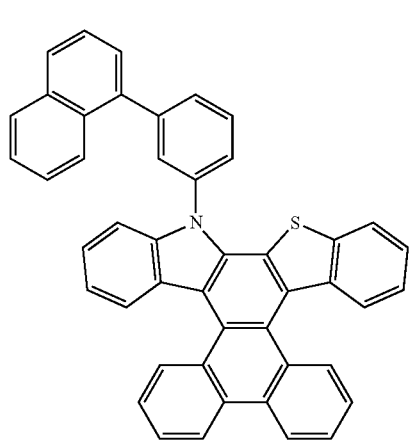
19
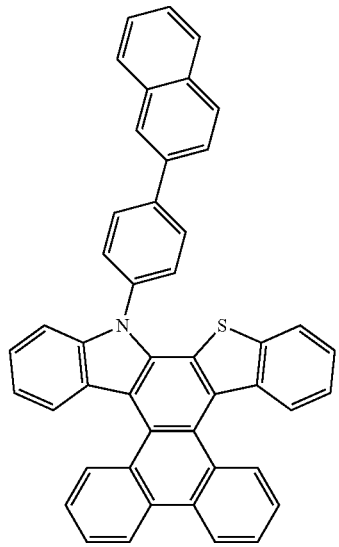
17
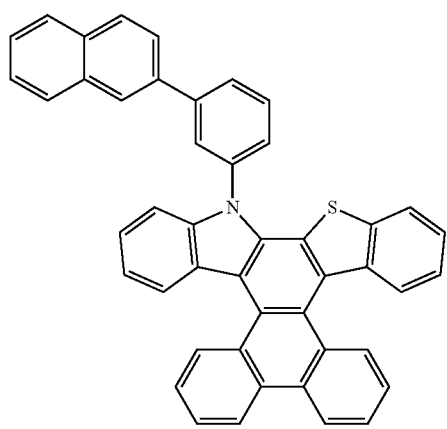
20
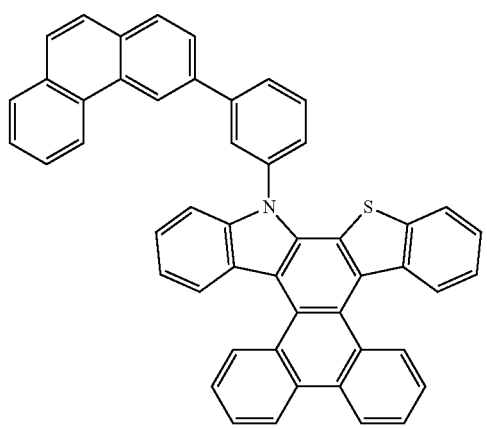
18
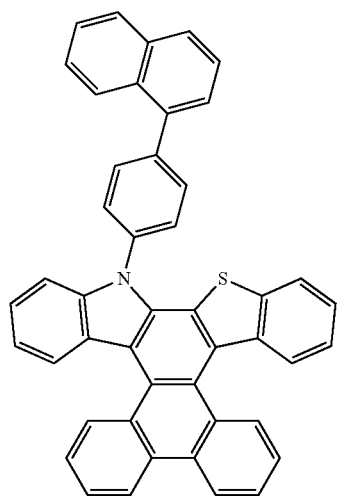
21
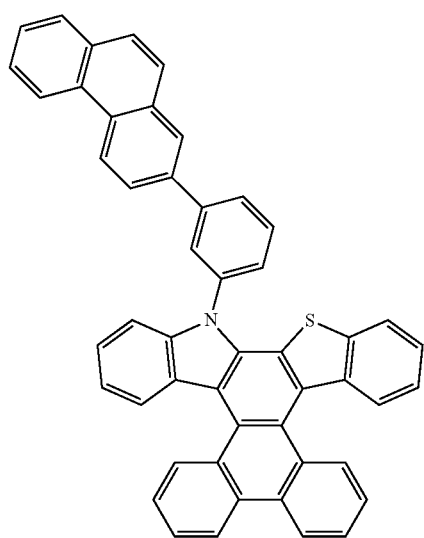

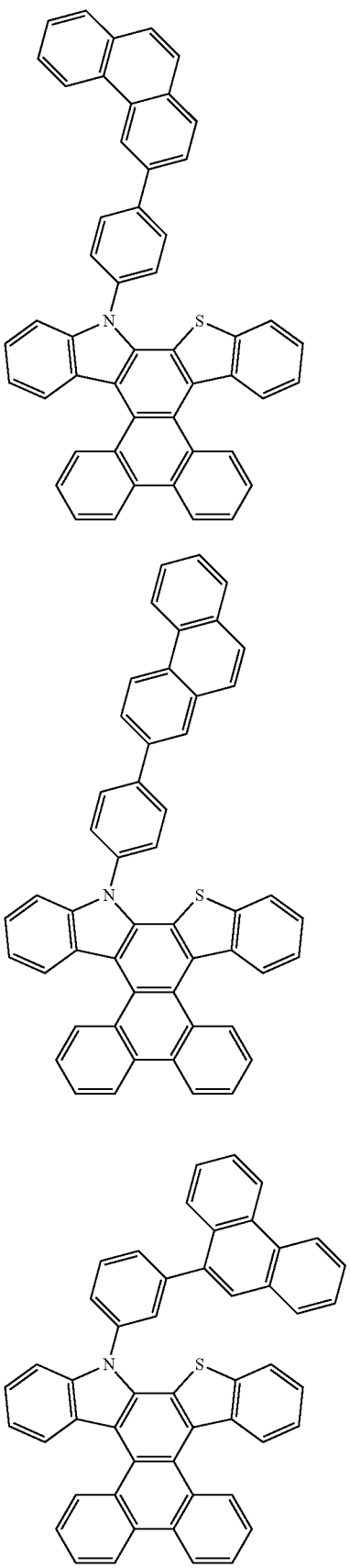
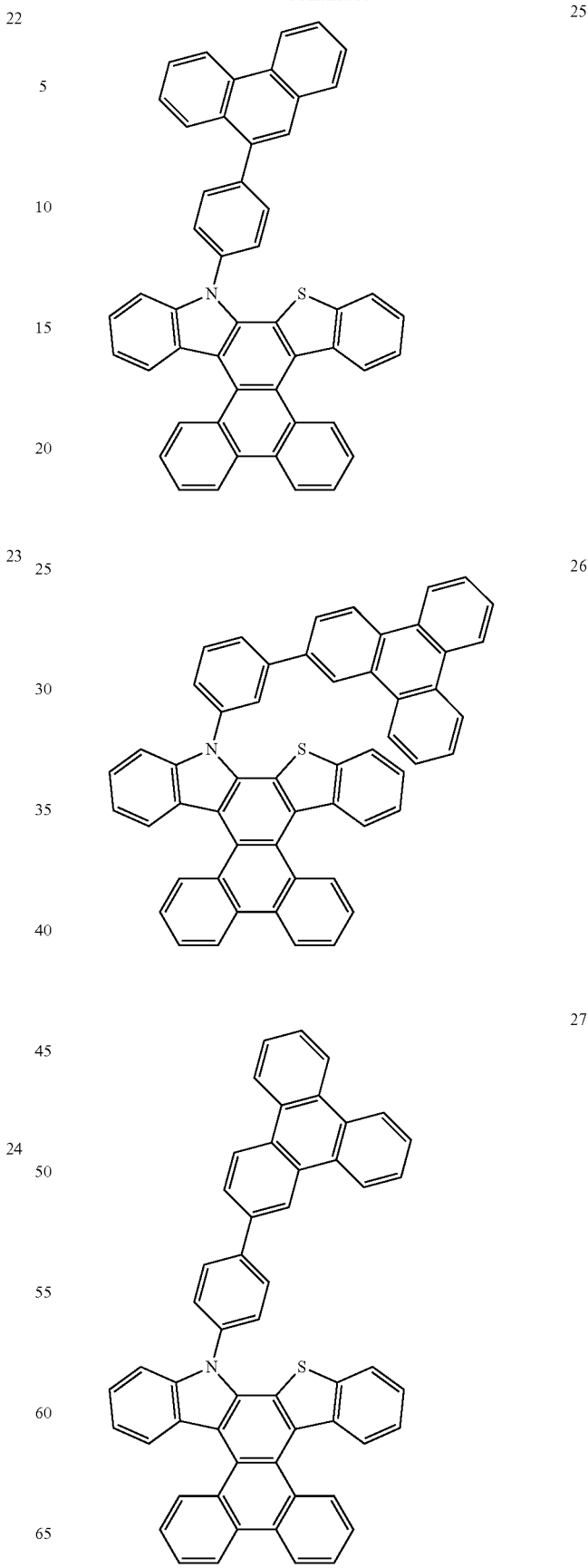

219
-continued
28
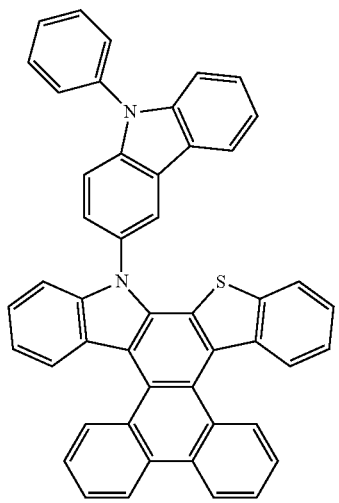
29
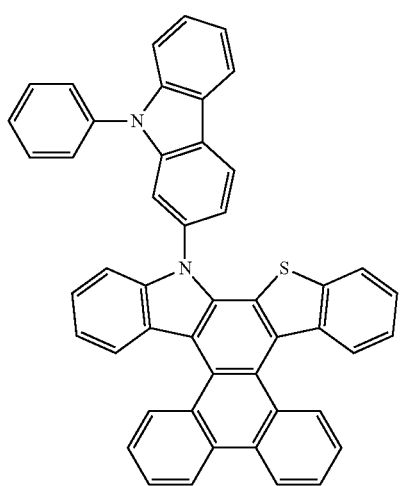
30
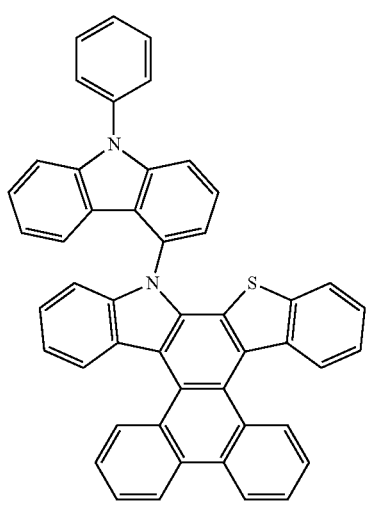
220
-continued
31
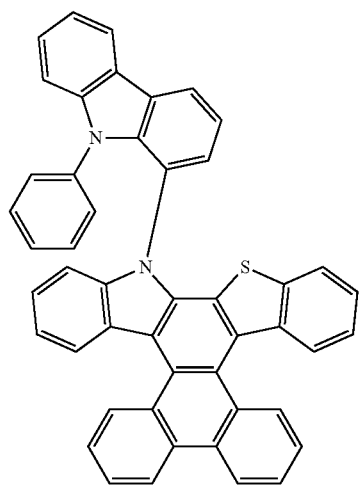
32
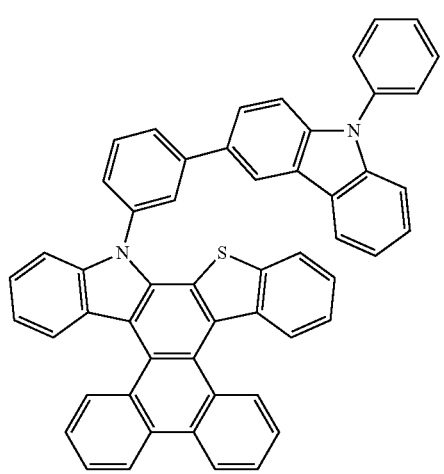
33
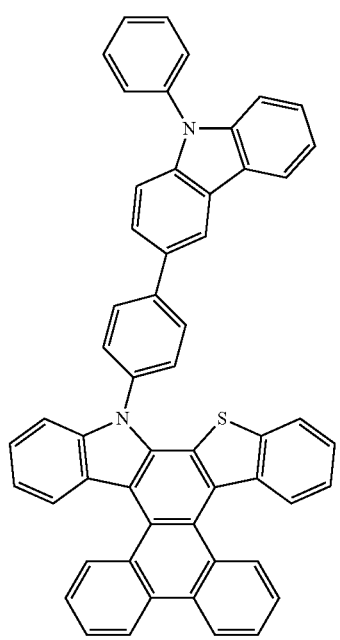

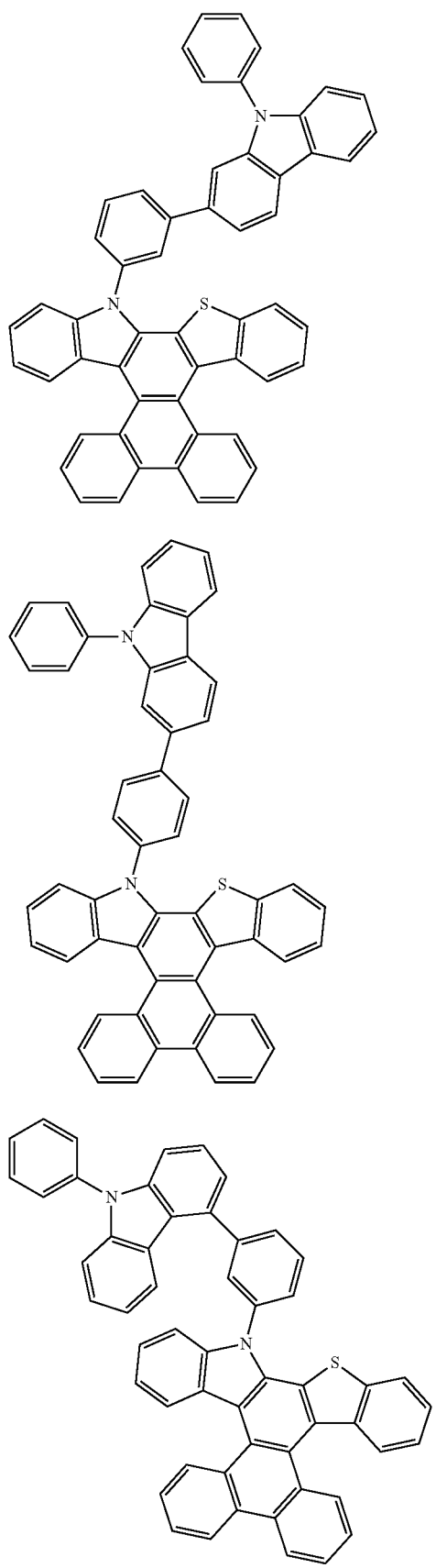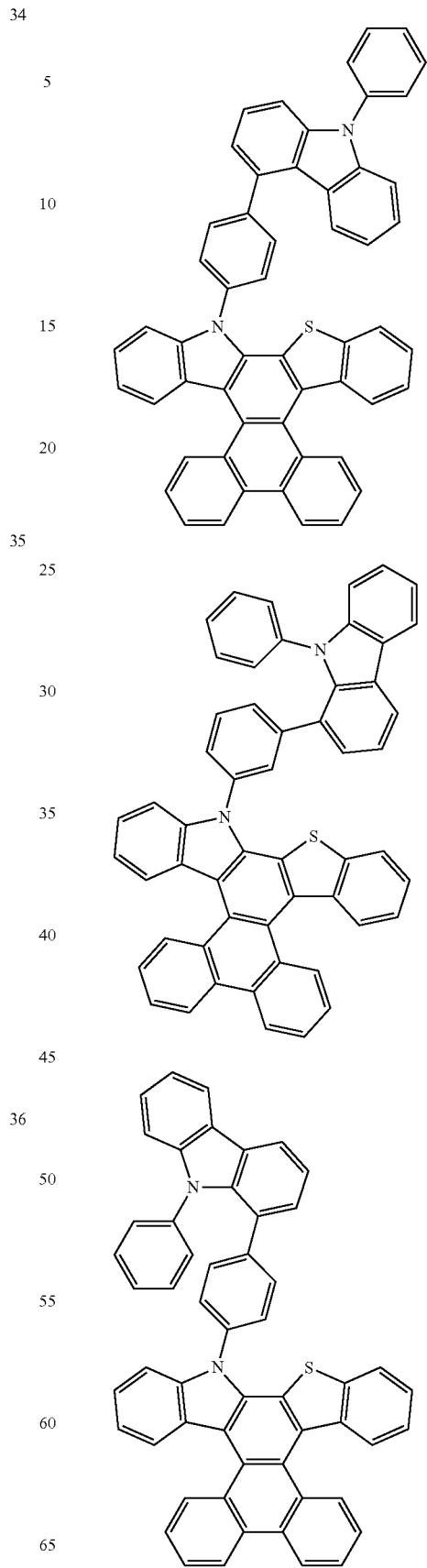

223
-continued
224
-continued
40
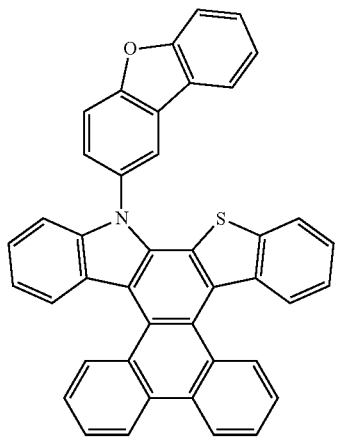
41
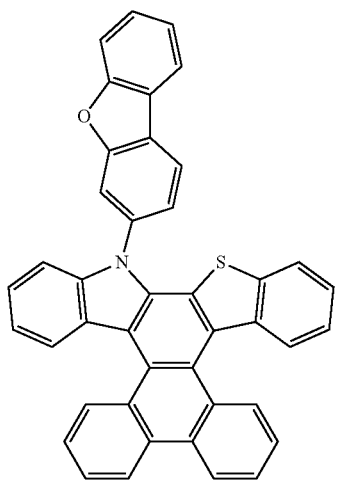
42
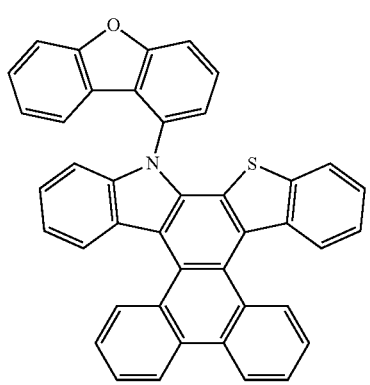
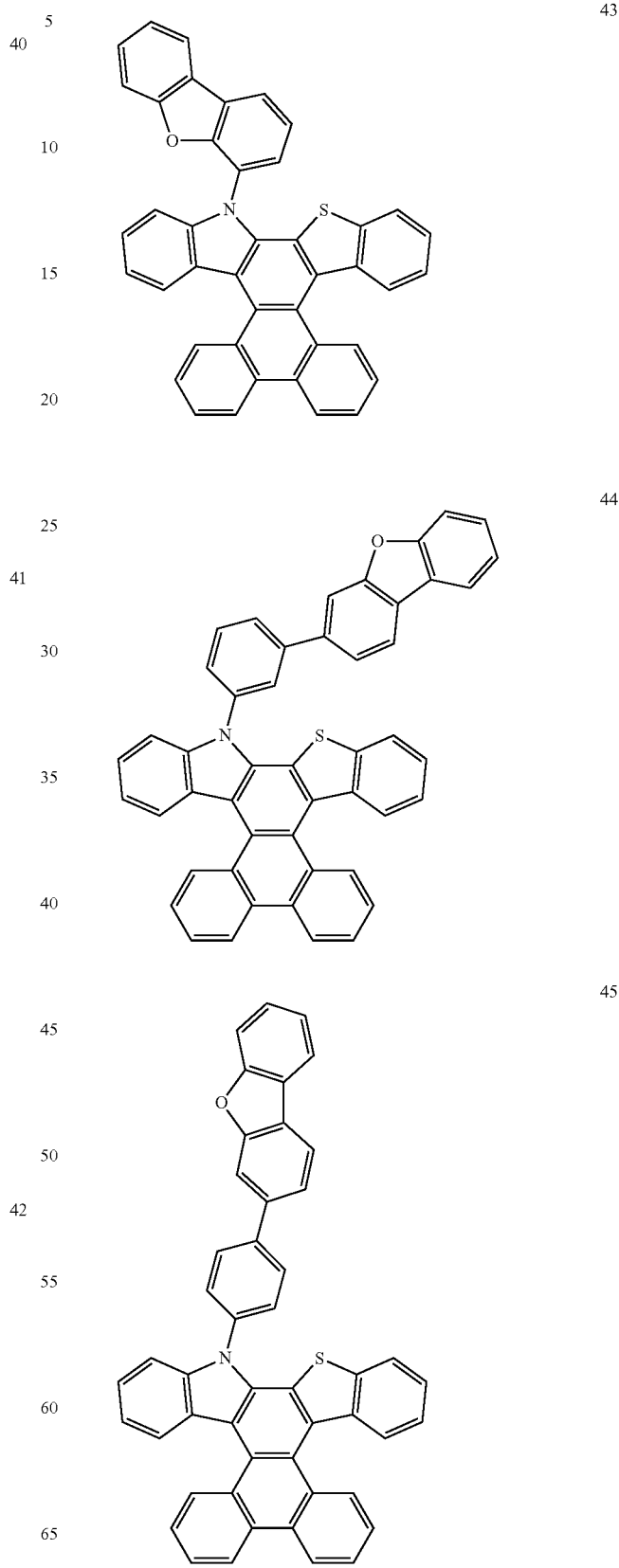

46
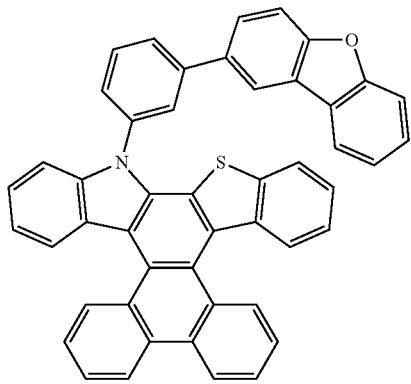
47
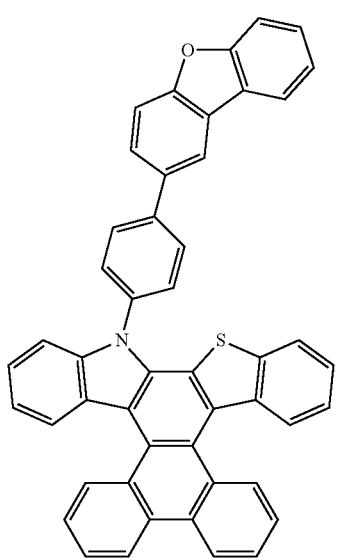
48
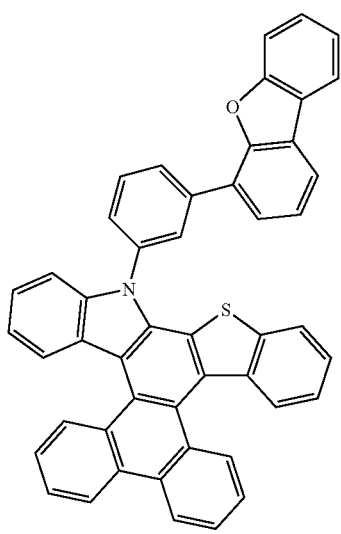
49
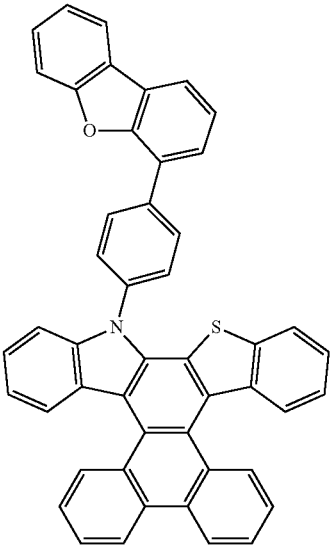
50
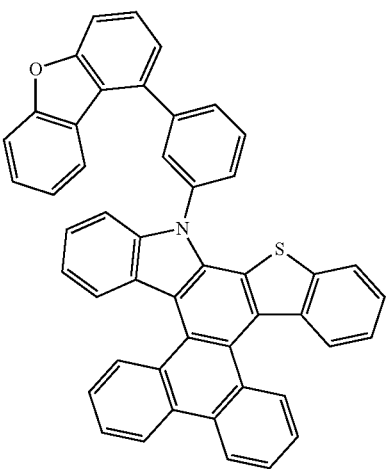
51
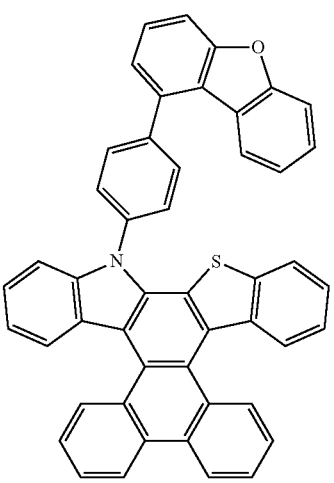

227
-continued
228
-continued
52
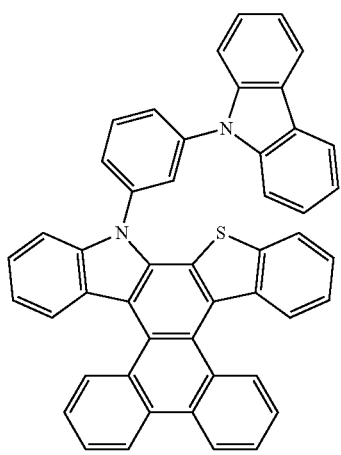
53
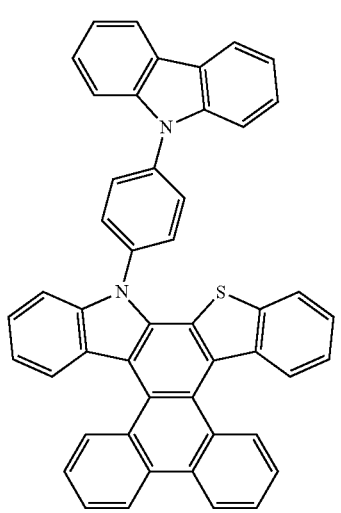
54
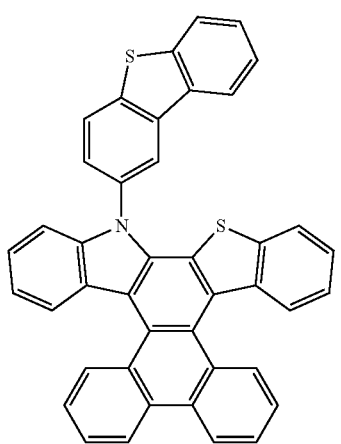
55
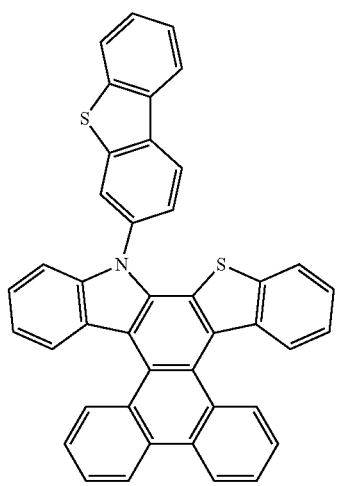
56
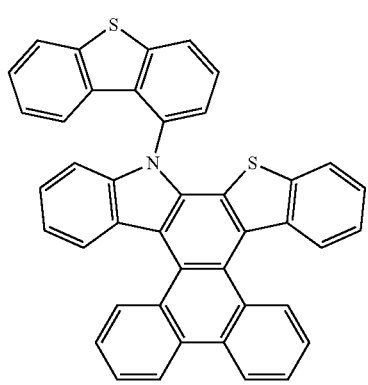
57
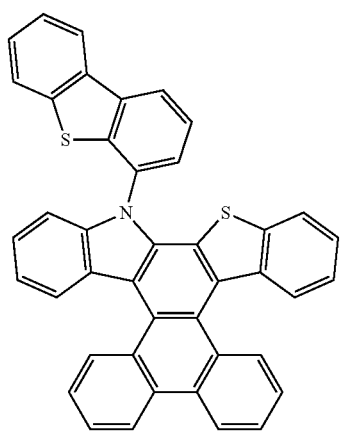

58
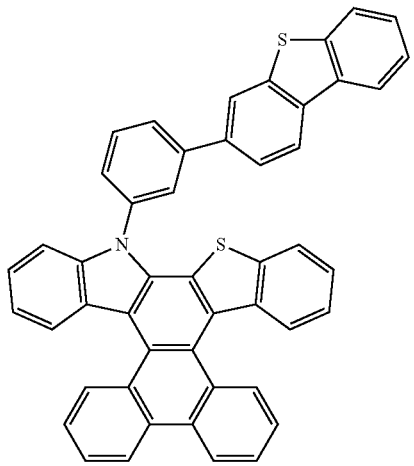
59
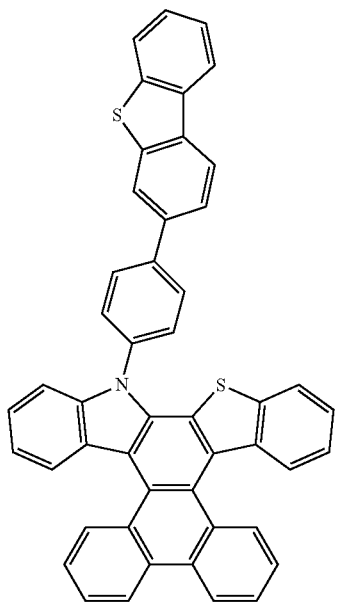
60
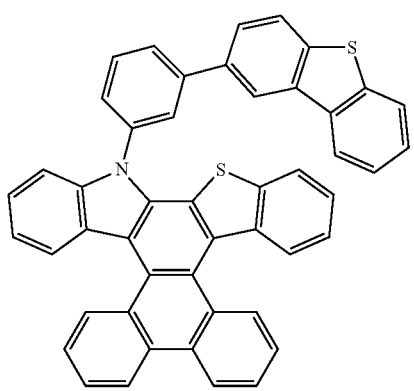
61
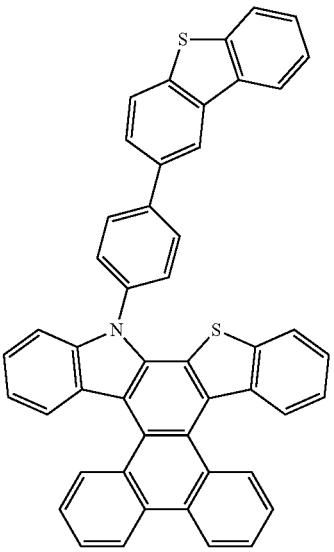
62
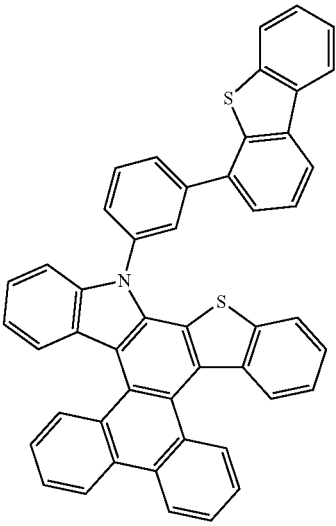
63
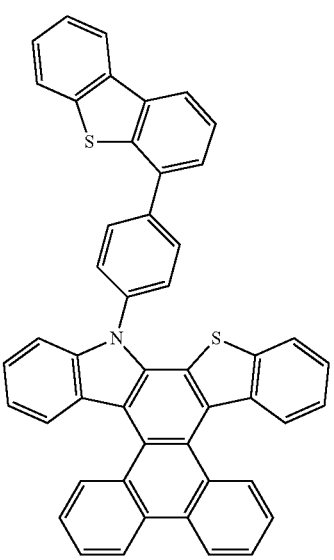

US 10,096,784 B2
231
-continued
232
-continued
64
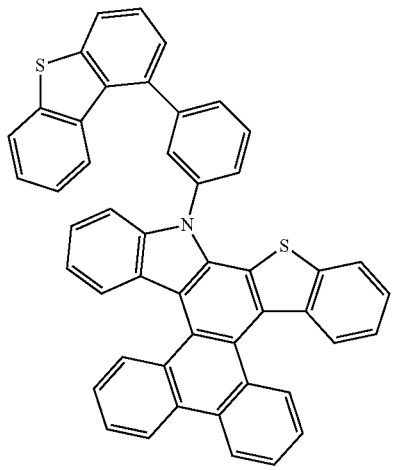
67
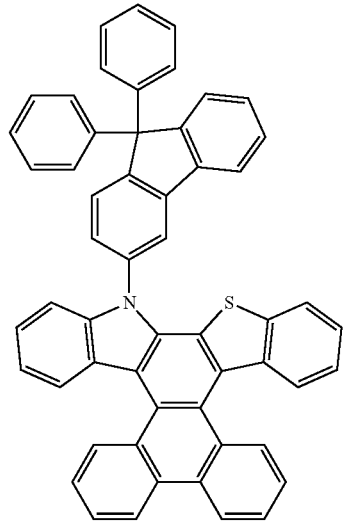
65
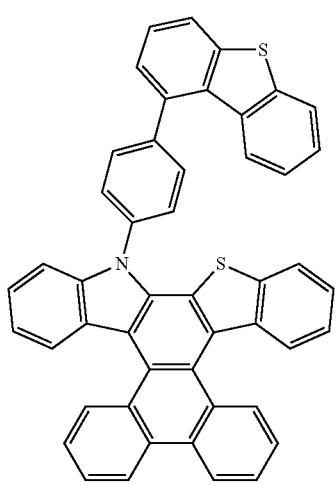
68
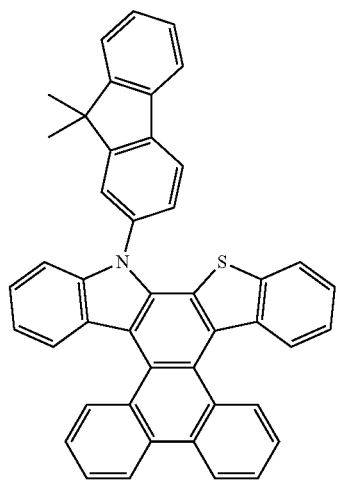
66
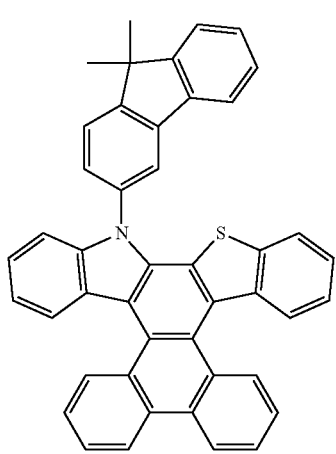
69
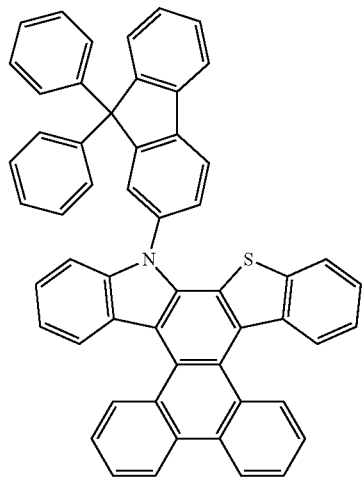

233
-continued
234
-continued
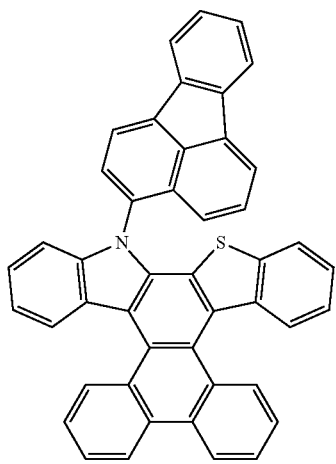
70
71
72
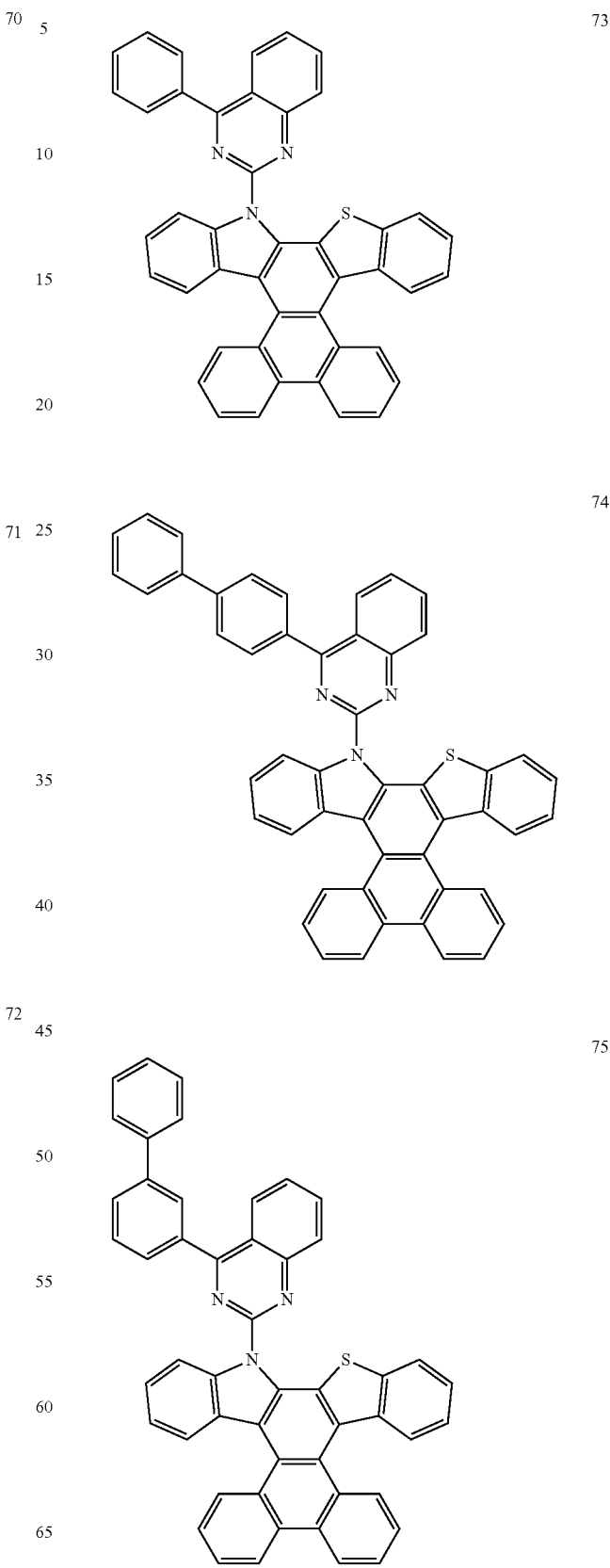
73
74
75

235
-continued
76
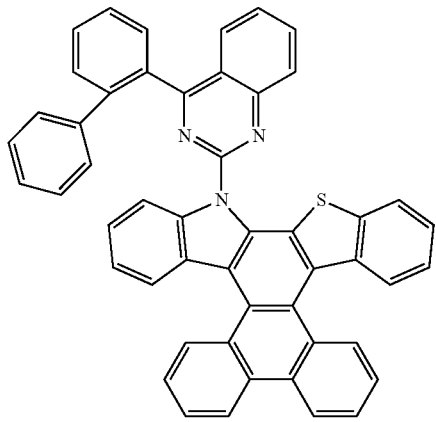
77
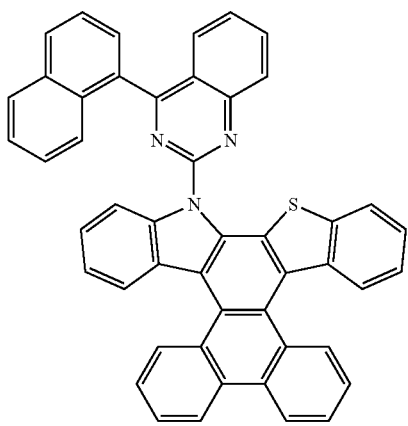
78
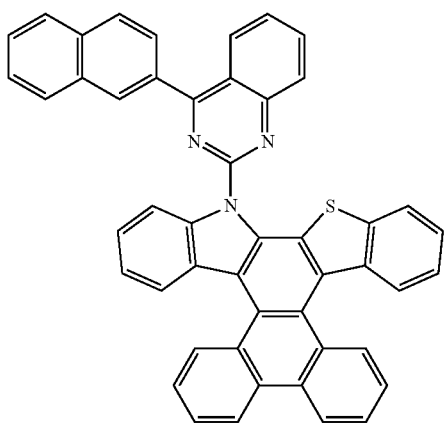
236
-continued
79
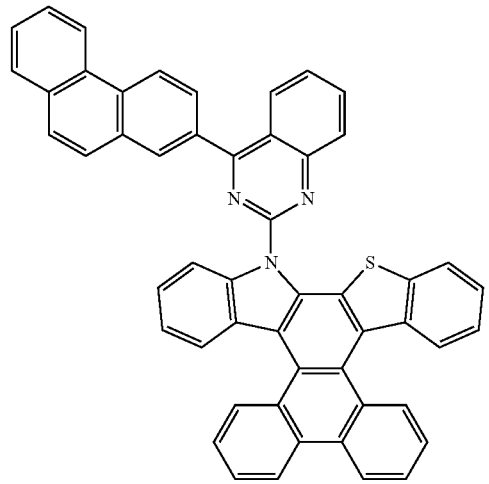
80
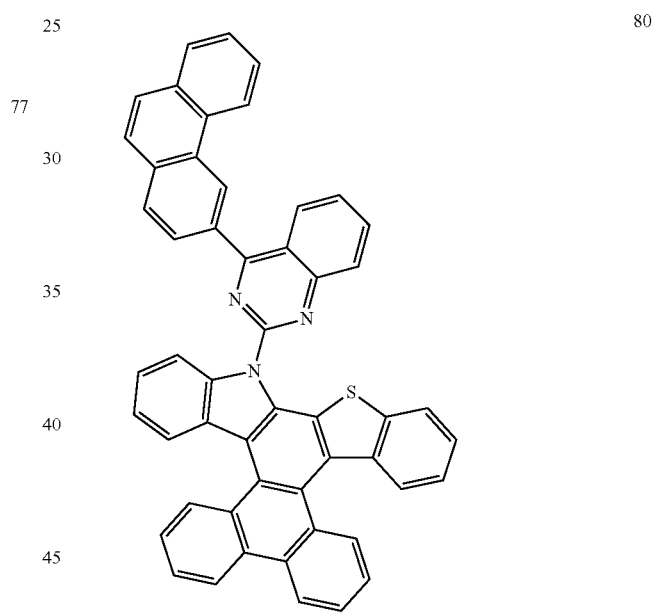
81
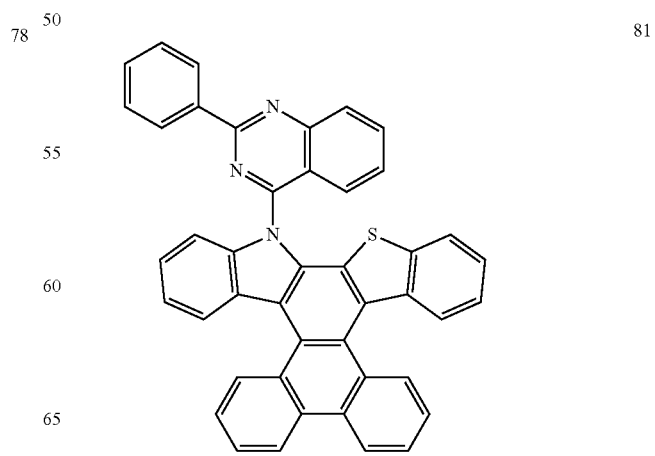

237
-continued
82
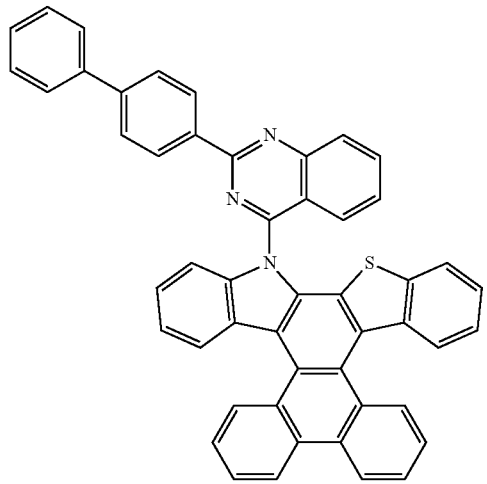
83
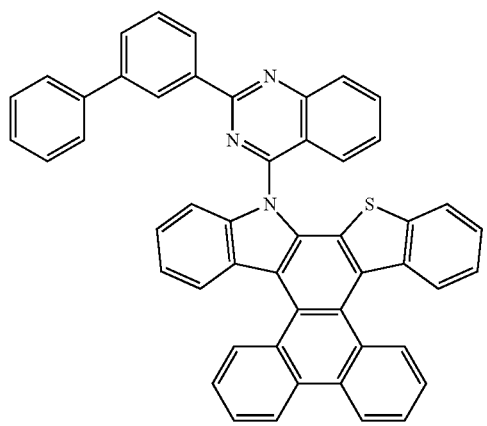
84
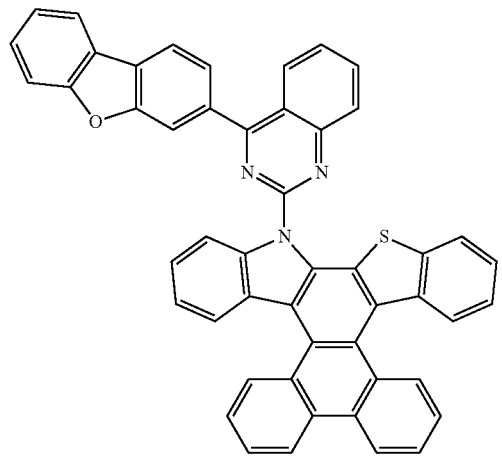
238
-continued
85
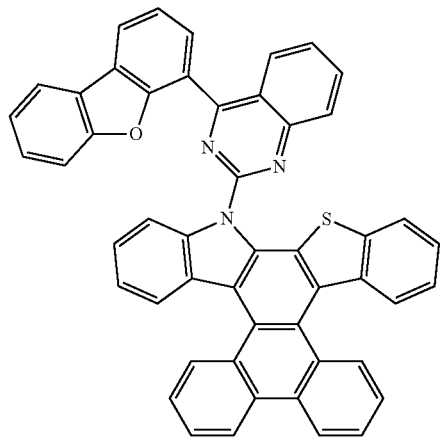
86
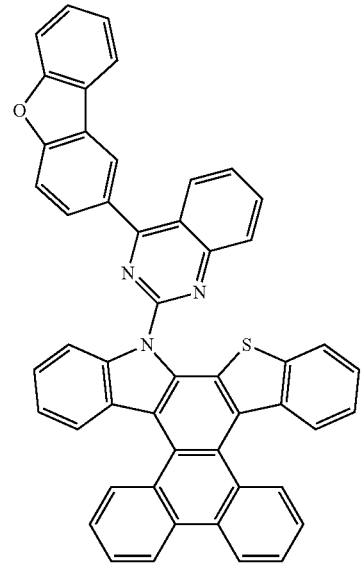
87
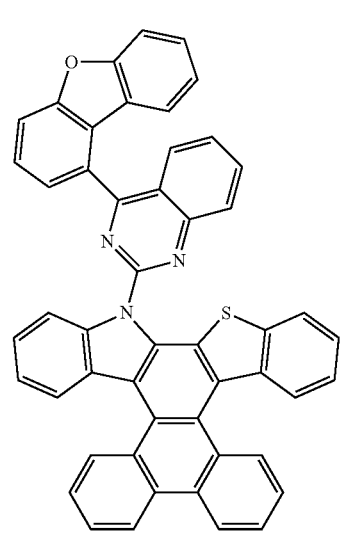

-continued
88
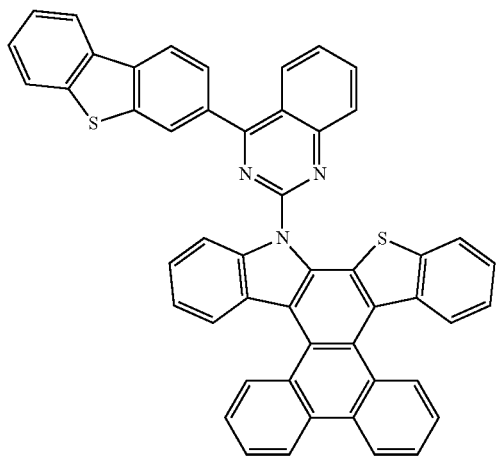
91
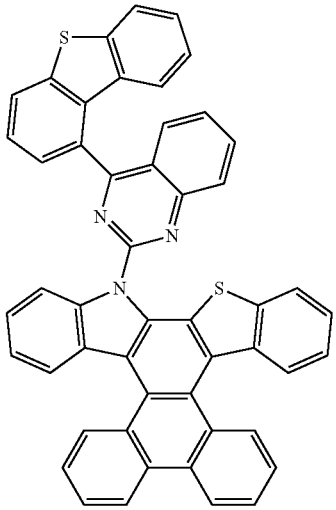
89
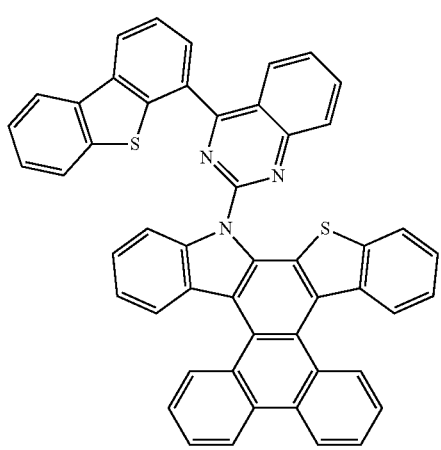
92
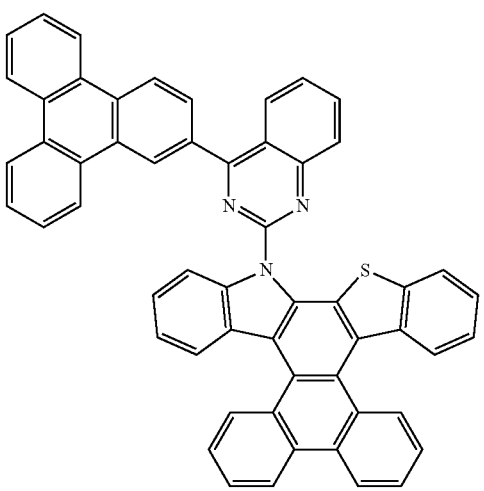
90
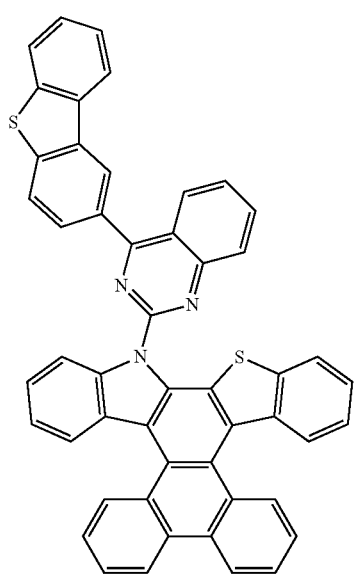
93
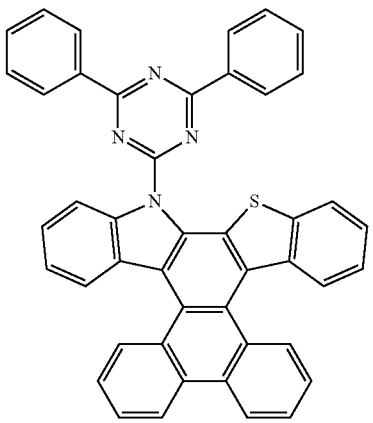

241
-continued
242
-continued
94
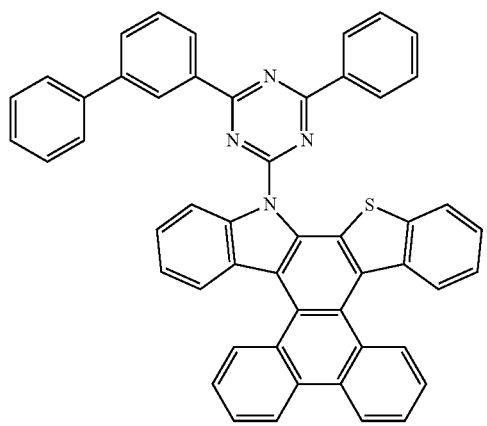
97
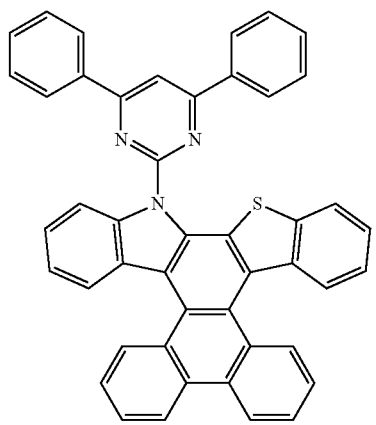
95
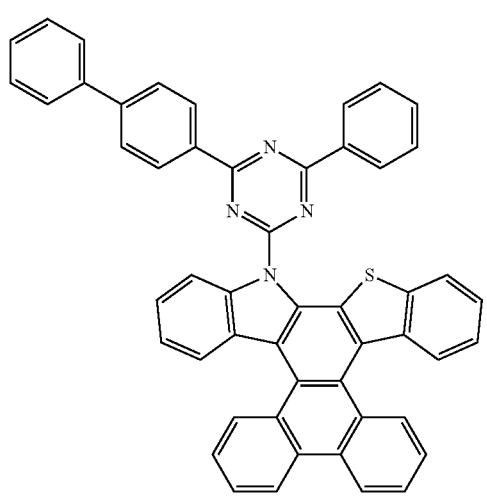
98
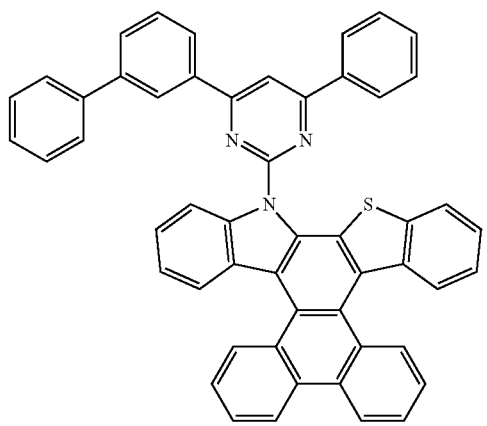
96
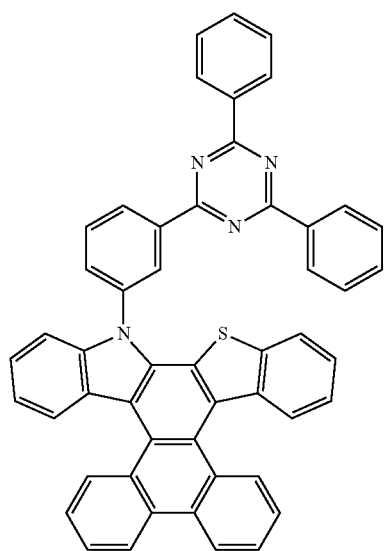
99
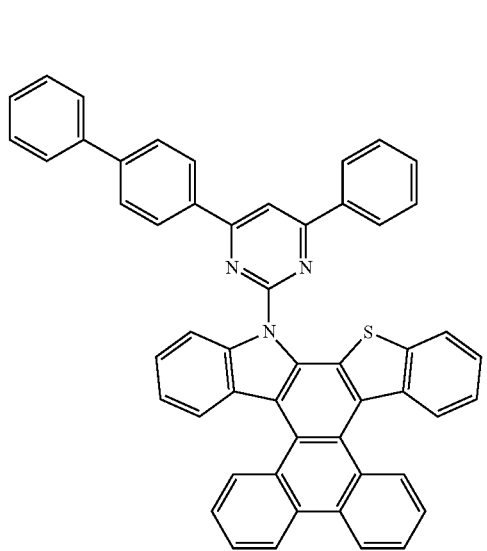

243
-continued
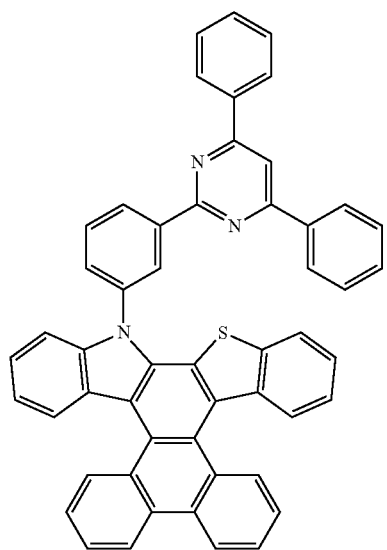
100
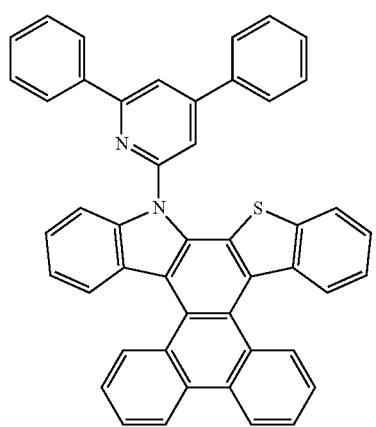
101
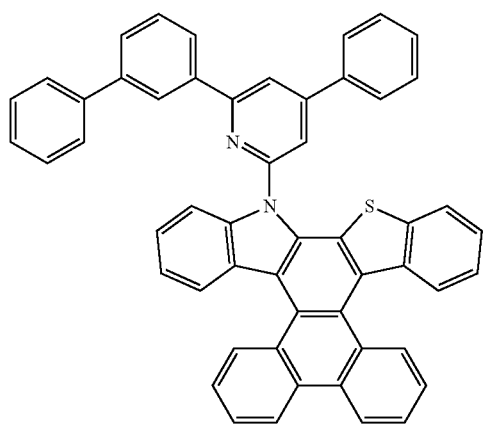
102
244
-continued
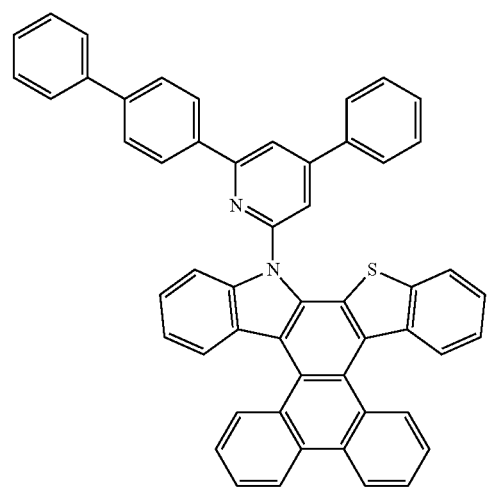
103
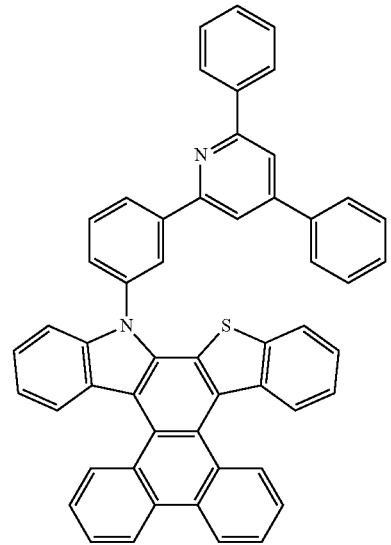
104
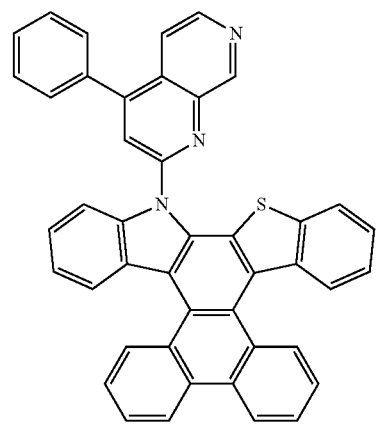
105

245
-continued
106
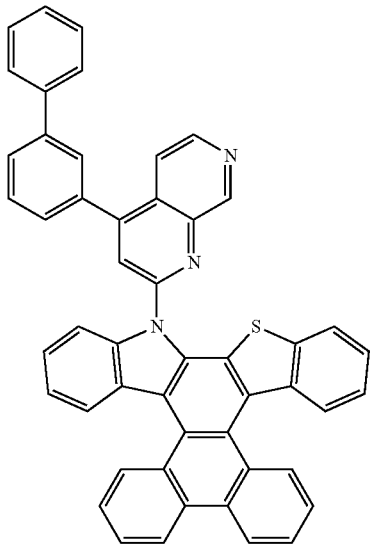
107
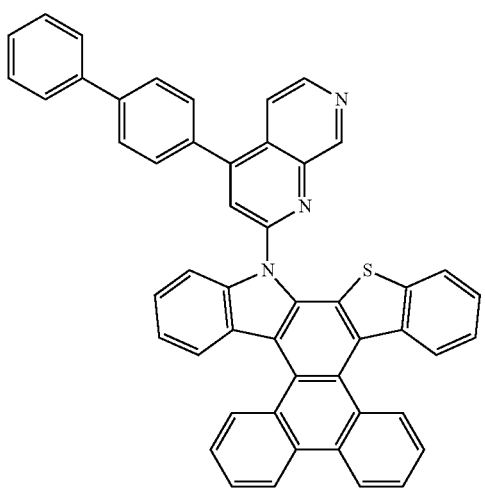
108
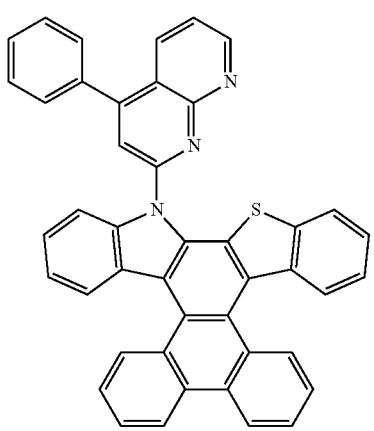
246
-continued
109
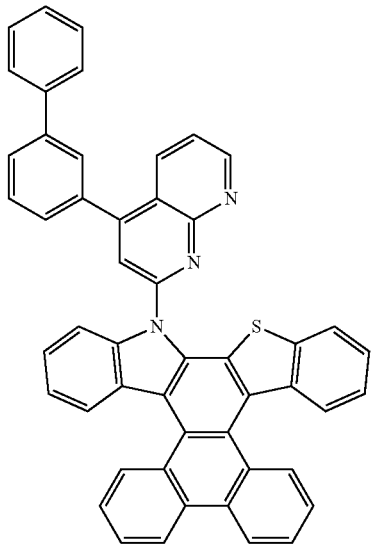
110
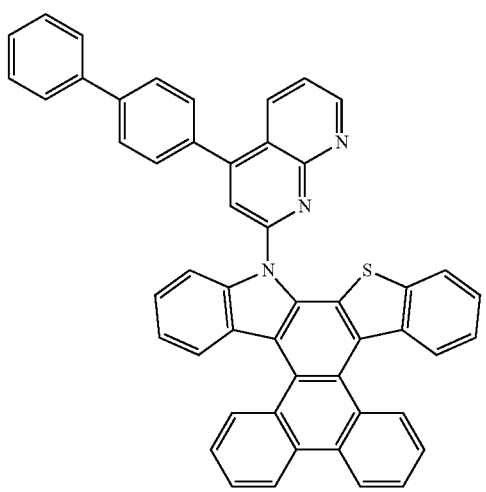
111
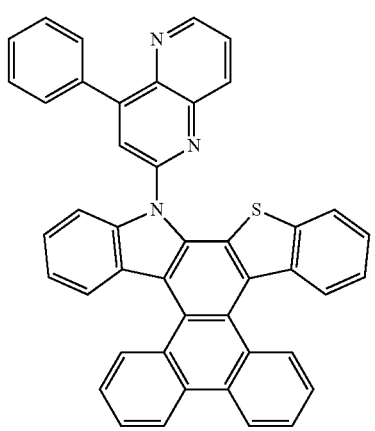

247
-continued
112
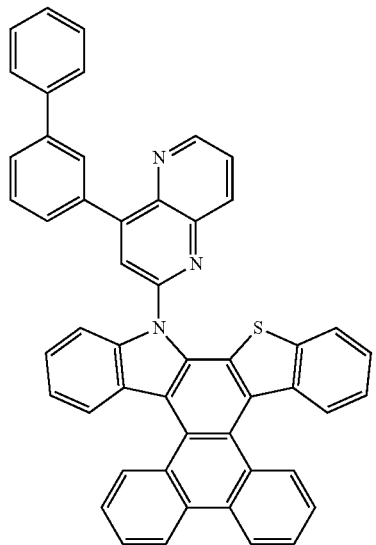
113
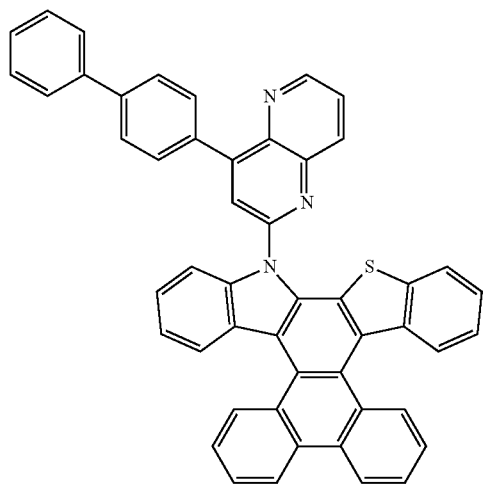
114
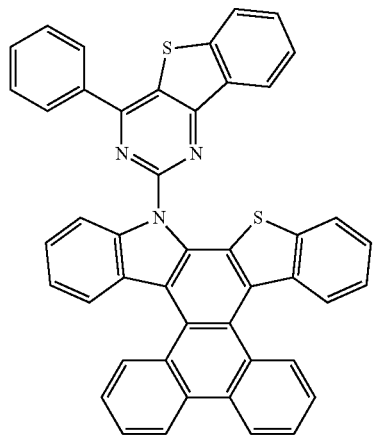
248
-continued
115
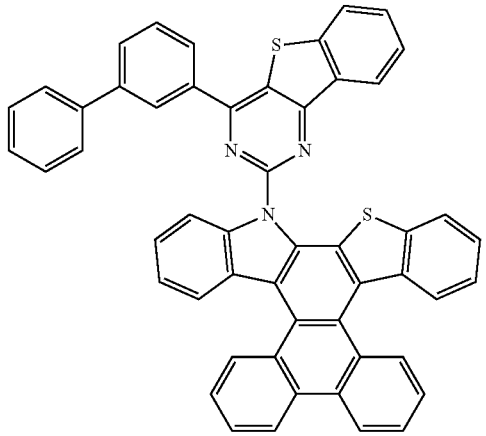
116
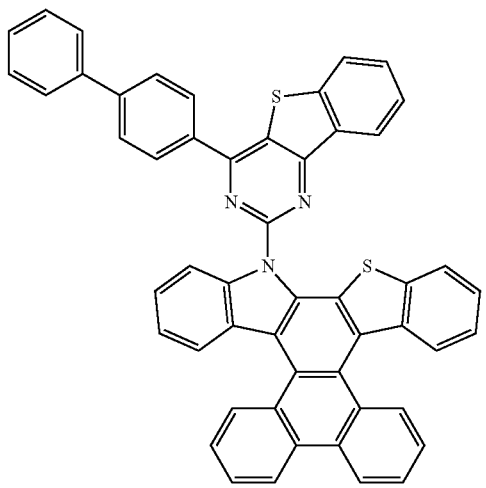
117
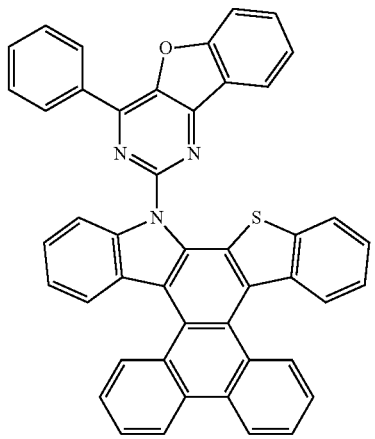

249
-continued
250
-continued
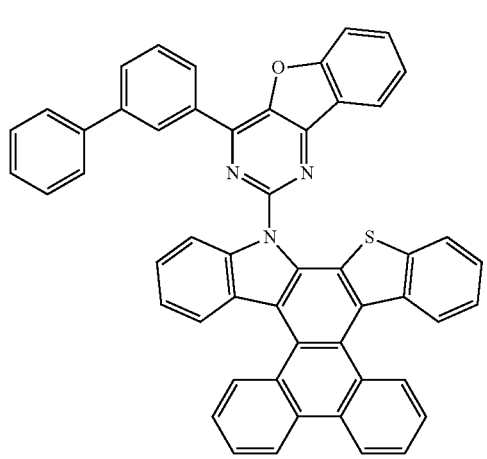
118
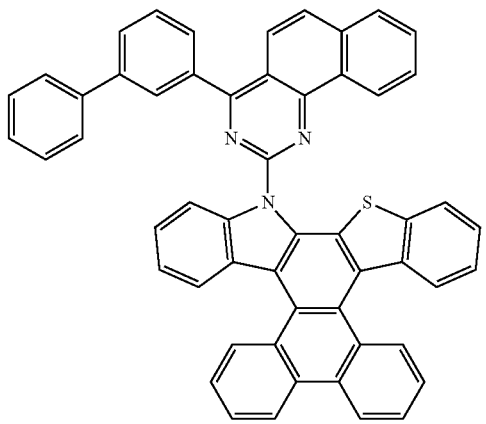
121
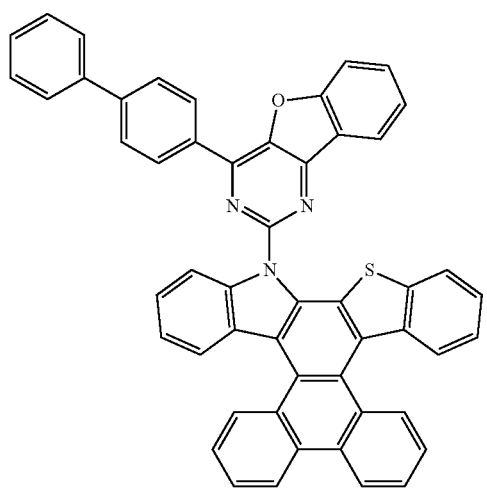
119
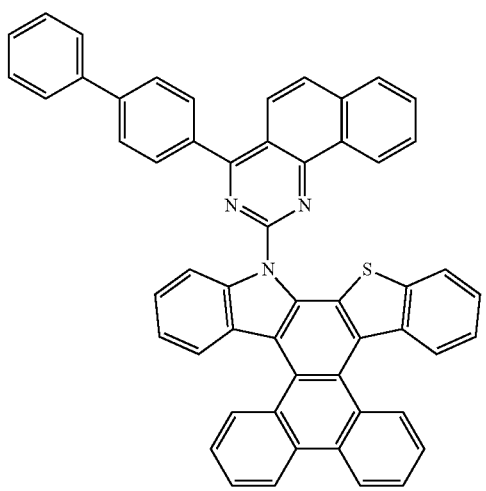
122
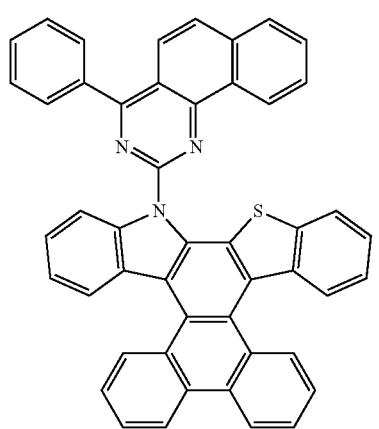
120
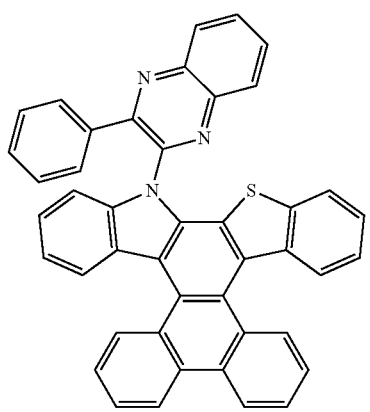
123

251
-continued
252
-continued
124
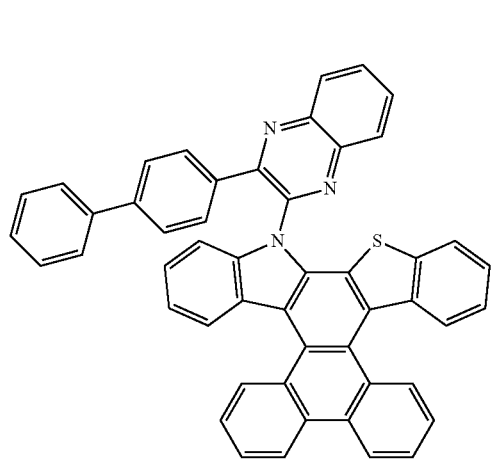
127
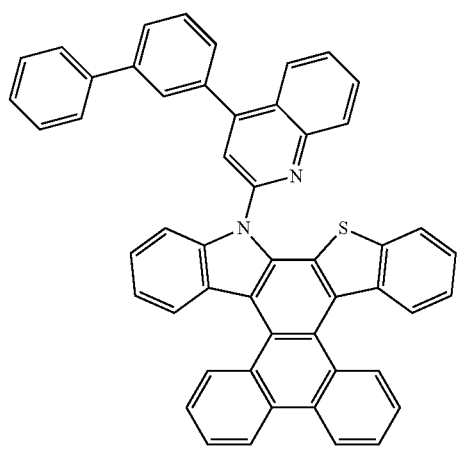
125
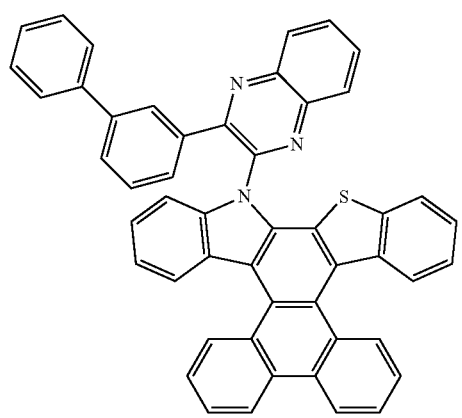
128
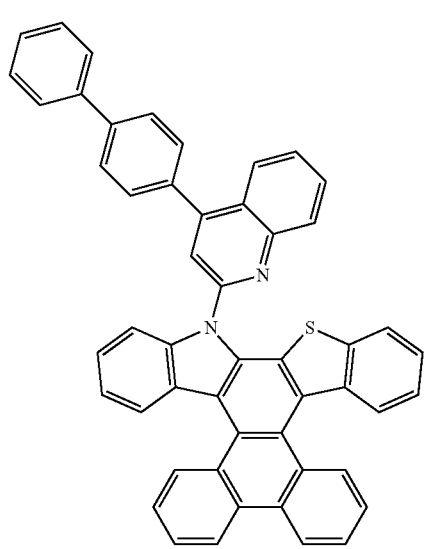
126
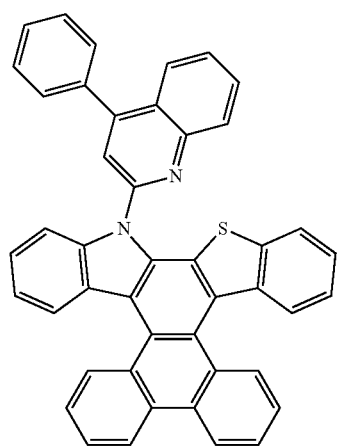
129
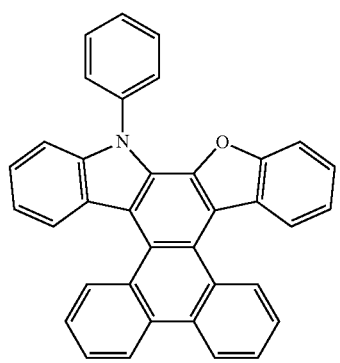

253
-continued
254
-continued
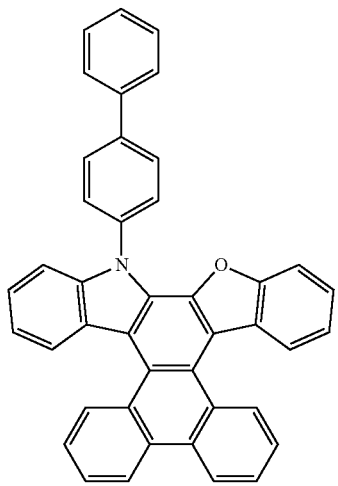
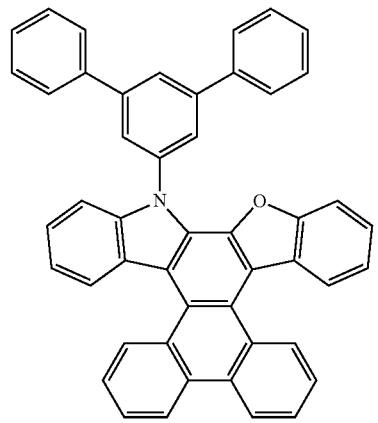
133
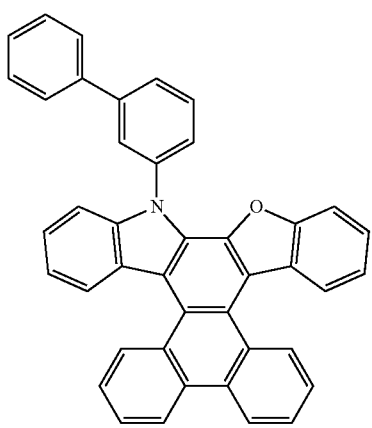
131
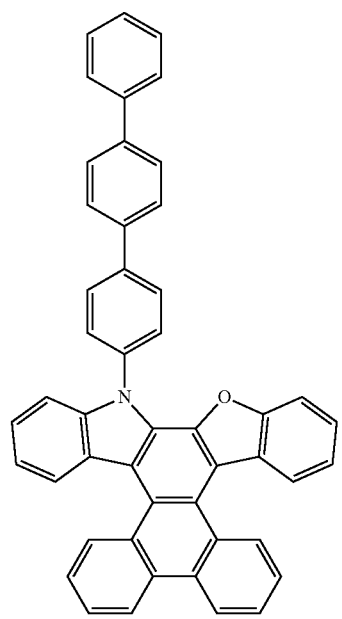
134
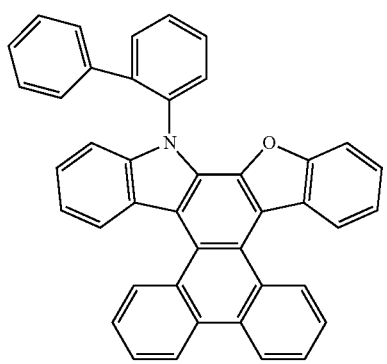
132
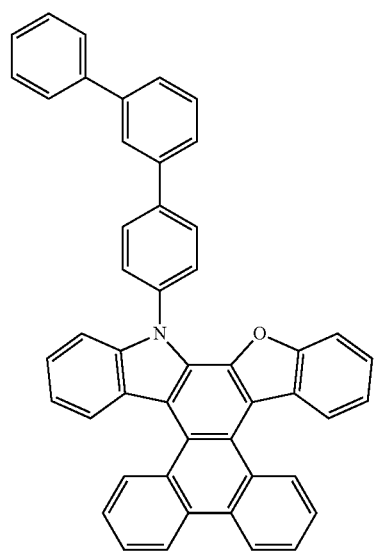
135

136
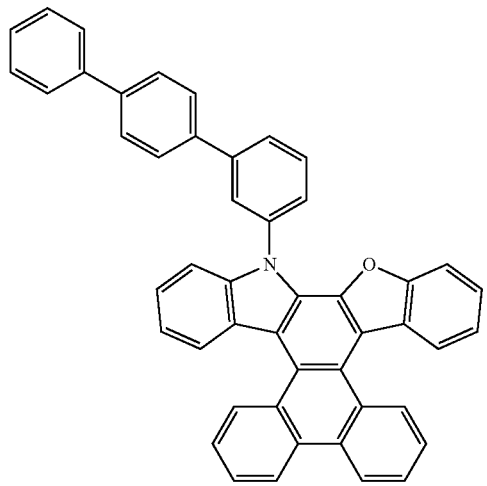
137
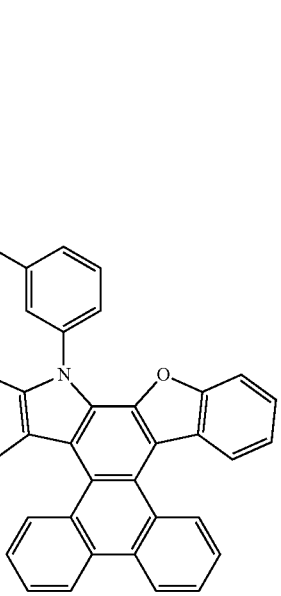
138
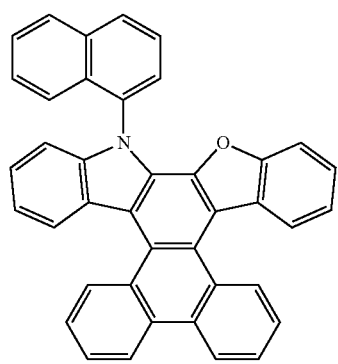
139
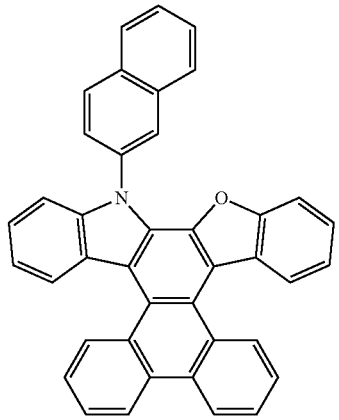
140
141
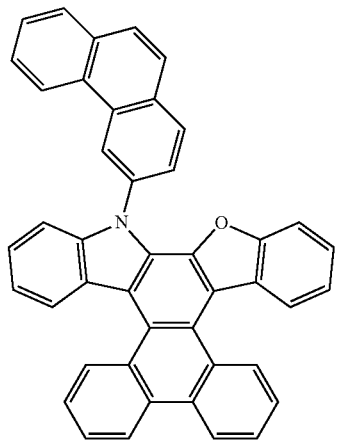

257
-continued
142
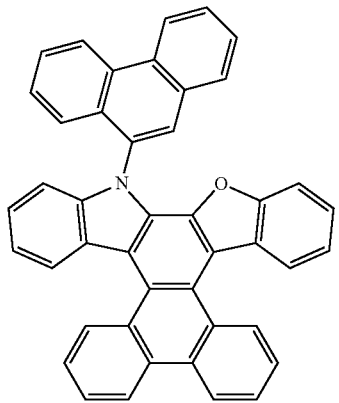
143
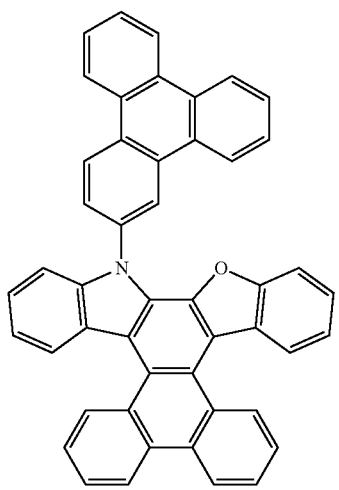
144
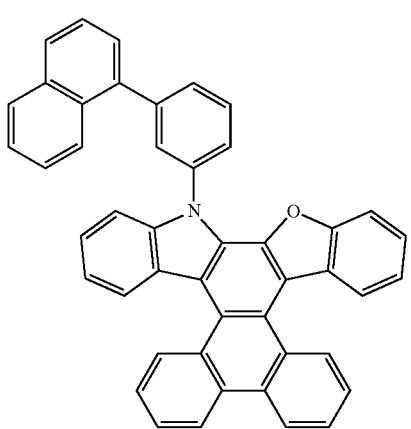
258
-continued
145
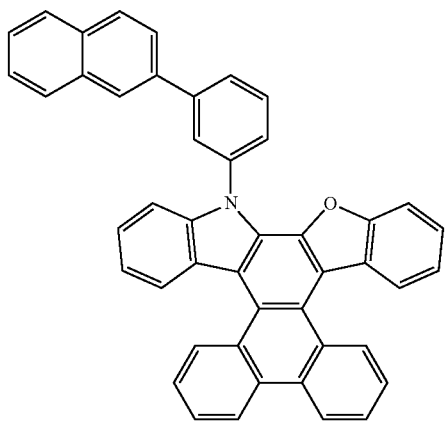
146
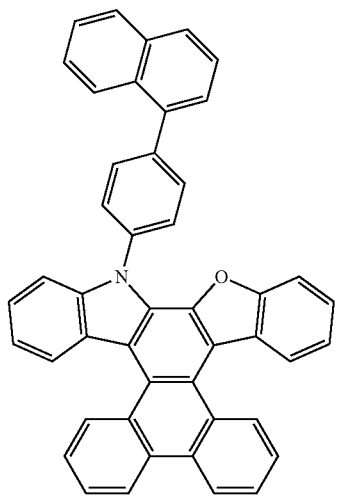
147
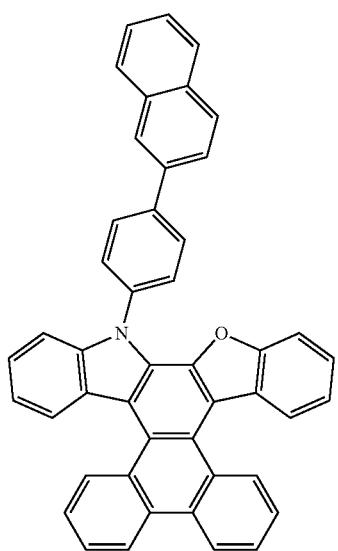

259
-continued
148
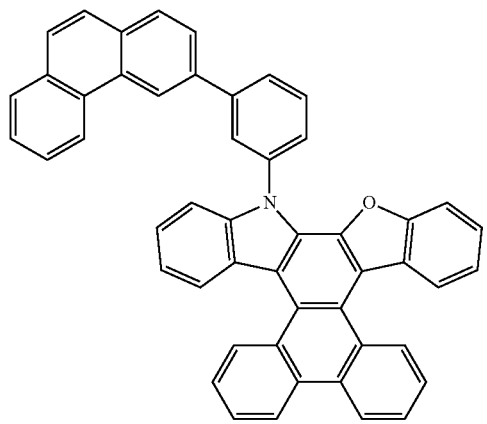
149
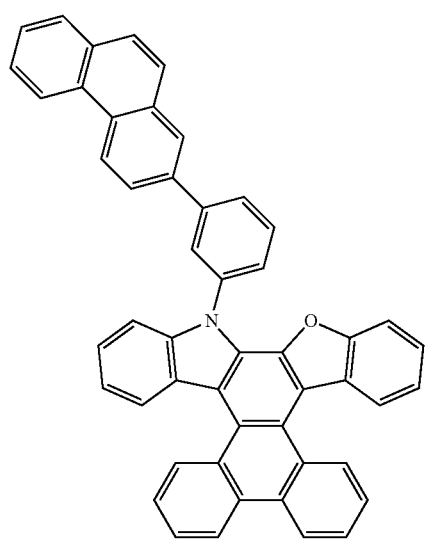
150
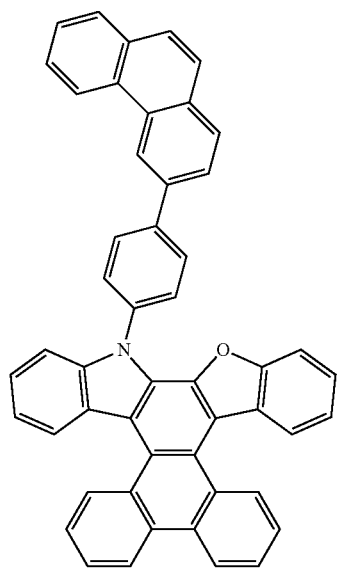
260
-continued
151
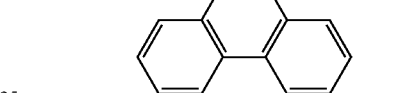
152
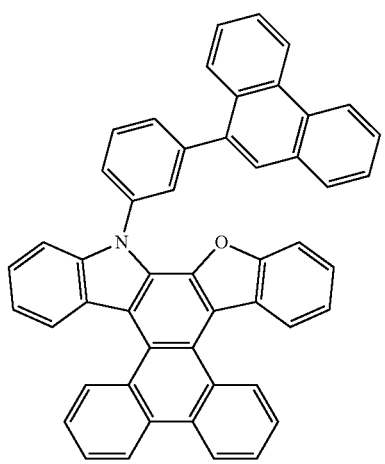
153
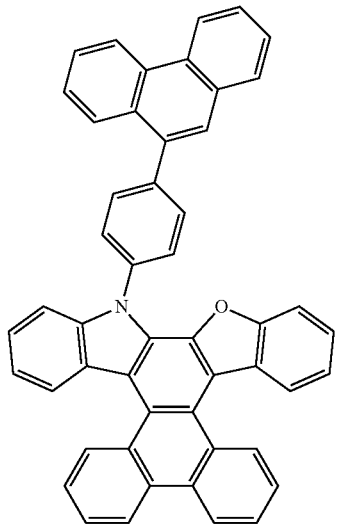

261
-continued
154
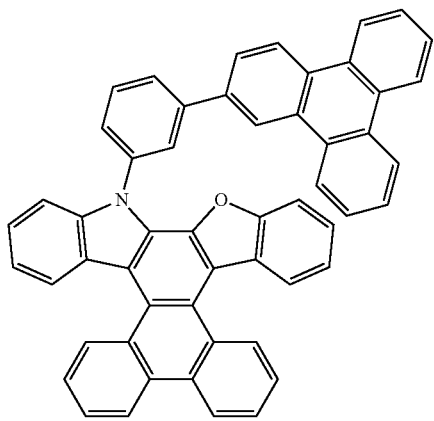
155
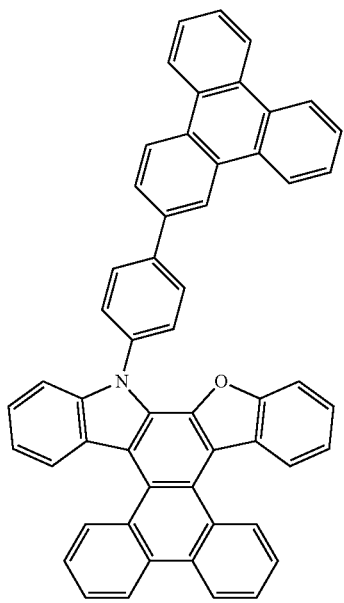
156
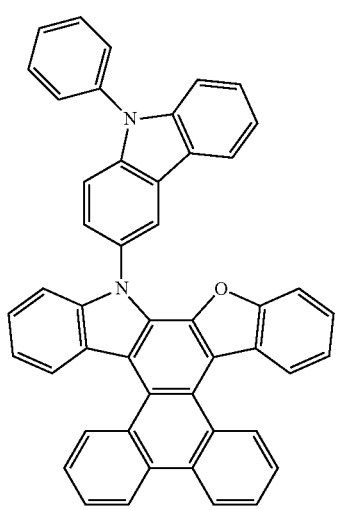
262
-continued
157
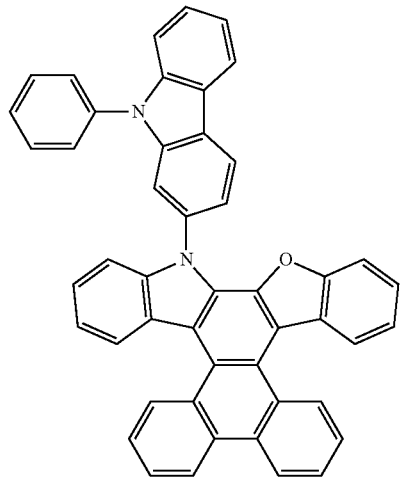
158
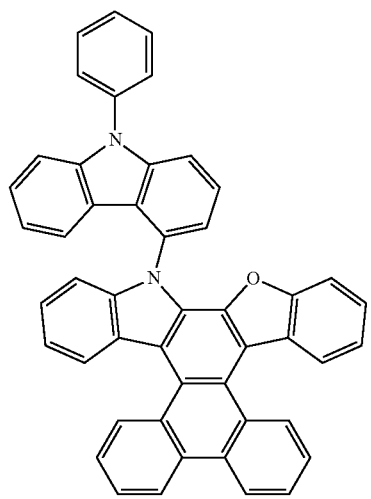
159
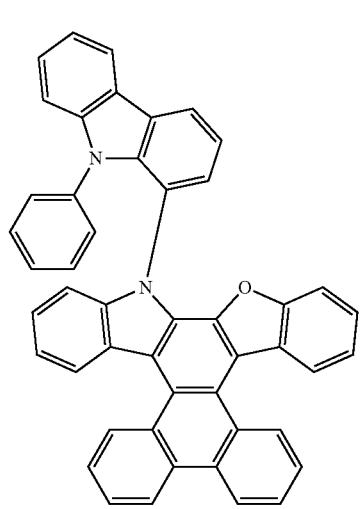

160
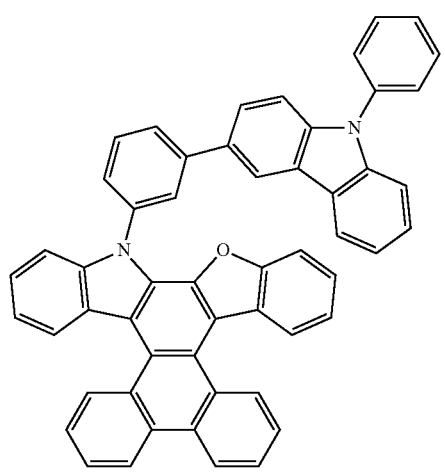
161
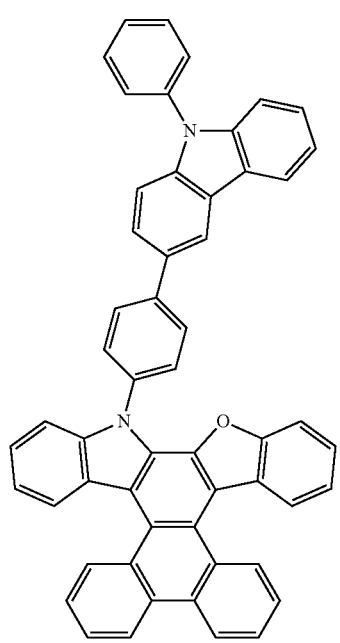
162
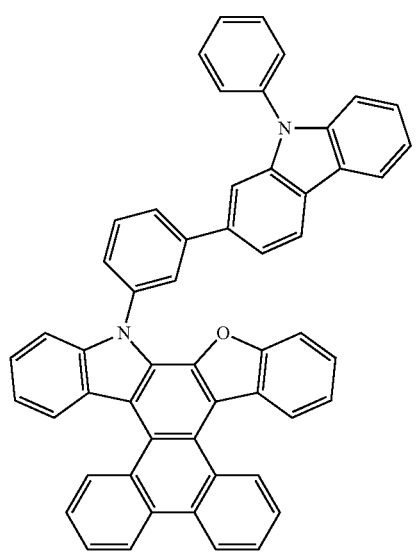
163
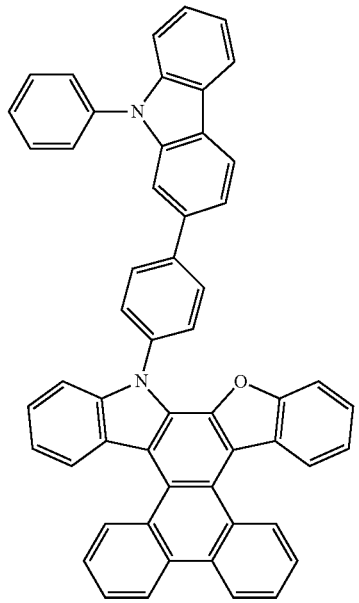
164
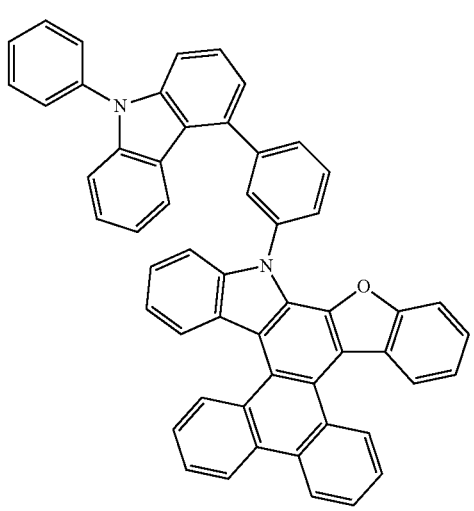
165
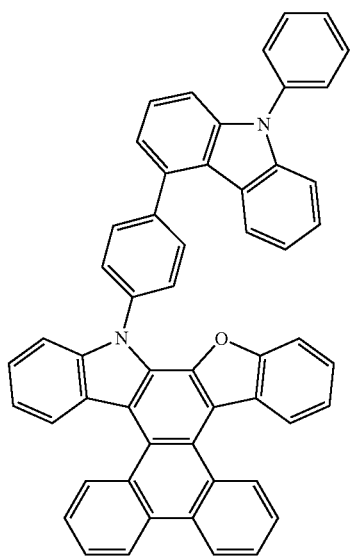

166
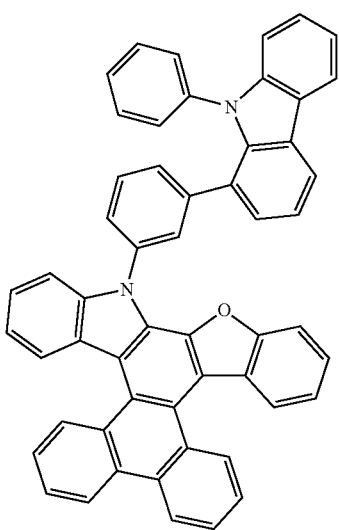
167
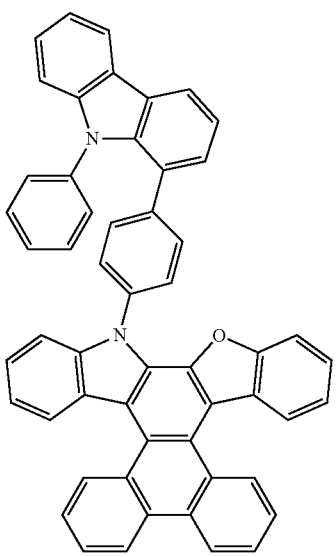
168
169
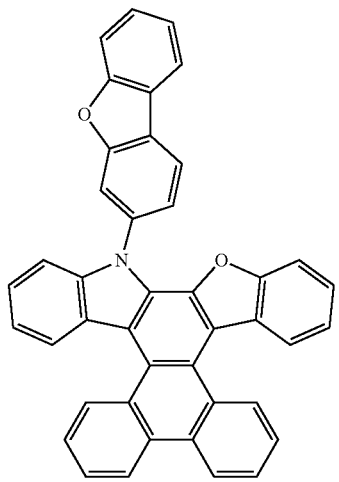
170
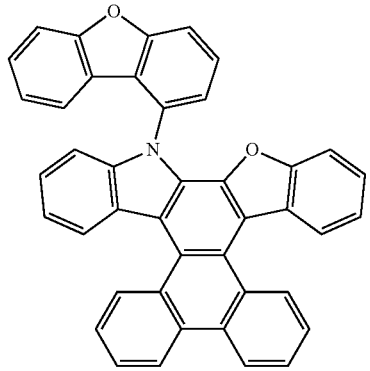
171
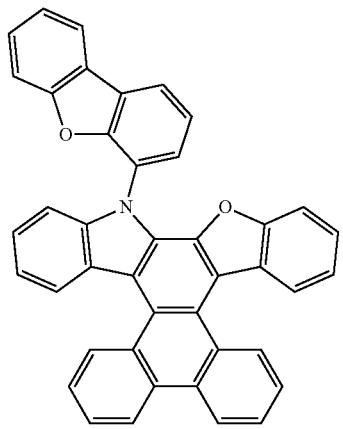

267
-continued
172 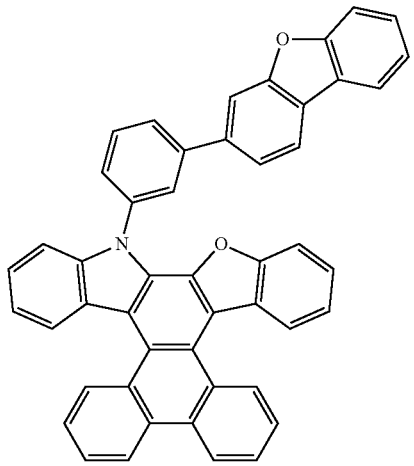
173 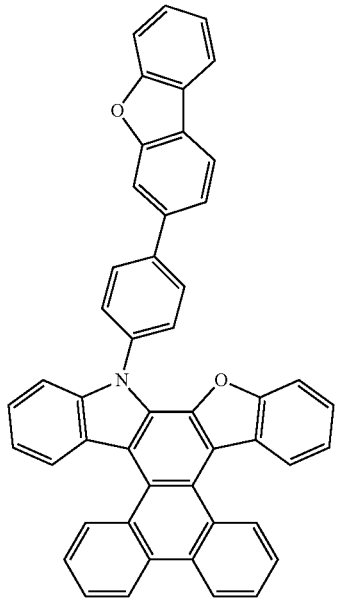
174 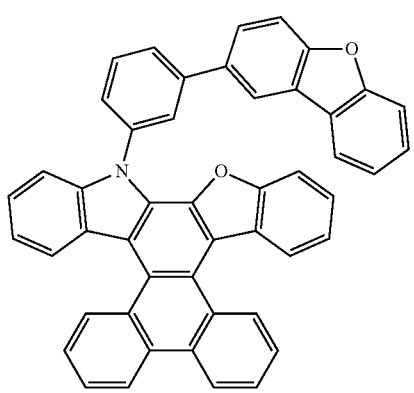
268
-continued
175 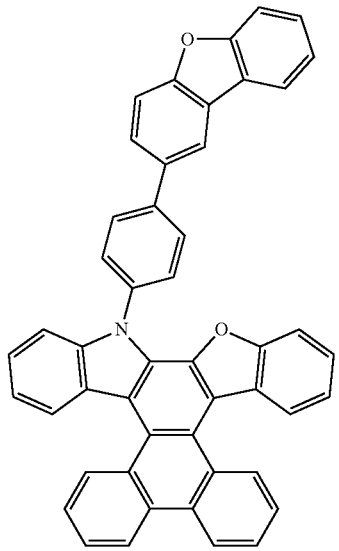
176 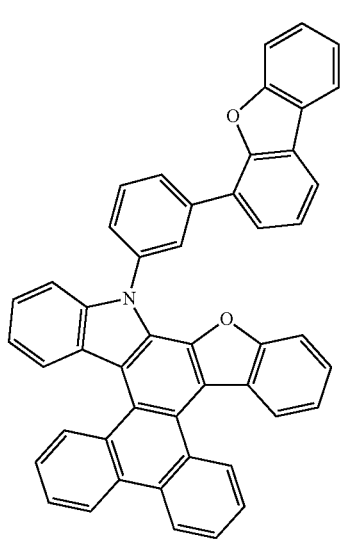
177 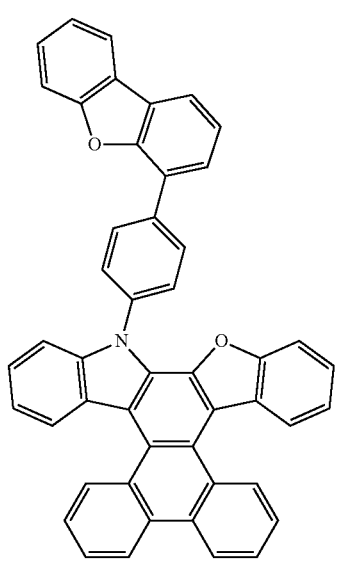

269
-continued
178
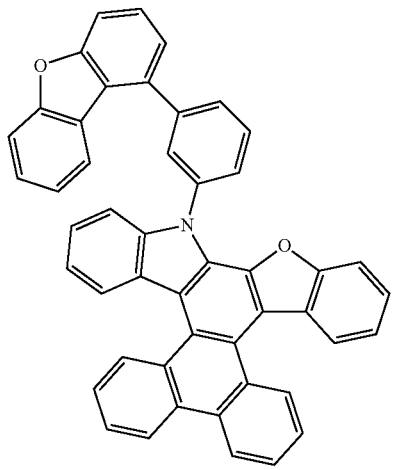
179
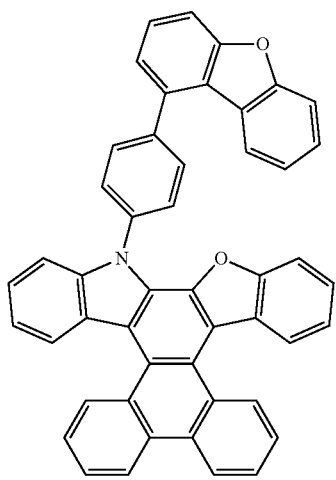
180
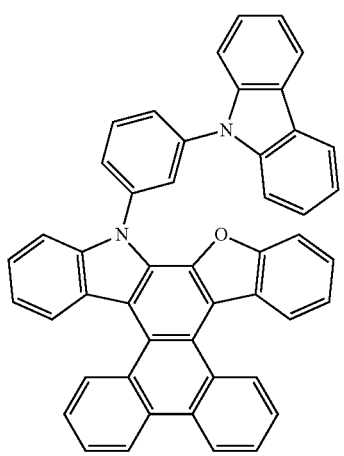
270
-continued
181
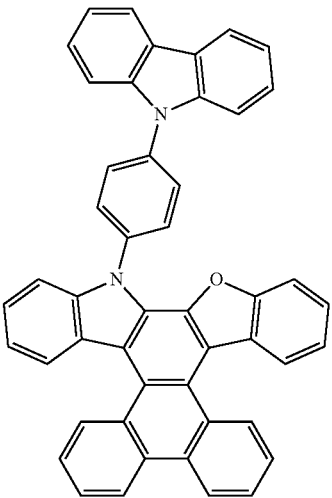
182
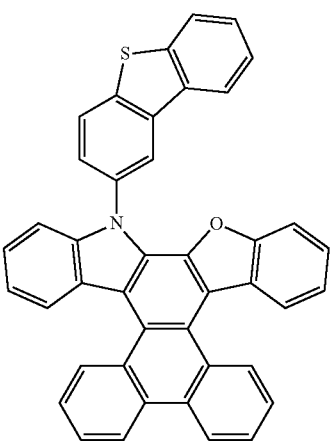
183
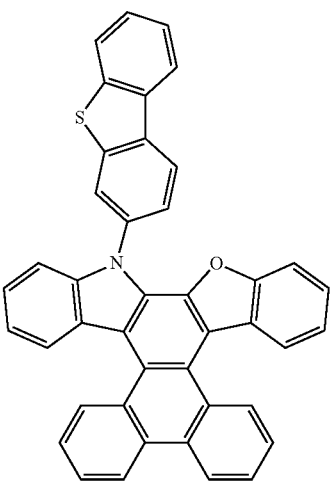

184
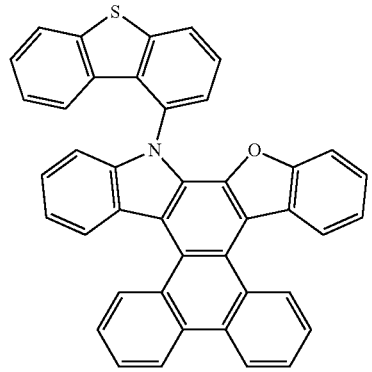
185
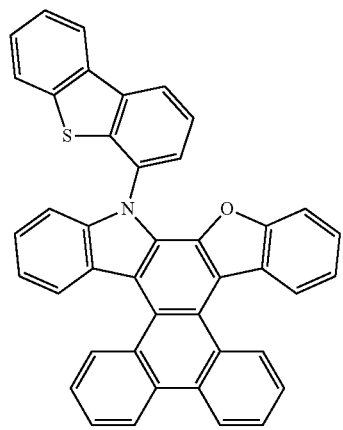
186
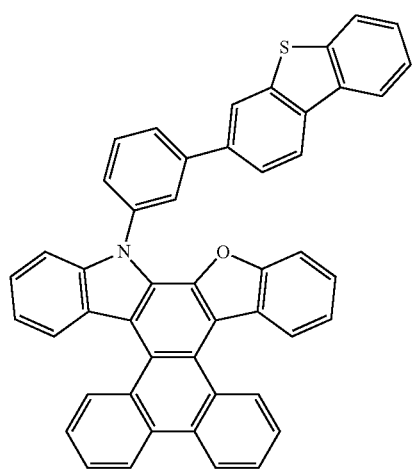
187
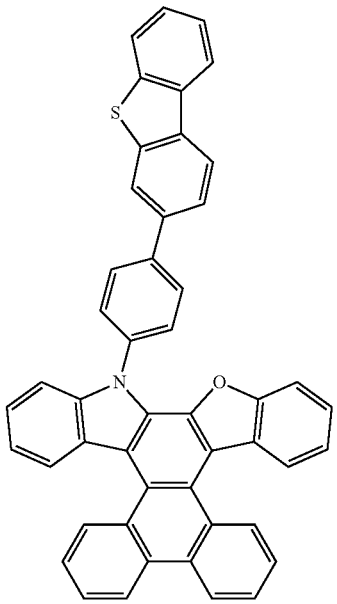
188
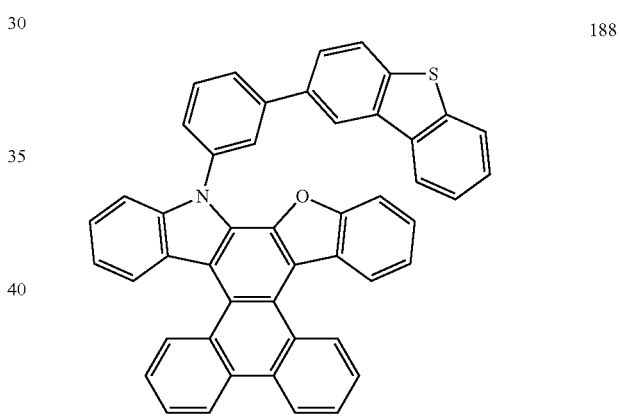
189
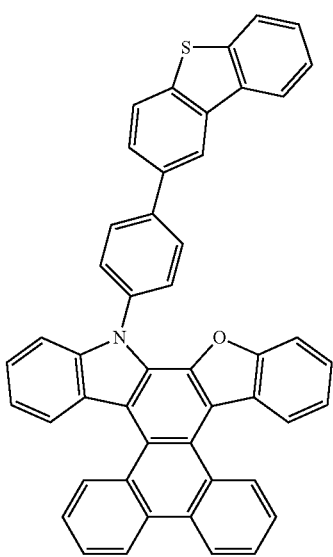

273
-continued
190
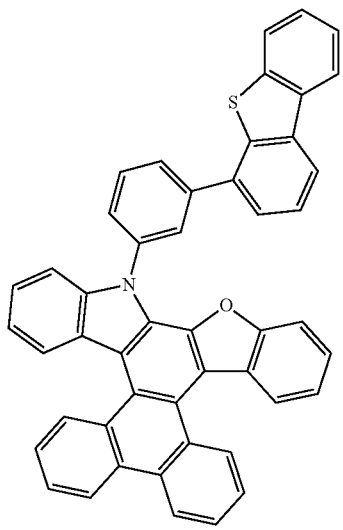
191
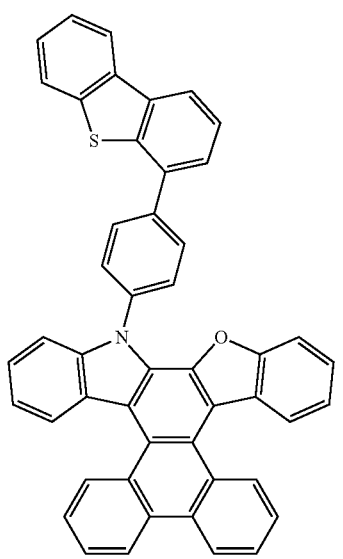
192
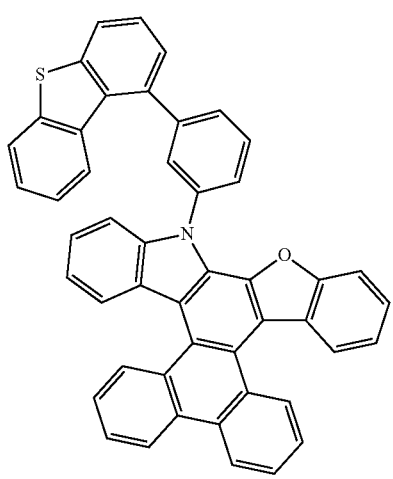
274
-continued
193
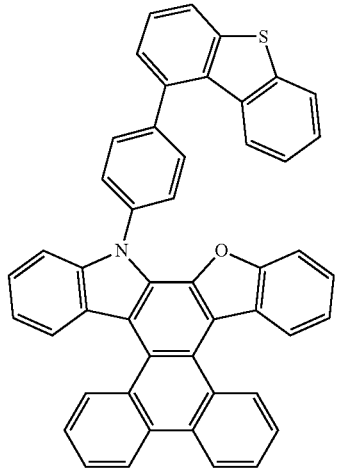
194
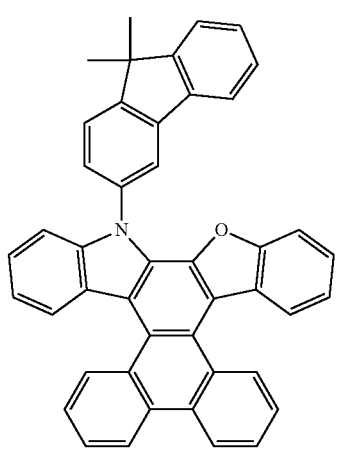
195
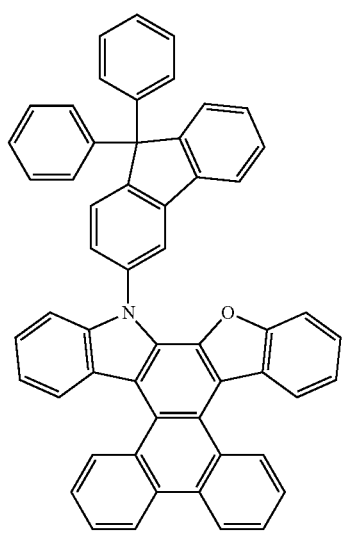

275
-continued
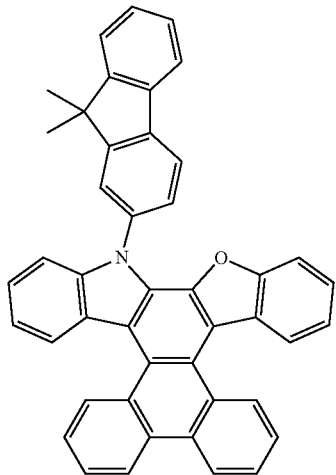
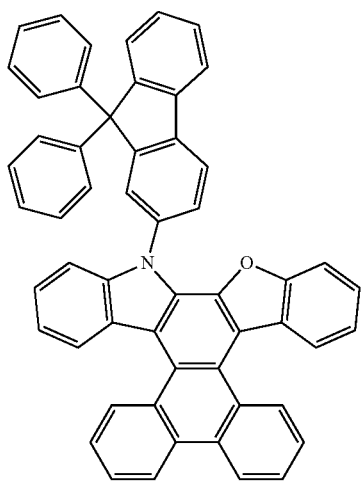
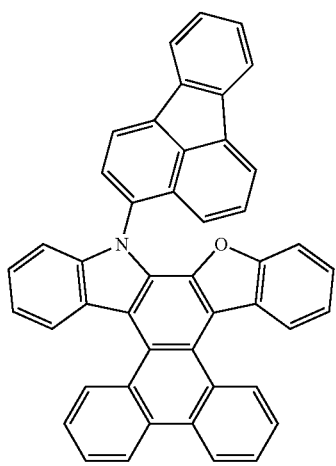
276
-continued
196
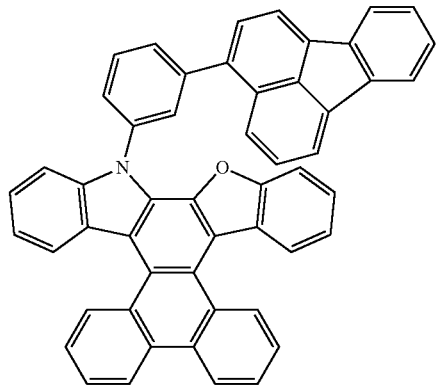
197
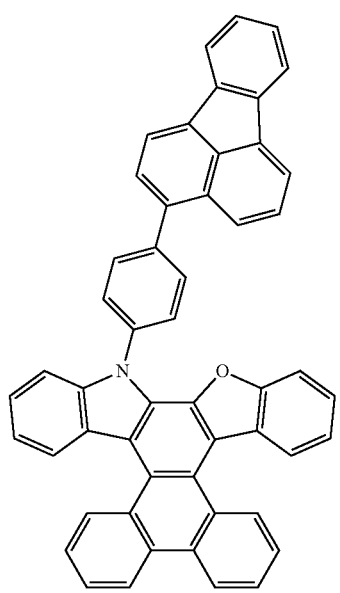
198
199
200
201
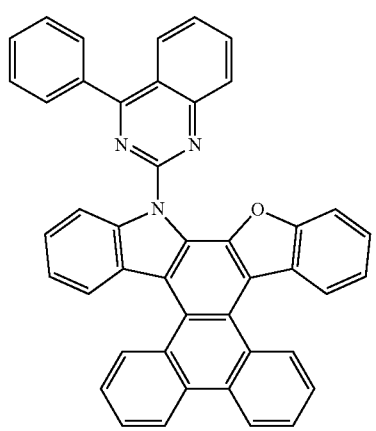

277
-continued
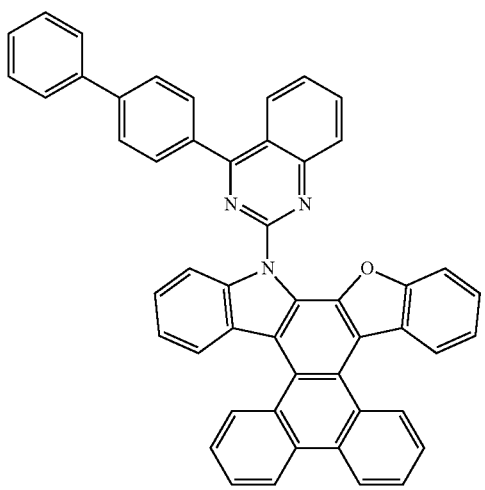
202
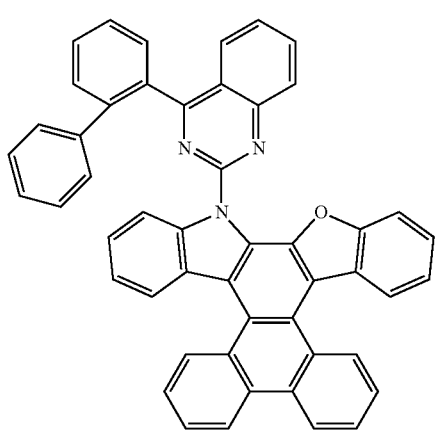
203
204
278
-continued
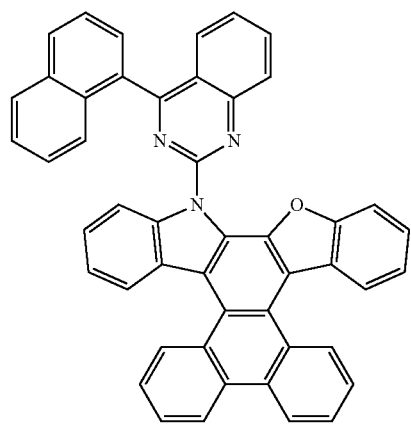
205
206
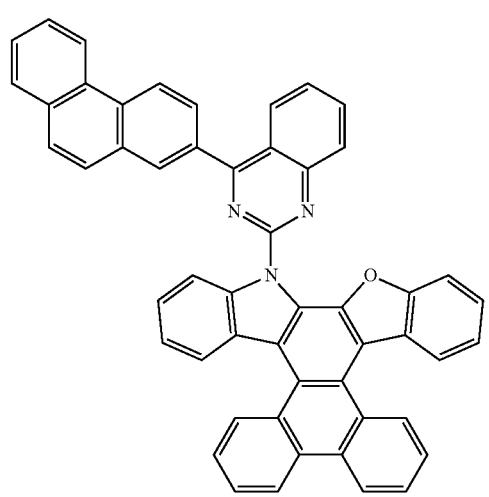
207

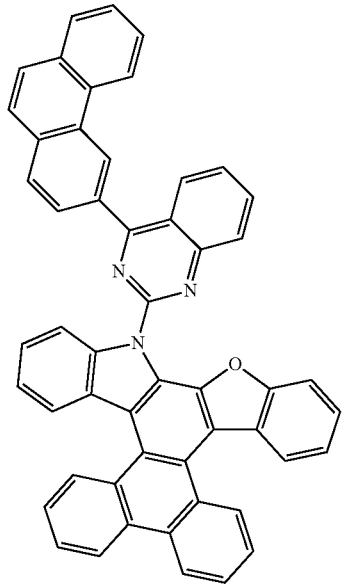
208
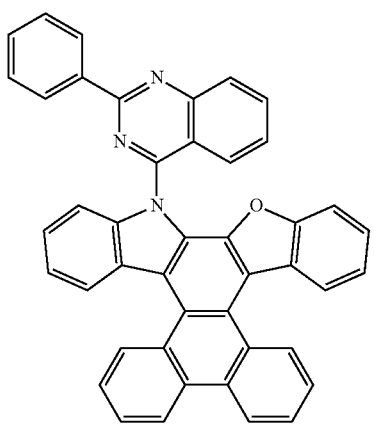
209
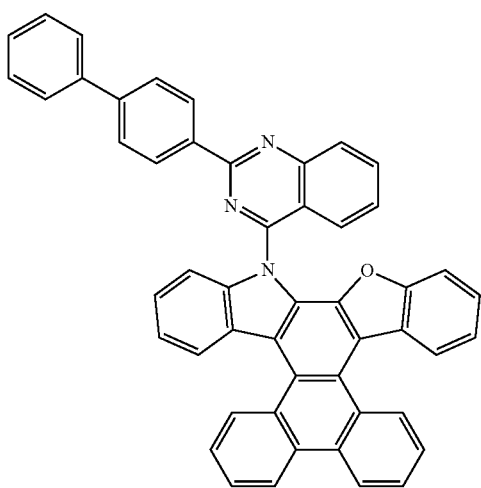
210
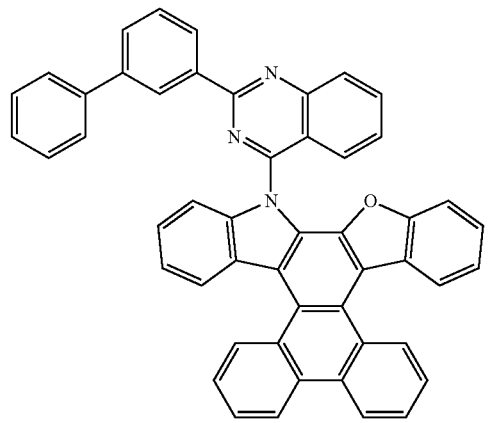
211
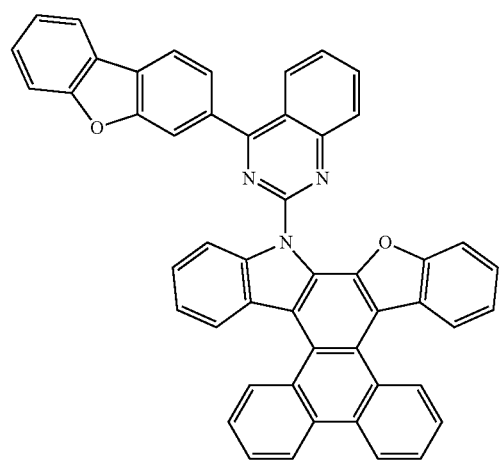
212
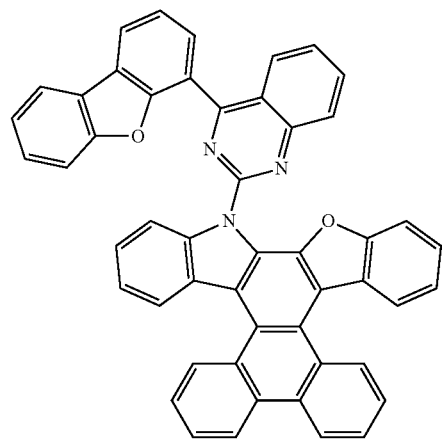
213

281
-continued
214
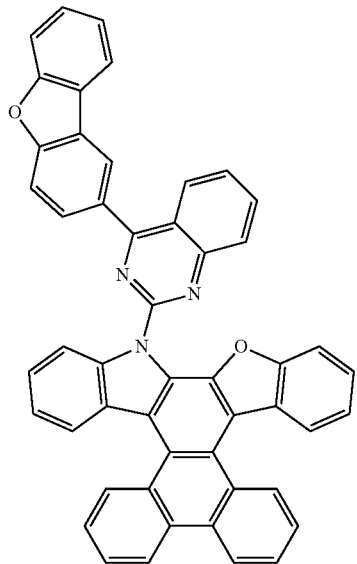
215
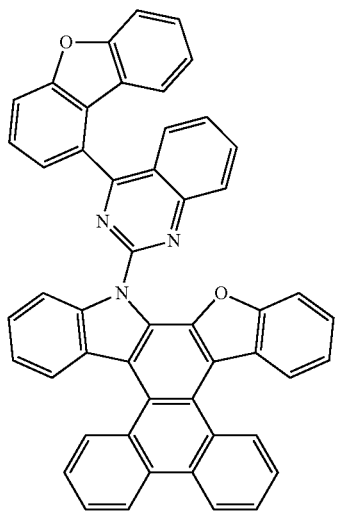
216
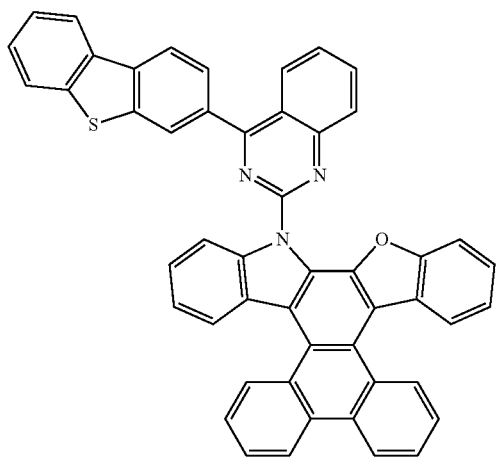
282
-continued
217
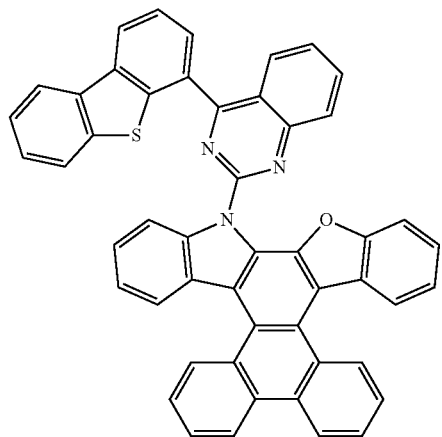
218
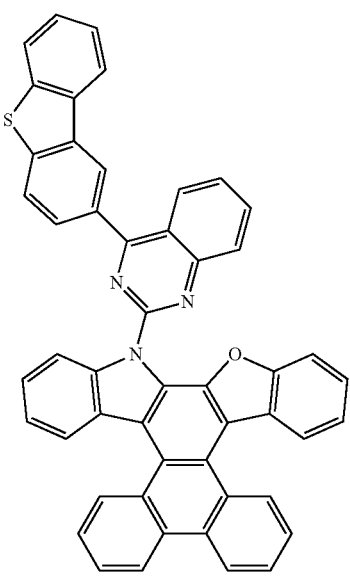
219
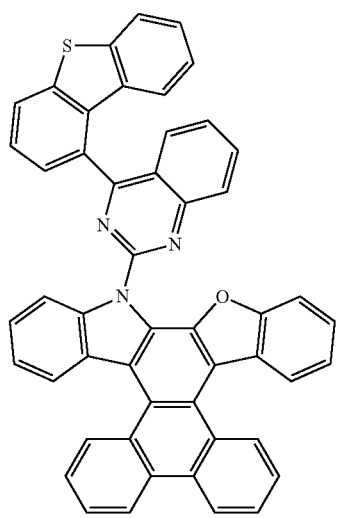

283
-continued
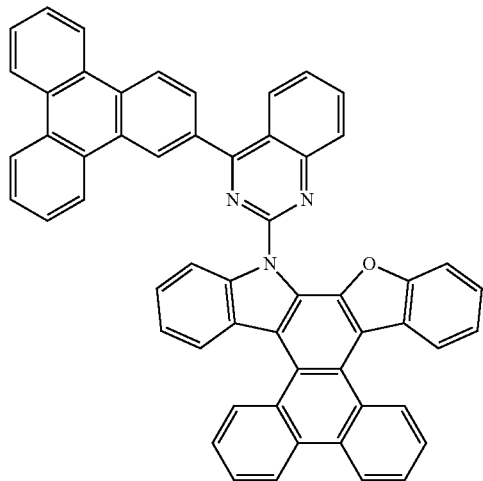
220
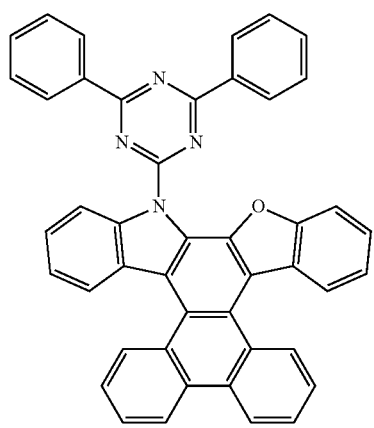
221
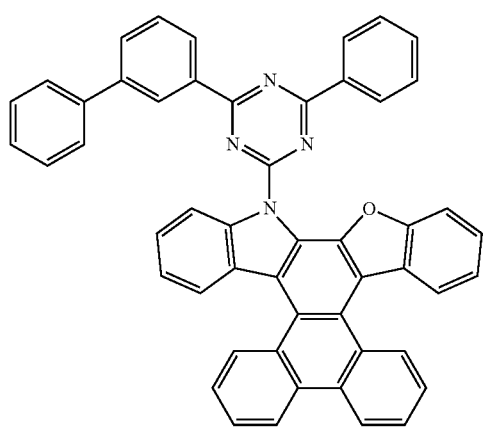
222
284
-continued
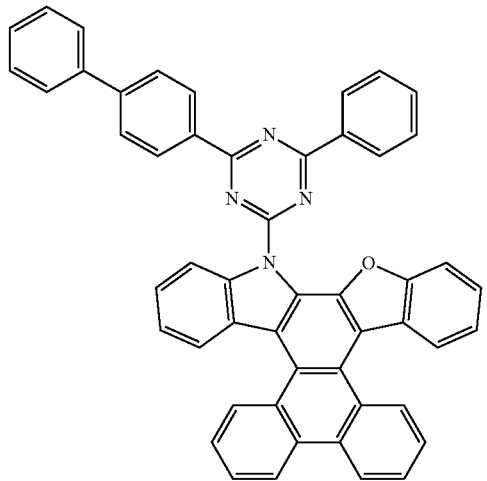
223
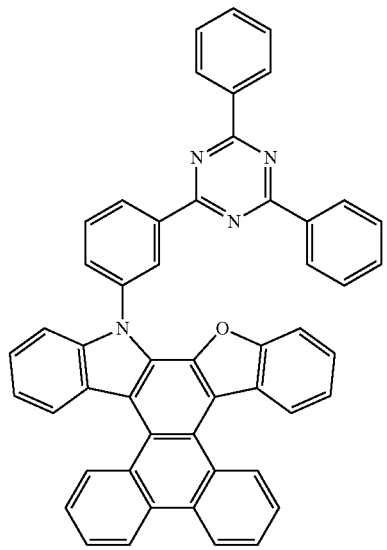
224
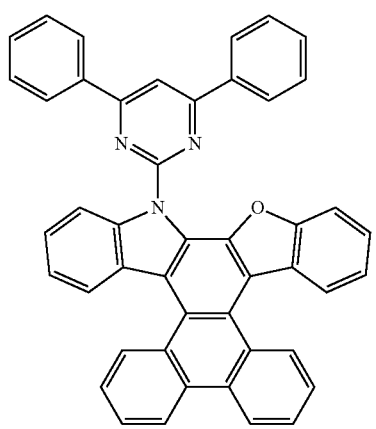
225

285
-continued
286
-continued
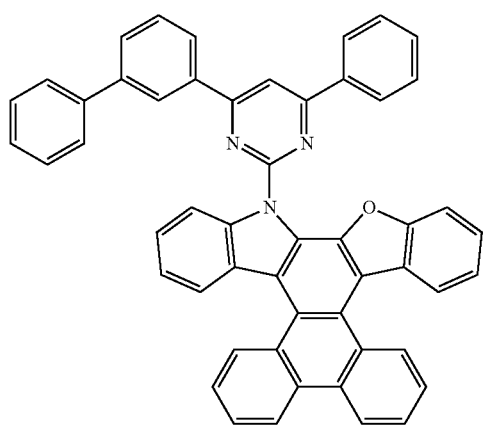
226
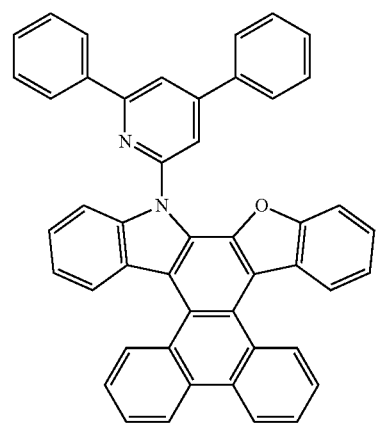
229
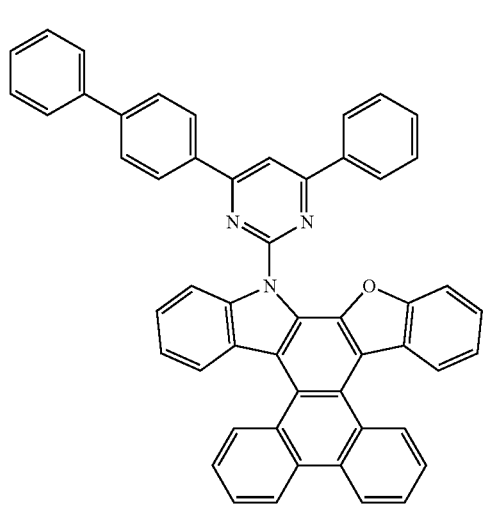
227
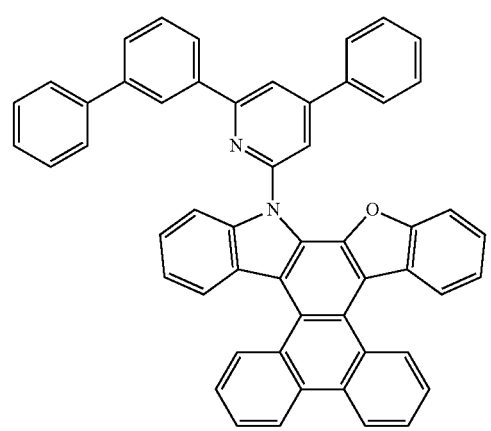
230
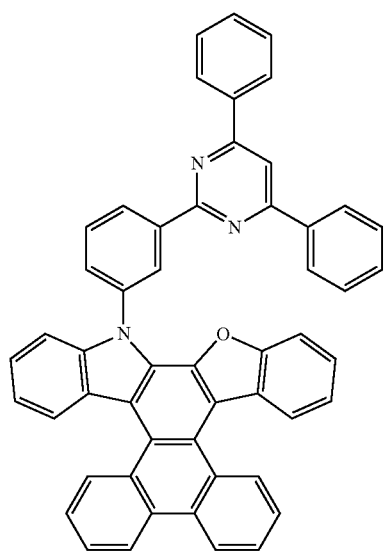
228
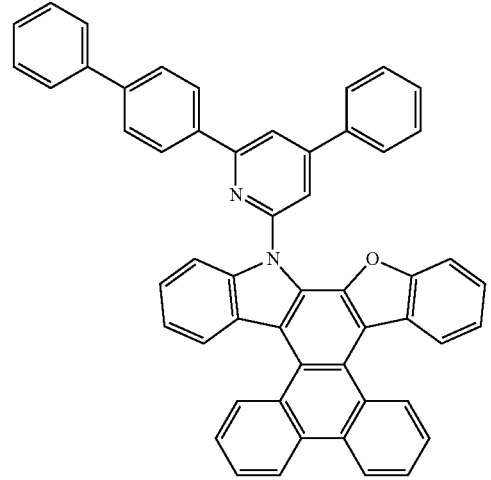
231

232
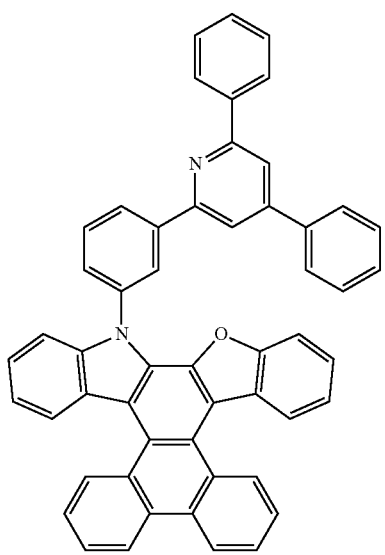
233
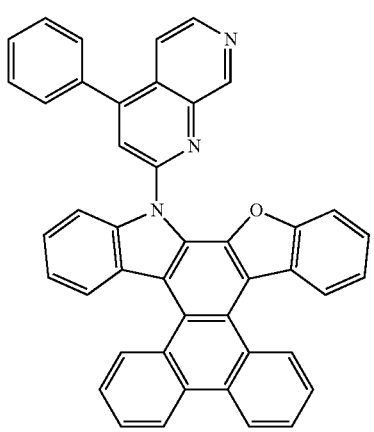
234
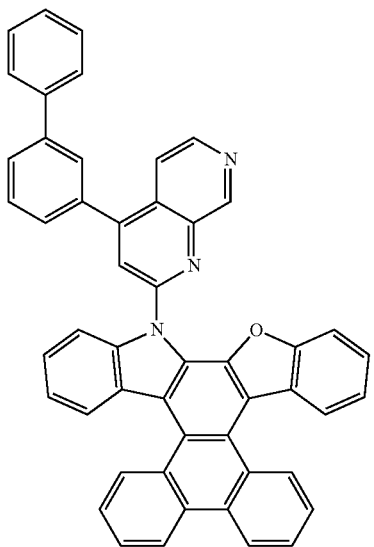
235
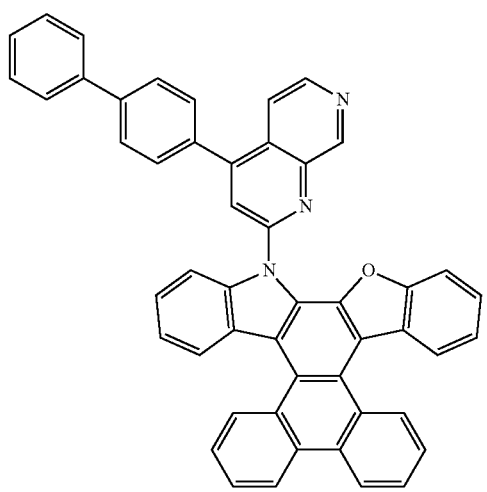
236
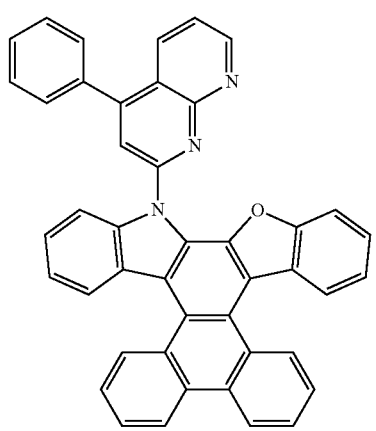
237
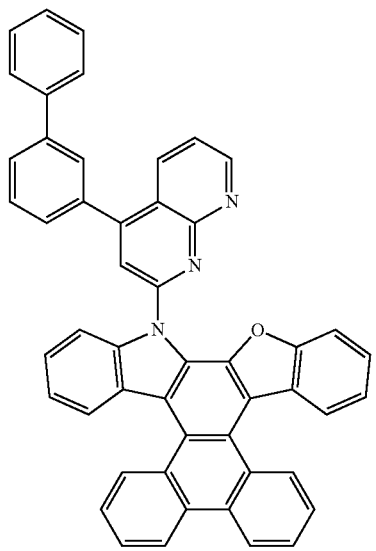

289
-continued
238
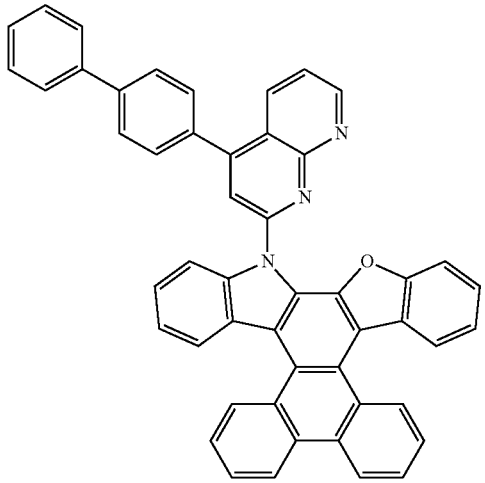
239
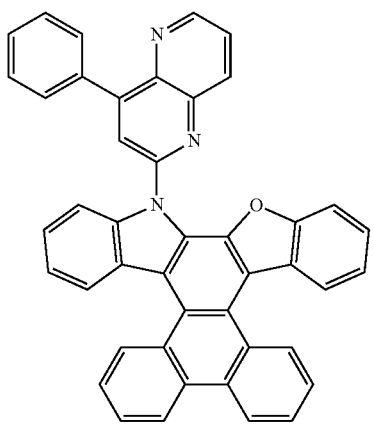
240
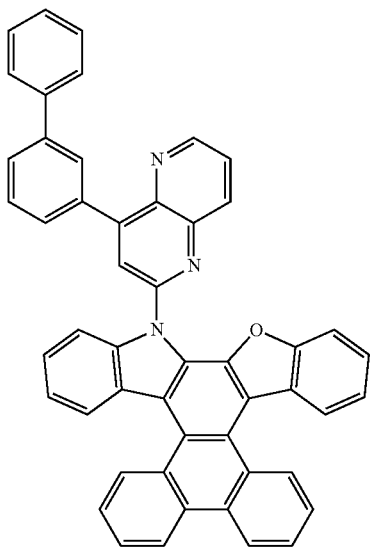
290
-continued
241
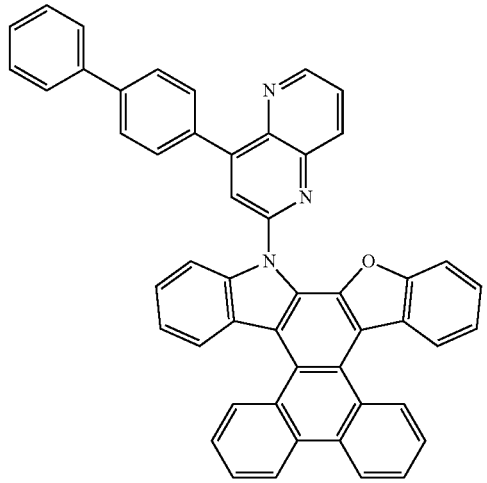
242
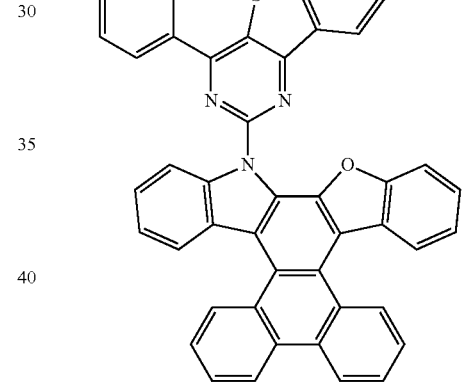
243
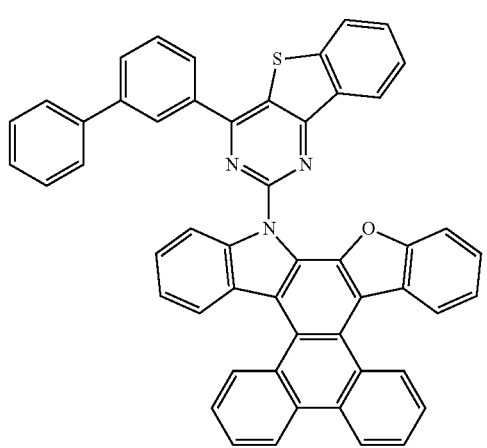

244
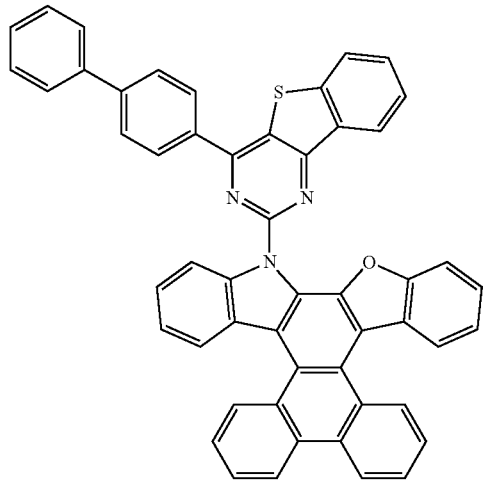
245
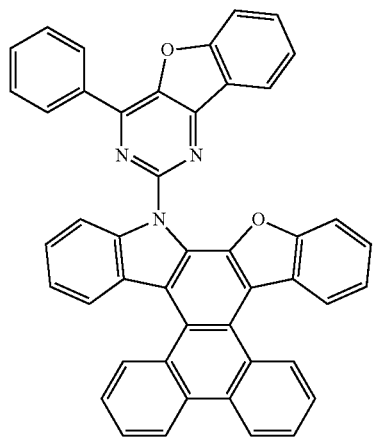
246
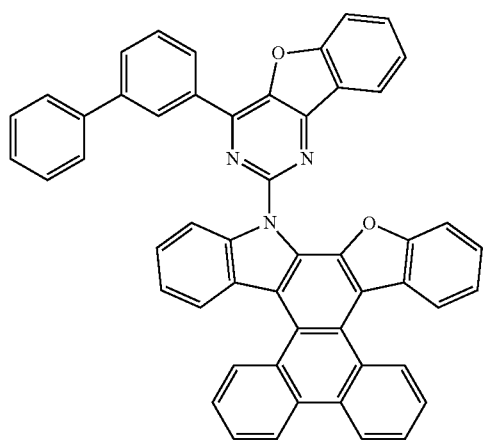
247
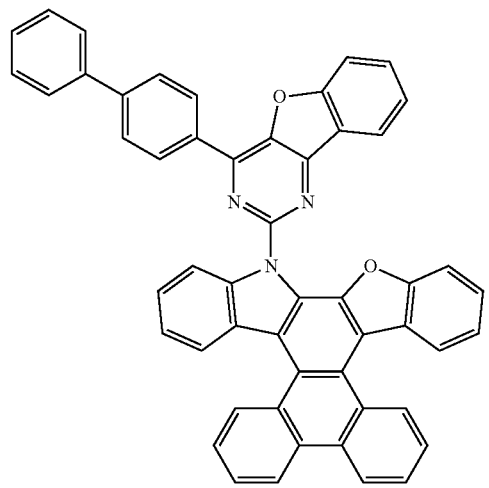
248
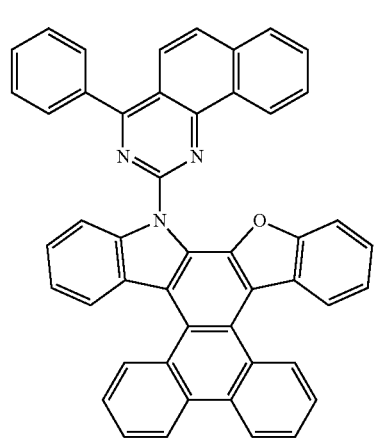
249
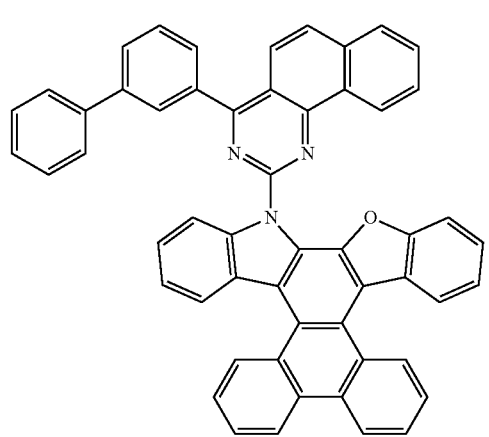

293
-continued
250
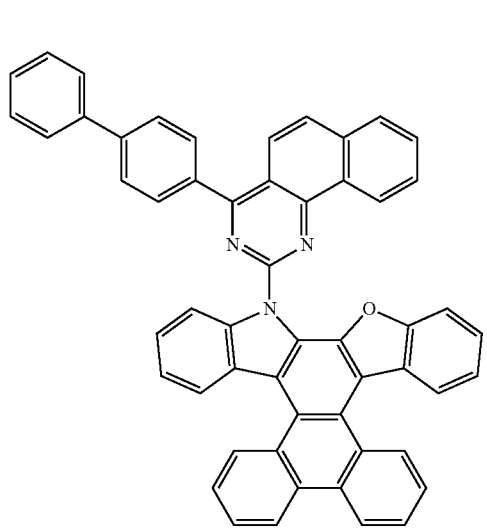
251
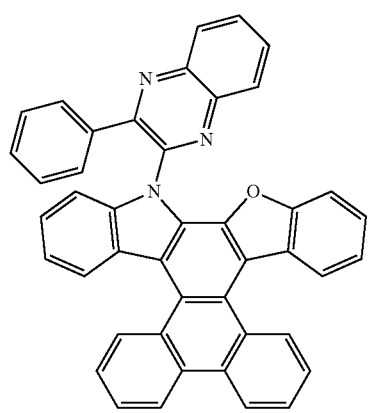
252
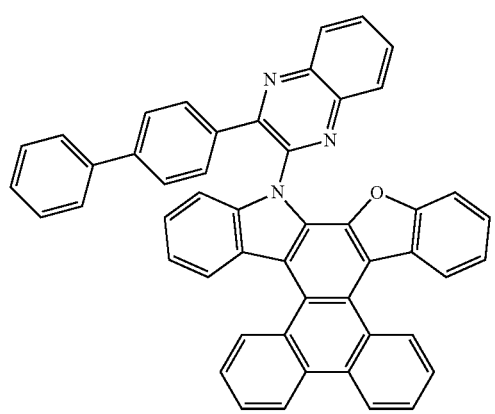
294
-continued
253
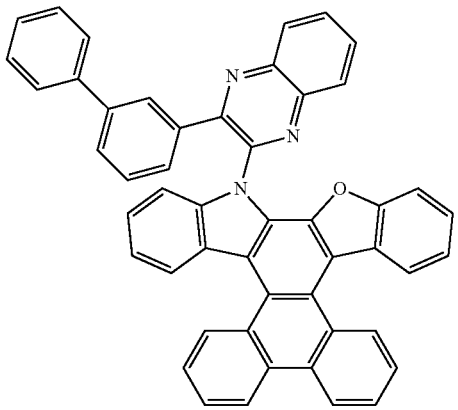
254
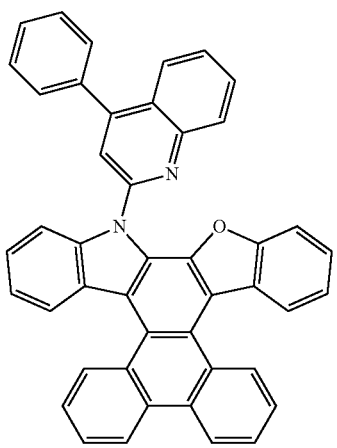
255
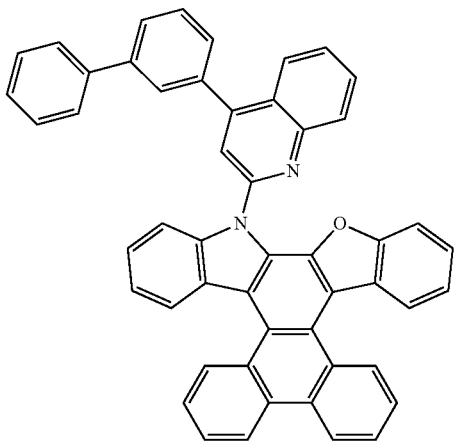

-continued

256

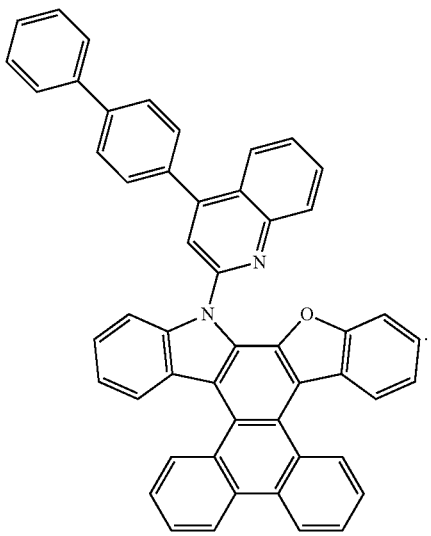

7. A composition for an organic optoelectric device, comprising
a first compound for an organic optoelectric device being the compound of claim 1; and
at least one second compound for an organic optoelectric device selected from a compound represented by Chemical Formula 2 and a compound consisting of a combination of a moiety represented by Chemical Formula 3 and a moiety represented by Chemical Formula 4:

[Chemical Formula 2]

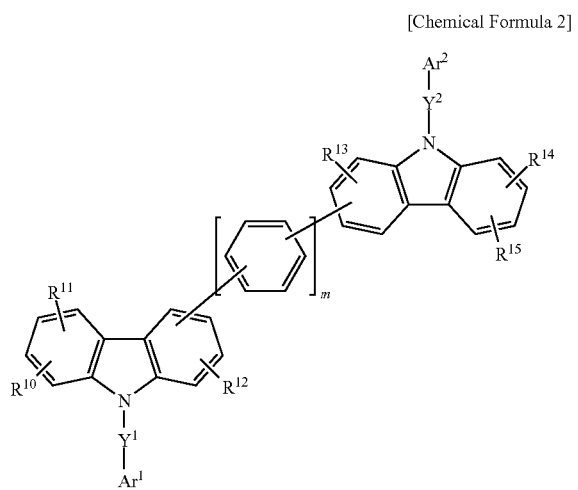

wherein, in Chemical Formula 2,
$Y^1$ and $Y^2$ are independently a single bond, a substituted or unsubstituted C6 to C30 arylene group, a substituted or unsubstituted C2 to C30 heteroarylene group, or a combination thereof,
$Ar^1$ and $Ar^2$ are independently a substituted or unsubstituted C6 to C30 aryl group, a substituted or unsubstituted C2 to C30 heterocyclic group, or a combination thereof,
$R^{10}$ to $R^{15}$ are independently hydrogen, deuterium, a substituted or unsubstituted C1 to C20 alkyl group, a substituted or unsubstituted C6 to C30 aryl group, a substituted or unsubstituted C2 to C50 heterocyclic group, or a combination thereof, and
m is an integer of 0 to 2;

[Chemical Formula 3]

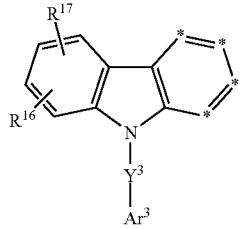

[Chemical Formula 4]

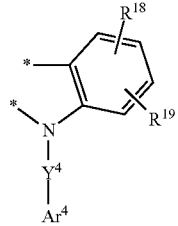

wherein, in Chemical Formulae 3 and 4,
$Y^3$ and $Y^4$ are independently a single bond, a substituted or unsubstituted C6 to C30 arylene group, a substituted or unsubstituted C2 to C30 heteroarylene group, or a combination thereof,
$Ar^3$ and $Ar^4$ are independently a substituted or unsubstituted C6 to C30 aryl group, a substituted or unsubstituted C2 to C30 heterocyclic group, or a combination thereof,
$R^{16}$ to $R^{19}$ are independently hydrogen, deuterium, a substituted or unsubstituted C1 to C20 alkyl group, a substituted or unsubstituted C6 to C50 aryl group, a substituted or unsubstituted C2 to C50 heterocyclic group, or a combination thereof,
two adjacent *'s of Chemical Formula 3 are C bound to two adjacent *'s of Chemical Formula 4 to provide a fused ring, and *'s not providing the fused ring in Chemical Formula 3 are independently $CR^a$, and
$R^a$ is hydrogen, deuterium, a substituted or unsubstituted C1 to C10 alkyl group, a substituted or unsubstituted C6 to C12 aryl group, a substituted or unsubstituted C2 to C12 heterocyclic group, or a combination thereof;
wherein the "substituted" refers to replacement of at least one hydrogen by deuterium, a C1 to C4 alkyl group, a C6 to C18 aryl group, or a C2 to C18 heteroaryl group.

8. The composition for an organic optoelectric device of claim 7, wherein $Ar^1$ and $Ar^2$ of Chemical Formula 2 are independently a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted triphenylenyl group, a substituted or unsubstituted pyridinyl group, a substituted or unsubstituted pyrimidinyl group, a substituted or unsubstituted quinazolyl group, a substituted or unsubstituted isoquinazolyl group, a substituted or unsubstituted dibenzothiophenyl group, a substituted or unsubstituted dibenzofuranyl group, a substituted or unsubstituted carbazolyl group, a substituted or unsubstituted fluorenyl group, or a combination thereof.

9. The composition for an organic optoelectric device of claim 7, wherein:
Chemical Formula 2 includes one of structures of Group III, and
the moieties *—Y$^1$—Ar$^1$ and *—Y$^2$—Ar$^2$ of Chemical Formula 2 are independently one of substituents of Group IV,
[Group III]
C-1
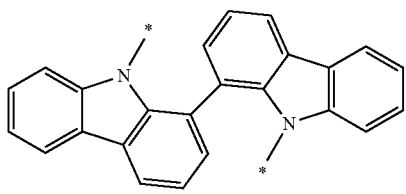
C-2
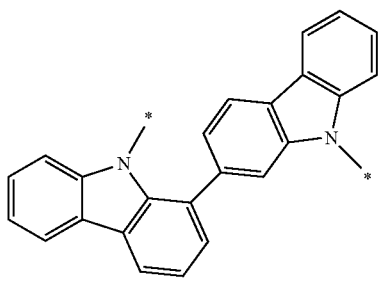
C-3
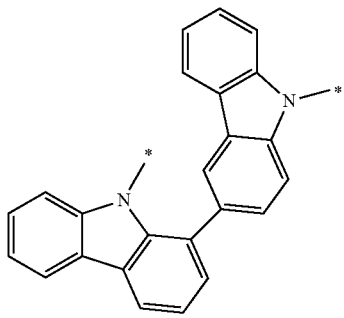
C-4
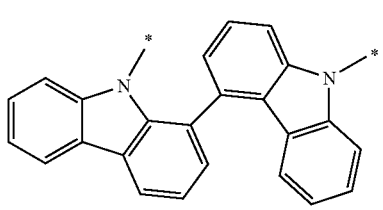
C-5
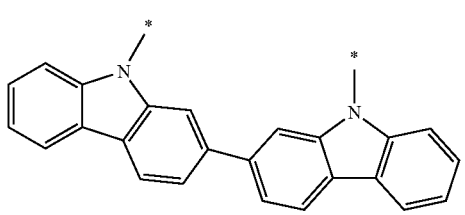
-continued
C-6
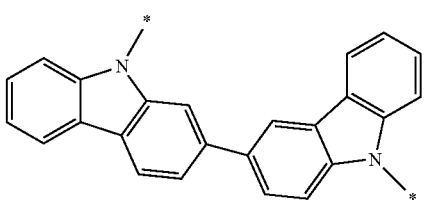
C-7
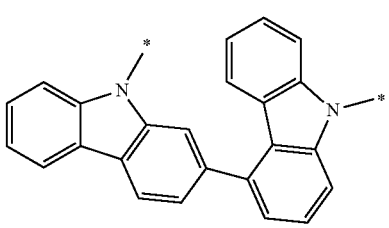
C-8
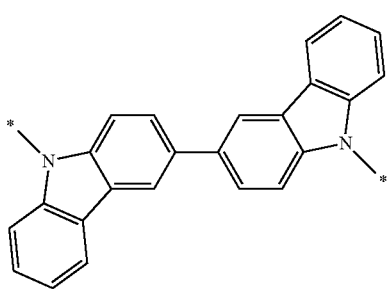
C-9
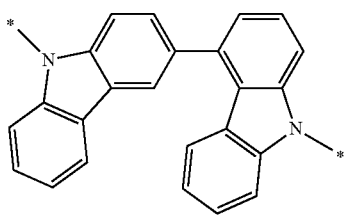
C-10
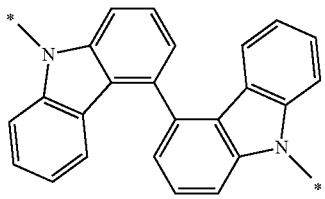
C-11
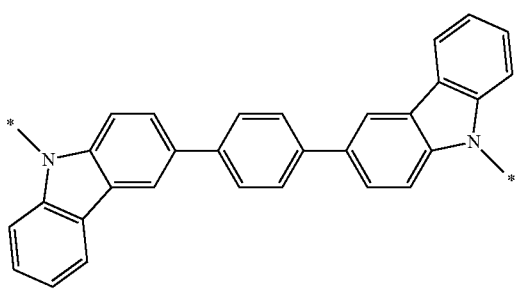

C-12
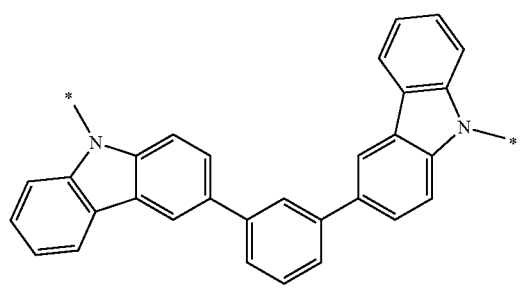
C-13
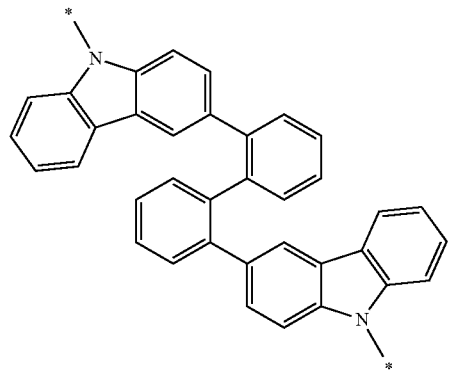
C-14
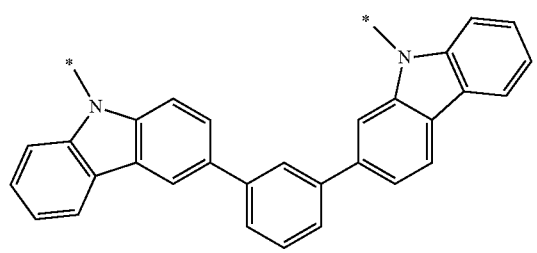
C-15
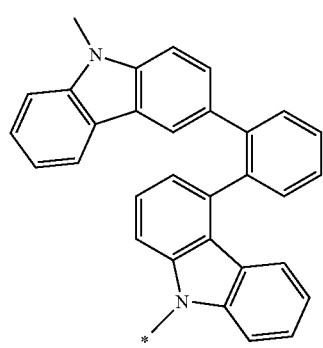
C-16
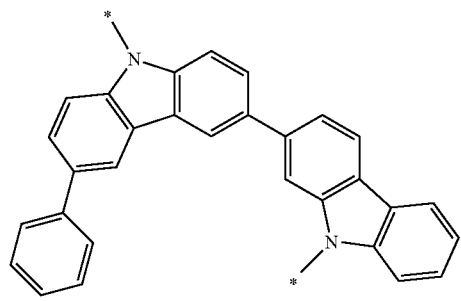
C-17
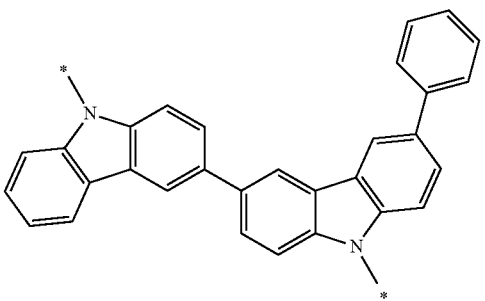
C-18
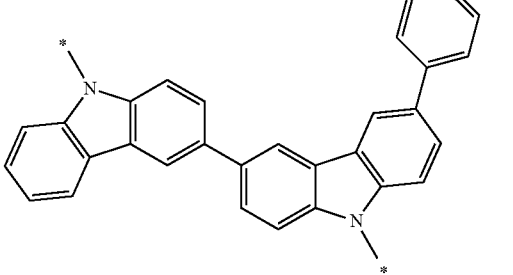
[Group IV]
B-1
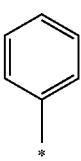
B-2
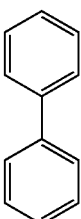
B-3
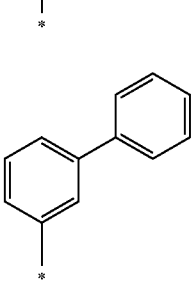

-continued
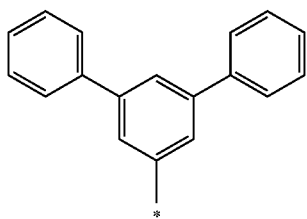
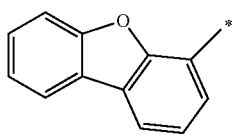
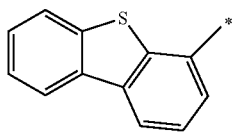
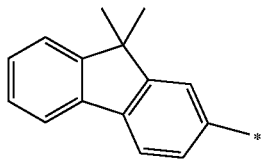
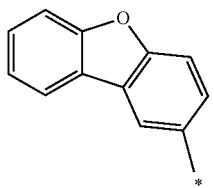
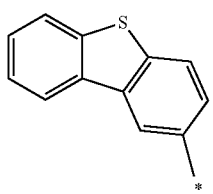
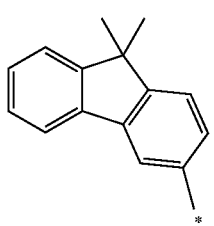
-continued
B-11
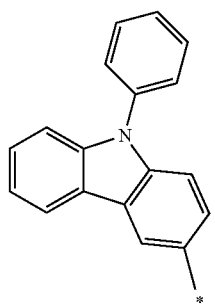
B-12
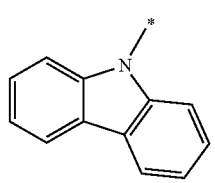
B-13
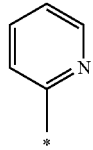
B-14
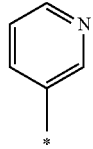
B-15
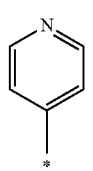
B-16
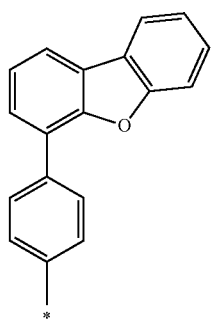

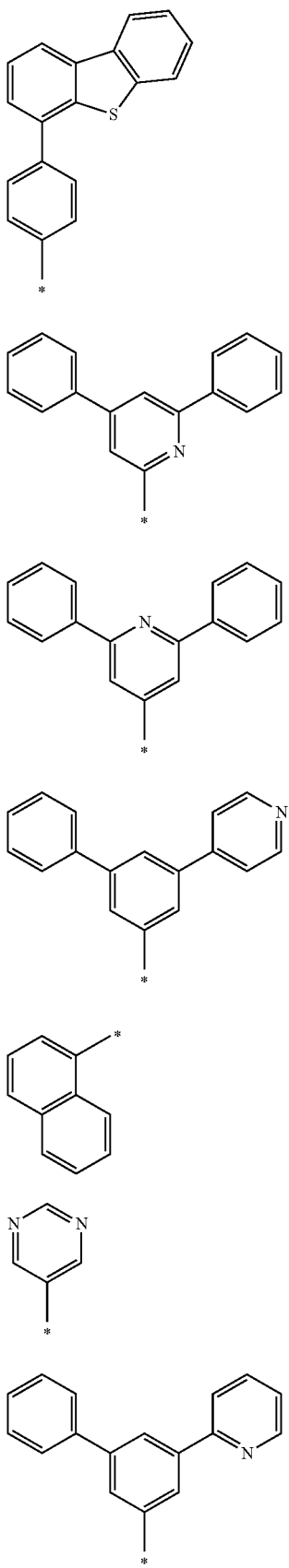
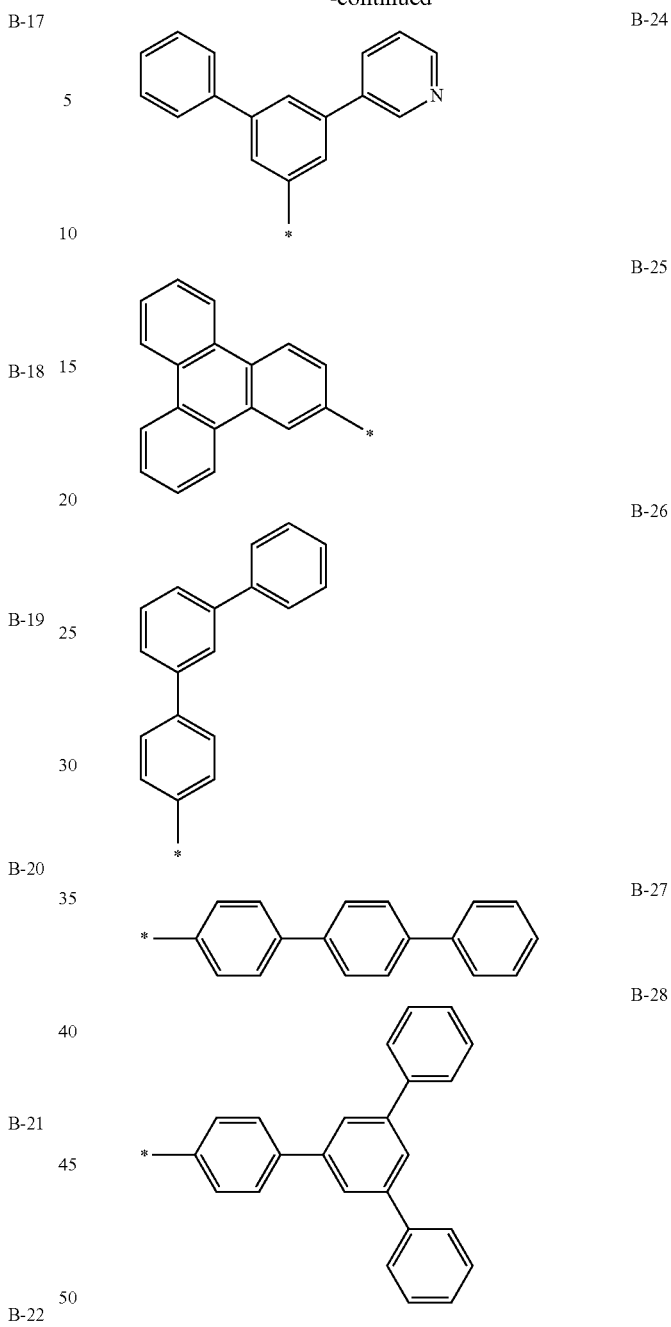

wherein, in Group III and Group IV, * is a linking point.

10. The composition for an organic optoelectric device of claim 9, wherein:

Chemical Formula 2 includes the structure represented by C-8 of Group III, and the moieties *—$Y^1$—$Ar^1$ and *—$Y^2$—$Ar^2$ of Chemical Formula 2 are independently represented by one of B-1 to B-4 of Group IV.

11. An organic optoelectric device, comprising:

an anode and a cathode facing each other, and an organic layer between the anode and the cathode, wherein the organic layer includes the compound for an organic optoelectric device of claim 1.

12. The organic optoelectric device of claim 11, wherein:
the organic layer includes a light emitting layer,
the compound for an organic optoelectric device is included as a host of the light emitting layer.

13. A display device comprising the organic optoelectric device of claim 11.

14. A composition for an organic optoelectric device, comprising
a first compound for an organic optoelectric device represented by Chemical Formula 1A; and
a second compound for an organic optoelectric device represented by Chemical Formula 1B:

[Chemical Formula 1A]

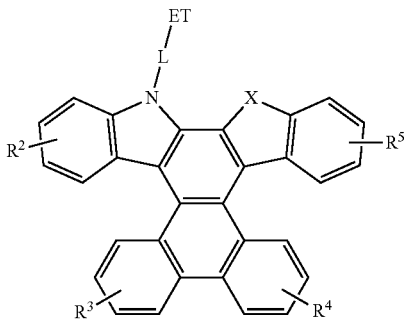

[Chemical Formula 1B]

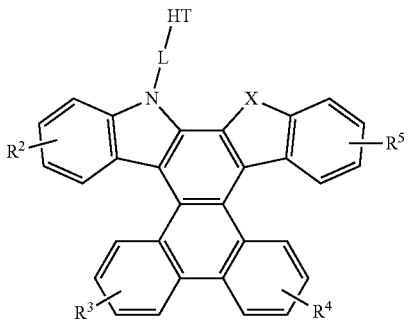

wherein, in Chemical Formula 1A and Chemical Formula 1B,

X is O, or S,

ET is a substituted or unsubstituted pyridinyl group, a substituted or unsubstituted pyrimidinyl group, a substituted or unsubstituted triazinyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzofuranpyrimidinyl group, a substituted or unsubstituted benzothiophenepyrimidinyl group, or a substituted or unsubstituted phenanthrolinyl group, HT is a substituted or unsubstituted phenyl group, a substituted or unsubstituted biphenyl group, a substituted or unsubstituted terphenyl group, a substituted or unsubstituted naphthyl group, a substituted or unsubstituted phenanthrenyl group, a substituted or unsubstituted triphenylene group, a substituted or unsubstituted fluorenyl group, a substituted or unsubstituted fluoranthenyl group, a substituted or unsubstituted carbazolyl group, a substituted or unsubstituted dibenzofuranyl group, or a substituted or unsubstituted dibenzothiophenyl group, $R^2$ to $R^9$ are independently hydrogen, deuterium, a substituted or unsubstituted C1 to C20 alkyl group, a substituted or unsubstituted C6 to C30 aryl group, a substituted or unsubstituted C2 to C30 heterocyclic group, or a combination thereof, and L is a single bond, a substituted or unsubstituted C6 to C30 arylene group, a substituted or unsubstituted C2 to C30 heteroarylene group, or a combination thereof.

15. The composition for an organic optoelectric device of claim 14, wherein:

ET is a substituted or unsubstituted quinazolinyl group,

HT is a substituted or unsubstituted phenyl group, a substituted or unsubstituted biphenyl group, a substituted or unsubstituted terphenyl group, a substituted or unsubstituted phenanthrene group, a substituted or unsubstituted dibenzofuranyl group, or a substituted or unsubstituted dibenzothiophenyl group, $R^2$ to $R^9$ are hydrogen, and the "substituted" refers to replacement of at least one hydrogen by deuterium, a C1 to C4 alkyl group, a phenyl group, a biphenyl group, a naphthyl group, a phenanthrenyl group, a triphenylene group, a fluoranthenyl group, a carbazolyl group, a dibenzofuranyl group, a dibenzothiophenyl group, a pyridinyl group, a pyrimidinyl group, or a triazinyl group.

16. An organic optoelectric device, comprising:
an anode and a cathode facing each other, and
an organic layer between the anode and the cathode,
wherein the organic layer includes the composition for an organic optoelectric device of claim 14.

17. The organic optoelectric device of claim 16, wherein:
the organic layer includes a light emitting layer, and
the composition for an organic optoelectric device is included as a host of the light emitting layer.

18. A display device comprising the organic optoelectric device of claim 16.

* * * * *